US008603473B2

(12) United States Patent
Glaser et al.

(10) Patent No.: US 8,603,473 B2
(45) Date of Patent: *Dec. 10, 2013

(54) MODIFIED BINDING MOLECULES COMPRISING CONNECTING PEPTIDES

(75) Inventors: Scott Glaser, San Diego, CA (US); Mitchell Reff, San Diego, CA (US); Tzung-Horng Yang, San Diego, CA (US); Xiufeng Wu, San Diego, CA (US); Paul Chinn, Carlsbad, CA (US)

(73) Assignee: Biogen Idec MA Inc., Cambridge, MA (US)

( * ) Notice: Subject to any disclaimer, the term of this patent is extended or adjusted under 35 U.S.C. 154(b) by 744 days.

This patent is subject to a terminal disclaimer.

(21) Appl. No.: 12/100,375

(22) Filed: Apr. 9, 2008

(65) Prior Publication Data

US 2009/0041758 A1 Feb. 12, 2009

Related U.S. Application Data

(63) Continuation of application No. 10/880,028, filed on Jun. 28, 2004, now abandoned.

(60) Provisional application No. 60/483,877, filed on Jun. 27, 2003, provisional application No. 60/508,810, filed on Oct. 3, 2003, provisional application No. 60/515,351, filed on Oct. 28, 2003, provisional application No. 60/516,030, filed on Oct. 30, 2003.

(51) Int. Cl.
*C07K 16/46* (2006.01)
*C07K 16/00* (2006.01)
*C07K 19/00* (2006.01)
*C07K 16/22* (2006.01)
*C07K 16/28* (2006.01)
*C07K 16/30* (2006.01)

(52) U.S. Cl.
USPC .......... 424/133.1; 424/134.1; 424/136.1; 424/143.1; 424/145.1; 424/155.1; 424/192.1; 530/324; 530/387.3; 530/387.7; 530/388.22; 530/388.8

(58) Field of Classification Search
None
See application file for complete search history.

(56) References Cited

U.S. PATENT DOCUMENTS

| 4,485,045 | A | 11/1984 | Regen |
| 4,544,545 | A | 10/1985 | Ryan et al. |
| 4,816,567 | A | 3/1989 | Cabilly et al. |
| 5,041,533 | A | 8/1991 | Wunsch et al. |
| 5,082,783 | A | 1/1992 | Ernst et al. |
| 5,166,322 | A | 11/1992 | Shaw et al. |
| 5,206,344 | A | 4/1993 | Katre et al. |
| 5,208,020 | A | 5/1993 | Chari et al. |
| 5,219,996 | A | 6/1993 | Bodmer et al. |
| 5,225,538 | A | 7/1993 | Capon et al. |
| 5,348,876 | A | 9/1994 | Michaelsen et al. |
| 5,530,101 | A | 6/1996 | Queen et al. |
| 5,618,920 | A | 4/1997 | Robinson et al. |
| 5,624,821 | A | 4/1997 | Winter et al. |
| 5,641,870 | A | 6/1997 | Rinderknecht et al. |
| 5,648,260 | A | 7/1997 | Winter et al. |
| 5,661,004 | A | 8/1997 | Browning et al. |
| 5,670,149 | A | 9/1997 | Browning et al. |
| 5,677,425 | A | 10/1997 | Bodmer et al. |
| 5,714,149 | A | 2/1998 | Rhind et al. |
| 5,766,897 | A | 6/1998 | Braxton |
| 5,795,964 | A | 8/1998 | Browning et al. |
| 5,821,333 | A | 10/1998 | Carter et al. |
| 5,834,597 | A | 11/1998 | Tso et al. |
| 5,837,821 | A | 11/1998 | Wu |
| 5,859,205 | A | 1/1999 | Adair et al. |
| 5,877,291 | A | 3/1999 | Mezes et al. |
| 5,892,019 | A | 4/1999 | Schlom et al. |
| 5,925,351 | A | 7/1999 | Browning et al. |
| 5,959,083 | A | 9/1999 | Bosslet et al. |
| 5,976,845 | A | 11/1999 | Mezes et al. |
| 6,011,138 | A | 1/2000 | Reff et al. |
| 6,063,905 | A | 5/2000 | Capra et al. |
| 6,066,719 | A | 5/2000 | Zapata |

(Continued)

FOREIGN PATENT DOCUMENTS

EP 0327378 A1 8/1989
EP 0509553 B1 10/1992

(Continued)

OTHER PUBLICATIONS

Brown et al, J Immunol 156(9): 3285-91, May 1996.*
Barrios et al, J Molecular Recognition 17: 332-338, 2004.*
Vajdos et al, J Mol Biol 320(2): 415-428, Jul. 5, 2002.*
Reiter, Yoram, et al., "Engineering interchain disulfide bonds into conserved framework regions of Fv Fragments: improved biochemical characteristics of recombinant immunotoxins containing disulfide-stabilized Fv," Protein Engineering, vol. 7(5):697-704 (1994).

(Continued)

*Primary Examiner* — Phuong Huynh
(74) *Attorney, Agent, or Firm* — Nelson Mullins Riley & Scarborough LLP; Debra J. Milasincic, Esq.

(57) ABSTRACT

The instant invention describes methods of separating or preferentially synthesizing dimers which are linked via at least one interchain disulfide linkage from dimers which are not linked via at least one interchain disulfide linkage from a mixture comprising the two types of polypeptide dimers. These forms can be separated from each other using hydrophobic interaction chromatography. In addition, the invention pertains to connecting peptides that result in the preferential biosynthesis of dimers that are linked via at least one interchain disulfide linkage or that are not linked via at least one interchain disulfide linkage. The invention also pertains to compositions in which a majority of the dimers are linked via at least one interchain disulfide linkage or are not linked via at least one interchain disulfide linkage. The invention still further pertains to novel binding molecules, e.g., comprising connecting peptides of the invention.

50 Claims, 42 Drawing Sheets

(56) References Cited

U.S. PATENT DOCUMENTS

| | | |
|---|---|---|
| 6,071,515 A | 6/2000 | Mezes et al. |
| 6,136,313 A | 10/2000 | Stevenson et al. |
| 6,165,476 A | 12/2000 | Strom et al. |
| 6,207,815 B1 | 3/2001 | Mezes et al. |
| 6,214,984 B1 | 4/2001 | Zapata |
| 6,218,149 B1 | 4/2001 | Morrison et al. |
| 6,284,536 B1 | 9/2001 | Morrison et al. |
| 6,312,691 B1 | 11/2001 | Browning et al. |
| 6,329,507 B1 | 12/2001 | Mezes et al. |
| 6,335,170 B1 | 1/2002 | Orntoft |
| 6,348,581 B1 | 2/2002 | Anderson et al. |
| 6,403,087 B1 | 6/2002 | Browning et al. |
| 6,413,777 B1 | 7/2002 | Reff et al. |
| 6,495,137 B1 | 12/2002 | Mezes et al. |
| 6,552,170 B1 | 4/2003 | Thompson et al. |
| 6,576,746 B2 | 6/2003 | McBride et al. |
| 6,642,356 B1 | 11/2003 | Humphreys et al. |
| 6,669,941 B1 | 12/2003 | Browning et al. |
| 6,737,056 B1 | 5/2004 | Presta |
| 6,759,518 B1 | 7/2004 | Kontermann et al. |
| 6,989,145 B2 | 1/2006 | Shitara et al. |
| 7,001,598 B2 | 2/2006 | Browning et al. |
| 7,026,446 B1 | 4/2006 | Atwell et al. |
| 7,030,080 B2 | 4/2006 | Browning et al. |
| 7,060,667 B1 | 6/2006 | Browning et al. |
| 7,247,302 B1 | 7/2007 | Rosok et al. |
| 7,276,585 B2 | 10/2007 | Lazar et al. |
| 7,317,091 B2 | 1/2008 | Lazar et al. |
| 7,318,924 B2 | 1/2008 | McKenzie et al. |
| 7,531,174 B2 | 5/2009 | Sanicola-Nadel et al. |
| 7,700,097 B2 * | 4/2010 | Braslawsky et al. ....... 424/133.1 |
| 8,084,026 B2 * | 12/2011 | Glaser et al. ............. 424/133.1 |
| 2002/0002271 A1 | 1/2002 | Rinderknecht et al. |
| 2002/0009446 A1 | 1/2002 | Magilavy |
| 2002/0028486 A1 | 3/2002 | Morrison et al. |
| 2002/0037558 A1 | 3/2002 | Lo et al. |
| 2002/0062010 A1 | 5/2002 | Arathoon et al. |
| 2002/0155109 A1 | 10/2002 | Lynch |
| 2002/0197254 A1 | 12/2002 | Browning et al. |
| 2003/0060444 A1 | 3/2003 | Finney et al. |
| 2003/0078385 A1 | 4/2003 | Arathoon et al. |
| 2003/0207346 A1 | 11/2003 | Arathoon et al. |
| 2004/0014690 A1 | 1/2004 | Ma et al. |
| 2004/0033511 A1 | 2/2004 | Pfizenmaier et al. |
| 2004/0058394 A1 | 3/2004 | Garber et al. |
| 2004/0082762 A1 | 4/2004 | Basi et al. |
| 2004/0101905 A1 | 5/2004 | Brekke et al. |
| 2004/0146940 A1 | 7/2004 | Sanicola-Nadel et al. |
| 2004/0176576 A1 | 9/2004 | McKenzie et al. |
| 2004/0198635 A1 | 10/2004 | Browning et al. |
| 2005/0037003 A1 | 2/2005 | Browning et al. |
| 2005/0097625 A1 | 5/2005 | Meade et al. |
| 2005/0152894 A1 | 7/2005 | Krummen et al. |
| 2005/0163782 A1* | 7/2005 | Glaser et al. ............. 424/155.1 |
| 2005/0163783 A1* | 7/2005 | Braslawsky et al. ....... 424/155.1 |
| 2005/0208045 A1 | 9/2005 | Vale et al. |
| 2005/0281811 A1 | 12/2005 | Browning et al. |
| 2006/0104971 A1 | 5/2006 | Garber et al. |
| 2006/0134102 A1 | 6/2006 | LePage et al. |
| 2006/0222644 A1 | 10/2006 | Garber et al. |
| 2006/0280722 A1 | 12/2006 | Browning et al. |
| 2007/0154476 A1 | 7/2007 | Browning et al. |
| 2007/0269371 A1 | 11/2007 | Krummen et al. |
| 2008/0166341 A1 | 7/2008 | Sanicola-Nadel et al. |
| 2009/0162380 A1* | 6/2009 | Glaser et al. ............. 424/172.1 |
| 2009/0285818 A1 | 11/2009 | Sanicola-Nadel et al. |
| 2010/0041032 A1 | 2/2010 | Orozco et al. |
| 2010/0202962 A1 | 8/2010 | Sanicola-Nadel et al. |

FOREIGN PATENT DOCUMENTS

| | | |
|---|---|---|
| EP | 0519596 B1 | 12/1992 |
| JP | 2001-46066 | 2/2001 |
| WO | 88/07089 A1 | 9/1988 |
| WO | 89/07142 A1 | 8/1989 |
| WO | 91/09967 A1 | 7/1991 |
| WO | 92/00329 A1 | 1/1992 |
| WO | 94/04679 A1 | 3/1994 |
| WO | 94/09817 A1 | 5/1994 |
| WO | 94/13808 A2 | 6/1994 |
| WO | 94/20625 A1 | 9/1994 |
| WO | 94/29351 A2 | 12/1994 |
| WO | 95/09917 A1 | 4/1995 |
| WO | 95/22389 | 8/1995 |
| WO | 96/22788 A1 | 8/1996 |
| WO | 97/03687 A1 | 2/1997 |
| WO | 97/11370 | 3/1997 |
| WO | 97/44362 A1 | 11/1997 |
| WO | 98/05787 A1 | 2/1998 |
| WO | 98/23289 A1 | 6/1998 |
| WO | 99/15549 A2 | 4/1999 |
| WO | 99/38525 A1 | 8/1999 |
| WO | 99/58572 A1 | 11/1999 |
| WO | 99/58679 A1 | 11/1999 |
| WO | 01/40309 A2 | 6/2001 |
| WO | 01/64754 A1 | 9/2001 |
| WO | 02/16413 A2 | 2/2002 |
| WO | 02/22680 A2 | 3/2002 |
| WO | 02/30986 A2 | 4/2002 |
| WO | 02/44215 A2 | 6/2002 |
| WO | 02/060955 A2 | 8/2002 |
| WO | 02/066516 A2 | 8/2002 |
| WO | 02/085946 A1 | 10/2002 |
| WO | 02/088170 A2 | 11/2002 |
| WO | 02/096948 A2 | 12/2002 |
| WO | 03/024392 A2 | 3/2003 |
| WO | 2004/003019 A2 | 1/2004 |
| WO | 2004/026427 A2 | 4/2004 |
| WO | 2004/029207 A2 | 4/2004 |
| WO | 2004/042017 A2 | 5/2004 |
| WO | 2004/074434 A2 | 9/2004 |
| WO | 2004/099249 A2 | 11/2004 |
| WO | 2005/000899 A2 | 1/2005 |
| WO | 2005/007809 A2 | 1/2005 |
| WO | 2005/027966 A2 | 3/2005 |
| WO | 2005/092927 A1 | 10/2005 |
| WO | 2006/074397 A2 | 7/2006 |
| WO | 2007/010231 A1 | 1/2007 |

OTHER PUBLICATIONS

Roux, K.H. et al., "Comparisons of the Ability of Human IgG3 Hinge Mutants, IgM, IgE, and IgA2, to Form Small Immune Complexes: A Role for Flexibility and Geometry," The Journal of Immunology, vol. 161:4083-4090 (1998).

Santos, Ameurfina D. et al., "Generation and Characterization of a Single Gene-encoded Single-Chain-Tetravalent Antitumor Antibody," Clinical Cancer Research, vol. 5:3118s-3123s (1999).

Schuurman, J. et al., "The inter-heavy chain disulfide bonds of IgG4 are in equilibrium with intra-chain disulfide bonds," Molecular Immunology, vol. 38:1-8 (2001).

Shopes, Bob, "A Genetically Engineered Human IgG Mutant with Enhanced Cytolytic Activity," The Journal of Immunology, vol. 148(9):2918-2922 (1992).

Shopes, Bob, "A Genetically Engineered Human IgG with Limited Flexibility Fully Initiates Cytolysis via Complement," Molecular Immunology, vol. 30(6):603-609 (1993).

Slavin-Chiorini, Dale C., et al., "Biological Properties of Chimeric Domain-deleted Anticarcinoma Immunoglobulin," Cancer Research, (Suppl.) vol. 55:5957s-5967s (1995).

Smith, Richard I.F., et al., "Recombinant Polymeric IgG: An Approach to Engineering More Potent Antibodies," Bio/Technology, vol. 12:683-688 (1994).

Tsutsumi, Yasuo, et al., "Site-specific chemical modification with polyethylene glycol of recombinant immunotoxin anti-Tac(Fv)-PE38 (LMB-2) improves antitumor activity and reduces animal toxicity and immunogenicity," PNAS, vol. 97(15):8548-8553 (2000).

Webber, Keith O., et al., "Preparation and Characterization of a Disulfide-Stabilized Fv Fragment of the Anti-Tac Antibody: Comparison with its Single-Chain Analog," Molecular Immunology, vol. 32(4):249-258 (1995).

(56) References Cited

OTHER PUBLICATIONS

Yazaki, Paul J., et al., "Mammalian expression and hollow fiber bioreactor production of recombinant anti-CEA diabody and minibody for clinical applications," Journal of Immunological Methods, vol. 253:195-208 (2001).
Zhao, Zhan G., et al., "Site-Specific Modification of a Single-Chain Antibody Using a Novel Glyoxylyl-Based Labeling Reagent," Bioconjugate Chem., vol. 10:424-430 (1999).
Aalberse, R.C. et al., "IgG4 breaking the rules," Immunology, vol. 105:9-19 (2002).
Adams, Gregory P., et al., "Highly Specific in Vivo Tumor Targeting by Monovalent and Divalent Forms of 741F8 Anti-c-erbB-2 Single-Chain Fv1," Cancer Research, vol. 53:4026-4034 (1993).
Adkins, Heather B. et al, "Antibody blockade of the Cripto CFC domain suppresses tumor cell growth in vivo," The Journal of Clinical Investigation, vol. 112(4):575-587 (2003).
Alt, Margitta, et al., "Novel tetravalent and bispecific IgG-like antibody molecules combining single-chain diabodies with the immunoglobulin gl Fc or CH3 region," FEBS Letters, vol. 454:90-94 (1999).
Angal, S. et al., "A Single Amino Acid Substitution Abolishes the Heterogeneity of Chimeric Mouse/Human (IgG4) Antibody," Molecular Immunology, vol. 30(1):105-108 (1993).
Benhar, Itai, et al., "Pseudomonas Exotoxin A Mutants," The Journal of Biological Chemistry, vol. 269(18):13398-13404 (1994).
Bera, Tapan K., et al., "A Bivalent Disulfide-stabilized Fv with Improved Antigen Binding to erbB2," J. Mol. Biol., vol. 281:475-483 (1998).
Bloom, James W., et al., "Interchain disulfide bond in the core hinge region of human IgG4," Protein Science, vol. 6:407-415 (1997).
Breeke, Ole Henrik, et al., "The structural requirements for complement activation by IgG: does it hinge on the hinge?" Immunology Today, vol. 16(2):85-90 (1995).
Caron, P.C. et al., "Engineered Humanized Dimeric Forms of IgG Are More Effective Antibodies," J. Exp. Med., vol. 176:1191-1195 (1992).
Carter, Paul, et al., "Engineering antibodies for imaging and therapy," Current Opinion in Biotechnology, vol. 8:449-454 (1997).
Chintalacharuvu, Koteswara R., et al., "Cysteine Residues Required for the Attachment of the Light Chain in Human IgA21," The Journal of Immunology, vol. 169:5072-5077 (2002).
Chintalacharuvu, Koteswara R., et al., "Hybrid IgA2/IgG1 Antibodies with Tailor-Made Effector Functions," Clinical Immunology, vol. 101(1):21-31 (2001).
Chintalacharuvu, Koteswara R., et al., "Production and characterization of recombinant IgA," Immunotechnology, vol. 4:165-174 (1999).
Chintalacharuvu, Koteswara R., et al., "Residues Critical for H-L Disulfide Bond Formation in Human IgA1 and IgA21," The Journal of Immunology, vol. 157:3443-3449 (1996).
Coloma, M. Josefina et al, "Design and production of novel tetravalent bispecific antibodies," Nature Biotechnology, vol. 15:159-163 (1997).
Coloma, M.J. et al., "The Hinge as a Spacer Contributes to Covalent Assembly and is Required for Function of IgG," The Journal of Immunology, vol. 158:733-740 (1997).
de Kruif, J. et al., Leucine Zipper Dimerized Bivalent and Bispecific scFv Antibodies from a Semi-synthetic Antibody Phage Display Library, The Journal of Biological Chemistry, vol. 271(13):7630-7634 (1996).
Dorai, Haimanti, et al., "Role of Inter-heavy and Light Chain Disulfide Bonds in the Effector Functions of Human Immunoglobulin IgG1," Molecular Immunology, vol. 29(12):1487-1491 (1992).
FitzGerald, Kevin, et al., "Improved tumour targeting by disulphide stabilized diabodies expressed in Pichia pastoris," Protein Engineering, vol. 10(10):1221-1225 (1997).
Gillies, Stephen D., et al., "Antigen binding and biological activities of engineered mutant chimeric antibodies with human tumor specificities," Hum. Antibod. Hybridomas, vol. 1(1):47-54 (1990).

Glockshuber, Rudi, et al., "A Comparison of Strategies to Stabilize Immunoglobulin FV-Fragments," Biochemistry, vol. 29:1362-1367 (1990).
Guan, Lufeng, et al., "Homogeneous immunoconjugates for boron neutron-capture therapy: Design, synthesis, and preliminary characterization," Proc. Natl. Acad. Sci. USA, vol. 95:13206-13210 (1998).
Haran, G., et al., "Doman motions in phosphoglycerate kinase: Determination of interdomain distance distributions by site-specific labeling and time-resolved fluorescence energy transfer," Proc. Natl. Acad. Sci. USA, vol. 89:11764-11768 (1992).
Hu, Xiu Feng et al, "Cripto Monoclonal Antibodies," Drug News Perspect., vol. 18(5):293-303 (2005).
Hu, S. et al., "Minibody: A Novel Engineered Anti-Carcinoembryonic Antigen Antibody Fragment (Single-Chain Fv-CH3) Which Exhibits Rapid, High-Level Targeting of Xenografts," Cancer Research, vol. 56:3055-3061 (1996).
Hudson, Peter J. et al., "High avidity scFv multimers; diabodies and triabodies," Journal of Immunological Methods, vol. 231:177-189 (1999).
Hudson, Peter J., "Recombinant antibody constructs in cancer therapy," Current Opinion in Immunology, vol. 11:548-557 (1999).
Humphreys, David P., et al., "F(ab')2 molecules made from *Escherichia coli* produced Fab' with hinge sequences conferring increased serum survival in an animal model," Journal of Immunological Methods, vol. 217:1-10 (1998).
Inouye, K. et al., "Single-step purification of F(ab') 2m fragments of mouse monoclonal antibodies (immunoglobulins M) by hydrophobic interaction high-performance liquid chromatography using TSKgel Ether-4PW," Journal of Biochemical and Biophysical Methods, vol. 26:27-39 (1993).
Jendreyko, Nina et al, "Intradiabodies, Bispecific, Tetravalent Antibodies for the Simultaneous Functional Knockout of Two Cell Surface Receptors," The Journal of Biological Chemistry, vol. 278(48):47812-47819 (2003).
Jue, Rodney, et al., "Addition of Sulfhydryl Groups to *Escherichia coli* Ribosomes by Protein Modification with 2-Iminothiolane (Methyl 4-Mercaptobutyrimidate)," Biochemistry, vol. 17(25):5399-5406 (1978).
Kipriyanov, Sergey M., et al., "Bacterial Expression and Refolding of Single-Chain Fv Fragments with C-Terminal Cysteines," Cell Biophysics, vol. 26:187-204 (1995).
Kreitman, Robert J., et al., "Site-Specific Conjugation to Interleukin 4 Containing Mutated Cysteine Residues Produces Interleukin 4-Toxin Conjugates with Improved Binding and Activity," Biochemistry, vol. 33:11637-11644 (1994).
Lee, C.V. et al., "Bivalent antibody phage display mimics natural immunoglobulin," Journal of Immunological Methods, vol. 284:119-132 (2004).
Lee, Hyun-Sil, et al., "Generation and characterization of a novel single-gene-encoded single-chain immunoglobulin molecule with antigen binding activity and effector functions," Molecular Immunology, vol. 36:61-71 (1999).
LePage, Doreen J. et al, "Inhibition of human tumor xenografts by anti-Cripto antibodies," Proceedings of the American Association for Cancer Research, vol. 44:145 (2003) Poster #749.
Leung, Shui-on et al, "The Effects of Domain Deletion, Glycosylation, and Long IgG, Hinge on the Biodistribution and Serum Stability Properties of a Humanized IgG, Immunoglobulin, hLL2, and Its Fragments," Clinical Cancer Research, vol. S:3106s-3116s (1999).
Lu, Dan et al, "Di-diabody: a novel tetravalent bispecific antibody molecule by design," Journal of Immunological Methods, vol. 279:219-232 (2003).
Lund, J. et al., "Multiple Interactions of "IgG with Its Core Oligosaccharide Can Modulate Recognition by Complement and Human Fcg Receptor I and Influence Synthesis of Its Oligosacharide Chains, The Journal of Immunology, vol. 157:4963-4969 (1996).
Lyons, Alan, et al., "Site-specific attachment to recombinant antibodies via introduced surface cysteine residues," Protein Engineering, vol. 3(8):703-708 (1990).
Michaelsen, T.E. et al., "Antibody Dependent Cell-Mediated Cytotoxicity Induced by Chimeric Mouse-Human IgG Subclasses and IgG3 Antibodies with Altered Hinge Region," Molecular Immunology, vol. 29(3):319-326 (1992).

(56) References Cited

OTHER PUBLICATIONS

Morimoto, K. et al., "Method for the preparation of bispecific F(ab')2m fragments from mouse monoclonal antibodies of the immunoglobulin M class and chararcterization of the fragments," Journal of Immunological Methods, vol. 224:43-50 (1999).

Morimoto, K. et al., "Single-step purification of F(ab')2 fragments of mouse monoclonal antibodies (immunoglobulins G1) by hydrophobic interaction high performance liquid chromatography using TSKgel Phenyl-4PW," Journal of Biochemical and Biophysical Methods, vol. 24:107-117 (1992).

Norderhaug, L. et al., "Chimeric mouse human IgG3 antibodies with an IgG4-like hinge region induce complement-mediated lysis more efficiently than IGG3 with normal hinge," Eur. J. Immunol., vol. 21:2379-2384 (1991).

Olafsen, Tove, et al., "Covalent disulfide-linked anti-CEA diabody allows site-specific conjugation and radiolabeling for tumor targeting applications," Protein Engineering, Design & Selection, vol. 17(1):21-27 (2004).

Palmer, Michael, et al., "*Staphylococcus aureus* a-Toxin," The Journal of Biological Chemistry, vol. 268 (16):11959-11962 (1993).

Plueckthun, Andreas et al, "New protein engineering approaches to multivalent and bispecific antibody fragments," Immunotechnology, vol. 3:83-105 (1997).

Queiroz, J.A., et al., "hydrophobic interaction chromatography of proteins," Journal of Biotechnology, vol. 87:143-159 (2001).

Reff, Mitchell E., et al., "A review of modifications to recombinant antibodies: attempt to increase efficacy in oncology applications," Critical Reviews in Oncology/Hematology, vol. 40:25-35 (2001).

Slepushkin, A.N. et al., "A comparative study of live and inactivated influenza vaccines: the organization of the observation and the results of a study of their reactogenicity and immunogenicity," Vopr. Virusol., vol. 39(3):128-131 (1994).

Smith, Craig A. et al., "A Receptor for Tumor Necrosis Factor Defines an Unusual Family of Cellular and Viral Proteins," Science, vol. 248:1019-1023 (1990).

Smith, Craig A. et al., "The TNF Receptor Superfamily of Cellular and Viral Proteins: Activation, Costimulation, and Death," Cell, vol. 76(6):959-962 (1994).

Smith-Gill, Sandra J. et al., "Contributions of Immunoglobulin Heavy and Light Chains to Antibody Specificity for Lysozyme and Two Haptens," The Journal of Immunology, vol. 139(12):4135-4144 (1987).

Smolen, Josef S., "Therapy of systemic lupus erythematosus: a look into the future," Arthritis Res., vol. 4(Suppl. 3): S25-S30 (2002).

Song, Mi-Kyung et al., "Light Chain of Natural Antibody Plays a Dominant Role in Protein Antigen Binding," Biochemical and Biophysical Research Communications, vol. 268:390-394 (2000).

Sugino, Yukio, "Biotechnology Series, Monoclonal Antibody," 40 pages (1986).

Talmadge, James E. et al., "Murine Models to Evaluate Novel and Conventional therapeutic Strategies for Cancer," The American Journal of Pathology, vol. 170(3):793-804 (2007).

Tartaglia, Louis A. et al., "Two TNF receptors," Immunology Today, vol. 13(5):151-153 (1992).

Tempest, Philip R. et al., "Reshaping a Human Monoclonal Antibody to Inhibit Human Respiratory Syncytial Virus Infection in Vivo," Bio/Technology, vol. 9:266-271 (1991).

Tew, John G. et al., "Follicular Dendritic Cells as Accessory Cells," Immunological Reviews, vol. 117:185-211 (1990).

Thurber, Greg M. et al., "Antibody tumor penetration: Transport opposed by systemic and antigen-mediated clearance," Advanced Drug Delivery Reviews, vol. 60:1421-1434 (2008).

Tibbetts, Randal S. et al., "Cardiac Antigen-Specific Autoantibody Production is Associated with Cardiomyopathy in Trypanosoma cruzi-infected mice," Journal of Immunology, vol. 152:1493-1499 (1994).

Toellner, Kai-Michael et al., "Immunoglobulin Swith Transcript Production In Vivo Related to the Site and Time of Antigen-specific B Cell Activation," J. Exp. Med., vol. 183:2303-2312 (1996).

Traunecker, Andréet al., "Highly efficient neutralization of HIV with recombinant CD4-immunoglobulin molecules," Nature, vol. 339:68-70 (1989).

Trethewey, Pat, "Systemic Lupus Erythematosus," Dimensions of Critical Care Nursing, vol. 23(3):111-115 (2004).

Ueda, Yutaka, et al., "Signal Transduction Inhibitor," Cancer and Chemotherapy (Gan to Kagaku Ryoho), vol. 28 (5):591-600 (2001).

Ullrich, Axel et al., "Signal Transduction by Receptors with Tyrosine Kinase Activity," Cell, vol. 61:203-212 (1990).

Van Dullemen, Hendrik M. et al., "Treatment of Crohn's Disease With Anti-Tumor Necrosis Factor Chimeric Monoclonal Antibody (cA2)," Gastroenterology, vol. 109:129-135 (1995).

Van Kooten, Cees et al., "CD40-CD40 Ligand: A Multifunctional Receptor—Ligand Pair," Advances in Immunology, vol. 61:1-77 (1996).

Van Vliet, Els et al., "Reticular Fibroblasts in Peripheral Lymphoid Organs Identified by a Monoclonal Antibody," The Journal of Histochemistry and Cytochemistry, vol. 34(7):883-890 (1986).

Voskoglou-Nomikos, Theodora et al., "Clinical Predictive Value of the in Vitro Cell Line, Human Xenograft, and Mouse Allograft Preclinical Cancer Models," Clinical Cancer Research, vol. 9:4227-4239 (2003).

Ward, E. Sally et al., "Binding activities of a repertoire of single immunoglobulin variable domains secreted from *Escherichia coli*," Nature, vol. 341(6242):544-546 (1989).

Ware, C.F. et al., "The Ligands and Receptors of the Lymphotoxin System," Curr. Top. Microbiol. Immunol., vol. 198:175-218 (1995).

Weinstein-Oppenheimer, Caroline R. et al., "The Raf signal transduction cascade as a target for chemotherapeutic intervention in growth factor-responsive tumors," Pharmacology & Therapeutics, vol. 88:229-279 (2000).

Welss, Thomas et al., "Molecular basis of basal cell carcinoma: Analysis of differential gene expression by differential display PCR and expression array," Int. J. Cancer, vol. 104:66-72 (2003).

Winter, Greg et al., "Man-made antibodies," Nature, vol. 349:293-299 (1991).

Wu, Herren et al., "Humanization of a Murine Monoclonal Antibody by Simultaneous Optimization of Framework and CDR Residues," J. Mol. Biol., vol. 294:151-162 (1999).

Wu, Qiang et al., "The Requirement of Membrane Lymphotoxin for the Presence of Dendritic Cells in Lymphoid Tissues," J. Exp. Med., vol. 190(5):629-638 (1999).

Xu, Jianchao et al., "Mice Deficient for teh CD40 Ligand," Immunity, vol. 1:423-431 (1994).

Yeo, Chang-Yeol et al., "Nodal Signals to Smads through Cripto-Dependent and Cripto-Independent Mechanisms," Molecular Cell, vol. 7:949-957 (2001).

Yonehara, Shin et al., "A Cell-killing monoclonal antibody (Anti-Fas) to a Cell Surface Antigen Co-downregulated with the Receptor of Tumor Necrosis Factor," J. Exp. Med., vol. 169:1747-1756 (1989).

Zhou, M. M et al., "Real-Time Measurements of Kinetics of EGF Binding to Soluble EGF Receptor Monomers and Dimers Support the Dimerization Model for Receptor Activation," Biochemistry, vol. 32:8193-8198 (1993).

MaClennan, I.C.M. et al., "The Structure and Function of Secondary Lymphoid Tissues," Clinical Aspects of Immunology, Blackwell Scientific Publications, 5th Edition, vol. 1, Chpt. 2, pp. 13-30 (1993).

Maeda, Kunihiko et al., "Murine Follicular Dendritic Cells and Low Affinity Fc Receptors for IgE (FceRII)," The Journal of Immunology, vol. 148(8):2340-2347 (1992).

Matsumoto, Mitsuru et al., "Affinity maturation without germinal centres in lymphotoxin-a-deficient mice," Nature, vol. 382:462-466 (1996).

Matsumoto, Mitsuru et al., "Distinct Roles of Lymphotoxin a and the Type 1 Tumor Necrosis Factor (TNF) Receptor in the Establishment of Follicular Dendritic Cells from the Non-Bone Marrow-derived Cells," J. Exp. Med., vol. 186 (12):1997-2004 (1997).

Matsumoto, Mitsuru et al., "Lymphotoxin-a-deficient and TNF receptor-I-deficient mice define developmental and functional characteristics of germinal centers," Immunological Reviews, vol. 156:137-144 (1997).

(56) References Cited

OTHER PUBLICATIONS

Matsumoto, Mitsuru et al., "Role of Lymphotoxin and the Type I TNF Receptor in the Formation of Germinal Centers," Science, vol. 271:1289-1291 (1996).
Mendlovic, Shlomo et al., "Induction of a systemic lupus erythematosus-like disease in mice by a common human anti-DNA idiotype," Proc. Natl. Acad. Sci. USA, vol. 85:2260-2264 (1988).
Miller, Glenn T. et al., "Specific Interaction of Lymphocyte Function-associated Antigen 3 with CD2 Can Inhibit T Cell Responses," J. Exp. Med., vol. 178:211-222 (1993).
Modlin, Robert L. et al., "Type 2 cytokines and negative immune regulation in human infections," Current Opinion in Immunology, vol. 5:511-517 (1993).
Mohan, Chandra et al., "Interaction Between CD40 and Its Ligand gp39 in the Development of Murine Lupus Nephritis," The Journal of Immunology, vol. 154:1470-1480 (1995).
Mohler, Kendall M. et al., "Suluble Tumor Necrosis Factor (TNF) Receptors Are Effective Therapeutic Agents in Lethal Endotoxemia and Function Simultaneously as Both TNF Carriers and TNF Antagonists," Journal of Immunology, vol. 151:1548-1561 (1993).
Morrison, Sherie L. et al., "Chimeric human antibody molecules: Mouse antigen-binding domains with human constant region domains," Proc. Natl. Acad. Sci. USA, vol. 81:6851-6855 (1984).
Morrison, Sherie L., "In Vitro Antibodies: Strategies for Production and Application," Annu. Rev. Immunol., vol. 10:239-265 (1992).
Morrissey, Philip J. et al., "CD4+ T Cells That Expess High Levels of CD45RB Induce Wasting Disease When Transferred into Congenic Severe Combined Immunodeficient Mice. Disease Development Is Prevented by Cotrasfer of Purified CD4+ T Cells," J. Exp. Med., vol. 178:237-244 (1993).
Muppidi, J.R. et al., "Ligand-independent redistribution of Fas (CD95) into lipid rafts mediates clonotypic T cell death," Nature Immunology, vol. 5(2):182-189 (2004).
Nakache, Maurice et al., "The mucosal vascular addressin is a tissue-specific endothelial cell adhesion molecule for circulating lymphocytes," Nature, vol. 337:179-181 (1989).
Neumann, Brigitte et al., "Defective Peyer's Patch Organogenesis in Mice Lacking the 55-kD Receptor for Tumor Necrosis Factor," J. Exp. Med., vol. 184:259-264 (1996).
Niederle, Norbert et al., "Long-Term Treatment of Chronic Myelogenous Leukemia with Different Interferons: Results from Three Studies," Leukemia and Lymphoma, vol. 9:111-119 (1993).
Onishi, Tetsuro et al., "A Study on Direct Antitumor Activity of Bropirimine (Oral Interferon Inducer) for Renal Cell Carcinoma," Acta Urol. Jpn., vol. 40:195-200 (1994).
Palmer, Michael et al., "*Staphylococcus aureus* alpha-Toxin, Production of Functionally Intact, Site-Spedifically Modifiable Protein by Introduction of Cysteine at Positions 69, 130, and 186," The Journal of Biological Chemistry, vol. 268(16):11959-11962 (1993).
Paul, William E., Fundamental Immunology, Third Edition, Raven Press, Chpt. 9, pp. 242, 292-295 (1993).
Pfeffer, Klaus et al., "Mice Deficient for the 55 kd Tumor Necrosis Factor Receptor Are Resistant to Endotoxic Shock, yet Succumb to L. monocytogenes Infection," Cell, vol. 73:457-467 (1993).
Picarella, Dominic E. et al., "Insulitis in transgenic mice expressing tumor necrosis factor b (lymphotoxin) in the pancreas," Proc. Natl. Acad. Sci. USA, vol. 89:10036-10040 (1992).
Picker, Louis J. et al., "Physiological and Molecular Mechanisms of Lymphocyte Homing," Annu. Rev. Immunol., vol. 10:561-591 (1992).
Pleskov, V.M. et al., "The receptor-mediated endocytosis of influenza viruses and low-density lipoproteins by tissue cells," Vopr. Virusol., vol. 39(3):121-125 (1994).
Powell, Kenneth L. et al., "The antiviral effects of nitric oxide," Trends in Microbiology, vol. 3(3):81-88 (1995).
Powrie, Fiona et al., "Inhibition of Th1 Responses Prevents Inflammatory Bowel Disease in scid Mice Reconstituted with CD45RBhi CD4+ T Cells," Immunity, vol. 1:553-562 (1994).
Powrie, Fiona et al., "Phenotypically distinct subsets of CD4+ T cells induce or protect from chronic intestinal inflammation in C. B-17 scid mice," International Immunology, vol. 5(11):1461-1471 (1993).
Queen, Cary et al., "A humanized antibody that binds to the interleukin 2 receptor," Proc. Natl. Acad. Sci. USA, vol. 86:10029-10033 (1989).
Raitano, Arthur B. et al., "Tumor Necrosis Factor Up-regulates g-Interferon Binding in a Human Carcinoma Cell Line," The Journal of Biological Chemistry, vol. 265(16):10466-10472 (1990).
Reed, Steven G. et al., "T-cell and cytokine responses in leishmaniasis," Current Opinion in Immunology, vol. 5:524-531 (1993).
Rennert, P.D. et al., "Normal Development of Lymph Nodes is Disrupted by Soluble LT beta Receptor—Ig Fusion Protein," European Cytokine Network, vol. 7(2):167, No. 17 (1996).
Rennert, Paul D. et al., "Surface Lymphotoxin a/b Complex Is Required for the Development of Peripheral Lymphoid Organs," J. Exp. Med., vol. 184:1999-2006 (1996).
Renshaw, Blair R. et al., "Humoral Immune Response in CD40 Ligand-deficient Mice," J. Exp. Med., vol. 180:1889-1900 (1994).
reutershealth, "Systemic Lupus Erythematosus," retrieved online at http://www.reutershealth.com/wellconnected/doc63.html (2002).
Riechmann, Lutz et al., "Reshaping human antibodies for therapy," Nature, vol. 332:323-327 (1988).
Roitt, Ivan M. et al., "Introduction to the Immune System," Immunology, Third Edition, Mosby, St. Louis, Chapter 1, pp. 1.1-1.12, Chpts. 19-22. pp. 19.1-22.12, Chapter 24, pp. 24.1-24.12 (1993).
Romagnani, Sergio, "Lymphokine Production by Human T Cells in Disease States," Annu. Rev. Immunol., vol. 12:227-257 (1994).
Rothe, Joachim et al., "Mice lacking the tumour necrosis factor receptor 1 are resistant to TNF-mediated toxicity but highly susceptible to infection by Listeria monocytogenes," Nature, vol. 364:798-802 (1993).
Ruddle, Nancy H. et al., "An Antibody to Lymphotoxin and Tumor Necrosis Factor Prevents Transfer of Experimetnal Allergic Encephalomyelitis," J. Exp. Med., vol. 172:1193-1200 (1990).
Rudikoff, Stuart et al., "Single amino acid substitution altering antigen-binding specificity," Proc. Natl. Acad. Sci. USA, vol. 79:1979-1983 (1982).
Rudnick, Stephen I. et al., "Affinity and Avidity in Antibody-Based Tumor Targeting," Cancer Biotherapy and Radiopharmaceuticals, vol. 24(2):155-161 (2009).
Sayegh, Mohamed H. et al., "CD28-B7 Blockade after Alloantigenic Challenge In Vivo Inhibits Th1 Cytokines but Spares Th2," J. Exp. Med., vol. 181:1869-1874 (1995).
Schiffer, Susan G. et al., "Fucosylation of Cripto Is Required for Its Ability to Facilitate Nodal Signaling," The Journal of Biological Chemistry, vol. 276(41):37769-37778 (2001).
Schiller, Joan H. et al., "Biological and Clinical Effects of Intravenous Tumor Necrosis Factor-a Administered Three Times Weekly," Cancer Research, vol. 51:1651-1658 (1991).
Schoenfeld, Hans-Joachim et al., "Efficient Purification of Recombinant Human Tumor Necrosis Factor b from *Escherichia coli* Yields Biologically Active Protein with a Trimeric Structure That Binds to Both Tumor Necrosis Factor Receptors," The Journal of Biological Chemistry, vol. 266(6):3863-3869 (1991).
Schriever, Folke et al., "The Central Role of Follicular Dendritic Cells in Lymphoid Tissues," Advances in Immunology, vol. 51:243-284 (1992).
Sebolt-Leopold, Judith S. et al., "Development of anticancer drugs targeting the MAP kinase pathway," Oncogene, vol. 19:6594-6599 (2000).
Selmaj, Krzysztof et al., "Identification of Lymphotoxin and Tumor Necrosis Factor in Multiple Sclerosis Lesions," J. Clin. Invest., vol. 87:949-954 (1991).
Sidman, Kenneth R. et al., "Controlled Release of Macromolecules and Pharmaceuticals from Synthetic Polypeptides Based on Glutamic Acid," Biopolymers, vol. 22:547-556 (1983).
Alderson, Mark R. et al., "Regulation of apoptosis and T cell activation by Fas-specific mAb," International Immunology, vol. 6(11):1799-1806 (1994).

(56) References Cited

OTHER PUBLICATIONS

Alimzhanov, Marat B. et al., "Abnormal development of secondary lymphoid tissues in lymphotoxin b-deficient mice," Proc. Natl. Acad. Sci. USA, vol. 94:9302-9307 (1997).
Androlewicz, Matthew J. et al., "Lymphotoxin Is Expressed as a Hetermeric Complex with a Distinct 33-kDa Glycoprotein on the Surface of an Activated Human T Cell Hybridoma," The Journal of Biological Chemistry, vol. 267 (4):2542-2547 (1992).
Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," J. Exp. Med., vol. 177:1439-1450 (1993).
Baens, Mathijs et al., "Construction and Evaluation of a hncDNA Library of Human 12p Transcribed Sequences Derived from a Somatic Cell Hybrid," Genomics, vol. 16:214-218 (1993).
Banks, Theresa A. et al., "Lymphotoxin-a-Deficient Mice," The Journal of Immunology, vol. 155:1685-1693 (1995).
Beckman, Robert A. et al., "Antibody Constructs in Cancer Therapy, Protein Engineering Strategies to Improve Exposure in Solid Tumors," Cancer, vol. 109(2):170-179 (2007).
Bernstein, David I. et al., "Effects of therapy with an immunomodulator (imiquimod, R-837) alone with the acyclovir on genital HSV-2 infection in guinea-pigs when begun after lesion development," Antiviral Research, vol. 20:45-55 (1993).
Bowie, James U. et al., "Deciphering the Message in Protein Sequences: Tolerance to Amino Acid Substitutions," Science, vol. 247:1306-1310 (1990).
Briskin, Michael J. et al., "MAdCAM-1 has homology to immunoglobulin and mucin-like adhesion receptors and to IgA1," Nature, vol. 363:461-464 (1993).
Browning, Jeffrey L. et al., "Characterization of Surface Lymphotoxin Forms, Use of Specific Monoclonal Antibodies and Soluble Receptors," The Journal of Immunology, vol. 154:33-46 (1995).
Browning, Jeffrey L. et al., "Lymphotoxin and an Associated 33-kDa Glycoprotein Are Expressed on the Surface of an Activated Human T Cell Hybridoma," The Journal of Immunology, vol. 147(4):1230-1237 (1991).
Browning, Jeffrey L. et al., "Lymphotoxin b, a Novel Member of the TNF Family That Forms a Heteromeric Complex with Lymphotoxin on the Cell Surface," Cell, vol. 72:847-856 (1993).
Browning, Jeffrey L. et al., "Signaling through the Lymphotoxin b Receptor Induces the Death of Some Adenocarcinoma Tumor Lines," J. Exp. Med., vol. 183:867-878 (1996).
Browning, Jeffrey L. et al., "Signaling through the lymphotoxin-b receptor in conjunction with interferon-? induces the death of a human tumor line," The 9th International Congress of Immunology, No. 4582 (1995).
Browning, Jeffrey et al., "Studies on the Differing Effects of Tumor Necrosis Factor and Lymphotoxin on the Growth of Several Human Tumor Lines," The Journal of Immunology, vol. 143(6):1859-1867 (1989).
Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111:2129-2138 (1990).
Campbell, Neil A. et al., "Methods: Monoclonal Antibody Technology," Biology, 5th Edition, Unit Seven, Animal Form and Function, Benjamin/Cummings, Laura Kennedy Ed., p. 856 (1999).
Casset, Florence et al., "A peptide mimetic of an anti-CD4 monoclonal antibody by rational design," Biochemical and Biophysical Research Communications, vol. 307:198-205 (2003).
Cavert, Winston et al., "Kinetics of Response in Lymphoid Tissues to Antiretroviral Therapy of HIV-1 Infection," Science, vol. 276:960-964 (1997).
Cespedes, Maria Virtudes et al., "Mouse models in oncogenesis and cancer therapy," Clin. Transl. Oncol.., vol. 8 (5):318-329 (2006).

Champier, Jacques et al., "Identification of differentially expressed genes in human pineal parenchymal tumors by microarray analysis," Acta Neuropathol., vol. 109:306-313 (2005).
Chen, Chyi-Ying A. et al., "AU-rich elements: characterization and importance in mRNA degradation," TIBS, vol. 20:465-470 (1995).
Chen, Yvonne et al., "Selection and Analysis of an Optimized Anti-VEGF Antibody: Crystal Structure of an Affinity-matured Fab in Complex with Antigen," J. Mol. Biol., vol. 293:865-881 (1999).
Cher, Daniel J. et al., "Two Types of Murine Helper T Cell Clone, II. Delayed-Type Hypersensitivity is Mediated by TH1 Clones," The Journal of Immunology, vol. 138(11):3688-3694 (1987).
Chisholm, Patricia L. et al., "Monoclonal antibodies to the integrin a-4 subunit inhibit the murine contact hypersensitivity response," Eur. J. Immunol., vol. 23:682-688 (1993).
Ciardiello, Fortunato et al., "Antitumor Activity of Combined Blockade of Epidermal Growth Factor Receptor and Protein Kinase A," Journal of National Cancer Institute, vol. 88(23):1770-1776 (1996).
Crowe, Paul D. et al., "A Lymphotoxin-b-Specific Receptor," Science, vol. 264:707-708 (1994).
Crowe, Paul D. et al., "Production of lymphotoxin (LTa) and a soluble dimeric form of its receptor using the baculovirus expression system," Journal of Immunological Methods, vol. 168:79-89 (1994).
Co, Man Sung et al., "Humanized antibodies for therapy," Nature, vol. 351:501-502 (1991).
Colman, P.M., "Effects of amino acid sequence changes on antibody-antigen interactions," Research in Immunology, vol. 145:33-36 (1994).
Couto, Joseph R. et al., "Humanization of KC4G3, an Anti-Human Carcinoma Antibody," Hybridoma, vol. 13 (3):215-219 (1994).
Dennis, Carina, "Off by a whisker," Nature, vol. 442(7104):739-741 (2006).
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).
De Togni, Pietro et al., "Abnormal Development of Peripheral Lymphoid Organs in Mice Deficient in Lymphotoxin," Science, vol. 264:703-707 (1994).
Dhein, Jens et al., "Induction of Apoptosis by Monoclonal Antibody Anti-APO-1 Class Switch Variants is Dependent on Cross-linking of APO-1 Cell Surface Antigens," The Journal of Immunology, vol. 149(10):3166-3173 (1992).
Dighe, Anand S. et al., "Enhanced In Vivo Growth and Resistance to Rejection of Tumor Cells Expressing Dominant Negative IFNg Receptors," Immunity, vol. 1:447-456 (1994).
Dijkstra, Christine D. et al., "Marginal zone macrophages identified by a monoclonal antibody: characterization of immuno- and enzyme-histochemical properties and functional capacities," Immunology, vol. 55:23-30 (1985).
Dono, Rosanna et al., "Isolation and Characterization of the CRIPTO Autosomal Gene and Its X-linked Related Sequence," Am. J. Hum. Genet., vol. 49:555-565 (1991).
Düzgünes, Nejat et al., "Liposome Targeting to HIV-Infected Cells Via Recombinant Soluble CD4 and CD4-IgG (Immunoadhesin)," Journal of Cellular Biochemistry, vol. 16:77, No. Q514 (1992).
Endres, Robert et al., "Mature Follicular Dendritic Cell Networks Depend on Expression of Lymphotoxin b Receptor by Radioresistant Stromal Cells and of Lymphotoxin b and Tumor Necrosis Factor by B Cells," J. Exp. Med., vol. 189 (1):159-167 (1999).
Eppstein, Deborah A. et al., "Biological activity of liposome-encapsulated murine interferon g is mediated by a cell membrane receptor," Proc. Natl. Acad. Sci. USA, vol. 82:3688-3692 (1985).
Erickson, Sharon L. et al., "Decreased sensitivity to tumour-necrosis factor but normal T-cell development in TNF receptor-2-deficient mice," Nature, vol. 372:560-563 (1994).
Ettinger, Rachel et al., "Disrupted splenic architecture, but normal lymph node development in mice expressing a soluble lymphotoxin-b receptor-IgG1 fusion protein," Proc. Natl. Acad. Sci. USA, vol. 93:13102-13107 (1996).
Fägerstam, Lars G. et al., "Surface Plasmon Resonance Detection in Affinity Technologies," Handbook of Affinity Chromatography, Chpt. 9, pp. 229-252 (1993).

(56) References Cited

OTHER PUBLICATIONS

Fitch, F.W. et al., "Differential Regulation of Murine T Lymphocyte Subsets," Annu. Rev. Immunol., vol. 11:29-48 (1993).
Force, Walker R. et al., "Mouse Lymphotoxin-b Receptor," The Journal of Immunology, vol. 155:5280-5288 (1995).
Foy, Teresa M. et al., "gp39-CD40 Interactions Are Essential for Germinal Center Formation and the Development of B Cell Memory," J. Exp. Med., vol. 180:157-163 (1994).
Friess, Helmut et al., "CRIPTO, a Member of the Epidermal Growth Factor Family, is Over-expressed in Human Pancreatic Cancer and Chronic Pancreatitis," Int. J. Cancer, vol. 56:668-674 (1994).
Fu, Yang-Xin et al., "B Lymphocytes Induce the Formation of Follicular Dendritic Cell Clusters in a Lymphotoxin a-dependent Fashion," J. Exp. Med., vol. 187(7):1009-1018 (1998).
Fu, Yang-Xin et al., "Development and Maturation of Secondary Lymphoid Tissues," Annu. Rev. Immunol., vol. 17:399-433 (1999).
Fu, Yang-Xin et al., "Lymphotoxin-a (LTa) Supports Development of Splenic Follicular Structure That Is Required for IgG Responses," J. Exp. Med., vol. 185(12):2111-2120 (1997).
Fujimori, Kenji et al., "A Modeling Analysis of Monoclonal Antibody Percolation Through Tumors: A Binding-Site Barrier," J. Mucl. Med., vol. 31:1191-1198 (1990).
Fukushima, Keiko et al., "N-Linked Sugar Chain Structure of Recombinant Human Lymphotoxin Produced by CHO Cells: The Functional Role of Carbohydrate as to Its Lectin-like Character and Clearance Velocity," Archives of Biochemistry and Biophysics, vol. 304(1):144-153 (1993).
Fütterer, Agnes et al., "The Lymphotoxin b Receptor Controls Organogenesis and Affinity Maturation in Peripheral Lymphoid Tissues," Immunity, vol. 9:59-70 (1998).
GenBank Accession No. AAK57792, Salcedo, I. et al., "Persistent polyclonal B lymphocytosis: an expansion of cells showing IgVH gene mutations and phenotypic features of normal lymphocytes from the CD27+ marginal zone B-cell compartment," Br. J. Haematol., vol. 116(3):662-666 (2002), 2 pages (2002).
GenBank Accession No. BAC01733, Akahori, Y. et al., "Construction and characterization of antibody libraries: isolation of therapeutic human antibodies and application to functional genomics," 3 pages (2002).
Gommerman, Jennifer L. et al., "Lymphotoxin/Light, Lymphoid Microenvironments and Autoimmune Disease," Nat. Rev. Immunol., vol. 3(8):642-655 (2003).
Gonzalez, Mercedes et al., "The Sequential Role of Lymphotoxin and B Cells in the Development of Splenic Follicles," J. Exp. Med., vol. 187(7):997-1007 (1998).
Goodwin, Raymond G. et al., "Molecular and Biological Characterization of a Ligand for CD27 Defines a New Family of Cytokines with Homology to Tumor Necrosis Factor," Cell, vol. 73:447-456 (1993).
Györfy, Z. et al., "Alteration of the TNF Sensitivity and Membrane Viscosity of Target Cells," Eur. Cytokine Netw., vol. 7(2):167 (1996).
Foote, Jefferson et al., "Antibody Framework Residues Affecting the Conformation of the Hypervariable Loops," J. Mol. Biol., vol. 224:487-499 (1992).
Han, Shuhua et al., "Cellular Interaction in Germinal Centers, Roles of CD40 Ligand and B7-2 in Established Germinal Centers," The Journal of Immunology, vol. 155:556-567 (1995).
He, Xiaozhong et al., "General Introduction to Modern Biological Technique," Publishing House of Beijing Normal University, 1st Edition, pp. 254-256 (1.8.3 &1.8.4).
Heath, Sonya L. et al., "Follicular dendritic cells and human immunodeficiency virus infectivity," Nature, vol. 377:740-744 (1995).
Hentschke, Moritz et al., "Germ Cell Nuclear Factor Is a Repressor of CRIPTO-1 and CRIPTO-3," The Journal of Biological Chemistry, vol. 281(44):33497-33504 (2006).
Hipp, Jason D. et al., "Cancer Vaccines: An Update," In Vivo, vol. 14:571-585 (2000).
Holm, Patrik et al., "Functional mapping and single chain construction of the anti-cytokeratin 8 monoclonal antibody TS1," Molecular Immunology, vol. 44:1075-1084 (2007).
Hu, X.F. et al., "Anti-Cripto Mab inhibit tumour growth and overcome MDR in a human leukaemia MDR cell line by inhibition of Akt and activation of JNK/SAPK and bad death pathways," British Journal of Cancer, vol. 96:918-927 (2007).
Huang, Sui et al., "Immune Response in Mice That Lack the Interferon-g Receptor," Science, vol. 259:1742-1745 (1993).
Hwang, Karl J. et al., "Hepatic uptake and degradation of unilamellar sphingomyelin/cholesterol liposomes: A kinetic study," Proc. Natl. Acad. Sci. USA, vol. 77(7):4030-4034 (1980).
Jain, Rakesh K., "Vascular and interstitial barriers to delivery of therapeutic agents in tumors," Cancer and Metastasis Reviews, vol. 9:753-766 (1990).
Johne, Berit et al., "Epitope mapping and binding kinetics of monoclonal antibodies studied by real time biospecific interaction analysis using surface plasmon resonance," Journal of Immunological Methods, vol. 160:191-198 (1993).
Juráková, Vera et al., "Interferon inducer, polyriboguanylic—polyribocytidylic acid, inhibits experimental hepatic metastases in mice," European Journal of Pharmacology, vol. 221:107-111 (1992).
Katz, Jonathan D. et al., "T Helper Cell Subsets in Insulin-Dependent Diabetes," Science, vol. 268:1185-1188 (1995).
Kawabe, Tsutomu et al., "The Immune Responses in CD40-Deficient Mice: Impaired Immunoglobulin Class Switching and Germinal Center Formation," Immunity, vol. 1:167-178 (1994).
Kohno, Tadahiko et al., "A second tumor necrosis factor receptor gene product can shed a naturally occurring tumor necrosis factor inhibitor," Proc. Natl. Acad. Sci. USA, vol. 87:8331-8335 (1990).
Kolanus, Waldemar et al., "T Cell Activation by Clustered Tyrosine Kinases," Cell, vol. 74:171-183 (1993).
Kolbinger, Frank et al., "Humanization of a mouse anti-human IgE antibody: a potential therapeutic for IgE-mediated allergies," Protein Engineering, vol. 6(8):971-980 (1993).
Kopp, William C. et al., "Immunomodulatory Effects of Interferon-g in Patients with Metastatic Malignant Melanoma," J. Immunother., vol. 13(3):181-190 (1993).
Kraal, Georg, "Cells in the Marginal Zone of the Spleen," International Review of Cytology, vol. 132:31-74 (1992).
Kraal, Georg et al., "Expression of the Mucosal Vascular Addressin, MAdCAM-1, on Sinus-Lining Cells in the Spleen," American Journal of Pathology, vol. 147(3):763-771 (1995).
Kraal, G. et al., "Lymphocyte migration in the spleen: the effect of macrophage elimination," Immunology, vol. 68:227-232 (1989).
Kraal, G. et al., "Marginal metallophilic cells of the mouse spleen identified by a monoclonal antibody," Immunology, vol. 58:665-669 (1986).
Kratz, Alexander et al., "Chronic Inflammation Caused by Lymphotoxin Is Lymphoid Neogenesis," J. Exp. Med., vol. 183:1461-1472 (1996).
Kreitman, Robert J. et al., "Immunotoxins for targeted cancer therapy," Advanced Drug Delivery Reviews, vol. 31:53-88 (1998).
Kumar, Sanjeev et al., "Molecular Cloning and Expression of the Fabs of Human Autoantibodies in the *Escherichia coli*," The Journal of Biological Chemistry, vol. 275(45):35129-35136 (2000).
Laman, Jon D. et al., "Functions of CD40 and Its Ligand, gp39 (CD40L)," Critical Reviews in Immunology, vol. 16:59-108 (1996).
Lane, Peter et al., "Activated human T cells express a ligand for the human B cell-associated antigen CD40 which participates in T cell-dependent activation of B lymphocytes," Eur. J. Immunol., vol. 22:2573-2578 (1992).
Langer, Robert et al., "Biocompatibility of polymeric delivery systems for macromolecules," Journal of Biomedical Materials Research, vol. 15:267-277 (1981).
Langer, Robert, "Controlled release of macromolecules," Chemtech, pp. 98-105 (1982).
Lawton, Pornsri et al., "Characterization of the Mouse Lymphotoxin-b Gene," The Journal of Immunology, vol. 154:239-246 (1995).

(56) References Cited

OTHER PUBLICATIONS

Lazar, Eliane et al. "Transforming Growth Factor a: Mutation of Aspartic Acid 47 and Leucine 48 Results in Different Biological Activities," Molecular and Cellular Biology, vol. 8(3):1247-1252 (1988).

Le Hir, Michel et al., "Differentiation of Follicular Dendritic Cells and Full Antibody Responses Require Tumor Necrosis Factor Receptor-1 Signaling," J. Exp. Med., vol. 183:2367-2372 (1996).

Ling, Leona E. et al., "Human Type I Interferon Receptor, IFNAR, Is a Heavily Glycosylated 120-130 kD Membrane Protein," Journal of Interferon and Cytokine Research, vol. 15:55-61 (1995).

Lo, Benny K.C., "Antibody Humanization by CDR Grafting," Methods in Molecular Biology, vol. 248: Antibody Engineering: Methods and Protocols, Humana Press Inc., Totowa, NJ, Chapter 7, pp. 135-159 (2004).

Loetscher, Hansruedi et al., "Recombinant 55-kDa Tumor Necrosis Factor (TNF) Receptor," The Journal of Biological Chemistry, vol. 266(27):18324-18329 (1991).

MacCallum, Robert M. et al., "Antibody-antigen interactions: Contact Analysis and Binding Site Topography," J. Mol. Biol., vol. 262:732-745 (1996).

MacKay, Fabienne et al., "Lymphotoxin but not tumor necrosis factor functions to maintain splenic architecture and humoral responsiveness in adult mice," Eur. J. Immunol., vol. 27:2033-2042 (1997).

MacKay, Fabienne et al., "Turning off follicular dendritic cells," Nature, vol. 395:26-27 (1998).

* cited by examiner

*Fig. 4*

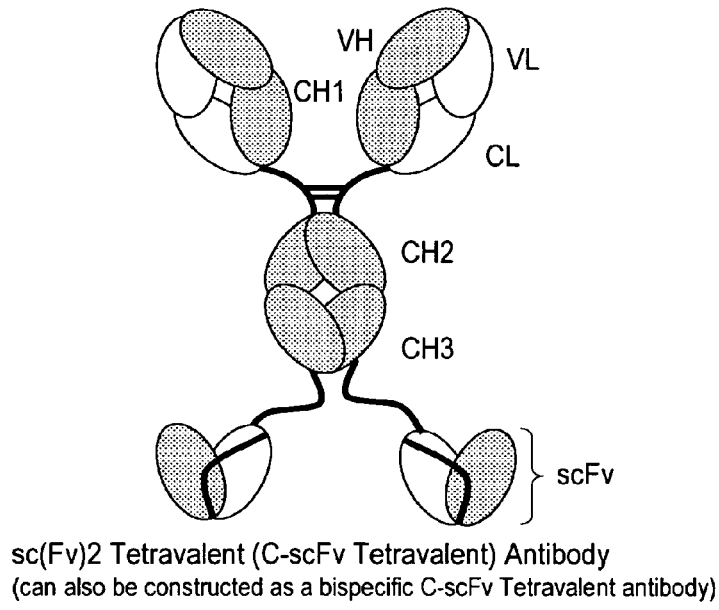

sc(Fv)2 Tetravalent (C-scFv Tetravalent) Antibody
(can also be constructed as a bispecific C-scFv Tetravalent antibody)

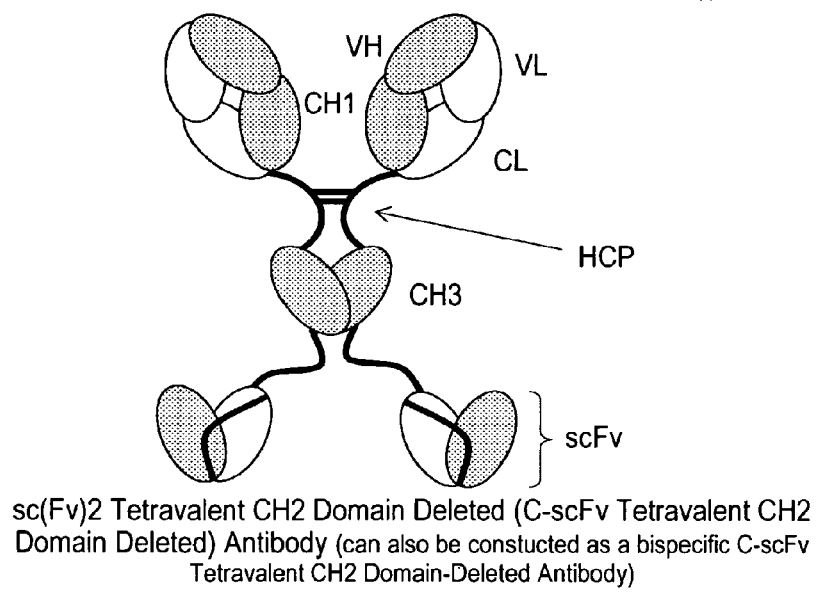

sc(Fv)2 Tetravalent CH2 Domain Deleted (C-scFv Tetravalent CH2
Domain Deleted) Antibody (can also be constucted as a bispecific C-scFv
Tetravalent CH2 Domain-Deleted Antibody)

V = Variable
C = Constant
L = Light
H = Heavy
HCP = Hinge Connecting Peptide
), ↶ = $G_4S$ flexible linkers Tetravalent or bi-specific tetravalent CH2 domain-deleted antibody
with a scFv appended to the N-terminus of the light chain.

N_L-scFv Tetravalent (or tetravalent bi-specific) CH2 Domain Deleted Antibody

V = Variable
C = Constant
L = Light
H = Heavy
HCP = Hinge Connecting Peptide

⟩ = G$_4$S flexible linker

⟨ = (G$_4$S)$_4$G$_3$AS flexible linker

Tetravalent or bi-specific tetravalent CH2 domain-deleted antibody with a scFv appended to the N-terminus of the heavy chain.

$N_H$-scFv Tetravalent (or tetravalent bi-specific) CH2 Domain Deleted Antibody

V = Variable
C = Constant
L = Light
H = Heavy
HCP = Hinge Connecting Peptide

⟩ = $G_4S$ flexible linker

⟍ = $(G_4S)_4G_3AS$ flexible linker

C- scFv tetravalent (or tetravalent bispecific) minibody

V = Variable
C = Constant
L = Light
H = Heavy
HCP = Hinge Connecting Peptide
⟩,⌐ = $(G_4S)_3$ flexible linkers Single-stranded DNA sequence of heavy chain huCC49 CH2 domain-deleted sc(Fv)2
tetravalent (C-scFv tetravalent CH2 domain deleted) antibody gene CAGGTCCAGCTGGTGCAGTCCGGCGCTGAGGTGGTGAAACCTGGGGCTTCCGTGAAGATT
TCCTGCAAGGCAAGCGGCTACACCTTCACTGATCACGCAATCCACTGGGTGAAACAGAAT
CCTGGACAGCGCCTGGAGTGGATTGGATATTTCTCTCCCGGAAACGATGATTTTAAGTAC
AATGAGAGGTTCAAGGGCAAGGCCACACTGACTGCAGACACATCTGCCAGCACTGCCTAC
GTGGAGCTCTCCAGCCTGAGATCCGAGGATACTGCAGTGTACTTCTGCACAAGATCCCTG
AATATGGCCTACTGGGGACAGGGAACCCTGGTCACCGTCTCCAGCGCTAGCACCAAGGGC
CCATCGGTCTTCCCCCTGGCACCCTCCTCCAAGAGCACCTCTGGGGGCACAGCGGCCCTG
GGCTGCCTGGTCAAGGACTACTTCCCCGAACCGGTGACGGTGTCGTGGAACTCAGGCGCC
CTGACCAGCGGCGTGCACACCTTCCCGGCTGTCCTACAGTCCTCAGGACTCTACTCCCTC
AGCAGCGTGGTGACCGTGCCCTCCAGCAGCTTGGGCACCCAGACCTACATCTGCAACGTG
AATCACAAGCCCAGCAACACCAAGGTGGACAAGAAAGTTGAGCCCAAATCTTGTGACAAA
ACTCACACATGCCCACCGTGCGGAGGTGGCTCGAGTGGAGGCGGTTCCGGAGGGCAGCCC
CGAGAACCACAGGTGTACACCCTGCCCCCATCCCGGGATGAGCTGACCAAGAACCAGGTC
AGCCTGACCTGCCTGGTCAAAGGCTTCTATCCCAGCGACATCGCCGTGGAGTGGGAGAGC
AATGGGCAGCCGGAGAACAACTACAAGACCACGCCTCCCGTGCTGGACTCCGACGGCTCC
TTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTG
TCTCCGGGTAAATCCGGCGGGGGTGGATCCGGTGGAGGGGGCTCCGGCGGTGGCGGGTCC
GACATCGTGATGAGCCAGTCTCCAGACTCCCTGGCCGTGTCCCTGGGCGAGAGGGTGACT
CTGAATTGCAAGTCCAGCCAGTCCCTGCTCTATAGCGGAAATCAGAAGAACTATCTCGCC
TGGTATCAGCAGAAACCAGGGCAGAGCCCTAAACTGCTGATTTACTGGGCATCCGCTAGG
GAATCCGGCGTGCCTGATCGCTTCAGCGGCAGCGGATCTGGGACAGACTTCACTCTGACA
ATCAGCAGCGTGCAGGCAGAAGACGTGGCAGTCTATTATTGTCAGCAGTATTATAGCTAT
CCCCTCACATTCGGCGCTGGCACCAAGCTGGAACTTAAGGGCGGTGGCGGGTCCGGTGGG
GGTGGCTCCGGGGGCGGTGGCTCCCAGGTCCAGCTGGTGCAGTCCGGCGCTGAGGTGGTG
AAACCTGGGGCTTCCGTGAAGATTTCCTGCAAGGCAAGCGGCTACACCTTCACTGATCAC
GCAATCCACTGGGTGAAACAGAATCCTGGACAGCGCCTGGAGTGGATTGGATATTTCTCT
CCCGGAAACGATGATTTTAAGTACAATGAGAGGTTCAAGGGCAAGGCCACACTGACTGCA
GACACATCTGCCAGCACTGCCTACGTGGAGCTCTCCAGCCTGAGATCCGAGGATACTGCA
GTGTACTTCTGCACAAGATCCCTGAATATGGCCTACTGGGGACAGGGAACCCTGGTCACC
GTCTCCAGC

*Fig. 8A*

Single-stranded DNA sequence of heavy chain huCC49 CH2 domain-deleted sc(Fv)2 tetravalent (C-scFv tetravalent CH2 domain deleted) antibody gene containing the G1/G3/Pro243Ala244Pro245 + [Gly/Ser] hinge connecting peptide.

CAGGTCCAGCTGGTGCAGTCCGGCGCTGAGGTGGTGAAACCTGGGGCTTCCGTGAAG
ATTTCCTGCAAGGCAAGCGGCTACACCTTCACTGATCACGCAATCCACTGGGTGAAA
CAGAATCCTGGACAGCGCCTGGAGTGGATTGGATATTTCTCTCCCGGAAACGATGAT
TTTAAGTACAATGAGAGGTTCAAGGGCAAGGCCACACTGACTGCAGACACATCTGCC
AGCACTGCCTACGTGGAGCTCTCCAGCCTGAGATCCGAGGATACTGCAGTGTACTTC
TGCACAAGATCCCTGAATATGGCCTACTGGGGACAGGGAACCCTGGTCACCGTCTCC
AGCGCTAGCACCAAGGGCCCATCGGTCTTCCCCCTGGCACCCTCCTCCAAGAGCACC
TCTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGC
TTGGGCACCCAGACCTACATCTGCAACGTGAATCACAAGCCCAGCAACACCAAGGTG
GACAAGAAAGTTGAGCCCAAATCTTGTGACAAAACTCACACATGCCCACCGTGCCCA
GAGCCCAAATCTTGTGACACACCTCCCCCATGCCCACGGTGCCCAGGAGGTGGCTCG
AGTGGAGGCGGTTCCGGAGGGCAGCCCCGAGAACCACAGGTGTACACCCTGCCCCCA
TCCCGGGATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTAC
AAGACCACGCCTCCCGTGCTGGACTCCGACGGCTCCTTCTTCCTCTACAGCAAGCTC
ACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATCC
GGCGGGGGTGGATCCGGTGGAGGGGGCTCCGGCGGTGGCGGGTCCGACATCGTGATG
AGCCAGTCTCCAGACTCCCTGGCCGTGTCCCTGGGCGAGAGGGTGACTCTGAATTGC
AAGTCCAGCCAGTCCCTGCTCTATAGCGGAAATCAGAAGAACTATCTCGCCTGGTAT
CAGCAGAAACCAGGGCAGAGCCCTAAACTGCTGATTTACTGGGCATCCGCTAGGGAA
TCCGGCGTGCCTGATCGCTTCAGCGGCAGCGGATCTGGGACAGACTTCACTCTGACA
ATCAGCAGCGTGCAGGCAGAAGACGTGGCAGTCTATTATTGTCAGCAGTATTATAGC
TATCCCCTCACATTCGGCGCTGGCACCAAGCTGGAACTTAAGGGCGGTGGCGGGTCC
GGTGGGGGTGGCTCCGGGGCGGTGGCTCCCAGGTCCAGCTGGTGCAGTCCGGCGCT
GAGGTGGTGAAACCTGGGGCTTCCGTGAAGATTTCCTGCAAGGCAAGCGGCTACACC
TTCACTGATCACGCAATCCACTGGGTGAAACAGAATCCTGGACAGCGCCTGGAGTGG
ATTGGATATTTCTCTCCCGGAAACGATGATTTTAAGTACAATGAGAGGTTCAAGGGC
AAGGCCACACTGACTGCAGACACATCTGCCAGCACTGCCTACGTGGAGCTCTCCAGC
CTGAGATCCGAGGATACTGCAGTGTACTTCTGCACAAGATCCCTGAATATGGCCTAC
TGGGGACAGGGAACCCTGGTCACCGTCTCCAGC

*Fig. 8B*

Single-stranded DNA sequence of light chain huCC49 CH2 domain-deleted sc(Fv)2 tetravalent (C-scFv tetravalent CH2 domain deleted) antibody gene GACATCGTGATGAGCCAGTCTCCAGACTCCCTGGCCGTGTCCCTGGGCGAGAGG
GTGACTCTGAATTGCAAGTCCAGCCAGTCCCTGCTCTATAGCGGAAATCAGAAG
AACTATCTCGCCTGGTATCAGCAGAAACCAGGGCAGAGCCCTAAACTGCTGATT
TACTGGGCATCCGCTAGGGAATCCGGCGTGCCTGATCGCTTCAGCGGCAGCGGA
TCTGGGACAGACTTCACTCTGACAATCAGCAGCGTGCAGGCAGAAGACGTGGCA
GTCTATTATTGTCAGCAGTATTATAGCTATCCCTCACATTCGGCGCTGGCACC
AAGCTGGAACTGAAACGTACGGTGGCTGCACCATCTGTCTTCATCTTCCCGCCA
TCTGATGAGCAGTTGAAATCTGGAACTGCCTCTGTTGTGTGCCTGCTGAATAAC
TTCTATCCCAGAGAGGCCAAAGTACAGTGGAAGGTGGATAACGCCCTCCAATCG
GGTAACTCCCAGGAGAGTGTCACAGAGCAGGACAGCAAGGACAGCACCTACAGC
CTCAGCAGCACCCTGACGCTGAGCAAAGCAGACTACGAGAAACACAAAGTCTAC
GCCTGCGAAGTCACCCATCAGGGCCTGAGCTCGCCCGTCACAAAGAGCTTCAAC
AGGGGAGAGTGTTGA

*Fig. 8C*

Amino acid sequence of heavy chain huCC49 CH2 domain-deleted sc(Fv)2 tetravalent
(C-scFv tetravalent CH2 domain deleted) antibody

```
QVQLVQSGAEVVKPGASVKISCKASGYTFTDHAIHWVKQNPGQRLEWIGYFSPGND
DFKYNERFKGKATLTADTSASTAYVELSSLRSEDTAVYFCTRSLNMAYWGQGTLVT
VSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTC
PPCGGGSSGGGSGGQPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQK
SLSLSPGKSGGGGSGGGGSGGGGSDIVMSQSPDSLAVSLGERVTLNCKSSQSLLYS
GNQKNYLAWYQQKPGQSPKLLIYWASARESGVPDRFSGSGSGTDFTLTISSVQAED
VAVYYCQQYYSYPLTFGAGTKLELKGGGGSGGGGSGGGGSQVQLVQSGAEVVKPGA
SVKISCKASGYTFTDHAIHWVKQNPGQRLEWIGYFSPGNDDFKYNERFKGKATLTA
DTSASTAYVELSSLRSEDTAVYFCTRSLNMAYWGQGTLVTVSS*
```

*Fig. 9A*

Amino acid sequence of heavy chain huCC49 CH2 domain-deleted sc(Fv)2 tetravalent
(C-scFv tetravalent CH2 domain deleted) antibody containing the G1/G3/Pro243Ala244Pro245 +
[Gly/Ser] hinge connecting peptide.

QVQLVQSGAEVVKPGASVKISCKASGYTFTDHAIHWVKQNPGQRLEWIGYFSPGND
DFKYNERFKGKATLTADTSASTAYVELSSLRSEDTAVYFCTRSLNMAYWGQGTLVT
VSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTC
PPCPEPKSCDTPPPCPRCPAPGGGSSGGGSGGQPREPQVYTLPPSRDELTKNQVSL
TCLVKGFYPSDIAVEWESNGQPENNYKTTPPVLDSDGSFFLYSKLTVDKSRWQQGN
VFSCSVMHEALHNHYTQKSLSLSPGKSGGGGSGGGGSGGGGSDIVMSQSPDSLAVS
LGERVTLNCKSSQSLLYSGNQKNYLAWYQQKPGQSPKLLIYWASARESGVPDRFSG
SGSGTDFTLTISSVQAEDVAVYYCQQYYSYPLTFGAGTKLELKGGGGSGGGGSGGG
GSQVQLVQSGAEVVKPGASVKISCKASGYTFTDHAIHWVKQNPGQRLEWIGYFSPG
NDDFKYNERFKGKATLTADTSASTAYVELSSLRSEDTAVYFCTRSLNMAYWGQGTL
VTVSS*

*Fig. 9B*

Amino acid sequence of light chain huCC49 CH2 domain-deleted sc(Fv)2 tetravalent
(C-scFv tetravalent CH2 domain deleted) antibody DIVMSQSPDSLAVSLGERVTLNCKSSQSLLYSGNQKNYLAWYQQKPGQSPKLLI
YWASARESGVPDRFSGSGSGTDFTLTISSVQAEDVAVYYCQQYYSYPLTFGAGT
KLELKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFN
RGEC*

*Fig. 9C*

Single-stranded DNA sequence of CH2 domain-deleted huCC49 tetravalent minibody (N-scFv tetravalent minibody or 2sc(Fv)2 Tetravalent antibody) gene.

```
GACATCGTGATGAGCCAGTCTCCAGACTCCCTGGCCGTGTCCCTGGGCGAGAGGGTGAC
TCTGAATTGCAAGTCCAGCCAGTCCCTGCTCTATAGCGGAAATCAGAAGAACTATCTCG
CCTGGTATCAGCAGAAACCAGGGCAGAGCCCTAAACTGCTGATTTACTGGGCATCCGCT
AGGGAATCCGGCGTGCCTGATCGCTTCAGCGGCAGCGGATCTGGGACAGACTTCACTCT
GACAATCAGCAGCGTGCAGGCAGAAGACGTGGCAGTCTATTATTGTCAGCAGTATTATA
GCTATCCCCTCACATTCGGCGCTGGCACCAAGCTGGAACTTAAGGGCGGTGGCGGGTCC
GGTGGGGGTGGCTCCGGGGCGGTGGCTCCCAGGTCCAGCTGGTGCAGTCCGGCGCTGA
GGTGGTGAAACCTGGGGCTTCCGTGAAGATTTCCTGCAAGGCAAGCGGCTACACCTTCA
CTGATCACGCAATCCACTGGGTGAAACAGAATCCTGGACAGCGCCTGGAGTGGATTGGA
TATTTCTCTCCCGGAAACGATGATTTTAAGTACAATGAGAGGTTCAAGGGCAAGGCCAC
ACTGACTGCAGACACATCTGCCAGCACTGCCTACGTGGAGCTCTCCAGCCTGAGATCCG
AGGATACTGCAGTGTACTTCTGCACAAGATCCCTGAATATGGCCTACTGGGGACAGGGT
ACCCTGGTCACCGTCTCCAGCGGCGGTGGAGGGTCCGGTGGAGGGGGCTCTGGAGGGGG
CGGTTCAGGGGGCGGTGGATCGGGCGGAGGTGCTAGCGACATCGTGATGAGCCAGTCTC
CAGACTCCCTGGCCGTGTCCCTGGGCGAGAGGGTGACTCTGAATTGCAAGTCCAGCCAG
TCCCTGCTCTATAGCGGAAATCAGAAGAACTATCTCGCCTGGTATCAGCAGAAACCAGG
GCAGAGCCCTAAACTGCTGATTTACTGGGCATCCGCTAGGGAATCCGGCGTGCCTGATC
GCTTCAGCGGCAGCGGATCTGGGACAGACTTCACTCTGACAATCAGCAGCGTGCAGGCA
GAAGACGTGGCAGTCTATTATTGTCAGCAGTATTATAGCTATCCCCTCACATTCGGCGC
TGGCACCAAGCTGGAACTTAAGGGCGGTGGCGGGTCCGGTGGGGGTGGCTCCGGGGCG
GTGGCTCCCAGGTCCAGCTGGTGCAGTCCGGCGCTGAGGTGGTGAAACCTGGGGCTTCC
GTGAAGATTTCCTGCAAGGCAAGCGGCTACACCTTCACTGATCACGCAATCCACTGGGT
GAAACAGAATCCTGGACAGCGCCTGGAGTGGATTGGATATTTCTCTCCCGGAAACGATG
ATTTTAAGTACAATGAGAGGTTCAAGGGCAAGGCCACACTGACTGCAGACACATCTGCC
AGCACTGCCTACGTGGAGCTCTCCAGCCTGAGATCCGAGGATACTGCAGTGTACTTCTG
CACAAGATCCCTGAATATGGCCTACTGGGGACAGGGAACCCTGGTCACCGTCTCCAGCG
TCGACCCCAAATCTTGTGACAAAACTCACACATGCCCACCGTGCGGAGGTGGCTCGAGT
GGAGGCGGATCCGGAGGGCAGCCCCGAGAACCACAGGTGTACACCCTGCCCCCATCCCG
GGATGAGCTGACCAAGAACCAGGTCAGCCTGACCTGCCTGGTCAAAGGCTTCTATCCCA
GCGACATCGCCGTGGAGTGGGAGAGCAATGGGCAGCCGGAGAACAACTACAAGACCACG
CCTCCCGTGCTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGGCTCTGCACA
ACCACTACACGCAGAAGAGCCTCTCCCTGTCTCCGGGTAAATGA
```

*Fig. 10A*

Single-stranded DNA sequence of CH2 domain-deleted huCC49 tetravalent minibody (N-scFv tetravalent minibody or 2sc(Fv)2 Tetravalent antibody) gene containing the G1/G3/Pro243Ala244Pro245 + [Gly/Ser] hinge connecting peptide.

GACATCGTGATGAGCCAGTCTCCAGACTCCCTGGCCGTGTCCCTGGGCGAGAGGGT
GACTCTGAATTGCAAGTCCAGCCAGTCCCTGCTCTATAGCGGAAATCAGAAGAACT
ATCTCGCCTGGTATCAGCAGAAACCAGGGCAGAGCCCTAAACTGCTGATTTACTGG
GCATCCGCTAGGGAATCCGGCGTGCCTGATCGCTTCAGCGGCAGCGGATCTGGGAC
AGACTTCACTCTGACAATCAGCAGCGTGCAGGCAGAAGACGTGGCAGTCTATTATT
GTCAGCAGTATTATAGCTATCCCCTCACATTCGGCGCTGGCACCAAGCTGGAACTT
AAGGGCGGTGGCGGGTCCGGTGGGGGTGGCTCCGGGGGCGGTGGCTCCCAGGTCCA
GCTGGTGCAGTCCGGCGCTGAGGTGGTGAAACCTGGGGCTTCCGTGAAGATTTCCT
GCAAGGCAAGCGGCTACACCTTCACTGATCACGCAATCCACTGGGTGAAACAGAAT
CCTGGACAGCGCCTGGAGTGGATTGGATATTTCTCTCCCGGAAACGATGATTTTAA
GTACAATGAGAGGTTCAAGGGCAAGGCCACACTGACTGCAGACACATCTGCCAGCA
CTGCCTACGTGGAGCTCTCCAGCCTGAGATCCGAGGATACTGCAGTGTACTTCTGC
ACAAGATCCCTGAATATGGCCTACTGGGGACAGGGTACCCTGGTCACCGTCTCCAG
CGGCGGTGGAGGGTCCGGTGGAGGGGGCTCTGGAGGGGGCGGTTCAGGGGGCGGTG
GATCGGGCGGAGGTGCTAGCGACATCGTGATGAGCCAGTCTCCAGACTCCCTGGCC
GTGTCCCTGGGCGAGAGGGTGACTCTGAATTGCAAGTCCAGCCAGTCCCTGCTCTA
TAGCGGAAATCAGAAGAACTATCTCGCCTGGTATCAGCAGAAACCAGGGCAGAGCC
CTAAACTGCTGATTTACTGGGCATCCGCTAGGGAATCCGGCGTGCCTGATCGCTTC
AGCGGCAGCGGATCTGGGACAGACTTCACTCTGACAATCAGCAGCGTGCAGGCAGA
AGACGTGGCAGTCTATTATTGTCAGCAGTATTATAGCTATCCCCTCACATTCGGCG
CTGGCACCAAGCTGGAACTTAAGGGCGGTGGCGGGTCCGGTGGGGGTGGCTCCGGG
GGCGGTGGCTCCCAGGTCCAGCTGGTGCAGTCCGGCGCTGAGGTGGTGAAACCTGG
GGCTTCCGTGAAGATTTCCTGCAAGGCAAGCGGCTACACCTTCACTGATCACGCAA
TCCACTGGGTGAAACAGAATCCTGGACAGCGCCTGGAGTGGATTGGATATTTCTCT
CCCGGAAACGATGATTTTAAGTACAATGAGAGGTTCAAGGGCAAGGCCACACTGAC
TGCAGACACATCTGCCAGCACTGCCTACGTGGAGCTCTCCAGCCTGAGATCCGAGG
ATACTGCAGTGTACTTCTGCACAAGATCCCTGAATATGGCCTACTGGGGACAGGGA
ACCCTGGTCACCGTCTCCAGCGTCGACCCCAAATCTTGTGACAAAACTCACACATG
CCCACCGTGCCCAGAGCCCAAATCTTGTGACACACCTCCCCCATGCCCACGGTGCC
CAGGAGGTGGCTCGAGTGGAGGCGGATCCGGAGGGCAGCCCCGAGAACCACAGGTG
TACACCCTGCCCCCATCCCGGGATGAGCTGACCAAGAACCAGGTCAGCCTGACCTG
CCTGGTCAAAGGCTTCTATCCCAGCGACATCGCCGTGGAGTGGGAGAGCAATGGGC
AGCCGGAGAACAACTACAAGACCACGCCTCCCGTGCTGGACTCCGACGGCTCCTTC
TTCCTCTACAGCAAGCTCACCGTGGACAAGAGCAGGTGGCAGCAGGGGAACGTCTT
CTCATGCTCCGTGATGCATGAGGCTCTGCACAACCACTACACGCAGAAGAGCCTCT
CCCTGTCTCCGGGTAAATGA

*Fig. 10B*

Amino acid sequence of CH2 domain-deleted huCC49 tetravalent minibody (N-scFv tetravalent minibody or 2sc(Fv)2 Tetravalent antibody).

DIVMSQSPDSLAVSLGERVTLNCKSSQSLLYSGNQKNYLAWYQQKPGQSPKLLIYW
ASARESGVPDRFSGSGSGTDFTLTISSVQAEDVAVYYCQQYYSYPLTFGAGTKLEL
KGGGGSGGGGSGGGGSQVQLVQSGAEVVKPGASVKISCKASGYTFTDHAIHWVKQN
PGQRLEWIGYFSPGNDDFKYNERFKGKATLTADTSASTAYVELSSLRSEDTAVYFC
TRSLNMAYWGQGTLVTVSSGGGGSGGGGSGGGGSGGGGSGGGASDIVMSQSPDSLA
VSLGERVTLNCKSSQSLLYSGNQKNYLAWYQQKPGQSPKLLIYWASARESGVPDRF
SGSGSGTDFTLTISSVQAEDVAVYYCQQYYSYPLTFGAGTKLELKGGGGSGGGGSG
GGGSQVQLVQSGAEVVKPGASVKISCKASGYTFTDHAIHWVKQNPGQRLEWIGYFS
PGNDDFKYNERFKGKATLTADTSASTAYVELSSLRSEDTAVYFCTRSLNMAYWGQG
TLVTVSSVDPKSCDKTHTCPPCGGGSSGGGSGGQPREPQVYTLPPSRDELTKNQVS
LTCLVKGFYPSDIAVEWESNGQPENNYKTTPPVLDSDGSFFLYSKLTVDKSRWQQG
NVFSCSVMHEALHNHYTQKSLSLSPGK*

*Fig. 11A*

Amino acid sequence of CH2 domain-deleted huCC49 tetravalent minibody (N-scFv tetravalent minibody or 2sc(Fv)2 Tetravalent antibody) containing the G1/G3/Pro243Ala244Pro245 + [Gly/Ser] hinge connecting peptide.

DIVMSQSPDSLAVSLGERVTLNCKSSQSLLYSGNQKNYLAWYQQKPGQSPKLLIYW
ASARESGVPDRFSGSGSGTDFTLTISSVQAEDVAVYYCQQYYSYPLTFGAGTKLEL
KGGGGSGGGGSGGGGSQVQLVQSGAEVVKPGASVKISCKASGYTFTDHAIHWVKQN
PGQRLEWIGYFSPGNDDFKYNERFKGKATLTADTSASTAYVELSSLRSEDTAVYFC
TRSLNMAYWGQGTLVTVSSGGGGSGGGGSGGGGSGGGGSGGGASDIVMSQSPDSLA
VSLGERVTLNCKSSQSLLYSGNQKNYLAWYQQKPGQSPKLLIYWASARESGVPDRF
SGSGSGTDFTLTISSVQAEDVAVYYCQQYYSYPLTFGAGTKLELKGGGGSGGGGSG
GGGSQVQLVQSGAEVVKPGASVKISCKASGYTFTDHAIHWVKQNPGQRLEWIGYFS
PGNDDFKYNERFKGKATLTADTSASTAYVELSSLRSEDTAVYFCTRSLNMAYWGQG
TLVTVSSVDPKSCDKTHTCPPCPEPKSCDTPPPCPRCPAPGGGSSGGGSGGQPREP
QVYTLPPSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK*

*Fig. 11B*

Single-stranded DNA sequence of heavy chain CH2 domain-deleted PRIMATIZED® p5E8 sc(Fv)2 tetravalent (C-scFv tetravalent CH2 domain deleted) antibody gene containing the G1/G3/Pro243Ala244Pro245 + [Gly/Ser] connecting peptide

GAGGTGCAGCTGGTGGAGTCTGGGGGCGGCTTGGCAAAGCCTGGGGGGTCCCTGAG
ACTCTCCTGCGCAGCCTCCGGGTTCAGGTTCACCTTCAATAACTACTACATGGACT
GGGTCCGCCAGGCTCCAGGGCAGGGGCTGGAGTGGGTCTCACGTATTAGTAGTAGT
GGTGATCCCACATGGTACGCAGACTCCGTGAAGGGCAGATTCACCATCTCCAGAGA
GAACGCCAAGAACACACTGTTTCTTCAAATGAACAGCCTGAGAGCTGAGGACACGG
CTGTCTATTACTGTGCGAGCTTGACTACAGGGTCTGACTCCTGGGGCCAGGGAGTC
CTGGTCACCGTCTCCTCAGCTAGCACCAAGGGCCCATCGGTCTTCCCCCTGGCACC
CTCCTCCAAGAGCACCTCTGGGGGCACAGCGGCCCTGGGCTGCCTGGTCAAGGACT
ACTTCCCCGAACCGGTGACGGTGTCGTGGAACTCAGGCGCCCTGACCAGCGGCGTG
CACACCTTCCCGGCTGTCCTACAGTCCTCAGGACTCTACTCCCTCAGCAGCGTGGT
GACCGTGCCCTCCAGCAGCTTGGGCACCCAGACCTACATCTGCAACGTGAATCACA
AGCCCAGCAACACCAAGGTGGACAAGAAAGTTGAGCCCAAATCTTGTGACAAAACT
CACACATGCCCACCGTGCCCAGAGCCCAAATCTTGTGACACACCTCCCCCATGCCC
ACGGTGCCCAGCACCTGGAGGTGGCTCGAGTGGAGGCGGTTCCGGAGGGCAGCCCC
GAGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGTG
GGAGAGCAATGGGCAGCCGGAGAACAACTACAAGACCACGCCTCCCGTGCTGGACT
CCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACAC
GCAGAAGAGCCTCTCCCTGTCTCCGGGTAAATCCGGCGGGGGTGGATCCGGTGGAG
GGGGCTCCGGCGGTGGCGGGTCCGACATCCAGATGACCCAGTCTCCATCTTCCCTG
TCTGCATCTGTAGGGGACAGAGTCACCATCACTTGCAGGGCAAGTCAGGACATTAG
GTATTATTTAAATTGGTATCAGCAGAAACCAGGAAAAGCTCCTAAGCTCCTGATCT
ATGTTGCATCCAGTTTGCAAAGTGGGGTCCCATCAAGGTTCAGCGGCAGTGGATCT
GGGACAGAGTTCACTCTCACCGTCAGCAGCCTGCAGCCTGAAGATTTTGCGACTTA
TTACTGTCTACAGGTTTATAGTACCCCTCGGACGTTCGGCCAAGGGACCAAGGTGG
AAATCAAAGGCGGTGGCGGGTCCGGTGGGGGTGGCTCCGGGGGCGGTGGCTCCGAG
GTGCAGCTGGTGGAGTCTGGGGGCGGCTTGGCAAAGCCTGGGGGGTCCCTGAGACT
CTCCTGCGCAGCCTCCGGGTTCAGGTTCACCTTCAATAACTACTACATGGACTGGG
TCCGCCAGGCTCCAGGGCAGGGGCTGGAGTGGGTCTCACGTATTAGTAGTAGTGGT
GATCCCACATGGTACGCAGACTCCGTGAAGGGCAGATTCACCATCTCCAGAGAGAA
CGCCAAGAACACACTGTTTCTTCAAATGAACAGCCTGAGAGCTGAGGACACGGCTG
TCTATTACTGTGCGAGCTTGACTACAGGGTCTGACTCCTGGGGCCAGGGAGTCCTG
GTCACCGTCTCCTCATGA

*Fig. 12A*

Single-stranded DNA sequence of light chain CH2 domain-deleted PRIMATIZED® p5E8
sc(Fv)2 tetravalent (C-scFv tetravalent CH2 domain deleted) antibody containing the
G1/G3/Pro243Ala244Pro245 + [Gly/Ser] connecting peptide gene GACATCCAGATGACCCAGTCTCCATCTTCCCTGTCTGCATCTGTAGGGGACAGAGTC
ACCATCACTTGCAGGGCAAGTCAGGACATTAGGTATTATTTAAATTGGTATCAGCAG
AAACCAGGAAAAGCTCCTAAGCTCCTGATCTATGTTGCATCCAGTTTGCAAAGTGGG
GTCCCATCAAGGTTCAGCGGCAGTGGATCTGGGACAGAGTTCACTCTCACCGTCAGC
AGCCTGCAGCCTGAAGATTTTGCGACTTATTACTGTCTACAGGTTTATAGTACCCCT
CGGACGTTCGGCCAAGGGACCAAGGTGGAAATCAAACGTACGGTGGCTGCACCATCT
GTCTTCATCTTCCCGCCATCTGATGAGCAGTTGAAATCTGGAACTGCCTCTGTTGTG
TGCCTGCTGAATAACTTCTATCCCAGAGAGGCCAAAGTACAGTGGAAGGTGGATAAC
GCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAA
GTCTACGCCTGCGAAGTCACCCATCAGGGCCTGAGCTCGCCCGTCACAAAGAGCTTC
AACAGGGGAGAGTGTTGA

*Fig. 12B*

Amino acid sequence of heavy chain CH2 domain-deleted PRIMATIZED® p5E8 sc(Fv)2 tetravalent (C-scFv tetravalent CH2 domain deleted) antibody containing the G1/G3/Pro243Ala244Pro245 + [Gly/Ser] connecting peptide EVQLVESGGGLAKPGGSLRLSCAASGFRFTFNNYYMDWVRQAPGQGLEWVSRISSSGD
PTWYADSVKGRFTISRENAKNTLFLQMNSLRAEDTAVYYCASLTTGSDSWGQGVLVTV
SSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKKVEPKSCDKTHTCPPCPE
PKSCDTPPPCPRCPAPGGGSSGGGSGGQPREPQVYTLPPSRDELTKNQVSLTCLVKGF
YPSDIAVEWESNGQPENNYKTTPPVLDSDGSFFLYSKLTVDKSRWQQGNVFSCSVMHE
ALHNHYTQKSLSLSPGKSGGGGSGGGGSGGGGSDIQMTQSPSSLSASVGDRVTITCRA
SQDIRYYLNWYQQKPGKAPKLLIYVASSLQSGVPSRFSGSGSGTEFTLTVSSLQPEDF
ATYYCLQVYSTPRTFGQGTKVEIKGGGGSGGGGSGGGGSEVQLVESGGGLAKPGGSLR
LSCAASGFRFTFNNYYMDWVRQAPGQGLEWVSRISSSGDPTWYADSVKGRFTISRENA
KNTLFLQMNSLRAEDTAVYYCASLTTGSDSWGQGVLVTVSS

*Fig. 13A*

Amino acid sequence of light chain CH2 domain-deleted PRIMATIZED® p5E8 sc(Fv)2 tetravalent (C-scFv tetravalent CH2 domain deleted) antibody containing the G1/G3/Pro243Ala244Pro245 + [Gly/Ser] connecting peptide DIQMTQSPSSLSASVGDRVTITCRASQDIRYYLNWYQQKPGKAPKLLIYVASSLQ
SGVPSRFSGSGSGTEFTLTVSSLQPEDFATYYCLQVYSTPRTFGQGTKVEIKRTV
AAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC*

*Fig. 13B*

Single-stranded DNA sequence of PRIMATIZED® p5E8 minibody gene (VL → VH orientation) containing the G1/G3/Pro243Ala244Pro245 + [Gly/Ser] connecting peptide GACATCCAGATGACCCAGTCTCCATCTTCCCTGTCTGCATCTGTAGGGGACAGAGTCA
CCATCACTTGCAGGGCAAGTCAGGACATTAGGTATTATTTAAATTGGTATCAGCAGAA
ACCAGGAAAAGCTCCTAAGCTCCTGATCTATGTTGCATCCAGTTTGCAAAGTGGGGTC
CCATCAAGGTTCAGCGGCAGTGGATCTGGGACAGAGTTCACTCTCACCGTCAGCAGCC
TGCAGCCTGAAGATTTTGCGACTTATTACTGTCTACAGGTTTATAGTACCCCTCGGAC
GTTCGGCCAAGGGACCAAGGTGGAAATCAAAGGCGGTGGCGGGTCCGGTGGGGTGGC
TCCGGGGCGGTGGCTCCGAGGTGCAGCTGGTGGAGTCTGGGGGCGGCTTGGCAAAGC
CTGGGGGGTCCCTGAGACTCTCCTGCGCAGCCTCCGGGTTCAGGTTCACCTTCAATAA
CTACTACATGGACTGGGTCCGCCAGGCTCCAGGGCAGGGGCTGGAGTGGGTCTCACGT
ATTAGTAGTAGTGGTGATCCCACATGGTACGCAGACTCCGTGAAGGGCAGATTCACCA
TCTCCAGAGAGAACGCCAAGAACACACTGTTTCTTCAAATGAACAGCCTGAGAGCTGA
GGACACGGCTGTCTATTACTGTGCGAGCTTGACTACAGGGTCTGACTCCTGGGGCCAG
GGAGTCCTGGTCACCGTCTCCTCAGTCGACCCCAAATCTTGTGACAAAACTCACACAT
GCCCACCGTGCCCAGAGCCCAAATCTTGTGACACACCTCCCCCATGCCCACGGTGCCC
AGCACCTGGAGGTGGCTCGAGTGGAGGCGGATCCGGAGGGCAGCCCCGAGAACCACAG
GTGTACACCCTGCCCCCATCCCGGGATGAGCTGACCAAGAACCAGGTCAGCCTGACCT
GCCTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTTC
CTCTACAGCAAGCTCACCGTGGACAAGAGCAGGTGGCAGCAGGGGAACGTCTTCTCAT
GCTCCGTGATGCATGAGGCTCTGCACAACCACTACACGCAGAAGAGCCTCTCCCTGTC
TCCGGGTAAATGA

*Fig. 14*

Single-stranded DNA sequence of PRIMATIZED® p5E8 minibody gene (VH → VL orientation) containing the G1/G3/Pro243Ala244Pro245 + [Gly/Ser] connecting peptide GAGGTGCAGCTGGTGGAGTCTGGGGGCGGCTTGGCAAAGCCTGGGGGGTCCCTGAGA
CTCTCCTGCGCAGCCTCCGGGTTCAGGTTCACCTTCAATAACTACTACATGGACTGG
GTCCGCCAGGCTCCAGGGCAGGGGCTGGAGTGGGTCTCACGTATTAGTAGTAGTGGT
GATCCCACATGGTACGCAGACTCCGTGAAGGGCAGATTCACCATCTCCAGAGAGAAC
GCCAAGAACACACTGTTTCTTCAAATGAACAGCCTGAGAGCTGAGGACACGGCTGTC
TATTACTGTGCGAGCTTGACTACAGGGTCTGACTCCTGGGGCCAGGGAGTCCTGGTC
ACCGTCTCCTCAGGCGGTGGCGGGTCCGGTGGGGGTGGCTCCGGGGCGGTGGCTCC
GACATCCAGATGACCCAGTCTCCATCTTCCCTGTCTGCATCTGTAGGGGACAGAGTC
ACCATCACTTGCAGGGCAAGTCAGGACATTAGGTATTATTTAAATTGGTATCAGCAG
AAACCAGGAAAAGCTCCTAAGCTCCTGATCTATGTTGCATCCAGTTTGCAAAGTGGG
GTCCCATCAAGGTTCAGCGGCAGTGGATCTGGGACAGAGTTCACTCTCACCGTCAGC
AGCCTGCAGCCTGAAGATTTTGCGACTTATTACTGTCTACAGGTTTATAGTACCCCT
CGGACGTTCGGCCAAGGGACCAAGGTGGAAATCAAAGTCGACCCCAAATCTTGTGAC
AAAACTCACACATGCCCACCGTGCCCAGAGCCCAAATCTTGTGACACACCTCCCCCA
TGCCCACGGTGCCCAGCACCTGGAGGTGGCTCGAGTGGAGGCGGATCCGGAGGGCAG
CCCCGAGAACCACAGGTGTACACCCTGCCCCCATCCCGGGATGAGCTGACCAAGAAC
CAGGTCAGCCTGACCTGCCTGGTCAAAGGCTTCTATCCCAGCGACATCGCCGTGGAG
TGGGAGAGCAATGGGCAGCCGGAGAACAACTACAAGACCACGCCTCCCGTGCTGGAC
TCCGACGGCTCCTTCTTCCTCTACAGCAAGCTCACCGTGGACAAGAGCAGGTGGCAG
CAGGGGAACGTCTTCTCATGCTCCGTGATGCATGAGGCTCTGCACAACCACTACACG
CAGAAGAGCCTCTCCCTGTCTCCGGGTAAATGA

*Fig. 15*

Amino acid sequence of PRIMATIZED® p5E8 minibody (VL → VH orientation)
containing the G1/G3/Pro243Ala244Pro245 + [Gly/Ser] connecting peptide DIQMTQSPSSLSASVGDRVTITCRASQDIRYYLNWYQQKPGKAPKLLIYVASSLQS
GVPSRFSGSGSGTEFTLTVSSLQPEDFATYYCLQVYSTPRTFGQGTKVEIKGGGGS
GGGGSGGGGSEVQLVESGGGLAKPGGSLRLSCAASGFRFTFNNYYMDWVRQAPGQG
LEWVSRISSSGDPTWYADSVKGRFTISRENAKNTLFLQMNSLRAEDTAVYYCASLT
TGSDSWGQGVLVTVSSVDPKSCDKTHTCPPCPEPKSCDTPPPCPRCPAPGGGSSGG
GSGGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGK

*Fig. 16*

Amino acid sequence of PRIMATIZED® p5E8 minibody (VH → VL orientation) containing
the G1/G3/Pro243Ala244Pro245 + [Gly/Ser] connecting peptide EVQLVESGGGLAKPGGSLRLSCAASGFRFTFNNYYMDWVRQAPGQGLEWVSRISSS
GDPTWYADSVKGRFTISRENAKNTLFLQMNSLRAEDTAVYYCASLTTGSDSWGQGV
LVTVSSGGGGSGGGGSGGGGSDIQMTQSPSSLSASVGDRVTITCRASQDIRYYLNW
YQQKPGKAPKLLIYVASSLQSGVPSRFSGSGSGTEFTLTVSSLQPEDFATYYCLQV
YSTPRTFGQGTKVEIKVDPKSCDKTHTCPPCPEPKSCDTPPPCPRCPAPGGGSSGG
GSGGQPREPQVYTLPPSRDELTKNQVSLTCLVKGFYPSDIAVEWESNGQPENNYKT
TPPVLDSDGSFFLYSKLTVDKSRWQQGNVFSCSVMHEALHNHYTQKSLSLSPGK

*Fig. 17*

Western blot of huCC49 CH2 domain-deleted
sc(Fv)2 tetravalent G1/G3/PAP

1. MW Marker
2. huCC49 CH2 domain-deleted sc(Fv)2 tetravalent G1/G3/PAP-non-reduced
3. huCC49 CH2 domain-deleted sc(Fv)2 tetravalent-non-reduced huCC49 CH2 domain-deleted sc(Fv)2 tetravalent antibody containing the G1/G3/Pro243Ala244Pro245 + [Gly/Ser] (SEQ ID NO:9) connecting peptide 1. Mark 12 Marker
2. huCC49 CH2 domain-deleted sc(Fv)2 tetravalent antibody G1/G3/PAP non-reduced
3. Mark 12 Marker
4. huCC49 CH2 domain-deleted sc(Fv)2 tetravalent antibody G1/G3/PAP reduced huCC49 CH2 domain-deleted sc(Fv)2 tetravalent
G1/G3/Pro243Ala244Pro245 antibody 1. Mark 12 Marker
2. HuCC49 2sc(Fv)2 tetravalent anti body
   (N-scFv tetravalent huCC49 minibody)
3. huCC49 minibody
4. huCC49 control 1. Mark 12 Marker
2. HuCC49 2sc(Fv)2 tetravalent antibody (N-scFv tetravalent huCC49 minibody)
3. HuCC49 2sc(Fv)2 tetravalent antibody (N-scFv tetravalent huCC49 minibody) G1/G3/PAP Lane 1   Marker
Lane 2   huCC49 2 sc(Fv)2 tetravalent antibody (N-scFv tetravalent huCC49 minibody) G1/G3/PAP - non-reduced
Lane 3   huCC49 2 sc(Fv)2 tetravalent antibody (N-scFv tetravalent huCC49 minibody) G1/G3/PAP - reduced

SEQUENCE LISTING

```
<160> NUMBER OF SEQ ID NOS: 49

<210> SEQ ID NO 1
<211> LENGTH: 10
<212> TYPE: PRT
<213> ORGANISM: Artificial Sequence
<220> FEATURE:
<223> OTHER INFORMATION: synthetic construct

<400> SEQUENCE: 1

Gly Gly Gly Ser Ser Gly Gly Gly Ser Gly
 1               5                   10

<210> SEQ ID NO 2
<211> LENGTH: 10
<212> TYPE: PRT
```

-continued

```
<213> ORGANISM: Artificial Sequence
<220> FEATURE:
<223> OTHER INFORMATION: synthetic construct

<400> SEQUENCE: 2

Glu Pro Lys Ser Cys Asp Lys Thr His Thr
1               5                   10

<210> SEQ ID NO 3
<211> LENGTH: 5
<212> TYPE: PRT
<213> ORGANISM: Artificial Sequence
<220> FEATURE:
<223> OTHER INFORMATION: synthetic construct

<400> SEQUENCE: 3

Cys Pro Pro Cys Pro
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic construct

<400> SEQUENCE: 4

Ala Pro Glu Leu Leu Gly Gly Pro
1               5

<210> SEQ ID NO 5
<211> LENGTH: 12
<212> TYPE: PRT
<213> ORGANISM: Artificial Sequence
<220> FEATURE:
<223> OTHER INFORMATION: synthetic construct

<400> SEQUENCE: 5

Glu Leu Lys Thr Pro Leu Gly Asp Thr Thr His Thr
1               5                   10

<210> SEQ ID NO 6
<211> LENGTH: 20
<212> TYPE: PRT
<213> ORGANISM: Artificial Sequence
<220> FEATURE:
<223> OTHER INFORMATION: synthetic construct

<400> SEQUENCE: 6

Cys Pro Arg Cys Pro Glu Pro Lys Ser Cys Asp Thr Pro Pro Pro Cys
1               5                   10                  15

Pro Arg Cys Pro
            20

<210> SEQ ID NO 7
<211> LENGTH: 24
<212> TYPE: PRT
<213> ORGANISM: Artificial Sequence
<220> FEATURE:
<223> OTHER INFORMATION: synthetic construct

<400> SEQUENCE: 7

Glu Pro Lys Ser Cys Asp Lys Thr His Thr Cys Pro Pro Cys Gly Gly
1               5                   10                  15

Gly Ser Ser Gly Gly Gly Ser Gly
            20
```

```
<210> SEQ ID NO 8
<211> LENGTH: 40
<212> TYPE: PRT
<213> ORGANISM: Artificial Sequence
<220> FEATURE:
<223> OTHER INFORMATION: synthetic construct

<400> SEQUENCE: 8

Glu Pro Lys Ser Cys Asp Lys Thr His Thr Cys Pro Pro Cys Pro Glu
 1               5                  10                  15

Pro Lys Ser Cys Asp Thr Pro Pro Cys Pro Arg Cys Pro Gly Gly
            20                  25                  30

Gly Ser Ser Gly Gly Gly Ser Gly
        35                  40

<210> SEQ ID NO 9
<211> LENGTH: 42
<212> TYPE: PRT
<213> ORGANISM: Artificial Sequence
<220> FEATURE:
<223> OTHER INFORMATION: synthetic construct

<400> SEQUENCE: 9

Glu Pro Lys Ser Cys Asp Lys Thr His Thr Cys Pro Pro Cys Pro Glu
 1               5                  10                  15

Pro Lys Ser Cys Asp Thr Pro Pro Cys Pro Arg Cys Pro Ala Pro
            20                  25                  30

Gly Gly Gly Ser Ser Gly Gly Gly Ser Gly
        35                  40

<210> SEQ ID NO 10
<211> LENGTH: 25
<212> TYPE: PRT
<213> ORGANISM: Artificial Sequence
<220> FEATURE:
<223> OTHER INFORMATION: synthetic construct

<400> SEQUENCE: 10

Glu Pro Lys Ser Cys Asp Lys Thr His Thr Ser Pro Pro Cys Pro Gly
 1               5                  10                  15

Gly Gly Ser Ser Gly Gly Gly Ser Gly
            20                  25

<210> SEQ ID NO 11
<211> LENGTH: 27
<212> TYPE: PRT
<213> ORGANISM: Artificial Sequence
<220> FEATURE:
<223> OTHER INFORMATION: synthetic construct

<400> SEQUENCE: 11

Glu Pro Lys Ser Cys Asp Lys Thr His Thr Ser Pro Pro Cys Pro Ala
 1               5                  10                  15

Pro Gly Gly Gly Ser Ser Gly Gly Gly Ser Gly
            20                  25

<210> SEQ ID NO 12
<211> LENGTH: 25
<212> TYPE: PRT
<213> ORGANISM: Artificial Sequence
<220> FEATURE:
<223> OTHER INFORMATION: synthetic construct

<400> SEQUENCE: 12
```

```
Glu Pro Lys Ser Cys Asp Lys Thr His Thr Cys Pro Pro Ser Pro Gly
 1               5                  10                  15

Gly Gly Ser Ser Gly Gly Gly Ser Gly
            20                  25

<210> SEQ ID NO 13
<211> LENGTH: 27
<212> TYPE: PRT
<213> ORGANISM: Artificial Sequence
<220> FEATURE:
<223> OTHER INFORMATION: synthetic construct

<400> SEQUENCE: 13

Glu Pro Lys Ser Cys Asp Lys Thr His Thr Cys Pro Pro Ser Pro Ala
 1               5                  10                  15

Pro Gly Gly Gly Ser Ser Gly Gly Gly Ser Gly
            20                  25

<210> SEQ ID NO 14
<211> LENGTH: 27
<212> TYPE: PRT
<213> ORGANISM: Artificial Sequence
<220> FEATURE:
<223> OTHER INFORMATION: synthetic construct

<400> SEQUENCE: 14

Glu Pro Lys Ser Cys Asp Lys Thr His Thr Cys Pro Pro Cys Pro Ala
 1               5                  10                  15

Pro Gly Gly Gly Ser Ser Gly Gly Gly Ser Gly
            20                  25

<210> SEQ ID NO 15
<211> LENGTH: 25
<212> TYPE: PRT
<213> ORGANISM: Artificial Sequence
<220> FEATURE:
<223> OTHER INFORMATION: synthetic construct

<400> SEQUENCE: 15

Glu Pro Lys Ser Cys Asp Lys Thr His Thr Cys Pro Pro Cys Pro Gly
 1               5                  10                  15

Gly Gly Ser Ser Gly Gly Gly Ser Gly
            20                  25

<210> SEQ ID NO 16
<211> LENGTH: 1809
<212> TYPE: DNA
<213> ORGANISM: Artificial Sequence
<220> FEATURE:
<223> OTHER INFORMATION: synthetic construct

<400> SEQUENCE: 16
caggtccagc tggtgcagtc cggcgctgag gtggtgaaac ctggggcttc cgtgaagatt    60
tcctgcaagg caagcggcta caccttcact gatcacgcaa tccactgggt gaaacagaat   120
cctggacagc gcctggagtg gattggatat ttctctcccg aaacgatga ttttaagtac    180 aatgagaggt tcaagggcaa ggccacactg actgcagaca catctgccag cactgcctac   240
gtggagctct ccagcctgag atccgaggat actgcagtgt acttctgcac aagatccctg   300
aatatggcct actggggaca gggaaccctg gtcaccgtct ccagcgctag caccaagggc   360
ccatcggtct tccccctggc accctcctcc aagagcacct ctgggggcac agcggccctg   420
ggctgcctgg tcaaggacta cttccccgaa ccggtgacgg tgtcgtggaa ctcaggcgcc   480
```

```
ctgaccagcg gcgtgcacac cttcccggct gtcctacagt cctcaggact ctactccctc     540
agcagcgtgg tgaccgtgcc ctccagcagc ttgggcaccc agacctacat ctgcaacgtg     600
aatcacaagc ccagcaacac caaggtggac aagaaagttg agcccaaatc ttgtgacaaa     660
actcacacat gcccaccgtg cggaggtggc tcgagtggag gcggttccgg agggcagccc     720
cgagaaccac aggtgtacac cctgcccca tcccgggatg agctgaccaa gaaccaggtc     780
agcctgacct gcctggtcaa aggcttctat cccagcgaca tcgccgtgga gtgggagagc     840
aatgggcagc cggagaacaa ctacaagacc acgcctcccg tgctggactc cgacggctcc     900
ttcttcctct acagcaagct caccgtggac aagagcaggt ggcagcaggg gaacgtcttc     960
tcatgctccg tgatgcatga ggctctgcac aaccactaca cgcagaagag cctctccctg    1020
tctccgggta atccggcgg gggtggatcc ggtggagggg gctccggcgg tggcgggtcc    1080
gacatcgtga tgagccagtc tccagactcc ctggccgtgt ccctgggcga gagggtgact    1140
ctgaattgca gtccagcca gtccctgctc tatagcggaa atcagaagaa ctatctcgcc    1200
tggtatcagc agaaaccagg gcagagccct aaactgctga tttactgggc atccgctagg    1260
gaatccggcg tgcctgatcg cttcagcggc agcggatctg ggacagactt cactctgaca    1320
atcagcagcg tgcaggcaga agacgtggca gtctattatt gtcagcagta ttatagctat    1380
cccctcacat cggcgctgg caccaagctg gaacttaagg gcggtggcgg gtccggtggg    1440
ggtggctccg ggggcggtgg ctcccaggtc cagctggtgc agtccggcgc tgaggtggtg    1500
aaacctgggg cttccgtgaa gatttcctgc aaggcaagcg gctacacctt cactgatcac    1560
gcaatccact gggtgaaaca gaatcctgga cagcgcctgg agtggattgg atatttctct    1620
cccggaaacg atgatttaa gtacaatgag aggttcaagg gcaaggccac actgactgca    1680
gacacatctg ccagcactgc ctacgtggag ctctccagcc tgagatccga ggatactgca    1740
gtgtacttct gcacaagatc cctgaatatg gcctactggg gacagggaac cctggtcacc    1800
gtctccagc                                                          1809
```

<210> SEQ ID NO 17
<211> LENGTH: 1857
<212> TYPE: DNA
<213> ORGANISM: Artificial Sequence
<220> FEATURE:
<223> OTHER INFORMATION: synthetic construct

<400> SEQUENCE: 17

```
caggtccagc tggtgcagtc cggcgctgag gtggtgaaac ctggggcttc cgtgaagatt      60
tcctgcaagg caagcggcta caccttcact gatcacgcaa tccactgggt gaaacagaat     120
cctggacagc gcctggagtg gattggatat ttctctcccg gaaacgatga ttttaagtac     180
aatgagaggt tcaagggcaa ggccacactg actgcagaca catctgccag cactgcctac    240
gtggagctct ccagcctgag atccgaggat actgcagtgt acttctgcac aagatccctg    300
aatatggcct actggggaca gggaaccctg gtcaccgtct ccagcgctag caccaagggc    360
ccatcggtct tccccctggc accctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgacaaa    660
actcacacat gcccaccgtg cccagagccc aaatcttgtg acacacctcc cccatgccca    720
```

| | | |
|---|---|---|
| cggtgcccag gaggtggctc gagtggaggc ggttccggag ggcagcccccg agaaccacag | 780 | |
| gtgtacaccc tgcccccatc ccgggatgag ctgaccaaga accaggtcag cctgacctgc | 840 | |
| ctggtcaaag gcttctatcc cagcgacatc gccgtggagt gggagagcaa tgggcagccg | 900 | |
| gagaacaact acaagaccac gcctcccgtg ctggactccg acggctcctt cttcctctac | 960 | |
| agcaagctca ccgtggacaa gagcaggtgg cagcagggga acgtcttctc atgctccgtg | 1020 | |
| atgcatgagg ctctgcacaa ccactacacg cagaagagcc tctccctgtc tccgggtaaa | 1080 | |
| tccggcgggg gtggatccgg tggagggggc tccggcggtg gcgggtccga catcgtgatg | 1140 | |
| agccagtctc cagactccct ggccgtgtcc ctgggcgaga gggtgactct gaattgcaag | 1200 | |
| tccagccagt ccctgctcta tagcggaaat cagaagaact atctcgcctg gtatcagcag | 1260 | |
| aaaccagggc agagccctaa actgctgatt tactgggcat ccgctaggga atccggcgtg | 1320 | |
| cctgatcgct tcagcggcag cggatctggg acagacttca ctctgacaat cagcagcgtg | 1380 | |
| caggcagaag acgtggcagt ctattattgt cagcagtatt atagctatcc cctcacattc | 1440 | |
| ggcgctggca ccaagctgga acttaagggc ggtggcgggt ccggtggggg tggctccggg | 1500 | |
| ggcggtggct cccaggtcca gctggtgcag tccggcgctg aggtggtgaa acctggggct | 1560 | |
| tccgtgaaga tttcctgcaa ggcaagcggc tacaccttca ctgatcacgc aatccactgg | 1620 | |
| gtgaaacaga tcctggaca gcgcctggag tggattggat atttctctcc cggaaacgat | 1680 | |
| gattttaagt acaatgagag gttcaagggc aaggccacac tgactgcaga cacatctgcc | 1740 | |
| agcactgcct acgtggagct ctccagcctg agatccgagg atactgcagt gtacttctgc | 1800 | |
| acaagatccc tgaatatggc ctactgggga cagggaaccc tggtcaccgt ctccagc | 1857 | |

<210> SEQ ID NO 18
<211> LENGTH: 663
<212> TYPE: DNA
<213> ORGANISM: Artificial Sequence
<220> FEATURE:
<223> OTHER INFORMATION: synthetic construct

<400> SEQUENCE: 18

| | | |
|---|---|---|
| gacatcgtga tgagccagtc tccagactcc ctggccgtgt ccctgggcga gagggtgact | 60 | |
| ctgaattgca gtccagcca gtccctgctc tatagcggaa atcagaagaa ctatctcgcc | 120 | |
| tggtatcagc agaaaccagg gcagagccct aaactgctga tttactgggc atccgctagg | 180 | |
| gaatccggcg tgcctgatcg cttcagcggc agcggatctg ggacagactt cactctgaca | 240 | |
| atcagcagcg tgcaggcaga agacgtggca gtctattatt gtcagcagta ttatagctat | 300 | |
| cccctcacat tcggcgctgg caccaagctg gaactgaaac gtacggtggc tgcaccatct | 360 | |
| gtcttcatct tcccgccatc tgatgagcag ttgaaatctg gaactgcctc tgttgtgtgc | 420 | |
| ctgctgaata acttctatcc cagagaggcc aaagtacagt ggaaggtgga taacgccctc | 480 | |
| caatcgggta actcccagga gagtgtcaca gagcaggaca gcaaggacag cacctacagc | 540 | |
| ctcagcagca ccctgacgct gagcaaagca gactacgaga acacaaagt ctacgcctgc | 600 | |
| gaagtcaccc atcagggcct gagctcgccc gtcacaaaga gcttcaacag gggagagtgt | 660 | |
| tga | 663 | |

<210> SEQ ID NO 19
<211> LENGTH: 603
<212> TYPE: PRT
<213> ORGANISM: Artificial Sequence
<220> FEATURE:
<223> OTHER INFORMATION: synthetic construct

<400> SEQUENCE: 19

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Gly Gly Gly Ser Gly Gly Gly Ser Gly Gly Gln Pro
225                 230                 235                 240

Arg Glu Pro Gln Val Tyr Thr Leu Pro Pro Ser Arg Asp Glu Leu Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys Ser Gly Gly Gly Gly Ser Gly Gly
            340                 345                 350

Gly Gly Ser Gly Gly Gly Ser Asp Ile Val Met Ser Gln Ser Pro
        355                 360                 365

Asp Ser Leu Ala Val Ser Leu Gly Glu Arg Val Thr Leu Asn Cys Lys
370                 375                 380

Ser Ser Gln Ser Leu Leu Tyr Ser Gly Asn Gln Lys Asn Tyr Leu Ala
385                 390                 395                 400

Trp Tyr Gln Gln Lys Pro Gly Gln Ser Pro Lys Leu Leu Ile Tyr Trp
                405                 410                 415

```
Ala Ser Ala Arg Glu Ser Gly Val Pro Asp Arg Phe Ser Gly Ser Gly
            420                 425                 430

Ser Gly Thr Asp Phe Thr Leu Thr Ile Ser Ser Val Gln Ala Glu Asp
        435                 440                 445

Val Ala Val Tyr Tyr Cys Gln Gln Tyr Ser Tyr Pro Leu Thr Phe
450                 455                 460

Gly Ala Gly Thr Lys Leu Glu Leu Lys Gly Gly Gly Ser Gly Gly
465                 470                 475                 480

Gly Gly Ser Gly Gly Gly Ser Gln Val Gln Leu Val Gln Ser Gly
            485                 490                 495

Ala Glu Val Val Lys Pro Gly Ala Ser Val Lys Ile Ser Cys Lys Ala
            500                 505                 510

Ser Gly Tyr Thr Phe Thr Asp His Ala Ile His Trp Val Lys Gln Asn
        515                 520                 525

Pro Gly Gln Arg Leu Glu Trp Ile Gly Tyr Phe Ser Pro Gly Asn Asp
    530                 535                 540

Asp Phe Lys Tyr Asn Glu Arg Phe Lys Gly Lys Ala Thr Leu Thr Ala
545                 550                 555                 560

Asp Thr Ser Ala Ser Thr Ala Tyr Val Glu Leu Ser Ser Leu Arg Ser
                565                 570                 575

Glu Asp Thr Ala Val Tyr Phe Cys Thr Arg Ser Leu Asn Met Ala Tyr
            580                 585                 590

Trp Gly Gln Gly Thr Leu Val Thr Val Ser Ser
            595                 600

<210> SEQ ID NO 20
<211> LENGTH: 621
<212> TYPE: PRT
<213> ORGANISM: Artificial Sequence
<220> FEATURE:
<223> OTHER INFORMATION: synthetic construct

<400> SEQUENCE: 20

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Gly Gln Arg Leu Glu Trp Ile
        35                  40                  45

Gly Tyr Phe Ser Pro Gly Asn Asp Asp Phe Lys Tyr Asn Glu Arg Phe
    50                  55                  60

Lys Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
```

-continued

```
                180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
            210                 215                 220
Pro Pro Cys Pro Glu Pro Lys Ser Cys Asp Thr Pro Pro Pro Cys Pro
225                 230                 235                 240
Arg Cys Pro Ala Pro Gly Gly Gly Ser Gly Gly Gly Ser Gly Gly Gly
                245                 250                 255
Gln Pro Arg Glu Pro Gln Val Tyr Thr Leu Pro Pro Ser Arg Asp Glu
                260                 265                 270
Leu Thr Lys Asn Gln Val Ser Leu Thr Cys Leu Val Lys Gly Phe Tyr
            275                 280                 285
Pro Ser Asp Ile Ala Val Glu Trp Glu Ser Asn Gly Gln Pro Glu Asn
            290                 295                 300
Asn Tyr Lys Thr Thr Pro Pro Val Leu Asp Ser Asp Gly Ser Phe Phe
305                 310                 315                 320
Leu Tyr Ser Lys Leu Thr Val Asp Lys Ser Arg Trp Gln Gln Gly Asn
                325                 330                 335
Val Phe Ser Cys Ser Val Met His Glu Ala Leu His Asn His Tyr Thr
                340                 345                 350
Gln Lys Ser Leu Ser Leu Ser Pro Gly Lys Ser Gly Gly Gly Gly Ser
            355                 360                 365
Gly Gly Gly Gly Ser Gly Gly Gly Ser Asp Ile Val Met Ser Gln
            370                 375                 380
Ser Pro Asp Ser Leu Ala Val Ser Leu Gly Glu Arg Val Thr Leu Asn
385                 390                 395                 400
Cys Lys Ser Ser Gln Ser Leu Leu Tyr Ser Gly Asn Gln Lys Asn Tyr
                405                 410                 415
Leu Ala Trp Tyr Gln Gln Lys Pro Gly Gln Ser Pro Lys Leu Leu Ile
                420                 425                 430
Tyr Trp Ala Ser Ala Arg Glu Ser Gly Val Pro Asp Arg Phe Ser Gly
            435                 440                 445
Ser Gly Ser Gly Thr Asp Phe Thr Leu Thr Ile Ser Ser Val Gln Ala
            450                 455                 460
Glu Asp Val Ala Val Tyr Tyr Cys Gln Gln Tyr Tyr Ser Tyr Pro Leu
465                 470                 475                 480
Thr Phe Gly Ala Gly Thr Lys Leu Glu Leu Lys Gly Gly Gly Gly Ser
                485                 490                 495
Gly Gly Gly Gly Ser Gly Gly Gly Ser Gln Val Gln Leu Val Gln
            500                 505                 510
Ser Gly Ala Glu Val Val Lys Pro Gly Ala Ser Val Lys Ile Ser Cys
            515                 520                 525
Lys Ala Ser Gly Tyr Thr Phe Thr Asp His Ala Ile His Trp Val Lys
            530                 535                 540
Gln Asn Pro Gly Gln Arg Leu Glu Trp Ile Gly Tyr Phe Ser Pro Gly
545                 550                 555                 560
Asn Asp Asp Phe Lys Tyr Asn Glu Arg Phe Lys Gly Lys Ala Thr Leu
                565                 570                 575
Thr Ala Asp Thr Ser Ala Ser Thr Ala Tyr Val Glu Leu Ser Ser Leu
            580                 585                 590
Arg Ser Glu Asp Thr Ala Val Tyr Phe Cys Thr Arg Ser Leu Asn Met
            595                 600                 605
```

```
Ala Tyr Trp Gly Gln Gly Thr Leu Val Thr Val Ser Ser
            610                 615                 620
```

```
<210> SEQ ID NO 21
<211> LENGTH: 220
<212> TYPE: PRT
<213> ORGANISM: Artificial Sequence
<220> FEATURE:
<223> OTHER INFORMATION: synthetic construct

<400> SEQUENCE: 21
```

```
Asp Ile Val Met Ser Gln Ser Pro Asp Ser Leu Ala Val Ser Leu Gly
  1               5                  10                  15

Glu Arg Val Thr Leu Asn Cys Lys Ser Ser Gln Ser Leu Leu Tyr Ser
             20                  25                  30

Gly Asn Gln Lys Asn Tyr Leu Ala Trp Tyr Gln Lys Pro Gly Gln
         35                  40                  45

Ser Pro Lys Leu Leu Ile Tyr Trp Ala Ser Ala Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                 85                  90                  95

Tyr Tyr Ser Tyr Pro Leu Thr Phe Gly Ala Gly Thr Lys Leu Glu Leu
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

```
<210> SEQ ID NO 22
<211> LENGTH: 1932
<212> TYPE: DNA
<213> ORGANISM: Artificial Sequence
<220> FEATURE:
<223> OTHER INFORMATION: synthetic construct

<400> SEQUENCE: 22
```

```
gacatcgtga tgagccagtc tccagactcc ctggccgtgt ccctgggcga gagggtgact     60
ctgaattgca gtccagcca gtccctgctc tatagcggaa atcagaagaa ctatctcgcc    120
tggtatcagc agaaaccagg gcagagccct aaactgctga tttactgggc atccgctagg    180
gaatccggcg tgcctgatcg cttcagcggc agcggatctg gacagactt cactctgaca    240 atcagcagcg tgcaggcaga agacgtggca gtctattatt gtcagcagta ttatagctat    300
cccctcacat cggcgctgg caccaagctg gaacttaagg cggtggcgg tccggtggg    360 ggtggctccg gggcggtgg ctcccaggtc agctggtgc agtccggcgc tgaggtggtg    420
aaacctgggg cttccgtgaa gatttcctgc aaggcaagcg gctacacctt cactgatcac    480
```

```
gcaatccact gggtgaaaca gaatcctgga cagcgcctgg agtggattgg atatttctct    540
cccggaaacg atgattttaa gtacaatgag aggttcaagg gcaaggccac actgactgca    600
gacacatctg ccagcactgc ctacgtggag ctctccagcc tgagatccga ggatactgca    660
gtgtacttct gcacaagatc cctgaatatg gcctactggg gacagggtac cctggtcacc    720
gtctccagcg gcggtggagg gtccggtgga gggggctctg gaggggggcgg ttcagggggc    780 ggtggatcgg gcggaggtgc tagcgacatc gtgatgagcc agtctccaga ctccctggcc    840
gtgtccctgg gcgagagggt gactctgaat tgcaagtcca gccagtccct gctctatagc    900
ggaaatcaga agaactatct cgcctggtat cagcagaaac agggcagag ccctaaactg    960 ctgatttact gggcatccgc tagggaatcc ggcgtgcctg atcgcttcag cggcagcgga   1020
tctgggacag acttcactct gacaatcagc agcgtgcagg cagaagacgt ggcagtctat   1080
tattgtcagc agtattatag ctatccccctc acattcggcg ctggcaccaa gctgaactt    1140 aagggcggtg gcgggtccgg tggggtggc tccgggggcg gtggctccca ggtccagctg    1200
gtgcagtccg gcgctgaggt ggtgaaacct ggggcttccg tgaagatttc ctgcaaggca   1260
agcggctaca ccttcactga tcacgcaatc cactgggtga acagaatcc tggacagcgc    1320 ctggagtgga ttggatattt ctctcccgga aacgatgatt ttaagtacaa tgagaggttc    1380
aagggcaagg ccacactgac tgcagacaca tctgccagca ctgcctacgt ggagctctcc    1440
agcctgagat ccgaggatac tgcagtgtac ttctgcacaa gatccctgaa tatggcctac    1500
tggggacagg gaaccctggt caccgtctcc agcgtcgacc ccaaatcttg tgacaaaact    1560
cacacatgcc caccgtgcgg aggtggctcg agtggaggcg gatccggagg cagccccga    1620 gaaccacagg tgtacaccct gcccccatcc cgggatgagc tgaccaagaa ccaggtcagc    1680
ctgacctgcc tggtcaaagg cttctatccc agcgacatcg ccgtggagtg ggagagcaat   1740
gggcagccgg agaacaacta caagaccacg cctcccgtgc tggactccga cggctccttc    1800
ttcctctaca gcaagctcac cgtggacaag agcaggtggc agcaggggaa cgtcttctca    1860
tgctccgtga tgcatgaggc tctgcacaac cactacacgc agaagagcct ctccctgtct   1920
ccgggtaaat ga    1932
```

<210> SEQ ID NO 23
<211> LENGTH: 1980
<212> TYPE: DNA
<213> ORGANISM: Artificial Sequence
<220> FEATURE:
<223> OTHER INFORMATION: synthetic construct

<400> SEQUENCE: 23

```
gacatcgtga tgagccagtc tccagactcc ctggccgtgt ccctgggcga gagggtgact     60
ctgaattgca agtccagcca gtccctgctc tatagcggaa atcagaagaa ctatctcgcc    120
tggtatcagc agaaaccagg gcagagccct aaactgctga tttactgggc atccgctagg    180
gaatccggcg tgcctgatcg cttcagcggc agcggatctg gacagactt cactctgaca    240 atcagcagcg tgcaggcaga agacgtggca gtctattatt gtcagcagta ttatagctat    300
cccctcacat tcggcgctgg caccaagctg aacttaagg gcggtggcgg gtccggtggg    360
ggtggctccg gggcggtgg ctcccaggtc cagctggtgc agtccggcgc tgaggtggtg    420
aaacctgggg cttccgtgaa gatttcctgc aaggcaagcg gctacacctt cactgatcac    480
gcaatccact gggtgaaaca gaatcctgga cagcgcctgg agtggattgg atatttctct    540
cccggaaacg atgattttaa gtacaatgag aggttcaagg gcaaggccac actgactgca    600
```

```
gacacatctg ccagcactgc ctacgtggag ctctccagcc tgagatccga ggatactgca    660
gtgtacttct gcacaagatc cctgaatatg gcctactggg acagggtac cctggtcacc    720 gtctccagcg gcggtggagg gtccggtgga gggggctctg gagggggcgg ttcagggggc    780
ggtggatcgg gcggaggtgc tagcgacatc gtgatgagcc agtctccaga ctccctggcc    840
gtgtccctgg gcgagagggt gactctgaat tgcaagtcca gccagtccct gctctatagc    900
ggaaatcaga agaactatct cgcctggtat cagcagaaac cagggcagag ccctaaactg    960
ctgatttact gggcatccgc tagggaatcc ggcgtgcctg atcgcttcag cggcagcgga   1020
tctgggacag acttcactct gacaatcagc agcgtgcagg cagaagacgt ggcagtctat   1080
tattgtcagc agtattatag ctatccccctc acattcggcg ctggcaccaa gctggaactt   1140
aagggcggtg gcgggtccgg tggggtggc tccggggggcg gtggctccca ggtccagctg   1200
gtgcagtccg gcgctgaggt ggtgaaacct ggggcttccg tgaagatttc ctgcaaggca   1260
agcggctaca ccttcactga tcacgcaatc cactgggtga acagaatcc tggacagcgc   1320 ctggagtgga ttggatattt ctctcccgga aacgatgatt ttaagtacaa tgagaggttc   1380
aagggcaagg ccacactgac tgcagacaca tctgccagca ctgcctacgt ggagctctcc   1440
agcctgagat ccgaggatac tgcagtgtac ttctgcacaa gatccctgaa tatggcctac   1500
tggggacagg gaaccctggt caccgtctcc agcgtcgacc ccaaatcttg tgacaaaact   1560
cacacatgcc caccgtgccc agagcccaaa tcttgtgaca cacctccccc atgcccacgg   1620
tgcccaggag gtggctcgag tggaggcgga tccgagggc agcccccgaga accacaggtg   1680 tacaccctgc ccccatcccg ggatgagctg accaagaacc aggtcagcct gacctgcctg   1740
gtcaaaggct tctatcccag cgacatcgcc gtggagtggg agagcaatgg gcagccggag   1800
aacaactaca agaccacgcc tcccgtgctg gactccgacg gctccttctt cctctacagc   1860
aagctcaccg tggacaagag caggtggcag caggggaacg tcttctcatg ctccgtgatg   1920
catgaggctc tgcacaacca ctacacgcag aagagcctct ccctgtctcc gggtaaatga   1980
```

<210> SEQ ID NO 24
<211> LENGTH: 643
<212> TYPE: PRT
<213> ORGANISM: Artificial Sequence
<220> FEATURE:
<223> OTHER INFORMATION: synthetic construct

<400> SEQUENCE: 24

```
Asp Ile Val Met Ser Gln Ser Pro Asp Ser Leu Ala Val Ser Leu Gly
  1               5                  10                  15

Glu Arg Val Thr Leu Asn Cys Lys Ser Ser Gln Ser Leu Leu Tyr Ser
             20                  25                  30

Gly Asn Gln Lys Asn Tyr Leu Ala Trp Tyr Gln Gln Lys Pro Gly Gln
         35                  40                  45

Ser Pro Lys Leu Leu Ile Tyr Trp Ala Ser Ala Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Val Gln Ala Glu Asp Val Ala Val Tyr Tyr Cys Gln Gln
                 85                  90                  95

Tyr Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125
```

```
Gln Val Gln Leu Val Gln Ser Gly Ala Glu Val Lys Pro Gly Ala
    130                 135                 140
Ser Val Lys Ile Ser Cys Lys Ala Ser Gly Tyr Thr Phe Thr Asp His
145                 150                 155                 160
Ala Ile His Trp Val Lys Gln Asn Pro Gly Gln Arg Leu Glu Trp Ile
                165                 170                 175
Gly Tyr Phe Ser Pro Gly Asn Asp Asp Phe Lys Tyr Asn Glu Arg Phe
            180                 185                 190
Lys Gly Lys Ala Thr Leu Thr Ala Asp Thr Ser Ala Ser Thr Ala Tyr
        195                 200                 205
Val Glu Leu Ser Ser Leu Arg Ser Glu Asp Thr Ala Val Tyr Phe Cys
    210                 215                 220
Thr Arg Ser Leu Asn Met Ala Tyr Trp Gly Gln Gly Thr Leu Val Thr
225                 230                 235                 240
Val Ser Ser Gly Gly Gly Gly Ser Gly Gly Gly Ser Gly Gly Gly
                245                 250                 255
Gly Ser Gly Gly Gly Gly Ser Gly Gly Gly Ala Ser Asp Ile Val Met
            260                 265                 270
Ser Gln Ser Pro Asp Ser Leu Ala Val Ser Leu Gly Glu Arg Val Thr
        275                 280                 285
Leu Asn Cys Lys Ser Ser Gln Ser Leu Leu Tyr Ser Gly Asn Gln Lys
    290                 295                 300
Asn Tyr Leu Ala Trp Tyr Gln Gln Lys Pro Gly Gln Ser Pro Lys Leu
305                 310                 315                 320
Leu Ile Tyr Trp Ala Ser Ala Arg Glu Ser Gly Val Pro Asp Arg Phe
                325                 330                 335
Ser Gly Ser Gly Ser Gly Thr Asp Phe Thr Leu Thr Ile Ser Ser Val
            340                 345                 350
Gln Ala Glu Asp Val Ala Val Tyr Tyr Cys Gln Gln Tyr Tyr Ser Tyr
        355                 360                 365
Pro Leu Thr Phe Gly Ala Gly Thr Lys Leu Glu Leu Lys Gly Gly Gly
    370                 375                 380
Gly Ser Gly Gly Gly Gly Ser Gly Gly Gly Gly Ser Gln Val Gln Leu
385                 390                 395                 400
Val Gln Ser Gly Ala Glu Val Val Lys Pro Gly Ala Ser Val Lys Ile
                405                 410                 415
Ser Cys Lys Ala Ser Gly Tyr Thr Phe Thr Asp His Ala Ile His Trp
            420                 425                 430
Val Lys Gln Asn Pro Gly Gln Arg Leu Glu Trp Ile Gly Tyr Phe Ser
        435                 440                 445
Pro Gly Asn Asp Asp Phe Lys Tyr Asn Glu Arg Phe Lys Gly Lys Ala
    450                 455                 460
Thr Leu Thr Ala Asp Thr Ser Ala Ser Thr Ala Tyr Val Glu Leu Ser
465                 470                 475                 480
Ser Leu Arg Ser Glu Asp Thr Ala Val Tyr Phe Cys Thr Arg Ser Leu
                485                 490                 495
Asn Met Ala Tyr Trp Gly Gln Gly Thr Leu Val Thr Val Ser Ser Val
            500                 505                 510
Asp Pro Lys Ser Cys Asp Lys Thr His Thr Cys Pro Pro Cys Gly Gly
        515                 520                 525
Gly Ser Ser Gly Gly Gly Ser Gly Gly Gln Pro Arg Glu Pro Gln Val
    530                 535                 540
Tyr Thr Leu Pro Pro Ser Arg Asp Glu Leu Thr Lys Asn Gln Val Ser
```

```
                545                 550                 555                 560
Leu Thr Cys Leu Val Lys Gly Phe Tyr Pro Ser Asp Ile Ala Val Glu
                565                 570                 575

Trp Glu Ser Asn Gly Gln Pro Glu Asn Asn Tyr Lys Thr Thr Pro Pro
                580                 585                 590

Val Leu Asp Ser Asp Gly Ser Phe Phe Leu Tyr Ser Lys Leu Thr Val
                595                 600                 605

Asp Lys Ser Arg Trp Gln Gln Gly Asn Val Phe Ser Cys Ser Val Met
                610                 615                 620

His Glu Ala Leu His Asn His Tyr Thr Gln Lys Ser Leu Ser Leu Ser
625                 630                 635                 640

Pro Gly Lys

<210> SEQ ID NO 25
<211> LENGTH: 661
<212> TYPE: PRT
<213> ORGANISM: Artificial Sequence
<220> FEATURE:
<223> OTHER INFORMATION: synthetic construct

<400> SEQUENCE: 25

Asp Ile Val Met Ser Gln Ser Pro Asp Ser Leu Ala Val Ser Leu Gly
1               5                   10                  15

Glu Arg Val Thr Leu Asn Cys Lys Ser Ser Gln Ser Leu Leu Tyr Ser
                20                  25                  30

Gly Asn Gln Lys Asn Tyr Leu Ala Trp Tyr Gln Gln Lys Pro Gly Gln
            35                  40                  45

Ser Pro Lys Leu Leu Ile Tyr Trp Ala Ser Ala Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110

Lys Gly Gly Gly Gly Ser Gly Gly Gly Gly Ser Gly Gly Gly Gly Ser
            115                 120                 125

Gln Val Gln Leu Val Gln Ser Gly Ala Glu Val Val Lys Pro Gly Ala
        130                 135                 140

Ser Val Lys Ile Ser Cys Lys Ala Ser Gly Tyr Thr Phe Thr Asp His
145                 150                 155                 160

Ala Ile His Trp Val Lys Gln Asn Pro Gly Gln Arg Leu Glu Trp Ile
                165                 170                 175

Gly Tyr Phe Ser Pro Gly Asn Asp Asp Phe Lys Tyr Asn Glu Arg Phe
                180                 185                 190

Lys Gly Lys Ala Thr Leu Thr Ala Asp Thr Ser Ala Ser Thr Ala Tyr
            195                 200                 205

Val Glu Leu Ser Ser Leu Arg Ser Glu Asp Thr Ala Val Tyr Phe Cys
        210                 215                 220

Thr Arg Ser Leu Asn Met Ala Tyr Trp Gly Gln Gly Thr Leu Val Thr
225                 230                 235                 240

Val Ser Ser Gly Gly Gly Gly Ser Gly Gly Gly Gly Ser Gly Gly Gly
                245                 250                 255

Gly Ser Gly Gly Gly Gly Ser Gly Gly Gly Ala Ser Asp Ile Val Met
                260                 265                 270
```

Ser Gln Ser Pro Asp Ser Leu Ala Val Ser Leu Gly Glu Arg Val Thr
            275                 280                 285

Leu Asn Cys Lys Ser Ser Gln Ser Leu Leu Tyr Ser Gly Asn Gln Lys
290                 295                 300

Asn Tyr Leu Ala Trp Tyr Gln Gln Lys Pro Gly Gln Ser Pro Lys Leu
305                 310                 315                 320

Leu Ile Tyr Trp Ala Ser Ala Arg Glu Ser Gly Val Pro Asp Arg Phe
                325                 330                 335

Ser Gly Ser Gly Ser Gly Thr Asp Phe Thr Leu Thr Ile Ser Ser Val
            340                 345                 350

Gln Ala Glu Asp Val Ala Val Tyr Tyr Cys Gln Gln Tyr Tyr Ser Tyr
        355                 360                 365

Pro Leu Thr Phe Gly Ala Gly Thr Lys Leu Glu Leu Lys Gly Gly Gly
    370                 375                 380

Gly Ser Gly Gly Gly Gly Ser Gly Gly Gly Gly Ser Gln Val Gln Leu
385                 390                 395                 400

Val Gln Ser Gly Ala Glu Val Val Lys Pro Gly Ala Ser Val Lys Ile
                405                 410                 415

Ser Cys Lys Ala Ser Gly Tyr Thr Phe Thr Asp His Ala Ile His Trp
            420                 425                 430

Val Lys Gln Asn Pro Gly Gln Arg Leu Glu Trp Ile Gly Tyr Phe Ser
        435                 440                 445

Pro Gly Asn Asp Asp Phe Lys Tyr Asn Glu Arg Phe Lys Gly Lys Ala
    450                 455                 460

Thr Leu Thr Ala Asp Thr Ser Ala Ser Thr Ala Tyr Val Glu Leu Ser
465                 470                 475                 480

Ser Leu Arg Ser Glu Asp Thr Ala Val Tyr Phe Cys Thr Arg Ser Leu
                485                 490                 495

Asn Met Ala Tyr Trp Gly Gln Gly Thr Leu Val Thr Val Ser Ser Val
            500                 505                 510

Asp Pro Lys Ser Cys Asp Lys Thr His Thr Cys Pro Pro Cys Pro Glu
        515                 520                 525

Pro Lys Ser Cys Asp Thr Pro Pro Cys Pro Arg Cys Pro Ala Pro
    530                 535                 540

Gly Gly Gly Ser Ser Gly Gly Gly Ser Gly Gly Gln Pro Arg Glu Pro
545                 550                 555                 560

Gln Val Tyr Thr Leu Pro Pro Ser Arg Asp Glu Leu Thr Lys Asn Gln
                565                 570                 575

Val Ser Leu Thr Cys Leu Val Lys Gly Phe Tyr Pro Ser Asp Ile Ala
            580                 585                 590

Val Glu Trp Glu Ser Asn Gly Gln Pro Glu Asn Asn Tyr Lys Thr Thr
        595                 600                 605

Pro Pro Val Leu Asp Ser Asp Gly Ser Phe Phe Leu Tyr Ser Lys Leu
    610                 615                 620

Thr Val Asp Lys Ser Arg Trp Gln Gln Gly Asn Val Phe Ser Cys Ser
625                 630                 635                 640

Val Met His Glu Ala Leu His Asn His Tyr Thr Gln Lys Ser Leu Ser
                645                 650                 655

Leu Ser Pro Gly Lys
            660

<210> SEQ ID NO 26
<211> LENGTH: 1866
<212> TYPE: DNA
<213> ORGANISM: Artificial Sequence

```
<220> FEATURE:
<223> OTHER INFORMATION: synthetic construct

<400> SEQUENCE: 26
gaggtgcagc tggtggagtc tgggggcggc ttggcaaagc ctggggggtc cctgagactc      60
tcctgcgcag cctccgggtt caggttcacc ttcaataact actacatgga ctgggtccgc     120
caggctccag ggcaggggct ggagtgggtc tcacgtatta gtagtagtgg tgatcccaca     180
tggtacgcag actccgtgaa gggcagattc accatctcca gagagaacgc caagaacaca     240
ctgtttcttc aaatgaacag cctgagagct gaggacacgg ctgtctatta ctgtgcgagc     300
ttgactacag ggtctgactc ctggggccag ggagtcctgg tcaccgtctc ctcagctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca gaaagttgag cccaaatct     660
tgtgacaaaa ctcacacatg cccaccgtgc ccagagccca atcttgtgac acacctccc     720
ccatgcccac ggtgcccagc acctggaggt ggctcgagtg gaggcggttc cggagggcag     780
ccccgagaac acaggtgta cccctgccc catcccggg atgagctgac caagaaccag     840
gtcagcctga cctgcctggt caaaggcttc tatcccagcg acatcgccgt ggagtgggag     900
agcaatgggc agccggagaa caactacaag accacgcctc ccgtgctgga ctccgacggc     960
tccttcttcc tctacagcaa gctcaccgtg gacaagagca ggtggcagca ggggaacgtc    1020
ttctcatgct ccgtgatgca tgaggctctg cacaaccact acacgcagaa gagcctctcc    1080
ctgtctccgg gtaaatccgg cggggggtgga tccggtggag ggggctccgg cggtggcggg    1140
tccgacatcc agatgaccca gtctccatct tccctgtctg catctgtagg ggacagagtc    1200
accatcactt gcagggcaag tcaggacatt aggtattatt taaattggta tcagcagaaa    1260
ccaggaaaag ctcctaagct cctgatctat gttgcatcca gtttgcaaag tggggtccca    1320
tcaaggttca gcggcagtgg atctgggaca gagttcactc tcaccgtcag cagcctgcag    1380
cctgaagatt ttgcgactta ttactgtcta caggtttata gtacccctcg gacgttcggc    1440
caagggacca aggtggaaat caaaggcggt ggcgggtccg gtggggtgg ctccgggggc    1500
ggtggctccg aggtgcagct ggtggagtct ggggggcggct tggcaaagcc tggggggtcc    1560
ctgagactct cctgcgcagc ctccgggttc aggttcacct tcaataacta ctacatggac    1620
tgggtccgcc aggctccagg gcaggggctg gagtgggtct cacgtattag tagtagtggt    1680
gatcccacat ggtacgcaga ctccgtgaag ggcagattca ccatctccag agagaacgcc    1740
aagaacacac tgtttcttca aatgaacagc ctgagagctg aggacacggc tgtctattac    1800
tgtgcgagct tgactacagg gtctgactcc tggggccagg gagtcctggt caccgtctcc    1860
tcatga                                                              1866

<210> SEQ ID NO 27
<211> LENGTH: 645
<212> TYPE: DNA
<213> ORGANISM: Artificial Sequence
<220> FEATURE:
<223> OTHER INFORMATION: synthetic construct

<400> SEQUENCE: 27
gacatccaga tgacccagtc tccatcttcc ctgtctgcat ctgtagggga cagagtcacc      60
```

```
atcacttgca gggcaagtca ggacattagg tattatttaa attggtatca gcagaaacca    120
ggaaaagctc ctaagctcct gatctatgtt gcatccagtt tgcaaagtgg ggtcccatca    180
aggttcagcg gcagtggatc tgggacagag ttcactctca ccgtcagcag cctgcagcct    240
gaagattttg cgacttatta ctgtctacag gtttatagta cccctcggac gttcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttga                   645
```

<210> SEQ ID NO 28
<211> LENGTH: 621
<212> TYPE: PRT
<213> ORGANISM: Artificial Sequence
<220> FEATURE:
<223> OTHER INFORMATION: synthetic construct

<400> SEQUENCE: 28

```
Glu Val Gln Leu Val Glu Ser Gly Gly Gly Leu Ala Lys Pro Gly Gly
  1               5                  10                  15

Ser Leu Arg Leu Ser Cys Ala Ala Ser Gly Phe Arg Phe Thr Phe Asn
             20                  25                  30

Asn Tyr Tyr Met Asp Trp Val Arg Gln Ala Pro Gly Gln Gly Leu Glu
         35                  40                  45

Trp Val Ser Arg Ile Ser Ser Gly Asp Pro Thr Trp Tyr Ala Asp
     50                  55                  60

Ser Val Lys Gly Arg Phe Thr Ile Ser Arg Glu Asn Ala Lys Asn Thr
 65                  70                  75                  80

Leu Phe Leu Gln Met Asn Ser Leu Arg Ala Glu Asp Thr Ala Val Tyr
                 85                  90                  95

Tyr Cys Ala Ser Leu Thr Thr Gly Ser Asp Ser Trp Gly Gln Gly Val
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Glu Pro Lys Ser Cys Asp Thr Pro Pro
225                 230                 235                 240

Pro Cys Pro Arg Cys Pro Ala Pro Gly Gly Gly Ser Ser Gly Gly Gly
                245                 250                 255

Ser Gly Gly Gln Pro Arg Glu Pro Gln Val Tyr Thr Leu Pro Pro Ser
```

```
                260                 265                 270
Arg Asp Glu Leu Thr Lys Asn Gln Val Ser Leu Thr Cys Leu Val Lys
            275                 280                 285
Gly Phe Tyr Pro Ser Asp Ile Ala Val Glu Trp Glu Ser Asn Gly Gln
        290                 295                 300
Pro Glu Asn Asn Tyr Lys Thr Thr Pro Pro Val Leu Asp Ser Asp Gly
305                 310                 315                 320
Ser Phe Phe Leu Tyr Ser Lys Leu Thr Val Asp Lys Ser Arg Trp Gln
                325                 330                 335
Gln Gly Asn Val Phe Ser Cys Ser Val Met His Glu Ala Leu His Asn
            340                 345                 350
His Tyr Thr Gln Lys Ser Leu Ser Leu Ser Pro Gly Lys Ser Gly Gly
        355                 360                 365
Gly Gly Ser Gly Gly Gly Ser Gly Gly Gly Ser Asp Ile Gln
    370                 375                 380
Met Thr Gln Ser Pro Ser Ser Leu Ser Ala Ser Val Gly Asp Arg Val
385                 390                 395                 400
Thr Ile Thr Cys Arg Ala Ser Gln Asp Ile Arg Tyr Tyr Leu Asn Trp
                405                 410                 415
Tyr Gln Gln Lys Pro Gly Lys Ala Pro Lys Leu Leu Ile Tyr Val Ala
            420                 425                 430
Ser Ser Leu Gln Ser Gly Val Pro Ser Arg Phe Ser Gly Ser Gly Ser
        435                 440                 445
Gly Thr Glu Phe Thr Leu Thr Val Ser Ser Leu Gln Pro Glu Asp Phe
    450                 455                 460
Ala Thr Tyr Tyr Cys Leu Gln Val Tyr Ser Thr Pro Arg Thr Phe Gly
465                 470                 475                 480
Gln Gly Thr Lys Val Glu Ile Lys Gly Gly Gly Gly Ser Gly Gly Gly
                485                 490                 495
Gly Ser Gly Gly Gly Ser Glu Val Gln Leu Val Glu Ser Gly Gly
            500                 505                 510
Gly Leu Ala Lys Pro Gly Gly Ser Leu Arg Leu Ser Cys Ala Ala Ser
        515                 520                 525
Gly Phe Arg Phe Thr Phe Asn Asn Tyr Tyr Met Asp Trp Val Arg Gln
    530                 535                 540
Ala Pro Gly Gln Gly Leu Glu Trp Val Ser Arg Ile Ser Ser Ser Gly
545                 550                 555                 560
Asp Pro Thr Trp Tyr Ala Asp Ser Val Lys Gly Arg Phe Thr Ile Ser
                565                 570                 575
Arg Glu Asn Ala Lys Asn Thr Leu Phe Leu Gln Met Asn Ser Leu Arg
            580                 585                 590
Ala Glu Asp Thr Ala Val Tyr Tyr Cys Ala Ser Leu Thr Thr Gly Ser
        595                 600                 605
Asp Ser Trp Gly Gln Gly Val Leu Val Thr Val Ser Ser
    610                 615                 620

<210> SEQ ID NO 29
<211> LENGTH: 214
<212> TYPE: PRT
<213> ORGANISM: Artificial Sequence
<220> FEATURE:
<223> OTHER INFORMATION: synthetic construct

<400> SEQUENCE: 29

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Ile Arg Tyr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Val Ser Ser Leu Gln Pro
65                  70                  75                  80

Glu Asp Phe Ala Thr Tyr Tyr Cys Leu Gln Val Tyr Ser Thr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 1173
<212> TYPE: DNA
<213> ORGANISM: Artificial Sequence
<220> FEATURE:
<223> OTHER INFORMATION: synthetic construct

<400> SEQUENCE: 30
gacatccaga tgacccagtc tccatcttcc ctgtctgcat ctgtagggga cagagtcacc      60
atcacttgca gggcaagtca ggacattagg tattatttaa attggtatca gcagaaacca     120
ggaaaagctc ctaagctcct gatctatgtt gcatccagtt tgcaaagtgg ggtcccatca     180
aggttcagcg gcagtggatc tgggacagag ttcactctca ccgtcagcag cctgcagcct     240
gaagattttg cgacttatta ctgtctacag gtttatagta cccctcggac gttcggccaa     300
gggaccaagg tggaaatcaa aggcggtggc ggtccggtg ggtggctc cggggcggt     360
ggctccgagg tgcagctggt ggagtctggg gcggcttgg caaagcctgg gggtccctg     420
agactctcct gcgcagcctc cgggttcagg ttcaccttca ataactacta catggactgg     480
gtccgccagg ctccagggca ggggctggag tgggtctcac gtattagtag tagtggtgat     540
cccacatggt acgcagactc cgtgaagggc agattcacca tctccagaga gaacgccaag     600
aacacactgt ttcttcaaat gaacagcctg agagctgagg acacggctgt ctattactgt     660
gcgagcttga ctacgggtc tgactcctgg gccagggag tcctggtcac cgtctcctca     720
gtcgacccca atcttgtga caaaactcac acatgcccac cgtgcccaga gcccaaatct     780
tgtgacacac ctcccccatg cccacggtgc ccagcacctg aggtggctc gagtggaggc     840
ggatccggag ggcagcccg agaaccacag gtgtacaccc tgcccccatc ccgggatgag     900

```
ctgaccaaga accaggtcag cctgacctgc ctggtcaaag gcttctatcc cagcgacatc    960
gccgtggagt gggagagcaa tgggcagccg gagaacaact acaagaccac gcctcccgtg   1020
ctggactccg acggctcctt cttcctctac agcaagctca ccgtggacaa gagcaggtgg   1080
cagcagggga acgtcttctc atgctccgtg atgcatgagg ctctgcacaa ccactacacg   1140
cagaagagcc tctccctgtc tccgggtaaa tga                                1173
```

<210> SEQ ID NO 31
<211> LENGTH: 1173
<212> TYPE: DNA
<213> ORGANISM: Artificial Sequence
<220> FEATURE:
<223> OTHER INFORMATION: synthetic construct

<400> SEQUENCE: 31

```
gaggtgcagc tggtggagtc tgggggcggc ttggcaaagc ctggggggtc cctgagactc     60
tcctgcgcag cctccgggtt caggttcacc ttcaataact actacatgga ctgggtccgc    120
caggctccag ggcaggggct ggagtgggtc tcacgtatta gtagtagtgg tgatcccaca    180
tggtacgcag actccgtgaa gggcagattc accatctcca gagagaacgc caagaacaca    240
ctgtttcttc aaatgaacag cctgagagct gaggacacgg ctgtctatta ctgtgcgagc    300
ttgactacag ggtctgactc ctggggccag gagtcctgg tcaccgtctc ctcaggcggt    360
ggcgggtccg gtgggggtgg ctccggggc ggtggctccg acatccagat gacccagtct    420
ccatcttccc tgtctgcatc tgtagggggac agagtcacca tcacttgcag ggcaagtcag    480
gacattaggt attatttaaa ttggtatcag cagaaaccag gaaaagctcc taagctcctg    540
atctatgttg catccagttt gcaaagtggg gtcccatcaa ggttcagcgg cagtggatct    600
gggacagagt tcactctcac cgtcagcagc ctgcagcctg aagattttgc gacttattac    660
tgtctacagg tttatagtac ccctcggacg ttcggccaag ggaccaaggt ggaaatcaaa    720
gtcgacccca atcttgtga caaaactcac acatgcccac cgtgcccaga gcccaaatct    780
tgtgacacac ctcccccatg cccacggtgc ccagcacctg aggtggctc gagtggaggc    840 ggatccggag ggcagcccg agaaccacag gtgtacaccc tgcccccatc ccgggatgag    900
ctgaccaaga accaggtcag cctgacctgc ctggtcaaag gcttctatcc cagcgacatc    960
gccgtggagt gggagagcaa tgggcagccg gagaacaact acaagaccac gcctcccgtg   1020
ctggactccg acggctcctt cttcctctac agcaagctca ccgtggacaa gagcaggtgg   1080
cagcagggga acgtcttctc atgctccgtg atgcatgagg ctctgcacaa ccactacacg   1140
cagaagagcc tctccctgtc tccgggtaaa tga                                1173
```

<210> SEQ ID NO 32
<211> LENGTH: 390
<212> TYPE: PRT
<213> ORGANISM: Artificial Sequence
<220> FEATURE:
<223> OTHER INFORMATION: synthetic construct

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Tyr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
```

```
                50                  55                  60
Ser Gly Ser Gly Thr Glu Phe Thr Leu Thr Val Ser Ser Leu Gln Pro
 65                  70                  75                  80

Glu Asp Phe Ala Thr Tyr Tyr Cys Leu Gln Val Tyr Ser Thr Pro Arg
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Ala Lys Pro Gly Gly Ser Leu Arg Leu Ser Cys
130                 135                 140

Ala Ala Ser Gly Phe Arg Phe Thr Phe Asn Asn Tyr Tyr Met Asp Trp
145                 150                 155                 160

Val Arg Gln Ala Pro Gly Gln Gly Leu Glu Trp Val Ser Arg Ile Ser
                165                 170                 175

Ser Ser Gly Asp Pro Thr Trp Tyr Ala Asp Ser Val Lys Gly Arg Phe
                180                 185                 190

Thr Ile Ser Arg Glu Asn Ala Lys Asn Thr Leu Phe Leu Gln Met Asn
                195                 200                 205

Ser Leu Arg Ala Glu Asp Thr Ala Val Tyr Tyr Cys Ala Ser Leu Thr
210                 215                 220

Thr Gly Ser Asp Ser Trp Gly Gln Gly Val Leu Val Thr Val Ser Ser
225                 230                 235                 240

Val Asp Pro Lys Ser Cys Asp Lys Thr His Thr Cys Pro Pro Cys Pro
                245                 250                 255

Glu Pro Lys Ser Cys Asp Thr Pro Pro Cys Pro Arg Cys Pro Ala
                260                 265                 270

Pro Gly Gly Gly Ser Ser Gly Gly Gly Ser Gly Gly Gln Pro Arg Glu
                275                 280                 285

Pro Gln Val Tyr Thr Leu Pro Pro Ser Arg Asp Glu Leu Thr Lys Asn
                290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
                340                 345                 350

Leu Thr Val Asp Lys Ser Arg Trp Gln Gln Gly Asn Val Phe Ser Cys
                355                 360                 365

Ser Val Met His Glu Ala Leu His Asn His Tyr Thr Gln Lys Ser Leu
370                 375                 380

Ser Leu Ser Pro Gly Lys
385                 390

<210> SEQ ID NO 33
<211> LENGTH: 390
<212> TYPE: PRT
<213> ORGANISM: Artificial Sequence
<220> FEATURE:
<223> OTHER INFORMATION: synthetic construct

<400> SEQUENCE: 33

Glu Val Gln Leu Val Glu Ser Gly Gly Gly Leu Ala Lys Pro Gly Gly
 1               5                  10                  15

Ser Leu Arg Leu Ser Cys Ala Ala Ser Gly Phe Arg Phe Thr Phe Asn
                20                  25                  30
```

Asn Tyr Tyr Met Asp Trp Val Arg Gln Ala Pro Gly Gln Gly Leu Glu
                35                  40                  45

Trp Val Ser Arg Ile Ser Ser Gly Asp Pro Thr Trp Tyr Ala Asp
 50                  55                  60

Ser Val Lys Gly Arg Phe Thr Ile Ser Arg Glu Asn Ala Lys Asn Thr
 65                  70                  75                  80

Leu Phe Leu Gln Met Asn Ser Leu Arg Ala Glu Asp Thr Ala Val Tyr
                85                  90                  95

Tyr Cys Ala Ser Leu Thr Thr Gly Ser Asp Ser Trp Gly Gln Gly Val
                100                 105                 110

Leu Val Thr Val Ser Gly Gly Gly Ser Gly Gly Gly Ser
                115                 120                 125

Gly Gly Gly Gly Ser Asp Ile Gln Met Thr Gln Ser Pro Ser Ser Leu
            130                 135                 140

Ser Ala Ser Val Gly Asp Arg Val Thr Ile Thr Cys Arg Ala Ser Gln
145                 150                 155                 160

Asp Ile Arg Tyr Tyr Leu Asn Trp Tyr Gln Gln Lys Pro Gly Lys Ala
                165                 170                 175

Pro Lys Leu Leu Ile Tyr Val Ala Ser Ser Leu Gln Ser Gly Val Pro
                180                 185                 190

Ser Arg Phe Ser Gly Ser Gly Ser Gly Thr Glu Phe Thr Leu Thr Val
                195                 200                 205

Ser Ser Leu Gln Pro Glu Asp Phe Ala Thr Tyr Tyr Cys Leu Gln Val
            210                 215                 220

Tyr Ser Thr Pro Arg Thr Phe Gly Gln Gly Thr Lys Val Glu Ile Lys
225                 230                 235                 240

Val Asp Pro Lys Ser Cys Asp Lys Thr His Thr Cys Pro Pro Cys Pro
                245                 250                 255

Glu Pro Lys Ser Cys Asp Thr Pro Pro Cys Pro Arg Cys Pro Ala
                260                 265                 270

Pro Gly Gly Gly Ser Ser Gly Gly Gly Ser Gly Gln Pro Arg Glu
            275                 280                 285

Pro Gln Val Tyr Thr Leu Pro Pro Ser Arg Asp Glu Leu Thr Lys Asn
290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
                340                 345                 350

Leu Thr Val Asp Lys Ser Arg Trp Gln Gln Gly Asn Val Phe Ser Cys
                355                 360                 365

Ser Val Met His Glu Ala Leu His Asn His Tyr Thr Gln Lys Ser Leu
370                 375                 380

Ser Leu Ser Pro Gly Lys
385                 390

<210> SEQ ID NO 34
<211> LENGTH: 10
<212> TYPE: PRT
<213> ORGANISM: Artificial Sequence
<220> FEATURE:
<223> OTHER INFORMATION: synthetic construct

<400> SEQUENCE: 34

```
<210> SEQ ID NO 35
<211> LENGTH: 15
<212> TYPE: DNA
<213> ORGANISM: Artificial Sequence
<220> FEATURE:
<223> OTHER INFORMATION: synthetic construct

<400> SEQUENCE: 35
ggggsggggs ggggs                                                     15

<210> SEQ ID NO 36
<211> LENGTH: 25
<212> TYPE: PRT
<213> ORGANISM: Artificial Sequence
<220> FEATURE:
<223> OTHER INFORMATION: synthetic construct

<400> SEQUENCE: 36
```

Gly Gly Gly Gly Ser Gly Gly Gly Ser Gly Gly Gly Ser Gly
1               5                   10                  15

Gly Gly Gly Ser Gly Gly Gly Ala Ser
            20                  25

```
<210> SEQ ID NO 37
<211> LENGTH: 35
<212> TYPE: DNA
<213> ORGANISM: Artificial Sequence
<220> FEATURE:
<223> OTHER INFORMATION: synthetic construct

<400> SEQUENCE: 37
agagagacat gtggcgacat ccagatgacc cagtc                              35

<210> SEQ ID NO 38
<211> LENGTH: 50
<212> TYPE: DNA
<213> ORGANISM: Artificial Sequence
<220> FEATURE:
<223> OTHER INFORMATION: synthetic construct

<400> SEQUENCE: 38
ggagccaccc ccaccggacc cgccaccgcc tttgatttcc accttggtcc              50

<210> SEQ ID NO 39
<211> LENGTH: 56
<212> TYPE: DNA
<213> ORGANISM: Artificial Sequence
<220> FEATURE:
<223> OTHER INFORMATION: synthetic construct

<400> SEQUENCE: 39
gggtccggtg ggggtggctc cggggggcggt ggctccgagg tgcagctggt ggagtc      56

<210> SEQ ID NO 40
<211> LENGTH: 33
<212> TYPE: DNA
<213> ORGANISM: Artificial Sequence
<220> FEATURE:
<223> OTHER INFORMATION: synthetic construct

<400> SEQUENCE: 40
agagaggtcg actgaggaga cggtgaccag gac                                33
```

Ile Gly Lys Thr Ile Ser Lys Lys Ala Lys
1               5                   10

```
<210> SEQ ID NO 41
<211> LENGTH: 86
<212> TYPE: DNA
<213> ORGANISM: Artificial Sequence
<220> FEATURE:
<223> OTHER INFORMATION: synthetic construct

<400> SEQUENCE: 41
agagagacat gtggcgaggt gcagctggtg gagtcggagc caccccacc ggacccgcca      60 ccgcctgagg agacggtgac caggac                                         86

<210> SEQ ID NO 42
<211> LENGTH: 51
<212> TYPE: DNA
<213> ORGANISM: Artificial Sequence
<220> FEATURE:
<223> OTHER INFORMATION: synthetic construct

<400> SEQUENCE: 42
ggagccaccc ccaccggacc cgccaccgcc tgaggagacg gtgaccagga c              51

<210> SEQ ID NO 43
<211> LENGTH: 56
<212> TYPE: DNA
<213> ORGANISM: Artificial Sequence
<220> FEATURE:
<223> OTHER INFORMATION: synthetic construct

<400> SEQUENCE: 43
gggtccggtg ggggtggctc cggggcggt ggctccgaca tccagatgac ccagtc         56

<210> SEQ ID NO 44
<211> LENGTH: 32
<212> TYPE: DNA
<213> ORGANISM: Artificial Sequence
<220> FEATURE:
<223> OTHER INFORMATION: synthetic construct

<400> SEQUENCE: 44
agagaggtcg actttgattt ccaccttggt cc                                  32

<210> SEQ ID NO 45
<211> LENGTH: 7
<212> TYPE: PRT
<213> ORGANISM: Artificial Sequence
<220> FEATURE:
<223> OTHER INFORMATION: synthetic construct

<400> SEQUENCE: 45

Glu Ser Lys Tyr Gly Pro Pro
 1               5

<210> SEQ ID NO 46
<211> LENGTH: 5
<212> TYPE: PRT
<213> ORGANISM: Artificial Sequence
<220> FEATURE:
<223> OTHER INFORMATION: synthetic construct

<400> SEQUENCE: 46

Cys Pro Ser Cys Pro
 1               5

<210> SEQ ID NO 47
<211> LENGTH: 8
<212> TYPE: PRT
<213> ORGANISM: Artificial Sequence
```

```
<220> FEATURE:
<223> OTHER INFORMATION: synthetic construct

<400> SEQUENCE: 47

Ala Pro Glu Phe Leu Gly Gly Pro
 1               5

<210> SEQ ID NO 48
<211> LENGTH: 29
<212> TYPE: PRT
<213> ORGANISM: Artificial Sequence
<220> FEATURE:
<223> OTHER INFORMATION: synthetic construct

<400> SEQUENCE: 48

Glu Ser Lys Tyr Gly Pro Pro Cys Pro Ser Cys Pro Glu Pro Lys Ser
 1               5                  10                  15

Cys Asp Thr Pro Pro Pro Cys Pro Arg Cys Pro Ala Pro
                20                  25

<210> SEQ ID NO 49
<211> LENGTH: 15
<212> TYPE: PRT
<213> ORGANISM: Artificial Sequence
<220> FEATURE:
<223> OTHER INFORMATION: synthetic construct

<400> SEQUENCE: 49

Cys Pro Glu Pro Lys Ser Cys Asp Thr Pro Pro Pro Cys Pro Arg
 1               5                  10                  15
```

MODIFIED BINDING MOLECULES COMPRISING CONNECTING PEPTIDES

RELATED APPLICATIONS

This application is a continuation of U.S. Ser. No. 10/880,028, filed on Jun. 8, 2004 (now abandoned), titled "Modified Binding Molecules Comprising Connecting Peptides" which claims priority to U.S. Ser. No. 60/483,877, titled "Purification and Preferential Synthesis of Polypeptides," filed on Jun. 27, 2003 and to U.S. Ser. No. 60/508,810, titled "Purification and Preferential Synthesis of Antigen Binding Polypeptides," filed Oct. 3, 2003. This application also claims priority to U.S. Ser. No. 60/515,351, titled "Modified Antibody Molecules Comprising Connecting Peptides," filed Oct. 28, 2003 and to U.S. Ser. No. 60/516,030, titled "Modified Antibody Molecules Comprising Connecting Peptides," filed Oct. 30, 2003. This application is also related to U.S. Ser. No. 10/880,320, titled "Purification and Preferential Synthesis of Binding Molecules," filed on Jun. 28, 2004. The contents of these applications are incorporated in their entirety by this reference.

BACKGROUND OF THE INVENTION

Antibodies are dimeric molecules; each monomer making up the dimer comprises one light and one heavy chain. Solutions of antibody molecules exist in two forms associated with hinge heterogeneity. Using SDS-PAGE analysis of purified Mab MAb, typically the two forms are observed as two protein bands, a major band (MW approximately 150-160 kDa) and a minor band (MW approximately 75-80 kDa). This latter form is typically observed after SDS-PAGE analysis of purified IgG4 preparations, but can be identified at much lower frequencies in all IgG isotypes, including purified, recombinant MAbs (Angal et al. 1993. *Mol. Immunol.* 30:105; Norderhaug et al. 1990. *Eur. J. Immunol.* 21:2370). The larger molecular weight isoform, referred to as Form A, contains covalent interchain disulfide bonds at positions corresponding to 239 and 242, Kabat numbering system (positions 226 and 229, EU numbering system) (Kabat, E, Wu, T T, Perry, H M, Gottesman, K S, Foeller, C: Sequences of Proteins of Immunological Interest. Bethesda, US Department of Health and Human Services, NIH, 1991). The second isoform, Form B, is thought to contain no covalent linkages between the two heavy chains and an intrachain disulfide bond between the two neighboring cysteine residues as evidenced by the 75-80 kDa seen in non-reducing SDS-PAGE electrophoresis. The two heavy chains of Form B are presumably held together by strong non-covalent (e.g., ionic) interactions associated with the CH3 domain region of the molecule. These mixtures of A and B forms are not present in solutions of MAb fragments that contain an intact hinge, but lack a CH3 domain, such as, for example, F(ab)$_2$ fragments. Typically, genetically engineered or enzymatically digested F(ab)$_2$ MAb preparations lack the B-form, since the molecule lacks the necessary domains for maintaining non-covalent interactions (e.g., hydrogen bonding). However, they are present in MAb preparations that do contain a CH3 domain, such as IgG4, CH2 domain deleted MAb fragments (e.g., as described in 02/060955 A2) and minibodies (see, e.g., Flu et al. 1996. Cancer Research 56:3055).

The application of protein engineering techniques to therapeutic antibody design has also produced a number of antibody formats that have been shown to have altered, and in some cases, improved pharmacodynamic, biodistribution, and activity profiles. Some altered antibody molecules have been made in which the number of cysteine residues in the hinge region is reduced to one to facilitate assembly of antibody molecules as it is only necessary to form a single disulfide bond. This also provides a specific target for attaching the hinge region either to another hinge region or to an effector or reporter molecule (U.S. Pat. No. 5,677,425). The number of cysteine residues in the antibody hinge has also been increased (U.S. Pat. No. 5,677,425). Other mutated antibodies have been constructed in which the IgG1 hinge region and the CH2 domain have been replaced with the human IgG3 hinge region. (WO 97/11370). These molecules contain 11 sulfhydryl groups for substitution of multiple haptens via thiol groups.

CH2 domain deleted antibodies have a molecular mass of approximately 120 kDa and have been shown to penetrate tumors significantly better than full length IgG. Minibodies, which also have deletion of the CH2 domain, have similar characteristics. These domain deleted molecules accumulate at tumor sites more efficiently than other MAb fragments, such as F(ab)'$_2$s, but without the unfavorable pharmacodynamic profiles seen with intact IgG antibody. CH2 domain deleted antibodies consist of a VLCL light chain and a VH1 heavy chain domain and a portion of the hinge region (e.g., the upper and middle hinge) genetically fused (either directly or through a modified peptide spacer) to a CH3 domain. As an example, the biosynthesis of recombinant CH2 domain deleted ddCC49, a domain deleted antibody that recognizes the tumor associated TAG72 antigen expressed on a variety of human carcinomas, produces the A and B isoforms in approximately 50:50 distribution in cell cultures. Cells engineered to express alternative forms of CH2 domain deleted antibodies, for example, tetravalent CH2 domain deleted antibodies, minibodies, or tetravalent minibodies also express a mixture consisting of A and B isoforms and/or monomeric half-mer molecules.

Form A and Form B are extremely difficult to separate even after MAb purification, since they are composed of identical amino acids and, therefore, have identical molecular weight and similar physical and chemical properties. They cannot be separated by standard gel filtration, affinity chromatography, or ion exchange chromatography typically used to purify antibody molecules, including recombinant MAb proteins. Current manufacturing processes discard at least 50% of the total antibody produced, having a negative impact on overall yield. Moreover, the presence of the two isoforms increases efforts required for downstream processing. Thus, a method of separating forms A and B or of increasing biosynthesis of one or the other form of antibody would be of great benefit.

SUMMARY OF THE INVENTION

The invention is based, at least in part, on the finding that in a composition comprising a mixture of dimeric polypeptide molecules comprising different isoforms (molecules comprising two heavy chain portions in which a fraction of the molecules comprise two heavy chain portions that are linked via at least one interchain disulfide linkage (Form A) and a portion of the molecules comprise two heavy chain portions that are not linked via at least one interchain disulfide linkage (Form B)) one form or the other can be preferentially obtained, e.g., by separation using hydrophobic interaction chromatography or by inclusion of synthetic connecting peptides which result in the preferential biosynthesis of either Form A or Form B.

In one embodiment, the binding molecules of the invention are tetravalent. The connecting peptides of the invention can be included in any dimeric molecule that tends to form both Form A and Form B, e.g., antibody molecules, domain deleted antibody molecules (e.g., lacking all or part of a CH2 domain), minibodies, diabodies, fusion proteins, etc. In a preferred embodiment, the formation of Form A is enhanced.

In another embodiment, the invention pertains to a composition comprising polypeptide dimers comprising at least four binding sites and at least two polypeptide chains, wherein said at least two polypeptide chains comprise at least one heavy chain portion and a synthetic connecting peptide, and wherein greater than about 50% of the dimers are linked via at least one interchain disulfide linkage.

In another embodiment, greater than about 90% of the dimers are linked via at least one interchain disulfide linkage.

In another embodiment, at least one of the polypeptide chains comprises a CH3 domain linked to a VL, VH or CH1 domain via the connecting peptide.

In another embodiment, the polypeptide chains lack all or part of a CH2 domain.

In another embodiment, the dimers are linked via two or more interchain disulfide linkages.

In another embodiment, the heavy chain portion is derived from an antibody of an isotype selected from the group consisting of: IgG1, IgG2, IgG3, and IgG4.

In another embodiment, the heavy chain portion comprises an amino acid sequence derived from a hinge region selected from the group consisting of: a γ1 hinge, a γ 2 hinge, a γ 3 hinge, and a γ 4 hinge.

In another embodiment, the molecules are bispecific.

In another embodiment, the molecules comprise at least one binding site specific for a soluble ligand.

In another embodiment, the molecules comprise at least one binding site specific for a cell surface molecule.

In another embodiment, the molecules comprise two binding sites specific for a tumor cell antigen and two binding sites specific for a prodrug.

In another embodiment, the binding sites specific for the prodrug are catalytic.

In another embodiment, the synthetic connecting peptide comprises a proline residue at position 243, Kabat numbering system.

In another embodiment, the synthetic connecting peptide further comprises an alanine residue at position 244 and a proline residue at position 245, Kabat numbering system.

In another embodiment, the heavy chain portion comprises a chimeric hinge.

In another embodiment, the synthetic connecting peptide comprises at least a portion of an IgG1 hinge domain, at least a portion of an IgG3 hinge domain.

In another embodiment, the connecting peptide comprises an amino acid sequence selected from the group consisting of: SEQ ID NOs: 8-15 and 48.

In a second aspect, the invention provides a method of treating a subject that would benefit from treatment with an antigen binding molecule comprising administering to the subject a composition comprising a mixture of dimeric polypeptide molecules comprising different isoforms, wherein one isoform or the other is preferentially obtained, such that treatment occurs.

In one embodiment, the subject is suffering from cancer.

In another embodiment, the subject is suffering from lymphoma.

In another embodiment, the subject is suffering from an autoimmune disease or disorder.

In another embodiment, the subject is suffering from an inflammatory disease or disorder.

In a third aspect, the invention provides a nucleic acid molecule comprising a nucleotide sequence encoding a polypeptide molecule comprising different isoforms (molecules comprising two heavy chain portions in which a fraction of the molecules comprise two heavy chain portions that are linked via at least one interchain disulfide linkage (Form A) and a portion of the molecules comprise two heavy chain portions that are not linked via at least one interchain disulfide linkage (Form B)) such that one form or the other can be preferentially obtained.

In one embodiment, the polypeptide dimers comprise four polypeptide chains and wherein two of the polypeptide chains comprise at least one heavy chain portion and a synthetic connecting peptide.

In another embodiment, the nucleic acid molecule comprises a nucleotide sequence shown in FIG. 8B (SEQ ID NO: 17).

In another embodiment, the nucleic acid molecule comprises a nucleotide sequence shown in FIG. 8C (SEQ ID NO: 18).

In another embodiment, the nucleic acid molecule comprises a nucleotide sequence shown in FIG. 10B (SEQ ID NO: 23).

In another embodiment, the nucleic acid molecule comprises a nucleotide sequence shown in FIG. 12A (SEQ ID NO:26).

In another embodiment, the nucleic acid molecule comprises a nucleotide sequence shown in FIG. 12B (SEQ ID NO:27).

In another embodiment, the nucleic acid molecule comprises a nucleotide sequence shown in FIG. 14 (SEQ ID NO:30).

In another embodiment, the nucleic acid molecule comprises a nucleotide sequence shown in FIG. 15 (SEQ ID NO:31).

In another embodiment, the nucleic acid molecule is in a vector. In still another embodiment, the vector is in a host cell.

In a fourth aspect, the invention provides binding molecules comprising an amino acid sequence encoding a polypeptide molecule comprising different isoforms (molecules comprising two heavy chain portions in which a fraction of the molecules comprise two heavy chain portions that are linked via at least one interchain disulfide linkage (Form A) and a portion of the molecules comprise two heavy chain portions that are not linked via at least one interchain disulfide linkage (Form B)) such that one form or the other can be preferentially obtained.

In one embodiment, the binding molecule comprises the amino acid sequence of FIG. 9B (SEQ ID NO: 20).

In another embodiment, the binding molecule comprises the amino acid sequence of FIG. 9C (SEQ ID NO: 21).

In another embodiment, the binding molecule comprises the amino acid sequence of FIG. 11B (SEQ ID NO: 25).

In another embodiment, the binding molecule comprises the amino acid sequence of FIG. 13A (SEQ ID NO: 28).

In another embodiment, the binding molecule comprises the amino acid sequence of FIG. 13B (SEQ ID NO: 29).

In another embodiment, the binding molecule comprises the amino acid sequence of FIG. 16 (SEQ ID NO: 32).

In another embodiment, the binding molecule comprises the amino acid sequence of FIG. 17 (SEQ ID NO: 33).

In a fifth aspect, the invention provides a composition comprising a mixture of dimeric polypeptide molecules comprising different isoforms (molecules comprising two heavy chain portions in which a fraction of the molecules comprise two heavy chain portions that are linked via at least one interchain disulfide linkage (Form A) and a portion of the molecules comprise two heavy chain portions that are not linked via at least one interchain disulfide linkage (Form B))

one form or the other can be preferentially obtained, and wherein said binding sites are individually selected from the group consisting of: an antigen binding site, a ligand binding portion of a receptor, and a receptor binding portion of a ligand.

In one embodiment, the polypeptide chains have at least one binding site derived from an antibody selected from the group consisting of: 2B8, Lym 1, Lym 2, LL2, Her2, B1, MB1, BH3, B4, B72.3, CC49, 5E8, B3F6, and 5E10.

In another embodiment, the polypeptide dimers are tetravalent minibody molecules.

In another embodiment, the polypeptide dimers are tetravalent domain deleted antibody molecules.

In another embodiment, the polypeptide dimers are diabodies.

In a sixth aspect, the invention provides a composition comprising minibody molecules comprising two polypeptide chains, wherein the polypeptide chains comprise a heavy chain portion and a synthetic connecting peptide, wherein the polypeptide chains lack all or part of a CH2 domain, and wherein greater than about 50% of the molecules are present in a form in which one of the polypeptide chains are linked via at least one interchain disulfide linkage.

In one embodiment, greater than about 90% of the dimers are linked via at least one interchain disulfide linkage.

In another embodiment, at least one of the polypeptide chains comprises a CH3 domain genetically fused to a VL, VH or CH1 domain via the connecting peptide.

In another embodiment, the polypeptide chains lack the entire CH2 domain.

In another embodiment, the dimers are linked via two or more interchain disulfide linkages.

In another embodiment, the heavy chain portion is derived from an antibody of an isotype selected from the group consisting of: IgG1, IgG2, IgG3, and IgG4.

In another embodiment, the heavy chain portion comprises an amino acid sequence is derived from a hinge region selected from the group consisting of: a γ1 hinge, a γ 2 hinge a γ 3 hinge, and a γ 4 hinge.

In another embodiment, the binding sites are individually selected from the group consisting of: an antigen binding site, a ligand binding portion of a receptor, and a receptor binding portion of a ligand.

In another embodiment, the molecules are bispecific.

In another embodiment, the connecting peptide comprises a proline residue at position 243, Kabat numbering system.

In another embodiment, the synthetic connecting peptide comprises a chimeric hinge.

In another embodiment, the synthetic connecting peptide comprises at least a portion of an IgG1 hinge domain, at least a portion of an IgG3 hinge domain. In a seventh aspect, the invention provides a method of treating a subject that would benefit from treatment with an antigen binding molecule comprising administering to the subject a composition comprising minibody molecules comprising two polypeptide chains, wherein the polypeptide chains comprise a heavy chain portion and a synthetic connecting peptide, wherein the polypeptide chains lack all or part of a CH2 domain, and wherein greater than about 50% of the molecules are present in a form in which one of the polypeptide chains are linked via at least one interchain disulfide linkage, such that treatment occurs.

In another aspect, the invention provides a nucleic acid molecule comprising a nucleotide sequence encoding a polypeptide chain comprising a heavy chain portion and a synthetic connecting peptide, wherein the polypeptide chains lack all or part of a CH2 domain, and wherein greater than about 50% of the molecules are present in a form in which one of the polypeptide chains are linked via at least one interchain disulfide linkage.

In still another aspect, the invention provides a composition comprising polypeptide dimers having at least four binding sites and at least two polypeptide chains, wherein said at least two polypeptide chains comprise at least one heavy chain portion and lacks all or part of a CH2 domain, wherein greater than 50% of the polypeptide dimers are linked via at least one interchain disulfide linkage.

BRIEF DESCRIPTION OF THE DRAWINGS

FIG. 4 shows a schematic diagram of a four chain dimeric tetravalent scFv antibody (C-scFv tetravalent antibody) and a four chain tetravalent scFv CH2 domain deleted antibody (C-scFv tetravalent CH2 domain deleted antibody) each comprising a scFv appended to the carboxyl terminus of $CH_3$ and a hinge connecting peptide. The orientation of the VH and VL domains in the scFv may be changed.

FIG. 8A (SEQ ID NO:16) shows the single-stranded DNA sequence of heavy chain CH2 domain-deleted sc(Fv)2 tetravalent (C-scFv tetravalent CH2 domain deleted) huCC49 gene. FIG. 8B (SEQ ID NO:17) shows the single-stranded DNA sequence of heavy chain tetravalent CH2 domain-deleted sc(Fv)2 tetravalent (C-scFv tetravalent CH2 domain deleted) huCC49 gene containing the synthetic G1/G3:/Pro243Ala244Pro245+[Gly/Ser] hinge connecting peptide. FIG. 8C (SEQ ID NO:18) shows the single-stranded DNA sequence of light chain CH2 domain-deleted sc(Fv)2 tetravalent (C-scFv tetravalent CH2 domain deleted) huCC49.

FIG. 9A (SEQ ID NO:19) shows the amino acid sequence of heavy chainCH2 domain-deleted sc(Fv)2 tetravalent (C-scFv tetravalent CH2 domain deleted) huCC49. FIG. 9B (SEQ ID NO:20) shows the amino acid sequence of heavy chain CH2 domain-deleted sc(Fv)2 tetravalent (C-scFv tetravalent CH2 domain deleted) huCC49 containing the synthetic G1/G3/Pro243Ala244Pro245+[Gly/Ser] hinge connecting peptide. FIG. 9C (SEQ ID NO:21) shows the amino acid sequence of light chain CH2 domain-deleted sc(Fv)2 tetravalent (C-scFv tetravalent CH2 domain deleted) huCC49

FIG. 10A (SEQ ID NO:22) shows the single-stranded DNA sequence of CH2 domain-deleted huCC49 tetravalent (N-scFv tetravalent) minibody gene. FIG. 10B (SEQ ID NO:23) shows the single-stranded DNA sequence of tetravalent CH2 domain-deleted (N-scFv tetravalent) huCC49 tetravalent minibody gene containing the synthetic G1/G3/Pro243Ala244Pro245+[Gly/Ser] hinge connecting peptide.

FIG. 11A (SEQ ID NO:24) shows the amino acid sequence of tetravalent CH2 domain-deleted (N-scFv tetravalent) huCC49 minibody. FIG. 11B (SEQ ID NO:25) shows the amino acid sequence of tetravalent CH2 domain-deleted (N-scFv tetravalent) huCC49 minibody containing the synthetic G1/G3/Pro243Ala244Pro245+[Gly/Ser] hinge connecting peptide.

FIG. 12A (SEQ ID NO:26) shows the single-stranded DNA sequence of heavy chain tetravalent CH2 domain-deleted PRIMATIZED® p5E8 sc(Fv)2 (C-scFv tetravalent CH2 domain deleted) antibody gene containing the G1/G3/Pro243Ala244Pro245+[Gly/Ser] hinge connecting peptide.

FIG. 12B (SEQ ID NO:27) shows the single-stranded DNA sequence of light chain tetravalent CH2 domain-deleted (C-scFv tetravalent CH2 domain deleted) PRIMATIZED® p5E8 sc(Fv)2 gene.

FIG. 13A (SEQ ID NO:28) shows the amino acid sequence of heavy chain tetravalent CH2 domain-deleted (C-scFv tetravalent CH2 domain deleted) PRIMATIZED® p5E8 sc(Fv)2 antibody containing the G1/G3/Pro243Ala244Pro245+[Gly/Ser] hinge connecting peptide.

FIG. 13B (SEQ ID NO:29) shows the amino acid sequence of light chain tetravalent CH2 domain-deleted (C-scFv tetravalent CH2 domain deleted) PRIMATIZED® p5E8 sc(Fv)2 antibody.

FIG. 14 (SEQ ID NO:30) shows the single-stranded DNA sequence of CH2 domain-deleted PRIMATIZED® p5E8 VL/VH minibody gene containing the G1/G3/Pro243Ala244Pro245+[Gly/Ser] hinge connecting peptide.

FIG. 15 (SEQ ID NO:31) shows the single-stranded DNA sequence of CH2 domain-deleted PRIMATIZED® p5E8 VH/VL minibody gene containing the G1/G3/Pro243Ala244Pro245+[Gly/Ser] hinge connecting peptide.

FIG. 16 (SEQ ID NO:32) shows the amino acid sequence of CH2 domain-deleted PRIMATIZED® p5E8 VL/VH minibody containing the G1/G3/Pro243Ala244Pro245+[Gly/Ser] hinge connecting peptide.

FIG. 17 (SEQ ID NO:33) shows the amino acid sequence of CH2 domain-deleted PRIMATIZED® p5E8 VH/VL minibody containing the G1/G3/Pro243Ala244Pro245+[Gly/Ser] hinge connecting peptide.

FIG. 35 B shows the same tumor retention data normalized to peak antibody accumulation.

DETAILED DESCRIPTION OF THE INVENTION

Figure 1:
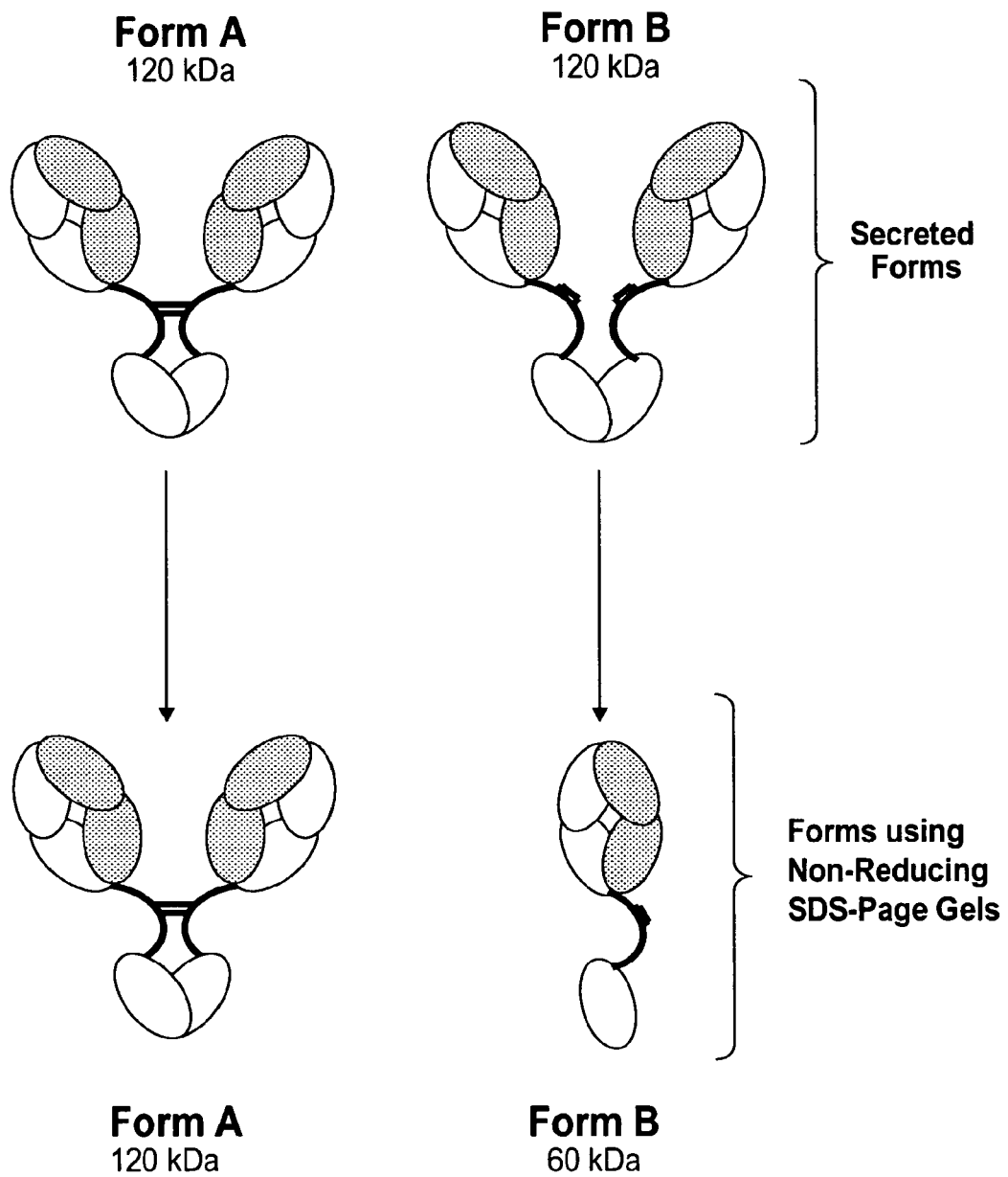
FIG. 1 shows Form A which appears as a 120 kDa dimer and Form B which appears as a 60 kDa monomer in domain deleted antibodies.

Human immunoglobulins (Igs), including monoclonal antibodies (MAbs), can exist in two forms that are associated with hinge heterogeneity. In native solutions, both of these forms are present as dimeric proteins (each monomer comprising one heavy chain and one light chain). One immunoglobulin molecule comprises a stable four chain construct of approximately 150-160 kDa in which the dimers are held together by an interchain heavy chain disulfide bond (Form A) and one comprises form in which the dimers are not linked via interchain disulfide bonds (Form B). Form B also forms a stable dimer under native conditions, but can be identified under denaturing, non-reducing conditions, in which the heavy chains dissociate yielding a 75-80 kDa molecule. These forms have been extremely difficult to separate, even after MAb affinity purification.

The frequency of appearance of the B form in various intact IgG isotypes is due to, but not limited to, structural differences associated with the hinge region isotype of the MAb molecule. In fact, a single amino acid substitution in the hinge region of the human IgG4 hinge can significantly reduce the appearance of the B form (Angal et al. 1993. Molecular Immunology 30:105) to levels typically observed using a human IgG1 hinge. However, applying this same amino acid substitution to MAb fragments in which the CH3 domain was retained did not eliminate Form B from preparations. Typically, all recombinant CH2 domain deleted antibodies produced in cell cultures often result in hinge heterogeneity which is not corrected via similar molecular mutations in the hinge.

The instant invention advances the state of the art by providing methods of, e.g., separating a first dimeric polypeptide from a second dimeric polypeptide wherein the first and second polypeptides comprise at least two polypeptide chains and at least two of the polypeptide chains comprise at least one heavy chain portion. In one embodiment, the polypeptides of the invention lack all or part of a CH2 domain. The monomers are linked via at least one interchain disulfide linkage (referred to herein as "Form A") and the monomers of the second polypeptide are not linked via at least one interchain disulfide linkage (referred to herein as "Form B"). These forms can be separated from each other using hydrophobic interaction chromatography. In addition, the invention pertains to polypeptides that comprise connecting peptides. The inclusion of certain connecting peptides results in the preferential biosynthesis of polypeptide dimers comprising polypeptide chains that are linked via at least one interchain disulfide linkage or that are not linked via at least one interchain disulfide linkage.

Before further description of the invention, for convenience, certain terms are described below:

I. DEFINITIONS

The polypeptides of the invention are binding molecules, i.e., polypeptide molecules or the nucleic acid molecules that encode them, that comprise at least one binding domain which comprises a binding site that specifically binds to a target molecule (such as an antigen or binding partner). For example, in one embodiment, a binding molecule of the invention comprises an immunoglobulin antigen binding site or the portion of a receptor molecule responsible for ligand binding or the portion of a ligand molecule that is responsible for receptor binding. The binding molecules of the invention are polypeptides or the nucleic acid molecules which encode them.

In one embodiment, the binding molecules comprise at least two binding sites. In one embodiment, the binding molecules comprise two binding sites. In one embodiment, the binding molecules comprise three binding sites. In another embodiment, the binding molecules comprise four binding sites.

The polypeptides of the invention are multimers. For example, in one embodiment, the polypeptides of the invention are dimers. In one embodiment, the dimers of the invention are homodimers, comprising two identical monomeric subunits. In another embodiment, the dimers of the invention are heterodimers, comprising two non-identical monomeric subunits. The subunits of the dimer may comprise one or more polypeptide chains. For example, in one embodiment, the dimers comprise at least two polypeptide chains. In one embodiment, the dimers comprise two polypeptide chains. In another embodiment, the dimers comprise four polypeptide chains (e.g., as in the case of antibody molecules).

The polypeptides of the invention comprise at least one amino acid sequence derived from an immunoglobulin domain. A polypeptide or amino acid sequence "derived from" a designated protein refers to the origin of the polypeptide. Preferably, the polypeptide or amino acid sequence which is derived from a particular starting polypeptide or amino acid sequence has an amino acid sequence that is essentially identical to that of the starting sequence, or a portion thereof wherein the portion consists of at least 10-20 amino acids, preferably at least 20-30 amino acids, more preferably at least 30-50 amino acids, or which is otherwise identifiable to one of ordinary skill in the art as having its origin in the starting sequence.

Preferred binding polypeptides comprise an amino acid sequence derived from a human amino acid sequence. However, binding polypeptides may comprise one or more amino acids from another mammalian species. For example, a primate heavy chain portion, hinge portion, or binding site may be included in the subject binding polypeptides and/or connecting polypeptides. Alternatively, one or more murine amino acids may be present in a binding polypeptide, e.g., in an antigen binding site of a binding molecule. Preferred binding molecules of the invention are not immunogenic.

It will also be understood by one of ordinary skill in the art that the binding molecules of the invention (e.g., the heavy chain or light chain portions or binding portions of the subject polypeptides) may be modified such that they vary in amino acid sequence from the naturally occurring immunoglobulin molecule from which they were derived. For example, nucleotide or amino acid substitutions leading to conservative substitutions or changes at "non-essential" amino acid residues may be made.

An isolated nucleic acid molecule encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Alternatively, in another embodiment, mutations may be introduced randomly along all or part of the immunoglobulin coding sequence, such as by saturation mutagenesis, and the resultant mutants can be incorporated into polypeptides of the invention and screened for their ability to bind to the desired antigen.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, a polypeptide of the invention comprises a polypeptide chain comprising a CH1 domain, at least a portion of a hinge domain, and a CH2 domain. In another embodiment, a polypeptide of the invention comprises a polypeptide chain comprising a CH1 domain and a CH3 domain. In another embodiment, a polypeptide of the invention comprises a polypeptide chain comprising a CH1 domain, at least a portion of a hinge domain, and a CH3 domain. In another embodiment, a polypeptide of the invention comprises a polypeptide chain comprising a CH3 domain. In one embodiment, a polypeptide of the invention lacks at least a portion of a CH2 domain (e.g., all or part of a CH2 domain). In another embodiment, a polypeptide of the invention comprises a complete Ig heavy chain. As set forth above, it will be understood by one of ordinary skill in the art that these domains (e.g., the heavy chain portions) may be modified such that they vary in amino acid sequence from the naturally occurring immunoglobulin molecule.

In one embodiment, at least two of the polypeptide chains of a binding molecule of the invention comprise at least one heavy chain portion derived from an antibody or immunoglobulin molecule. In one embodiment, at least two heavy chain portions of a polypeptide of the invention are present on different polypeptide chains and interact, e.g., via at least one disulfide linkage (Form A) or via non-covalent interactions (Form B) to form a dimeric polypeptide, each monomer of the dimer comprising at least one heavy chain portion.

In one embodiment, the heavy chain portions of one polypeptide chain of a dimer are identical to those on a second polypeptide chain of the dimer. In one embodiment, the monomers (or half-mers) of a dimer of the invention are identical to each other. In another embodiment, they are not identical. For example, each monomer may comprise a different target binding site.

In one embodiment, a dimer of the invention is held together by covalent interactions, e.g., disulfide bonds. In one embodiment, a dimer of the invention is held together by one or more disulfide bonds. In another embodiment, a dimer of the invention is held together by one or more, preferably two disulfide bonds. In another embodiment, a dimer of the invention is held together by one or more, preferably three disulfide bonds. In another embodiment, a dimer of the invention is held together by one or more, preferably four disulfide bonds. In another embodiment, a dimer of the invention is held together by one or more, preferably five disulfide bonds. In another embodiment a dimer of the invention is held together by one or more, preferably six disulfide bonds. In another embodiment, a dimer of the invention is held together by one or more, preferably seven disulfide bonds. In another embodiment, a dimer of the invention is held together by one or more, preferably eight disulfide bonds. In another embodiment, a dimer of the invention is held together by one or more, preferably nine disulfide bonds. In another embodiment, a dimer of the invention is held together by one or more, preferably ten disulfide bonds. In a further embodiment, a dimer of the invention is not held together by disulfide bonds, but is held together, e.g., by non-covalent interactions.

The heavy chain portions of a polypeptide may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule. As used herein, the term "light chain portion" includes amino acid sequences derived from an immunoglobulin light chain. Preferably, the light chain portion comprises at least one of a VL or CL domain.

In one embodiment a polypeptide of the invention comprises an amino acid sequence or one or more moieties not derived from an Ig molecule. Exemplary modifications are described in more detail below. For example, in one embodiment, a polypeptide of the invention may comprise a flexible linker sequence. In another embodiment, a polypeptide may be modified to add a functional moiety (e.g., PEG, a drug, or a label).

In one embodiment, a binding polypeptide of the invention is a fusion protein. Fusion proteins are chimeric molecules which comprise a binding domain comprising at least one target binding site and at least one heavy chain portion. In one embodiment, a fusion protein further comprises a synthetic connecting peptide.

A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric polypeptides include fusion proteins and the chimeric hinge connecting peptides of the invention.

The term "heterologous" as applied to a polynucleotide or a polypeptide, means that the polynucleotide or polypeptide is derived from a genotypically distinct entity from that of the rest of the entity to which it is being compared. For instance, a heterologous polynucleotide or antigen may be derived from a different species origin, different cell type, or the same type of cell of distinct individuals.

The term "ligand binding domain" or "ligand binding portion of a receptor" as used herein refers to any native receptor (e.g., cell surface receptor) or any region or derivative thereof retaining at least a qualitative ligand binding ability, and preferably the biological activity of a corresponding native receptor.

The term "receptor binding domain" or "receptor binding portion of a ligand" as used herein refers to any native ligand or any region or derivative thereof retaining at least a qualitative receptor binding ability, and preferably the biological activity of a corresponding native ligand.

In one embodiment, a binding molecule of the invention is a fusion protein. A fusion protein of the invention is a chimeric molecule that comprises a binding domain (which comprises at least one binding site) and a dimerization domain (which comprises at least one heavy chain portion). The heavy chain portion may be from any immunoglobulin, such as IgG1, IgG2, IgG3, or IgG4 subtypes, IgA, IgE, IgD or IgM.

In another embodiment of the invention, a binding molecule is an "antibody-fusion protein chimera." Such molecules comprise a molecule which combines at least one binding domain of an antibody with at least one fusion protein. Preferably, the interface between the two polypeptides is a CH3 domain of an immunoglobulin molecule.

In one embodiment, the binding molecules of the invention are "antibody" or "immunoglobulin" molecules, e.g., naturally occurring antibody or immunoglobulin molecules or genetically engineered antibody molecules that bind antigen in a manner similar to antibody molecules. As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. a tumor associated antigen). Antibodies and immunoglobulins comprise light and heavy chains, with or without an interchain covalent linkage between them. Basic immunoglobulin structures in vertebrate systems are relatively well understood.

As will be discussed in more detail below, the generic term "immunoglobulin" comprises five distinct classes of antibody that can be distinguished biochemically. All five classes of antibodies are clearly within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region allows the antibody to selectively recognize and specifically bind epitopes on antigens. That is, the $V_L$ domain and $V_H$ domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the $V_H$ and $V_L$ chains.

As used herein, the term "binding site" or "binding domain" comprises a region of a polypeptide which is responsible for selectively binding to a target molecule of interest (e.g. an antigen, ligand, receptor, substrate or inhibitor). Exemplary binding domains include an antibody variable domain, a receptor binding domain of a ligand, a ligand binding domain of a receptor or an enzymatic domain.

In one embodiment, the binding molecules have at least one binding site specific for a molecule targeted for reduction or elimination, e.g., a cell surface antigen or a soluble antigen.

In preferred embodiments, the binding domain is an antigen binding site. An antigen binding site is formed by variable regions that vary from one polypeptide to another. The polypeptides of the invention comprise at least two antigen binding sites. As used herein, the term "antigen binding site" includes a site that specifically binds (immunoreacts with) an antigen (e.g., a cell surface or soluble antigen). The antigen binding site includes an immunoglobulin heavy chain and light chain variable region and the binding site formed by these variable regions determines the specificity of the antibody. In one embodiment, an antigen binding molecule of the invention comprises at least one heavy or light chain CDR of an antibody molecule (e.g., the sequence of which is known in the art or described herein). In another embodiment, an antigen binding molecule of the invention comprises at least two CDRs from one or more antibody molecules. In another embodiment, an antigen binding molecule of the invention comprises at least three CDRs from one or more antibody molecules. In another embodiment, an antigen binding molecule of the invention comprises at least four CDRs from one or more antibody molecules. In another embodiment, an antigen binding molecule of the invention comprises at least five CDRs from one or more antibody molecules. In another embodiment, an antigen binding molecule of the invention comprises at least six CDRs from one or more antibody molecules. Exemplary antibody molecules comprising at least one CDR that can be included in the subject antigen binding molecules are known in the art and exemplary molecules are described herein.

The polypeptides comprising two heavy chain portions disclosed herein may be linked to form two associated Ys so there will be four binding sites forming a "tetravalent" molecule (see e.g., WO02/096948A2)). In another embodiment, tetravalent minibodies or domain deleted antibodies can be made.

The term "specificity" includes the number of potential binding sites which specifically bind (e.g., immunoreact with) a given target. A polypeptide may be monospecific and contain one or more binding sites which specifically bind a target or a polypeptide may be multispecific and contain two or more binding sites which specifically bind the same or different targets.

In one embodiment, a binding molecule of the invention is a bispecific molecule (e.g., antibody, minibody, domain deleted antibody, or fusion protein having binding specificity for more than one molecule, e.g., more than one antigen or more than one epitope on the same antigen. In one embodiment, the bispecific molecules have at least one target binding site specific for a molecule targeted for reduction or elimination and a targeting molecule on a cell. In another embodiment, the bispecific molecules have at least one target binding site specific for a molecule targeted for reduction or elimination and at least one target binding site specific for a drug. In yet another embodiment, the bispecific molecules have at least one target binding site specific for a molecule targeted for reduction or elimination and at least one target binding site specific for a prodrug. In a preferred embodiment, the bispecific molecules are tetravalent antibodies that have two target binding sites specific for one target and two target binding sites specific for the second target. A tetravalent bispecific molecule may be bivalent for each specificity. Further description of bispecific molecules is provided below.

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen).

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

As previously indicated, the subunit structures and three dimensional configuration of the constant regions of the various immunoglobulin classes are well known. As used herein, the term "VET domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; and Kabat E A et al. Sequences of Proteins of Immunological Interest. Bethesda, US Department of Health and Human Services, NIH. 1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083).

In one embodiment, a binding molecule of the invention comprises a connecting peptide. The connecting peptides of the invention are synthetic. As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

Connecting peptides of the invention connect two domains (e.g., a binding domain and a dimerization domain) of a binding molecule of the invention. For example, connecting peptides connect a heavy chain portion to a binding domain comprising a binding site. In one embodiment, a connecting peptide connects two heavy chain constant region domains, such as CH1 and CH2 domains; CH1 and CH3 domains; hinge and CH1 domains; hinge and CH3 domains; VH and hinge domains, or a CH3 domain and a non-immunoglobulin polypeptide) in a linear amino acid sequence of a polypeptide chain. Preferably, such connecting peptides provide flexibility to the polypeptide molecule and facilitate dimerization via disulfide bonding. In one embodiment, the connecting peptides of the invention are used to replace one or more heavy chain domains (e.g., at least a portion of a constant region domain (e.g., at least a portion of a CH2 domain) and/or at least a portion of the hinge region (e.g., at least a portion of the lower hinge region domain) in a domain deleted construct). For example, in one embodiment, a VH domain is fused to a CH3 domain via a connecting peptide (the C-terminus of the connecting peptide is attached to the N-terminus of the CH3 domain and the N-terminus of the connecting peptide is attached to the C-terminus of the VH domain). In another embodiment, a VL domain is fused to a CH3 domain via a connecting peptide (the C-terminus of the connecting peptide is attached to the N-terminus of the CH3 domain and the N-terminus of the connecting peptide is attached to the C-terminus of the VL domain. In another embodiment, a CH1 domain is fused to a CH3 domain via a connecting peptide (the C-terminus of the connecting peptide is attached to the N-terminus of the CH3 domain and the N-terminus of the connecting peptide is attached to the C-terminus of the CH1 domain).

In one embodiment, a synthetic connecting peptide comprises a portion of a constant region domain. For example, in one embodiment, a connecting peptide that replaces a CH2 domain can comprise a portion of the CH2 domain.

In one embodiment, a connecting peptide comprises or consists of a gly-ser linker. As used herein, the term "gly-ser linker" refers to a peptide that consists of glycine and serine residues An exemplary gly/ser linker comprises the amino acid sequence GGGSSGGGSG (SEQ ID NO:1). In one embodiment, a connecting peptide of the invention comprises at least a portion of an upper hinge region (e.g., derived from an IgG1, IgG3, or IgG4 molecule), at least a portion of a middle hinge region (e.g., derived from an IgG1, IgG3, or IgG4 molecule) and a series of gly/ser amino acid residues (e.g., a gly/ser linker such as GGGSSGGGSG (SEQ ID NO:1)). In one embodiment, the connecting peptide comprises a substitution of one or more amino acids as compared to naturally occurring IgG1 or IgG3 hinge regions. In another embodiment, a connecting peptide comprises an amino acid sequence such as described in WO 02/060955. Connecting peptides are described in more detail below.

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

It is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In one embodiment, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate compliment binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. More generally, those skilled in the art will realize that antibodies modified as described herein may exert a number of subtle effects that may or may not be readily appreciated. However the resulting physiological profile, bioavailability and other biochemical effects of the modifications, such as tumor localization, biodistribution and serum half-life, may easily be measured and quantified using well know immunological techniques without undue experimentation.

In one embodiment, modified forms of antibodies can be made from a whole precursor or parent antibody using techniques known in the art. Exemplary techniques are discussed in more detail below. In particularly preferred embodiments both the variable and constant regions of polypeptides of the invention are human. In one embodiment, fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make antibodies are described in U.S. Pat. Nos. 6,150,584; 6,458,592; 6,420,140. Other techniques are known in the art.

A polypeptide comprising a heavy chain portion may or may not comprise other amino acid sequences or moieties not derived from an immunoglobulin molecule. Such modifications are described in more detail below. For example, in one embodiment, a polypeptide of the invention may comprise a flexible linker sequence. In another embodiment, a polypeptide may be modified to add a functional moiety such as PEG.

The polypeptides of the instant invention comprise at least two binding sites that provide for the association of the polypeptide with the selected target molecule.

In one embodiment, a binding molecule of the invention comprises an antibody molecule, e.g., an intact antibody molecule, or a fragment of an antibody molecule. In another embodiment, binding molecule of the invention is a modified or synthetic antibody molecule. In one embodiment, a binding molecule of the invention comprises all or a portion of (e.g., at least one antigen binding site from, at least one CDR from, or at least one heavy chain portion from) a monoclonal antibody, a humanized antibody, a chimeric antibody, or a recombinantly produced antibody.

In embodiments where the binding molecule is an antibody or modified antibody, the antigen binding site and the heavy chain portions need not be derived from the same immunoglobulin molecule. In this regard, the variable region may or be derived from any type of animal that can be induced to mount a humoral response and generate immunoglobulins against the desired antigen. As such, the variable region of the polypeptides may be, for example, of mammalian origin e.g., may be human, murine, non-human primate (such as cynomolgus monkeys, macaques, etc.), lupine, camelid (e.g., from camels, llamas and related species). In another embodiment, the variable region may be condricthoid in origin (e.g., from sharks).

Polypeptides of the invention can be made using techniques that are known in the art. In one embodiment, the polypeptides of the invention are antibody molecules that have been "recombinantly produced," i.e., are produced using recombinant DNA technology. Exemplary techniques for making antibody molecules are discussed in more detail below.

In one embodiment, the polypeptides of the invention are modified antibodies. As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a binding molecule of the invention is a fusion protein comprising at least one heavy chain portion lacking a CH2 domain and comprising a binding domain of a polypeptide comprising the binding portion of one member of a ligand and its receptor.

In one embodiment, the term, "modified antibody" according to the present invention includes immunoglobulins, antibodies, or immunoreactive fragments or recombinants thereof, in which at least a fraction of one or more of the constant region domains has been deleted or otherwise altered so as to provide desired biochemical characteristics such as the ability to non-covalently dimerize, increased ability to localize at the site of a tumor, or reduced serum half-life when compared with a whole, unaltered antibody of approximately the same immunogenicity. In a preferred embodiment, the polypeptides of the present invention are domain deleted antibodies which comprise a polypeptide chain similar to an immunoglobulin heavy chain, but which lack at least a portion of one or more heavy chain domains. More preferably, one entire domain of the constant region of the modified antibody will be deleted and even more preferably all or part of the CH2 domain will be deleted.

In preferred embodiments, a polypeptide of the invention will not elicit a deleterious immune response in a human. Modifications to the constant region compatible with the instant invention comprise additions, deletions or substitutions of one or more amino acids in one or more domains. That is, the polypeptides of the invention disclosed herein may comprise alterations or modifications to one or more of the three heavy chain constant domains (CH1, CH2 or CH3) and/or to the light chain constant region domain (CL).

In one embodiment, the invention pertains to a modified antibody molecule comprising at least one CC49 binding site (specific for Tag72). For example, FIG. 8A (SEQ ID NO:16) shows the single-stranded DNA sequence of sc(Fv)2 heavy chain tetravalent $CH_2$ domain-deleted huCC49 gene. FIG. 8B (SEQ ID NO:17) shows the single-stranded DNA sequence of sc(Fv)2 heavy chain tetravalent $CH_2$ domain-deleted huCC49 gene containing the synthetic G1/G3/Pro243Ala244Pro245+ [Gly/Ser] hinge connecting peptide. FIG. 8C (SEQ ID NO:18) shows the single-stranded DNA sequence of sc(Fv)2 light chain $CH_2$ domain-deleted huCC49. FIG. 9A (SEQ ID NO:19) shows the amino acid sequence of heavy chain sc(Fv)2 tetravalent $CH_2$ domain-deleted huCC49. FIG. 9B (SEQ ID NO:20) shows the amino acid sequence of heavy chain tetravalent $CH_2$ domain-deleted sc(Fv)2 huCC49 containing the synthetic G1/G3/Pro243Ala244Pro245+[Gly/Ser] hinge connecting peptide. FIG. 9C (SEQ ID NO:21) shows the amino acid sequence of light chain $CH_2$ domain-deleted sc(Fv)2 huCC49. FIG. 10A (SEQ ID NO:22) shows the single-stranded DNA sequence of tetravalent $CH_2$ domain-deleted 2sc(Fv)2 huCC49 minibody gene. FIG. 10B (SEQ ID NO:23) shows the single-stranded DNA sequence of tetravalent $CH_2$ domain-deleted sc(Fv)2 huCC49 minibody gene containing the synthetic G1/G3/Pro243Ala244Pro245+ [Gly/Ser] hinge connecting peptide. FIG. 11A (SEQ ID NO:24) shows the amino acid sequence of tetravalent $CH_2$ domain-deleted sc(Fv)2 huCC49 minibody. FIG. 11B (SEQ ID NO:25) shows the amino acid sequence of tetravalent $CH_2$ domain-deleted sc(Fv)2 huCC49 minibody containing the synthetic G1/G3/Pro243Ala244Pro245+[Gly/Ser] hinge connecting peptide.

In another embodiment, the invention pertains to a modified antibody molecule comprising at least one p5E8 binding site (specific for CD23). FIG. 12A (SEQ ID NO:26) shows the single-stranded DNA sequence of heavy chain tetravalent CH2 domain-deleted PRIMATIZED® p5E8 sc(Fv)2 antibody gene containing the G1/G3/Pro243Ala244Pro245+ [Gly/Ser] hinge connecting peptide. FIG. 12B (SEQ ID NO:27) shows the single-stranded DNA sequence of light chain tetravalent CH2 domain-deleted PRIMATIZED® p5E8 sc(Fv)2 gene. FIG. 13A (SEQ ID NO:28) shows the amino acid sequence of heavy chain tetravalent CH2 domain-deleted PRIMATIZED® p5E8 sc(Fv)2 antibody containing the G1/G3/Pro243Ala244Pro245+[Gly/Ser] hinge connecting peptide. FIG. 13B (SEQ ID NO:29) shows the amino acid sequence of light chain tetravalent CH2 domain-deleted PRIMATIZED® p5E8 sc(Fv)2 antibody. FIG. 14 (SEQ ID NO:30) shows the single-stranded DNA sequence of CH2 domain-deleted PRIMATIZED® p5E8 VL/VH minibody gene containing the G1/G3/Pro243Ala244Pro245+[Gly/Ser] hinge connecting peptide. FIG. 15 (SEQ ID NO:31) shows the single-stranded DNA sequence of CH2 domain-deleted PRIMATIZED® p5E8 VH/VL minibody gene containing the G1/G3/Pro243Ala244Pro245+[Gly/Ser] hinge connecting peptide. FIG. 16 (SEQ ID NO:32) shows the amino acid sequence of CH2 domain-deleted PRIMATIZED® p5E8 VL/VH minibody containing the G1/G3/ Pro243Ala244Pro245+[Gly/Ser] hinge connecting peptide. FIG. 17 (SEQ ID NO:33) shows the amino acid sequence of CH2 domain-deleted PRIMATIZED® p5E8 VH/VL minibody containing the G1/G3/Pro243Ala244Pro245+[Gly/Ser] hinge connecting peptide.

In one embodiment, the polypeptides of the invention may be modified to reduce their immunogenicity using art-recognized techniques. For example, antibodies or polypeptides of the invention can be humanized, deimmunized, or chimeric antibodies can be made. These types of antibodies are derived from a non-human antibody, typically a murine antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci.* 81: 6851-5 (1984); Morrison et al., *Adv. Immunol.* 44: 65-92 (1988); Verhoeyen et al., *Science* 239: 1534-1536 (1988); Padlan, *Molec. Immun.* 28: 489-498 (1991); Padlan, *Molec. Immun.* 31: 169-217 (1994), and U.S. Pat. Nos. 5,585, 089, 5,693,761 and 5,693,762 all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of polypeptides of the invention that are tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified. In one embodiment, the binding molecule comprises a chimeric antibody. In the context of the present application the term "chimeric antibodies" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse) and the constant region is human. Preferably, the variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in U.S. Pat. Nos. 5,585, 089, 5,693,761 and 5,693,762, it will be well within the competence of those skilled in the art, either by carrying out routine experimentation or by trial and error testing to obtain a functional antibody with reduced immunogenicity.

As used herein the term "properly folded polypeptide" includes polypeptides (e.g., antigen binding molecules such as antibodies) in which all of the functional domains comprising the polypeptide are distinctly active. As used herein, the term "improperly folded polypeptide" includes polypeptides in which at least one of the functional domains of the polypeptide is not active. In one embodiment, a properly folded polypeptide comprises polypeptide chains linked by at least one disulfide bond and, conversely, an improperly folded polypeptide comprises polypeptide chains not linked by at least one disulfide bond.

As used herein, the term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas. The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

In one embodiment, a binding molecule of the invention binds to a tumor cell. Exemplary antibodies which comprise antigen binding sites that bind to antigens expressed on tumor cells are known in the art and one or more CDRs from such antibodies can be included in a binding molecule of the invention. Exemplary antibodies include: 2B8, Lym 1, Lym 2, LL2, Her2, B1, MB1, BH3, B4, B72.3, 5E8, B3F6 and 5E10. In a preferred embodiment, a polypeptide of the invention is a C2B8 antibody which binds to CD20. In another preferred embodiment, a polypeptide of the invention is a CC49 antibody which recognizes TAG72.

In one embodiment, a binding molecule of the invention binds to a molecule which is useful in treating an autoimmune or inflammatory disease or disorder.

As used herein, the term "autoimmune disease or disorder" refers to disorders or conditions in a subject wherein the immune system attacks the body's own cells, causing tissue destruction. Autoimmune diseases include general autoimmune diseases, i.e., in which the autoimmune reaction takes place simultaneously in a number of tissues, or organ specific autoimmune diseases, i.e., in which the autoimmune reaction targets a single organ. Examples of autoimmune diseases that can be diagnosed, prevented or treated by the methods and compositions of the present invention include, but are not limited to, Crohn's disease; Inflammatory bowel disease (IBD); systemic lupus erythematosus; ulcerative colitis; rheumatoid arthritis; goodpasture's syndrome; Grave's disease; Hashimoto's thyroiditis; pemphigus vulgaris; myasthenia gravis; scleroderma; autoimmune hemolytic anemia; autoimmune thrombocytopenic purpura; polymyositis and dermatomyositis; pernicious anemia; Sjögren's syndrome; ankylosing spondylitis; vasculitis; type I diabetes mellitus; neurological disorders, multiple sclerosis, and secondary diseases caused as a result of autoimmune diseases.

As used herein the term "inflammatory disease or disorder" includes diseases or disorders which are caused, at least in part, or exacerbated by inflammation, e.g., increased blood flow, edema, activation of immune cells (e.g., proliferation, cytokine production, or enhanced phagocytosis). Exemplary disorders include those in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, mitochondria, apoptosis, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories.

Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, osteoarthritis, rheumatoid arthritis, acute and chronic infections (bacterial, viral and fungal); acute and chronic bronchitis, sinusitis, and other respiratory infections, including the common cold; acute and chronic gastroenteritis and colitis; acute and chronic cystitis and urethritis; acute respiratory distress syndrome; cystic fibrosis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; and burns (thermal, chemical, and electrical).

As used herein the term "medium that separates polypeptides based on hydrophobic interaction" includes a medium comprising hydrophobic ligands (e.g., alkyl or aryl groups) covalently attached to a matrix. Such a medium can be used to separate polypeptides based on interaction between a solvent and accessible non-polar groups on the surface of the polypeptides and the hydrophobic ligands of the medium. An exemplary medium is Phenyl 5PW-HR available from Tosoh Bioscience.

As used herein, the term "conductivity" includes electrical conductivity of a solution as measured in microSiemens/cm (formerly micromhos/cm). The greater the ion content of a solution, the greater the conductivity of the solution. Conductivity can be readily measured using techniques that are well known in the art (e.g., by measuring the current passing between two electrodes).

The separation methods of the invention can be used with solutions having a pH ranging from acid to neutral, e.g., from about pH 3.5 to approximately neutral. As used herein, the term "approximately neutral pH" includes pH values of approximately 7. For example, in one embodiment, a separation method of the invention can be performed using a solution (e.g., a buffer) having a pH of about 3, about 4, about 5, about 6, about 7, or about 8. Preferably, the pH of the solution is about 6 or about 7. In one embodiment, the pH of the solution is about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, or about 8.0.

As used herein the term "affinity matrix" includes a matrix, such as agarose, controlled pore glass, or poly (styrenedivinyl)benzene to which an affinity ligand is attached. The affinity ligand binds to the desired polypeptide and the contaminating polypeptides are not bound to the affinity ligand. The desired polypeptide can be eluted from the affinity matrix using known protocols.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the binding molecules of the invention are engineered, e.g., to express a connecting peptide of the invention.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two ore more segments that correspond to polypeptides encoded by the original ORFs (which segments are not normally so joined in nature.) Although the reading frame is thus made continuous throughout the fused segments, the segments may be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

As used herein, the phrase "subject that would benefit from administration of a binding molecule" includes subjects, such as mammalian subjects, that would benefit from administration of a binding molecule used, e.g., for detection of an antigen recognized by a binding molecule (e.g., for a diagnostic procedure) and/or from treatment with a binding molecule to reduce or eliminate the target recognized by the binding molecule. For example, in one embodiment, the subject may benefit from reduction or elimination of a soluble or particulate molecule from the circulation or serum (e.g., a toxin or pathogen) or from reduction or elimination of a population of cells expressing the target (e.g., tumor cells). As described in more detail herein, the binding molecule can be used in unconjugated form or can be conjugated, e.g., to a drug, prodrug, or an isotope.

II. SYNTHETIC CONNECTING PEPTIDES

At least one polypeptide chain of a dimer of the invention can comprise a synthetic connecting peptide of the invention. In one embodiment, at least two chains of a dimer of the invention comprise a connecting peptide. In a preferred embodiment, two chains of a dimer of the invention comprise a connecting peptide.

In one embodiment, connecting peptides can be used to join two heavy chain portions in frame in a single polypeptide chain. For example, in one embodiment, a connecting peptide of the invention can be used to fuse a CH3 domain (or synthetic CH3 domain) to a hinge region (or synthetic hinge region). In another embodiment, a connecting peptide of the invention can be used to fuse a CH3 domain (or synthetic CH3 domain) to a CH1 domain (or synthetic CH1 domain). In still another embodiment, a connecting peptide can act as a peptide spacer between the hinge region (or synthetic hinge region) and a CH2 domain (or a synthetic CH2 domain).

In another embodiment, a CH3 domain can be fused to an extracellular protein domain (e.g., a VL domain (or synthetic domain), a VH domain (or synthetic domain), a CH1 domain (or synthetic domain), a hinge domain (or synthetic hinge), or to the ligand binding portion of a receptor or the receptor binding portion of a ligand). For example, in one embodiment, a VH or VL domain is fused to a CH3 domain via a connecting peptide (the C-terminus of the connecting peptide is attached to the N-terminus of the CH3 domain and the N-terminus of the connecting peptide is attached to the C-terminus of the VH or VL domain). In another embodiment, a CH1 domain is fused to a CH3 domain via a connecting peptide (the C-terminus of the connecting peptide is attached to the N-terminus of the CH3 domain and the N-terminus of the connecting peptide is attached to the C-terminus of the CH1 domain). In another embodiment, a connecting peptide of the invention can be used to fuse a CH3 domain (or synthetic CH3 domain) to a hinge region (or synthetic hinge region) or portion thereof. In still another embodiment, a connecting peptide can act as a peptide spacer between the hinge region (or synthetic hinge region) and a CH2 domain (or a synthetic CH2 domain).

In one embodiment, a connecting peptide can comprise or consist of a gly/ser spacer. For example, a domain deleted CC49 construct having a short amino acid spacer GGSSGGGGSG (SEQ. ID No. 1) substituted for the CH2 domain and the lower hinge region (CC49.ΔCH2 [gly/ser]) can be used. In another embodiment, a connecting peptide comprises the amino acid sequence IGKTISKKAK (SEQ ID NO:36).

In another embodiment, connecting peptide can comprise at least a portion of an immunoglobulin hinge region. For example, chimeric hinge domains can be constructed which combine hinge elements derived from different antibody isotypes. In one embodiment, a connecting peptide comprises at least a portion of an IgG1 hinge region. In another embodiment, a connecting peptide can comprise at least a portion of an IgG3 hinge region. In another embodiment, a connecting peptide can comprise at least a portion of an IgG1 hinge region and at least a portion of an IgG3 hinge region. In one embodiment, a connecting peptide can comprise an IgG1 upper and middle hinge and a single IgG3 middle hinge repeat motif.

Because the numbering of individual amino acids in such connecting peptides comprising an amino acid sequence derived from an immunoglobulin hinge region may vary depending upon the length of the connecting peptide, the numbering of amino acid positions in these molecules is given using Kabat numbering see, e.g., Table 2). Table 1 shows naturally occurring hinge sequence for IgG1, IgG3, and IgG4 molecules. Table 2 shows Kabat numbering for portions of these hinge molecules and also shows Kabat numbering for connecting peptide amino acid residues presented in that table.

In one embodiment, a connecting peptide of the invention comprises a non-naturally occurring immunoglobulin hinge region domain, e.g., a hinge region domain that is not naturally found in the polypeptide comprising the hinge region domain and/or a hinge region domain that has been altered so that it differs in amino acid sequence from a naturally occurring immunoglobulin hinge region domain. In one embodiment, mutations can be made to hinge region domains to make a connecting peptide of the invention. In one embodiment, a connecting peptide of the invention comprises a hinge domain which does not comprise a naturally occurring number of cysteines, i.e., the connecting peptide comprises either fewer cysteines or a greater number of cysteines than a naturally occurring hinge molecule. In a preferred embodiment, incorporation of a connecting peptide (e.g., comprising a non-naturally occurring number of cysteines) into a polypeptide results in a composition in which greater than 50%, 60%, 70%, 80% or 90% of the dimeric molecules present in a form in which the two heavy chain portions are linked via at least one interchain disulfide linkage.

In one embodiment of the invention, a connecting peptide comprises hinge region domain comprising a proline residue at an amino acid position corresponding to amino acid position 243 in the Kabat numbering system (position 230, EU numbering system). In one embodiment, a connecting peptide comprises an alanine residue at an amino acid position corresponding to position 244, Kabat numbering system (position 246, EU numbering system). In another embodiment, a connecting peptide of the invention comprises a proline residue at an amino acid position corresponding to position 245 (Kabat numbering system; position 247, EU numbering system)). In one embodiment, a connecting peptide comprises a cysteine residue at an amino acid position corresponding to position 239, Kabat numbering system (position 226, EU numbering system). In one embodiment, a connecting peptide comprises a serine residue at an amino acid position corresponding to position 239, Kabat numbering system (position 226, EU numbering system). In one embodiment, a connecting peptide comprises a cysteine residue at an amino acid position corresponding to position 242, Kabat numbering system (position 229, EU numbering system). In one embodiment, a connecting peptide comprises a serine residue at an amino acid position corresponding to position 242, Kabat numbering system (position 229, EU numbering system).

In one embodiment, the connecting peptide can be chosen to result in the preferential synthesis of a particular isoform of polypeptide, e.g., in which the two heavy chain portions are linked via disulfide bonds or are not linked via disulfide bonds. For example, as described in the instant examples, the G1/G3/Pro243+[gly/ser] linker (SEQ ID NO: 8), G1/G3/Pro243Ala244Pro245+[gly/ser] linker (SEQ ID NO: 9), Pro243+[gly/ser] linker (SEQ ID NO:15), and Pro243Ala244Pro245+[gly/ser] linker (SEQ ID NO: 14), connecting peptides resulted in the production of only Form A CH2 domain-deleted antibody with no detectable Form B. In contrast, CH2 domain-deleted Cys242Ser:Pro243 (SEQ ID NO: 12), and CH2 domain-deleted Cys242Ser:Pro243Ala244Pro245 (SEQ ID NO: 13), both resulted in a preference for the Form B isoform. These synthetic hinge region connecting peptides would thus be useful for favoring synthesis of Form A or B isoform. This is true for any isotype of antibody, (e.g., IgG1, IgG2, IgG3, or IgG4) based on the high degree of homology among the CH3 domains for all four human isotypes. (Including identical and conserved amino acid residues, IgG1 CH3 domain is 98.13% homologous to IgG2 CH3, 97.20% homologous to IgG3 CH3, and 96.26% homologous to IgG4 CH3). The parentheticals referring to connecting peptides and various binding molecules of the invention represent equivalent terminology unless otherwise indicated.

In one embodiment, a connecting peptide of the invention comprises a hinge region domain followed by a flexible gly/ser linker. Exemplary connecting peptides are shown in Table 2 and in SEQ ID NOs: 8-15, 48, and 49. It will be understood that variant forms of these exemplary connecting peptides can be created by introducing one or more nucleotide substitutions, additions or deletions into the nucleotide sequence encoding a connecting peptide such that one or more amino acid substitutions, additions or deletions are introduced into the connecting peptide. For example, mutations may be introduced by standard techniques, such as site-directed mutagenesis and PCR-mediated mutagenesis. Preferably, conservative amino acid substitutions are made at one or more nonessential amino acid residues such that the ability of the connecting peptide to preferentially enhance synthesis of Form A or Form B is not altered. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Connecting peptides of the invention can be of varying lengths. In one embodiment, a connecting peptide of the invention is from about 15 to about 50 amino acids in length. In another embodiment, a connecting peptide of the invention is from about 20 to about 45 amino acids in length. In another embodiment, a connecting peptide of the invention is from about 25 to about 40 amino acids in length. In another embodiment, a connecting peptide of the invention is from about 30 to about 35 amino acids in length. In another embodiment, a connecting peptide of the invention is from about 24 to about 27-amino acids in length. In another embodiment, a connecting peptide of the invention is from about 40 to about 42 amino acids in length.

Connecting peptides can be introduced into polypeptide sequences using techniques known in the art. For example, in one embodiment, the Splicing by Overlap Extension (SOE) method (Horton, R. M. 1993 Methods in Molecular Biology, Vol 15:PCR Protocols: Current Methods and applications. Ed. B. A. White) can be used. Modifications can be confirmed by DNA sequence analysis. Plasmid DNA can be used to transform host cells for stable production of the polypeptides produced.

In one embodiment, incorporation of one of the subject connecting peptides into a polypeptide yields a composition comprising polypeptide molecules having at least two binding sites and at least two polypeptide chains, wherein at least two of the polypeptide chains comprise a synthetic connecting peptide and wherein greater than 50% of the molecules are present in a form in which the two heavy chain portions are linked via at least one interchain disulfide linkage. In another embodiment, greater than 60% of the molecules are present in a form in which the two heavy chain portions are linked via at least one interchain disulfide linkage. In another embodiment, greater than 70% of the molecules are present in a form in which the two heavy chain portions are linked via at least one interchain disulfide linkage. In another embodiment, greater than 80% of the molecules are present in a form in which the two heavy chain portions are linked via at least one interchain disulfide linkage. In another embodiment, greater than 90% of the molecules are present in a form in which the two heavy chain portions are linked via at least one interchain disulfide linkage.

In one embodiment, incorporation of one of the subject connecting peptides into an IgG4 molecule yields a composition in which greater than 95% of the molecules are present in a form in which the two heavy chain portions are linked via at least one interchain disulfide linkage.

III. BINDING MOLECULES

The polypeptides of the invention comprise at least two binding sites which bind to a target molecule of interest. Exemplary binding sites include, e.g., sites which bind to an antigen (antigen binding sites), sites which bind to a receptor (receptor binding sites), or sites which bind to a ligand (ligand binding sites). In one embodiment, the binding molecules comprise at least two binding sites. In one embodiment, the binding molecules comprise two binding sites. In one embodiment, the binding molecules comprise three binding sites. In another embodiment, the binding molecules comprise four binding sites.

In one embodiment, the binding molecules have at least one target binding site specific for a molecule which mediates a biological effect (e.g., which modulates cellular activation (e.g., by binding to a cell surface receptor and resulting in transmission or inhibition of an activating or inhibitory signal), which results in death of the cell (e.g., by complement fixation or exposure to a payload present on the binding molecule), or which modulates a disease or disorder in a subject (e.g., by promoting lysis of a fibrin clot or promoting clot formation, or by modulating the amount of a substance which is bioavailable (e.g., by enhancing or reducing the amount of a ligand such as TNFα in the subject)).

In one embodiment, the binding molecules have at least one target binding site specific for an molecule targeted for reduction or elimination, e.g., a cell surface antigen or a soluble antigen. In one embodiment, binding of the binding molecule to the target results in reduction or elimination of the target, e.g., from a tissue or from the circulation. In another embodiment, the binding molecules have at least one binding site specific for a molecule that can be used to detect the presence of a target molecule (e.g., to detect a contaminant or diagnose a condition or disorder). In yet another embodiment, a binding molecule of the invention comprises at least one binding site that targets the binding molecule to a specific site in a subject (e.g., to a tumor cell or blood clot).

Exemplary binding sites that can be included in the binding domain of a binding molecule of the invention include: the receptor binding portion of a ligand, the ligand binding portion of a receptor, the substrate binding portion of an enzyme, the enzyme binding portion of a substrate, or one or more antigen binding portions of an antibody.

In one embodiment, at least one target binding site of a binding molecule (e.g., an antibody molecule, a bispecific antibody, or a modified antibody) is catalytic (Shokat and Schultz. 1990. Annu. Rev. Immunol. 8:335).

In one embodiment, a heavy chain variable portion and a light chain variable portion of a binding molecule are present in the same polypeptide, e.g., as in a single chain antibody or a minibody (see e.g., U.S. Pat. No. 5,837,821 or WO 94/09817A1). In another embodiment, the heavy chain portion and the light chain portion of a polypeptide are present in different polypeptide chains, e.g., as in antibody molecules.

The target binding polypeptides of the invention are multimeric molecules. In one embodiment, the target binding polypeptides are dimers. In one embodiment, the dimers of the invention are homodimers, comprising two identical monomeric subunits. In another embodiment, the dimers of the invention are heterodimers, comprising two non-identical monomeric subunits. The dimers comprise at least two polypeptide chains. In one embodiment, the binding molecules comprise two polypeptide chains. In another embodiment, the binding molecules comprise three polypeptide chains. In another embodiment, the binding molecules comprise four polypeptide chains.

In a preferred embodiment, a binding molecule of the invention comprises at least one CDR of an antibody, e.g., an antibody known in the art to bind to a target of interest. In another embodiment, a binding molecule of the invention comprises at least two CDRs. In another embodiment, a binding molecule of the invention comprises at least three CDRs. In another embodiment, a binding molecule of the invention comprises at least four CDRs. In another embodiment, a binding molecule of the invention comprises at least five CDRs. In another embodiment, a binding molecule of the invention comprises at least six CDRs. In a preferred embodiment, a binding molecule of the invention comprises at least one VH domain of an antibody, e.g., an antibody known in the art to bind to a target of interest. In a preferred embodiment, a binding molecule of the invention comprises at least one VL domain. In another preferred embodiment, a binding molecule of the invention comprises at least one VH domain and one VL domain of an antibody.

In one embodiment, an antigen binding site consists of a VH domain, e.g., derived from camelids, which is stable in the absence of a VL chain (Hamers-Casterman et al. 1993. Nature 363:446; Desmyter et al. 1996. Nat. Struct. Biol. 3:803; Desmyter, A., 1996. Nat. Struct. Biol. 3:803; Decanniere, K., et al. 1999. Structure 7:361; Davies et al. 1996. Protein Eng. 9:531; Kortt et al. 1995. J. Protein Chem. 14:167).

A. Fusion Proteins

The invention also pertains to binding molecules which comprise one or more immunoglobulin domains. The fusion proteins of the invention comprise a binding domain (which comprises at least one binding site) and a dimerization domain (which comprises at least one heavy chain portion). The subject fusion proteins may be bispecific (with one binding site for a first target and a second binding site for a second target) or may be multivalent (with two binding sites for the same target).

Exemplary fusion proteins reported in the literature include fusions of the T cell receptor (Gascoigne et al., Proc. Natl. Acad. Sci. USA 84:2936-2940 (1987)); CD4 (Capon et al., Nature 337:525-531 (1989); Traunecker et al., Nature 339:68-70 (1989); Zettmeissl et al., DNA Cell Biol. USA 9:347-353 (1990); and Byrn et al., Nature 344:667-670 (1990)); L-selectin (homing receptor) (Watson et al., J. Cell. Biol. 110:2221-2229 (1990); and Watson et al., Nature 349: 164-167 (1991)); CD44 (Aruffo et al., Cell 61:1303-1313 (1990)); CD28 and B7 (Linsley et al., J. Exp. Med. 173:721-730 (1991)); CTLA-4 (Lisley et al., J. Exp. Med. 174:561-569 (1991)); CD22 (Stamenkovic et al., Cell 66:1133-1144 (1991)); TNF receptor (Ashkenazi et al., Proc. Natl. Acad. Sci. USA 88:10535-10539 (1991); Lesslauer et al., Eur. J. Immunol. 27:2883-2886 (1991); and Peppel et al., J. Exp. Med. 174:1483-1489 (1991)); and IgE receptor a (Ridgway and Gorman, J. Cell. Biol. Vol. 115, Abstract No. 1448 (1991)).

In one embodiment a fusion protein combines the binding domain(s) of the ligand or receptor (e.g. the extracellular domain (ECD) of a receptor) with at least one heavy chain domain and a synthetic connecting peptide. In one embodiment, when preparing the fusion proteins of the present invention, nucleic acid encoding the binding domain of the ligand or receptor will be fused C-terminally to nucleic acid encoding the N-terminus of an immunoglobulin constant domain sequence. N-terminal fusions are also possible. In one embodiment, a fusion protein includes a CH2 and a CH3 domain. Fusions may also be made to the C-terminus of the Fc portion of a constant domain, or immediately N-terminal to the CH1 of the heavy chain or the corresponding region of the light chain.

In one embodiment, the sequence of the ligand or receptor domain is fused to the N-terminus of the Fc domain of an immunoglobulin molecule. It is also possible to fuse the entire heavy chain constant region to the sequence of the ligand or receptor domain. In one embodiment, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. The precise site at which the fusion is made is not critical; particular sites are well known and may be selected in order to optimize the biological activity, secretion, or binding characteristics of the molecule. Methods for making fusion proteins are known in the art.

For bispecific fusion proteins, the fusion proteins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Additional exemplary ligands and their receptors that may be included in the subject fusion proteins include the following:

Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, and interferons such as interferon-$\alpha$, $\beta$, or $\gamma$ (U.S. Pat. Nos. 4,925,793 and 4,929,554).

Cytokine receptors typically consist of a ligand-specific alpha chain and a common beta chain. Exemplary cytokine receptors include those for GM-CSF, IL-3 (U.S. Pat. No. 5,639,605), IL-4 (U.S. Pat. No. 5,599,905), IL-5 (U.S. Pat. No. 5,453,491), IFNγ (EP0240975), and the TNF family of receptors (e.g., TNFα (e.g. TNFR-1 (EP 417, 563), TNFR-2 (EP 417,014) lymphotoxin beta receptor).

Adhesion Proteins

Adhesion molecules are membrane-bound proteins that allow cells to interact with one another. Various adhesion proteins, including leukocyte homing receptors and cellular adhesion molecules, of receptor binding portions thereof, can be incorporated in a fusion protein of the invention. Leucocyte homing receptors are expressed on leucocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

Chemokines

Chemokines, chemotactic proteins which stimulate the migration of leucocytes towards a site of infection, can also be incorporated into a fusion protein of the invention. Exemplary chemokines include Macrophage inflammatory proteins (MIP-1-α and MIP-1-β), neutrophil chemotactic factor, and RANTES (regulated on activation normally T-cell expressed and secreted).

Growth Factors and Growth Factor Receptors

Growth factors or their receptors (or receptor binding or ligand binding portions thereof) may be incorporated in the fusion proteins of the invention. Exemplary growth factors include Vascular Endothelial Growth Factor (VEGF) and its isoforms (U.S. Pat. No. 5,194,596); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); stein-cell factor (SCF), thrombopoietin (c-Mpl ligand), and the Wnt polypeptides (U.S. Pat. No. 6,159,462). Exemplary growth factor receptors which may be used as targeting receptor domains of the invention include EGF receptors; VEGF receptors (e.g. Flt1 or Flk1/KDR), PDGF receptors (WO 90/14425); HGF receptors (U.S. Pat. Nos. 5,648,273, and 5,686,292), and neurotrophic receptors including the low affinity receptor (LNGFR), also termed as $p75^{NTR}$ or p75, which binds NGF, BDNF, and NT-3, and high affinity receptors that are members of the trk family of the receptor tyrosine kinases (e.g. trkA, trkB (EP 455,460), trkC (EP 522,530)).

Hormones

Exemplary growth hormones for use as targeting agents in the fusion proteins of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH), calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

Clotting Factors

Exemplary blood coagulation factors for use as targeting agents in the fusion proteins of the invention include the clotting factors (e.g., factors V, VII, VIII, X, IX, XI, XII and XIII, von Willebrand factor); tissue factor (U.S. Pat. Nos. 5,346,991, 5,349,991, 5,726,147, and 6,596,84); thrombin and prothrombin; fibrin and fibrinogen; plasmin and plasminogen; plasminogen activators, such as urokinase or human urine or tissue-type plasminogen activator (t-PA).

Other exemplary fusion proteins are taught, e.g., in WO0069913A1 and WO0040615A2. Another exemplary molecule that may be included in a fusion protein of the invention is IGSF9.

Fusion proteins can be prepared using methods that are well known in the art (see for example U.S. Pat. Nos. 5,116, 964 and 5,225,538). Ordinarily, the ligand or receptor domain is fused C-terminally to the N-terminus of the constant region of the heavy chain (or heavy chain portion) and in place of the variable region. Any transmembrane regions or lipid or phospholipids anchor recognition sequences of ligand binding receptor are preferably inactivated or deleted prior to fusion. DNA encoding the ligand or receptor domain is cleaved by a restriction enzyme at or proximal to the 5' and 3' ends of the DNA encoding the desired ORF segment. The resultant DNA fragment is then readily inserted into DNA encoding a heavy chain constant region. The precise site at which the fusion is made may be selected empirically to optimize the secretion or binding characteristics of the soluble fusion protein. DNA encoding the fusion protein is then transfected into a host cell for expression.

B. Antibodies or Portions Thereof

In one embodiment, a binding molecule, e.g., antigen binding molecule, of the invention is an antibody molecule. Using art recognized protocols, for example, antibodies are preferably raised in mammals by multiple subcutaneous or intraperitoneal injections of the relevant antigen (e.g., purified tumor associated antigens or cells or cellular extracts comprising such antigens) and an adjuvant. This immunization typically elicits an immune response that comprises production of antigen-reactive antibodies from activated splenocytes or lymphocytes. While the resulting antibodies may be harvested from the serum of the animal to provide polyclonal preparations, it is often desirable to isolate individual lymphocytes from the spleen, lymph nodes or peripheral blood to provide homogenous preparations of monoclonal antibodies (MAbs). Preferably, the lymphocytes are obtained from the spleen.

In this well known process (Kohler et al., Nature, 256:495 (1975)) the relatively short-lived, or mortal, lymphocytes from a mammal which has been injected with antigen are fused with an immortal tumor cell line (e.g. a myeloma cell line), thus, producing hybrid cells or "hybridomas" which are both immortal and capable of producing the genetically coded antibody of the B cell. The resulting hybrids are segregated into single genetic strains by selection, dilution, and regrowth with each individual strain comprising specific genes for the formation of a single antibody. They produce antibodies which are homogeneous against a desired antigen and, in reference to their pure genetic parentage, are termed "monoclonal."

Hybridoma cells thus prepared are seeded and grown in a suitable culture medium that preferably contains one or more substances that inhibit the growth or survival of the unfused, parental myeloma cells. Those skilled in the art will appreciate that reagents, cell lines and media for the formation, selection and growth of hybridomas are commercially available from a number of sources and standardized protocols are well established. Generally, culture medium in which the hybridoma cells are growing is assayed for production of monoclonal antibodies against the desired antigen. Preferably, the binding specificity of the monoclonal antibodies produced by hybridoma cells is determined by immunoprecipitation or by an in vitro assay, such as a radioimmunoassay (RIA) or enzyme-linked immunoabsorbent assay (ELISA). After hybridoma cells are identified that produce antibodies of the desired specificity, affinity and/or activity, the clones may be subcloned by limiting dilution procedures and grown by standard methods (Goding, *Monoclonal Antibodies: Principles and Practice*, pp 59-103 (Academic Press, 1986)). It will further be appreciated that the monoclonal antibodies secreted by the subclones may be separated from culture medium, ascites fluid or serum by conventional purification procedures such as, for example, protein-A, hydroxylapatite chromatography, gel electrophoresis, dialysis or affinity chromatography.

In another embodiment, DNA encoding a desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be modified as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Those skilled in the art will also appreciate that DNA encoding antibodies or antibody fragments may also be derived from antibody phage libraries, e.g., using pd phage or Fd phagemid technology. Exemplary methods are set forth, for example, in EP 368 684 B1; U.S. Pat. No. 5,969,108, Hoogenboom, H. R. and Chames. 2000. *Immunol. Today* 21:371; Nagy et al. 2002. *Nat. Med.* 8:801; Huie et al. 2001. *Proc. Natl. Acad. Sci. USA* 98:2682; Lui et al. 2002. *J. Mol. Biol.* 315:1063, each of which is incorporated herein by reference. Several publications (e.g., Marks et al. *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al. 2000. *Nat. Biotechnol.* 18:1287; Wilson et al. 2001. *Proc. Natl. Acad. Sci. USA* 98:3750; or Irving et al. 2001 *J. Immunol. Methods* 248:31. In yet another embodiment, cell surface libraries can be screened for antibodies (Boder et al. 2000. Proc. Natl. Acad. Sci. USA 97:10701; Daugherty et al. 2000 *J. Immunol. Methods* 243:211. Such procedures provide alternatives to traditional hybridoma techniques for the isolation and subsequent cloning of monoclonal antibodies.

Yet other embodiments of the present invention comprise the generation of human or substantially human antibodies in transgenic animals (e.g., mice) that are incapable of endogenous immunoglobulin production (see e.g., U.S. Pat. Nos. 6,075,181, 5,939,598, 5,591,669 and 5,589,369 each of which is incorporated herein by reference). For example, it has been described that the homozygous deletion of the antibody heavy-chain joining region in chimeric and germ-line mutant mice results in complete inhibition of endogenous antibody production. Transfer of a human immunoglobulin gene array to such germ line mutant mice will result in the production of human antibodies upon antigen challenge. Another preferred means of generating human antibodies using SCID mice is disclosed in U.S. Pat. No. 5,811,524 which is incorporated herein by reference. It will be appreciated that the genetic material associated with these human antibodies may also be isolated and manipulated as described herein.

Yet another highly efficient means for generating recombinant antibodies is disclosed by Newman, *Biotechnology*, 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

In another embodiment, lymphocytes can be selected by micromanipulation and the variable genes isolated. For example, peripheral blood mononuclear cells can be isolated from an immunized mammal and cultured for about 7 days in vitro. The cultures can be screened for specific IgGs that meet the screening criteria. Cells from positive wells can be isolated. Individual Ig-producing B cells can be isolated by FACS or by identifying them in a complement-mediated hemolytic plaque assay. Ig-producing B cells can be micromanipulated into a tube and the Vh and Vl genes can be amplified using, e.g., RT-PCR. The VH and VL genes can be cloned into an antibody expression vector and transfected into cells (e.g., eukaryotic or prokaryotic cells) for expression.

Moreover, genetic sequences useful for producing the polypeptides of the present invention may be obtained from a number of different sources. For example, as discussed extensively above, a variety of human antibody genes are available in the form of publicly accessible deposits. Many sequences of antibodies and antibody-encoding genes have been published and suitable antibody genes can be chemically synthesized from these sequences using art recognized techniques. Oligonucleotide synthesis techniques compatible with this aspect of the invention are well known to the skilled artisan and may be carried out using any of several commercially available automated synthesizers. In addition, DNA sequences encoding several types of heavy and light chains set forth herein can be obtained through the services of commercial DNA synthesis vendors. The genetic material obtained using any of the foregoing methods may then be altered or modified to provide obtain polypeptides of the present invention.

Alternatively, antibody-producing cell lines may be selected and cultured using techniques well known to the skilled artisan. Such techniques are described in a variety of laboratory manuals and primary publications. In this respect, techniques suitable for use in the invention as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

It will further be appreciated that the scope of this invention further encompasses all alleles, variants and mutations of antigen binding DNA sequences.

As is well known, RNA may be isolated from the original hybridoma cells or from other transformed cells by standard techniques, such as guanidinium isothiocyanate extraction and precipitation followed by centrifugation or chromatography. Where desirable, mRNA may be isolated from total RNA by standard techniques such as chromatography on oligo dT cellulose. Suitable techniques are familiar in the art.

Variable and constant region domains can be obtained from any source and be incorporated into a modified antibody of the invention. To clone antibodies, mRNA can be isolated from hybridoma, spleen, or lymph cells, reverse transcribed into DNA, and antibody genes amplified by PCR. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes. Numerous primer sets suitable for amplification of antibody genes are known in the art (e.g., 5' primers based on the N-terminal sequence of purified antibodies (Benhar and Pastan. 1994. Protein Engineering 7:1509); rapid amplification of cDNA ends (Ruberti, F. et al. 1994. J. Immunol. Methods 173:33); antibody leader sequences (Larrick et al. 1989 Biochem. Biophys. Res. Commun. 160:1250); or based on known variable region framework amino acid sequences from the Kabat (Kabat et al. 1991. Sequences of Proteins of Immunological Interest. Bethesda, Md.: JS Dep. Health Hum. Serv. 5$^{th}$ ed.) or the V-base databases (e.g., Orlandi et al. 1989. Proc. Natl. Acad. Sci. USA 86:3833; Sblattero et al. 1998. Immunotechnology 3:271; or Krebber et al. 1997. J. Immunol. Methods 201:35). Constant region domains can be selected having a particular effector function (or lacking a particular effector function) or with a particular modification to reduce immunogenicity. Variable and constant domains can be cloned, e.g., using the polymerase chain reaction and primers which are selected to amplify the domain of interest. PCR amplification methods are described in detail in U.S. Pat. Nos. 4,683,195; 4,683,202; 4,800,159; 4,965,188; and in, e.g., "PCR Protocols: A Guide to Methods and Applications" Innis et al. eds., Academic Press, San Diego, Calif. (1990); Ho et al. 1989. Gene 77:51; Horton et al. 1993. Methods Enzymol. 217:270).

Alternatively, V domains can be obtained from libraries of V gene sequences from an animal of choice. Libraries expressing random combinations of domains, e.g., VH and VL domains, can be screened with a desired antigen to identify elements which have desired binding characteristics. Methods of such screening are well known in the art. For example, antibody gene repertoires can be cloned into a λ bacteriophage expression vector (Huse, W D et al. 1989. Science 2476:1275). In addition, cells (Boder and Wittrup. 1997. Nat. Biotechnol. 15:553; Daugtherty, P. et al. 2000. J. Immunol. Methods. 243:211; Francisco et al. 1994. Proc. Natl. Acad. Sci. USA 90:10444; Georgiou et al. 1997. Nature Biotechnology 15:29) or viruses (e.g., Hoogenboom, HR. 1998 Immunotechnology 4:1 Winter et al. 1994. Annu. Rev. Immunol. 12:433; Griffiths, A D. 1998. Curr. Opin. Biotechnol. 9:102) expressing antibodies on their surface can be screened. Ribosomal display can also be used to screen antibody libraries (Hanes J., et al. 1998. Proc. Natl. Acad. Sci. USA 95:14130; Hanes, J. and Pluckthun. 1999. Cliff. Top. Microbiol. Immunol. 243:107; He, M. and Taussig. 1997. Nucleic Acids Research 25:5132).

Preferred libraries for screening are human V gene libraries. VL and VH domains from a non-human source may also be used. In one embodiment, such non-human V domains can be altered to reduce their immunogenicity using art recognized techniques.

Libraries can be naïve, from immunized subjects, or semi-synthetic (Hoogenboom, H. R. and Winter. 1992. J. Mol. Biol. 227:381; Griffiths, A D, et al. EMBO J. 13:3245; de Kruif, J. et al. 1995. J. Mol. Biol. 248:97; Barbas, C. F., et al. 1992. Proc. Natl. Acad. Sci. USA 89:4457).

In addition, the sequences of many antibody V and C domains are known and such domains can be synthesized using methods well known in the art.

In one embodiment, mutations can be made to immunoglobulin domains to create a library of nucleic acid molecules having greater heterogeneity (Thompson, J., et al. 1996. J. Mol. Biol. 256:77; Lamminmaki, U. et al. 1999. J. Mol. Biol. 291:589; Caldwell, R. C. and Joyce G F. 1992. PCR Methods Appl. 2:28; Caldwell R C and Joyce G F. 1994. PCR Methods Appl. 3:S136. Standard screening procedures can be used to select high affinity variants. In another embodiment, changes to VH and VL sequences can be made to increase antibody avidity, e.g., using information obtained from crystal structures using techniques known in the art.

C. Modified Antibodies

Exemplary constructs include, e.g., minibodies, diabodies, diabodies fused to CH3 molecules, tetravalent antibodies, intradiabodies (e.g., Jendreyko et al. 2003. J. Biol. Chem. 278:47813), bispecific antibodies, fusion proteins (e.g., antibody cytokine fusion proteins, proteins fused to at least a portion of an Fc receptor), bispecific antibodies. Other immunoglobulins (Ig) and certain variants thereof are described, for example in U.S. Pat. No. 4,745,055; EP 256,654; Faulkner et al., Nature 298:286 (1982); EP 120,694; EP 125,023; Morrison, J. Immun. 123:793 (1979); Kohler et al., Proc. Natl. Acad. Sci. USA 77:2197 (1980); Raso et al., Cancer Res. 41:2073 (1981); Morrison et al., Ann. Rev. Immunol. 2:239 (1984); Morrison, Science 229:1202 (1985); Morrison et al., Proc. Natl. Acad. Sci. USA 81:6851 (1984); EP 255,694; EP 266,663; and WO 88/03559. Reassorted immunoglobulin chains also are known. See, for example, U.S. Pat. No. 4,444,878; WO 88/03565; and EP 68,763 and references cited therein.

In one embodiment, a polypeptide of the invention comprises an immunoglobulin heavy chain having deletion or substitution of at least one amino acid. For example, the mutation of one or more single amino acid in selected areas of the CH2 domain may be enough to substantially reduce Fc binding and thereby increase tumor localization. Similarly, it may be desirable to simply delete that part of one or more constant region domains that control the effector function (e.g. complement binding) to be modulated. Such partial deletions of the constant regions may improve selected characteristics of the antibody (serum half-life) while leaving other desirable functions associated with the subject constant region domain intact. Accordingly, in one embodiment, a binding molecule of the invention lacks all or part of a CH2 domain. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other preferred embodiments may comprise the addition of one or more amino acids to the constant region to enhance desirable characteristics such as effector function or provide for more cytotoxin or carbohydrate attachment. In such embodiments it may be desirable to insert or replicate specific sequences derived from selected constant region domains.

In another embodiment, mutations to naturally occurring hinge regions can be made. Such modifications to the constant region in accordance with the instant invention may easily be made using well known biochemical or molecular engineering techniques well within the skill of the art.

In one embodiment, polypeptides of the invention comprise modified constant regions wherein one or more domains are partially or entirely deleted ("domain deleted antibodies"). In especially preferred embodiments compatible modified antibodies will comprise domain deleted constructs or variants wherein the entire CH2 domain has been removed. A variety of modified antibody constructs are described in more detail below.

i. Minibodies

Figure 2:
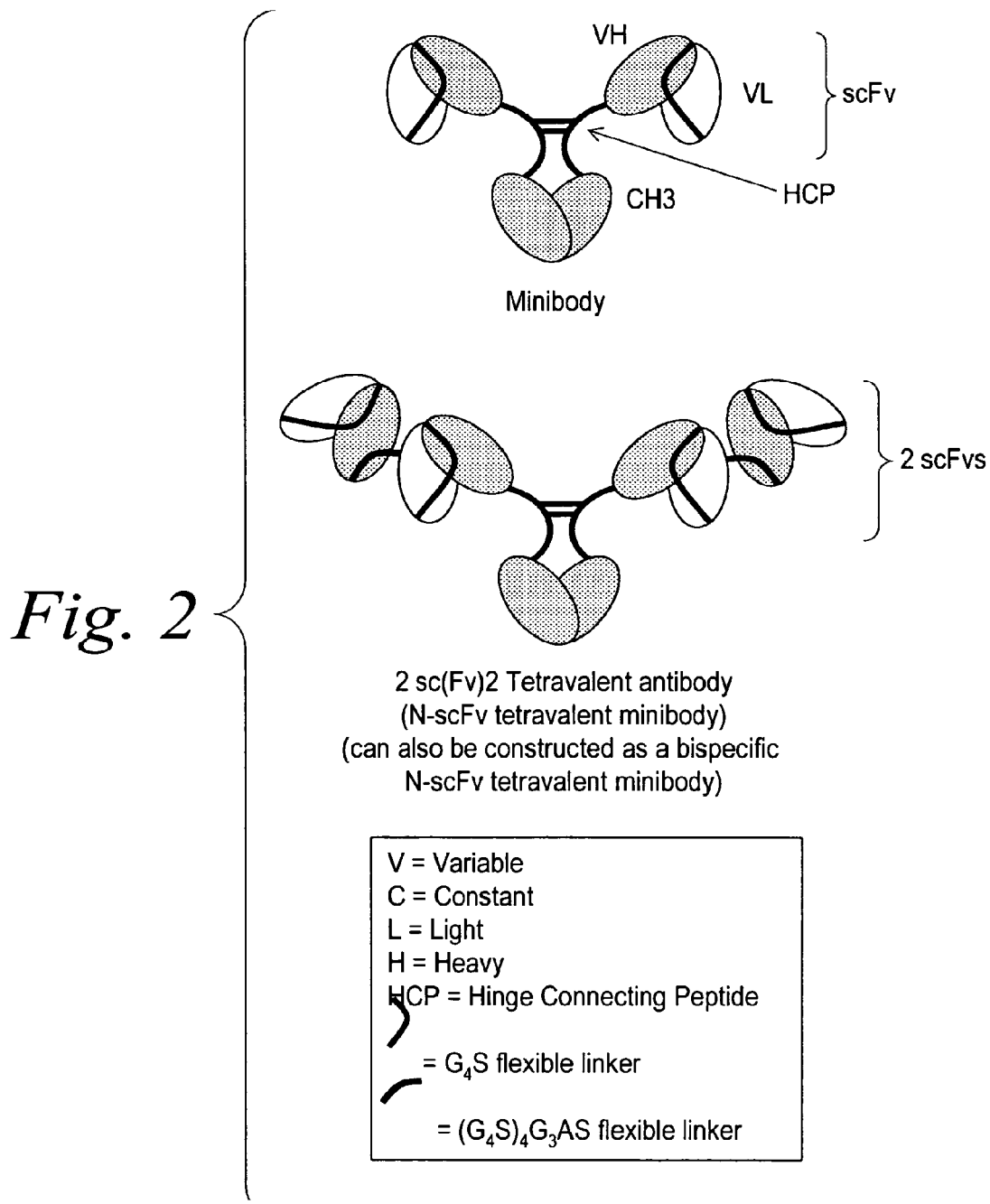
FIG. 2 shows a schematic diagram of an exemplary two chain dimeric minibody and an exemplary two chain dimeric tetravalent minibody each comprising a hinge connecting peptide (HCP). Other configurations are also possible, for example, the two chain dimeric tetravalent minibody comprising a connecting peptide (HCP) can also be constructed to be bispecific. In another embodiment, the orientation of the VH and VL domains in the scFv may be changed.
Figure 3:
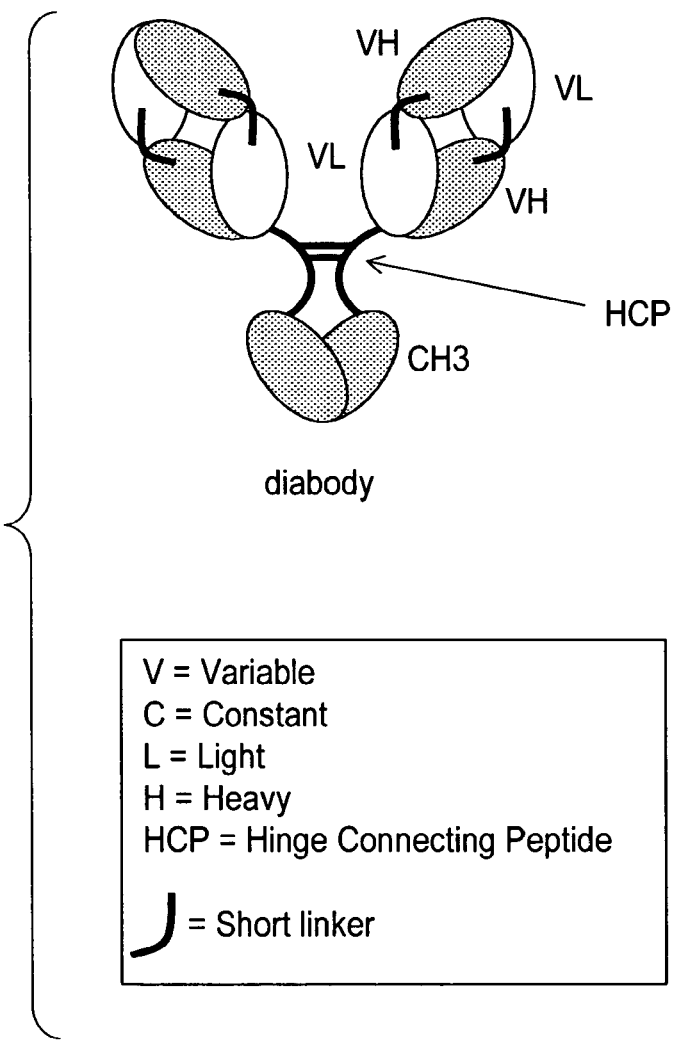
FIG. 3 shows a schematic diagram of a four chain dimeric diabody comprising a hinge connecting peptide (HCP). The four chain dimeric diabody comprising a hinge connecting peptide (HCP) can also be constructed to be bispecific. The orientation of the VH and VL domains may be changed.
Figure 5:
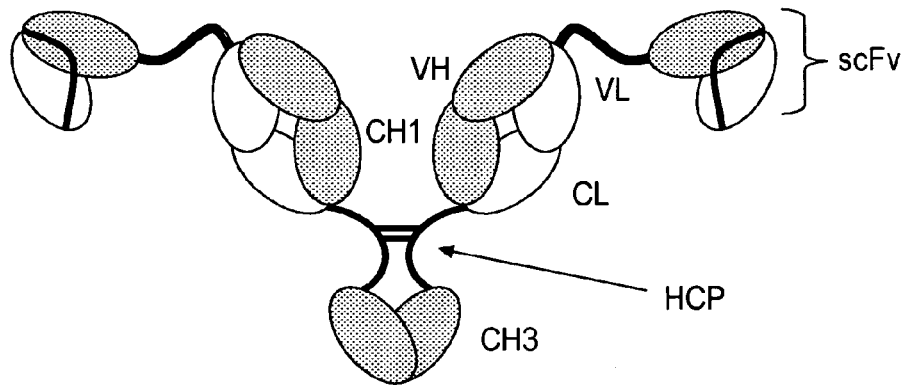
FIG. 5 shows a schematic diagram of a four chain dimeric CH2 domain deleted tetravalent ($N_L$-scFv CH2 domain deleted tetravalent) antibody comprising a hinge connecting peptide (HCP). The four chain dimeric CH2 domain deleted tetravalent antibody comprising a connecting peptide (HCP) can also be constructed to be bispecific. The orientation of the VH and VL domains in the scFv appended to the light chain may be changed.
Figure 6:
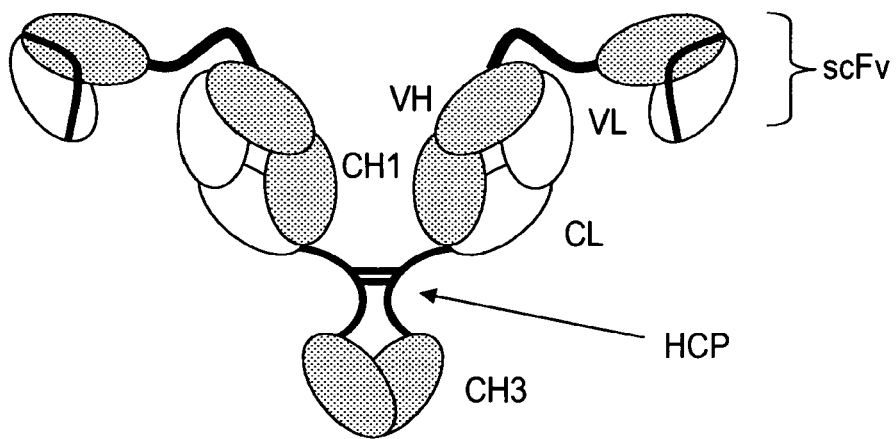
FIG. 6 shows a schematic diagram of a four chain dimeric CH2 domain deleted tetravalent ($N_H$-scFv CH2 domain deleted tetravalent) antibody comprising a hinge connecting peptide (HCP). The four chain dimeric CH2 domain deleted tetravalent antibody comprising a connecting peptide (HCP) can also be constructed to be bispecific. The orientation of the VET and VL domains in the scFv appended to the heavy chain may be changed.
Figure 7:
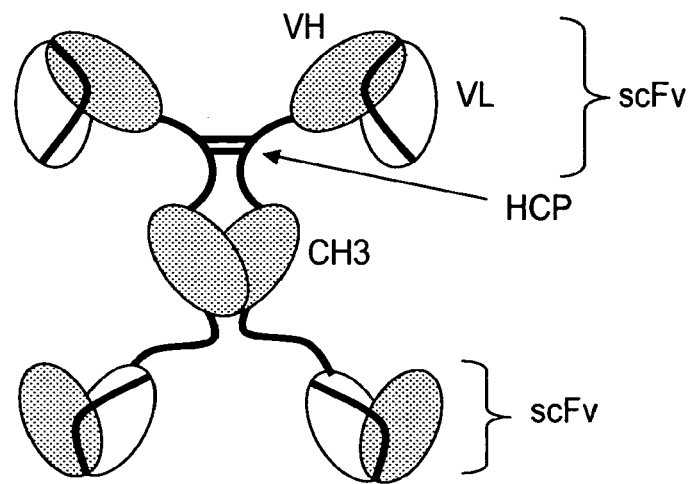
FIG. 7 shows a schematic diagram of a two chain dimeric tetravalent minibody (C-scFv tetravalent minibody) comprising a hinge connecting peptide (HCP). The two chain dimeric tetravalent minibody comprising a connecting peptide (HCP) can also be constructed to be bispecific. The orientation of the VH and VL domains in both scFvs may be changed.

In one embodiment, the modified antibodies of the invention are minibodies. Minibodies are dimeric molecules made up of two polypeptide chains each comprising an ScFv molecule (a single polypeptide comprising one or more antigen binding sites, e.g., a VL domain linked by a flexible linker to a VH domain fused to a CH3 domain via a connecting peptide. An exemplary minibody construct is shown in FIG. 2. In FIG. 2 a CH3 domain is fused at its N-terminus to a connecting peptide which is fused at its N-terminus to a VH domain which is fused via its N-terminus to a flexible linker which is fused at its N-terminus to a VL domain.

ScFv molecules can be constructed in a VH-linker-VL orientation or VL-linker-VH orientation.

The flexible hinge that links the VL and VH domains that make up the antigen binding site preferably comprises from about 10 to about 50 amino acid residues. An exemplary connecting peptide for this purpose is (Gly4Ser)$_3$ (SEQ ID NO:35) (Huston et al. 1988. Proc. Natl. Acad. Sci. USA 85:5879). Other connecting peptides are known in the art.

Methods of making single chain antibodies are well known in the art, e.g., Ho et al. 1989. Gene 77:51; Bird et al. 1988 Science 242:423; Pantoliano et al. 1991. *Biochemistry* 30:10117; Milenic et al. 1991. *Cancer Research* 51:6363; Takkinen et al. 1991. *Protein Engineering* 4:837.

Minibodies can be made by constructing an ScFv component and connecting peptide-CH3 component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis.

In one embodiment, a minibody of the invention comprises a connecting peptide. In one embodiment, the connecting peptide comprises a gly/ser linker, e.g., GGGSSGGGSGG (SEQ ID NO: 1).

In another embodiment, a tetravalent minibody can be constructed. Tetravalent minibodies can be constructed in the same manner as minibodies, except that two ScFv molecules are linked using a flexible linker, e.g., having an amino acid sequence (G4S)$_4$G3AS (SEQ ID NO: 36). An exemplary tetravalent minibody is illustrated in FIG. 2.

ii. Domain Deleted Antibodies

In another embodiment, the modified antibodies of the invention are CH2 domain deleted antibodies. Domain deleted constructs can be derived from a vector (e.g., from IDEC Pharmaceuticals, San Diego) encoding an IgG1 human constant domain (see, e.g., WO 02/060955A2 and WO02/096948A2). Essentially, the vector was engineered to delete the CH2 domain and provide a modified vector expressing a domain deleted IgG1 constant region. Genes encoding the murine variable region of the C2B8 antibody, 5E8 antibody, B3F6 antibody, or the variable region of the humanized CC49 antibody were then inserted in the modified vector and cloned. When expressed in transformed cells, these vectors provided C2B8.ΔCH2, 5E8.ΔCH2, B3F6.ΔCH2 or huCC49.ΔCH2 or respectively. These constructs exhibit a number of properties that make them particularly attractive candidates for monomeric subunits.

Besides the deletion of whole constant region domains, it will be appreciated that the antibodies of the present invention can be engineered to partially delete or substitute of a few amino acids or even a single amino acid. For example, the mutation of a single amino acid in selected areas of the $C_H2$ domain may be enough to substantially reduce Fc binding and thereby increase tumor localization. Similarly, it may be desirable to simply delete that part of one or more constant region domains that control the effector function (e.g. complement C1Q binding). Such partial deletions of the constant regions may improve selected characteristics of the antibody (serum half-life) while leaving other desirable functions associated with the subject constant region domain intact. Creation of a $C_H2$ domain deleted version can be accomplished by way of overlapping PCR mutagenesis. The gamma 1 constant domain begins with a plasmid encoded Nhe I site with is in translational reading frame with the immunoglobulin sequence. A 5' PCR primer was constructed encoding the Nhe I site as well as sequence immediately downstream. A 3' PCR primer mate was constructed such that it anneals with the 3' end to the immunoglobulin hinge region and encodes in frame the first several amino acids of the gamma 1 CH3 domain. A second PCR primer pair consisted of the reverse complement of the 3' PCR primer from the first pair (above) as the 5' primer and a 3' primer that anneals at a loci spanning the BsrG I restriction site within the $C_H3$ domain. Following each PCR amplification, the resultant products were utilized as template with the Nhe I and BsrG 15' and 3', respectively primers. The amplified product was then cloned back into N5KG1 to create the plasmid N5KG1Δ$C_H2$. This construction places the intact CH3 domain immediately downstream and in frame with the intact hinge region. A similar procedure can be used to create a domain deleted construct in which the CH3 domain is immediately downstream of a connecting peptide. For example, a domain deleted version of the C2B8 antibody was created in this manner as described in U.S. Pat. Nos. 5,648,267 and 5,736,137 each of which is incorporated herein by reference.

In one embodiment, tetravalent domain-deleted antibodies can be produced by combining a DNA sequence encoding a domain deleted antibody with a ScFv molecule. For example, in one embodiment, these sequences are combined such that the ScFv molecule is linked at its N-terminus to the CH3 domain of the domain deleted antibody via a flexible linker (e.g., a gly/ser linker such as (Gly4Ser)$_3$ (SEQ ID NO: 35).

In another embodiment a tetravalent antibody can be made by fusing an ScFv molecule to a connecting peptide, which is fused to a CH1 domain to construct an ScFv-Fab tetravalent molecule. (Coloma and Morrison. 1997. Nature Biotechnology. 15:159; WO 95/09917).

iii. Diabodies

Diabodies are similar to scFv molecules, but usually have a short (less than 10 and preferably 1-5) amino acid residue linker connecting both V-domains, such that the VL and VH domains on the same polypeptide chain can not interact. Instead, the VL and VH domain of one polypeptide chain interact with the VH and VL domain (respectively) on a second polypeptide chain (WO 02/02781). In one embodiment, a binding molecule of the invention is a diabody fused to at least one heavy chain portion. In a preferred embodiment, a binding molecule of the invention is a diabody fused to a CH3 domain.

In one embodiment a modified antibody of the invention a binding molecule comprises a tetravalent or bispecific tetravalent CH2 domain-deleted antibody with a scFv appended to the N-terminus of the light chain. In another embodiment of the invention, a binding molecule comprises a tetravalent or bispecific tetravalent CH2 domain-deleted antibody with a scFv appended to the N-terminus of the heavy chain. In one embodiment, the attachment of the scFv to the N-terminus results in reduced aggregation of the molecules as compared to molecules in which the scFv is attached at the carboxy-terminus. In one embodiment, less than about 30% aggregates are present in a composition of binding molecules produced by cells expressing a N-terminal fusion construct. In one embodiment, less than about 20% aggregates are present in a composition of binding molecules produced by cells expressing a N-terminal fusion construct. In one embodiment, less than about 10% aggregates are present in a composition of binding molecules produced by cells expressing a N-terminal fusion construct. In one embodiment, less than about 5% aggregates are present in a composition of binding molecules produced by cells expressing a N-terminal fusion construct.

Other forms of modified antibodies are also within the scope of the instant invention (e.g., WO 02/02781 A1; 5,959,083; 6,476,198 B1; US 2002/0103345 A1; WO 00/06605; Byrn et al. 1990. Nature. 344:667-70; Chamow and Ashkenazi. 1996. Trends Biotechnol. 14:52).

D. Catalytic Antibodies

In one embodiment, at least one binding specificity of a modified antibody molecule of the invention is catalytic. Catalytic binding specificities can be made using art recognized techniques (see, e.g., U.S. Pat. No. 6,590,080, U.S. Pat. No. 5,658,753). Catalytic binding specificities can work by a number of basic mechanisms similar to those identified for enzymes to stabilize the transition state, thereby reducing the free energy of activation. For example, general acid and base residues can be optimally positioned for participation in catalysis within catalytic active sites; covalent enzyme-substrate intermediates can be formed; catalytic antibodies can also be in proper orientation for reaction and increase the effective concentration of reactants by at least seven orders of magnitude (Fersht, A. R., et al., Am. Chem. Soc. 90 (1968): 5833) and thereby greatly reduce the entropy of a chemical reaction. Finally, catalytic antibodies can convert the energy obtained upon substrate binding to distort the reaction towards a structure resembling the transition state.

In one embodiment, acid or base residues can be brought into the binding site by using a complementary charged molecule as an immunogen. This technique proved successful for elicitation of antibodies with a hapten containing a positively-charged ammonium ion (Shokat, et al., Chem. Int. Ed. Engl. 27 (1988):269-271).

In another approach, antibodies can be elicited to stable compounds that resemble the size, shape, and charge of the transition state of a desired reaction (i.e., transition state analogs). See U.S. Pat. No. 4,792,446 and U.S. Pat. No. 4,963,355 which describe the use of transition state analogues to immunize animals and the production of catalytic antibodies. Both of these patents are hereby incorporated by reference. In one embodiment, such molecules can be administered as part of an immunoconjugate, e.g., with an immunogenic carrier molecule, such as KLH.

Exemplary catalytic binding specificities can have, e.g., esterase activity (involving a charged transition state whose electrostatic and shape characteristics can be mimicked by a phosphonate structure; Jacobs, et al., J. Am. Chem. Soc. 109 (1987):2174-2176; Durfor, et al., J. Am. Chem. Soc. 110 (1988):8713-8714; Tramontano, et al., J. Am. Chem. Soc. 110 (1988):2282; Pollack, et al., J. Am. Chem. Soc. 111 (1989):5961-5962); peptidase or amidase activity (Janda, et al., Science 241 (1988):1188-1191; Iverson, et al., Science 243 (1989):1184-1188; Paul, et al., Science 244 (1989):1158-1162); Claisen rearrangement (Jackson, et al., J. Am. Chem. Soc. 110 (1988):4841-4842; Hilvert, et al., Proc. Natl. Acad. Sci. USA 85 (1988):4953-4955; Hilvert, et al., J. Am. Chem. Soc. 110 (1988):5593-5594); redox reactions (Shokat, et al., Angew. Chem. Int. Ed. Engl. 27 (1989):269-271); photochemical cleavage of a thymine dimer (Cochran, et al., J. Am. Chem. Soc. 110 (1988):7888-7890); stereospecific transesterification rearrangements (Napper, et al., Science 237 (1987):1041-1043); or a bimolecular amide synthesis (Benkovic, et al., Proc. Natl. Acad. Sci. USA 85 (1988):5355-5358; Janda, et al., Science 241 (1988):1188-1191).

In another approach, conventional binding specificities can be mutated to render them catalytic.

Methods of screening for catalytic antibody activity are well known in the art (e.g., Reymond, J. L. 2002. Journal of Immunological Methods 269:125; Mouratou et al. 2002. J. of Immunological Methods. 269:147. In yet another embodiment, catalytic B cells can be selected, e.g., as described in U.S. Pat. No. 6,590,080 using a molecule can be constructed which facilitates selection of catalytic B cells.

In another embodiment, catalytic binding specificities can be developed as part of a two step process. Catalytic antibodies can be selected only if displaying the following binding features: binding both the substrate and a reactive group in such a way that the two groups are in a reactive position towards each other. Second, the selected antibodies can be chemically engineered by covalently binding a reactive group into the binding pocket of the antibody. J Immunol Methods. 2002. 269:81-98.

In one embodiment, a catalytic binding specificity is specific for a prodrug. Such a binding specificity can be used to catalyze the conversion of a prodrug into a drug which is effective in vivo. Preferably, the reaction catalyzed is one that cannot be accomplished by natural enzymes in vivo. Examples of prodrug activation by antibodies are known in the art (see, e.g., Miyashita et al. 1993. Proc. Natl. Acad. Sci. USA 90:5337).

In one embodiment, a modified antibody molecule of the invention comprises at least one binding specificity for a target cell and at least one binding specificity for a prodrug. For example, in a preferred embodiment, an modified antibody molecule of the invention comprises at least one binding specificity for a tumor cell and at least one binding specificity for a prodrug which can be converted to cytotoxic drug. In one example, a modified antibody of the invention comprises a binding specificity for a carbamate prodrug 44N,N,-bis(2-chloroethyl)1-aminophenyl-N-[(1S-(1,3-dicarboxy)propyl] carbamate and generates the corresponding cytotoxic nitrogen mustard (Wentworth et al. 1996. Proc Natl. Acad. Sci. USA. 93:799).

In one embodiment, the modified antibody is administered prior to administration of the prodrug to allow accumulation at the site of the target cell. Exemplary prodrugs are known in the art. Prodrugs can also be synthesized by incorporating a portion designed to be released by catalytic action, e.g., by sequential retro-aldol/retro-Michael reactions catalyzed by an antibody with aldolase activity. (Shabat et al. 2001. Proc. Natl. Acad. Sci. USA 98:7428). Such drug masking portions can be made, e.g., by modification of hydroxyl or thiol groups of drugs.

E. Multispecific Binding Molecules

In one embodiment, a binding molecule of the invention is multispecific, i.e., has at least one binding site that binds to a first molecule or epitope of a molecule and at least one second binding site that binds to a second molecule of epitope of a molecule.

In one embodiment, a binding molecule of the invention is bispecific. Bispecific molecules can bind to two different target sites, e.g., on the same target molecule or on different target molecules. For example, in the case of antibodies, bispecific molecules can bind to two different epitopes, e.g., on the same antigen or on two different antigens. Bispecific molecules can be used, e.g., in diagnostic and therapeutic applications. For example, they can be used to immobilize enzymes for use in immunoassays. They can also be used in diagnosis and treatment of cancer, e.g., by binding both to a tumor associated molecule and a detectable marker (e.g., a chelator which tightly binds a radionuclide. Bispecific molecules can also be used for human therapy, e.g., by directing cytotoxicity to a specific target (for example by binding to a pathogen or tumor cell and to a cytotoxic trigger molecule, such as the T cell receptor or the Fcγ receptor. Bispecific antibodies can also be used, e.g., as fibrinolytic agents or vaccine adjuvants.

Examples of bispecific binding molecules include those with at least two arms directed against tumor cell antigens; bispecific binding molecules with at least one arm directed against a tumor cell antigen and the at least one arm directed against a cytotoxic trigger molecule (such as anti-Fc.gamma.RI/anti-CD15, anti-p185.sup.HER2/Fc.gamma.RIII (CD16), anti-CD3/anti-malignant B-cell (1D10), anti-CD3/anti-p185.sup.HER2, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3); bispecific binding molecules with at least one which binds specifically to a tumor antigen and at least one which binds to a toxin (such as anti-saporin/anti-Id-1, anti-CD22/anti-saporin, anti-CD7/anti-saporin, anti-CD38/anti-saporin, anti-CEA/anti-ricin A chain, anti-interferon-.alpha.(IFN-.alpha.)/anti-hybridoma idiotype, anti-CEA/anti-vinca alkaloid); bispecific binding molecules for converting enzyme activated prodrugs (such as anti-CD30/anti-alkaline phosphatase (which catalyzes conversion of mitomycin phosphate prodrug to mitomycin alcohol)); bispecific binding molecules which can be used as fibrinolytic agents (such as anti-fibrin/anti-tissue plasminogen activator (tPA), anti-fibrin/anti-urokinase-type plasminogen activator (uPA)); bispecific binding molecules for targeting immune complexes to cell surface receptors (such as anti-low density lipoprotein (LDL)/anti-Fc receptor (e.g. Fc.gamma.RI, Fc.gamma.RII or Fc.gamma.RIII)); bispecific binding molecules for use in therapy of infectious diseases (such as anti-CD3/anti-herpes simplex virus (HSV), anti-T-cell receptor:CD3 complex/anti-influenza, anti-Fc-.gamma.R/anti-HIV; bispecific binding molecules for tumor detection in vitro or in vivo such as anti-CEA/anti-EOTUBE, anti-CEA/anti-DPTA, anti-p185HER2/anti-1-hapten); bispecific binding molecules as vaccine adjuvants (see Fanger et al., supra); and bispecific binding molecules as diagnostic tools (such as anti-rabbit IgG/anti-ferritin, anti-horse radish peroxidase (HRP)/anti-hormone, anti-somatostatin/anti-substance P, anti-HRP/anti-FITC, anti-CEA/anti-.beta.-galactosidase (see Nolan et al., supra)). Examples of trispecific antibodies include anti-CD3/anti-CD4/anti-CD37, anti-CD3/anti-CD5/anti-CD37 and anti-CD3/anti-CD8/anti-CD37.

In a preferred embodiment, a bispecific molecule of the invention binds to CRIPTO-I.

Bispecific molecules may be monovalent for each specificity or be multivalent for each specificity. For example, an antibody molecule or fusion protein may comprise one binding site that reacts with a first target molecule and one binding site that reacts with a second target molecule or it may comprise two binding sites that react with a first target molecule and two binding sites that react with a second target molecule. Methods of producing bispecific molecules are well known in the art. For example, recombinant technology can be used to produce bispecific molecules, e.g., diabodies, single-chain diabodies, tandem scFvs, etc. Exemplary techniques for producing bispecific molecules are known in the art (e.g., Kontermann et al. Methods in Molecular Biology Vol. 248: Antibody Engineering: Methods and Protocols. Pp 227-242 US 2003/0207346 A1 and the references cited therein). In one embodiment, a multimeric bispecific molecules are prepared using methods such as those described e.g., in US 2003/0207346 A1 or U.S. Pat. No. 5,821,333, or US2004/0058400.

As used herein the phrase "multispecific fusion protein" designates fusion proteins (as hereinabove defined) having at least two binding specificities (i.e. combining two or more binding domains of a ligand or receptor). Multispecific fusion proteins can be assembled as heterodimers, heterotrimers or heterotetramers, essentially as disclosed in WO 89/02922 (published Apr. 6, 1989), in EP 314, 317 (published May 3, 1989), and in U.S. Pat. No. 5,116,964 issued May 2, 1992. Preferred multispecific fusion proteins are bispecific. Examples of bispecific fusion proteins include CD4-IgG/TNFreceptor-IgG and CD4-IgG/L-selectin-IgG. The last mentioned molecule combines the lymph node binding function of the lymphocyte homing receptor (LHR, L-selectin), and the HIV binding function of CD4, and finds potential application in the prevention or treatment of HIV infection, related conditions, or as a diagnostic.

Target binding sites for the multispecific binding molecules of the invention can readily be selected by one of ordinary skill in the art. While not limiting in any way, exemplary binding sites include one or more epitopes of a tumor antigen. Other exemplary target molecules include one or more epitopes of, e.g., heparin sulfate, growth factors or their receptors (e.g., epidermal growth factor receptor, insulin-like growth factor receptor, hepatocyte growth factor (HGF/SF) receptor, MORE (See, e.g., Cao et al. Proc. Natl. Acad. Sci. 2001. 98:7443; Lu et al. 2004. J. Biol. Chem. 279:2856).

In another embodiment, the invention pertains to bispecific molecules, e.g., antibodies, which incorporate at least one binding site that binds to a known target and at least one binding site which recognizes an unknown target (for example, in one embodiment, the bispecific molecule incorporates binding sites selected from a semi-synthetic antibody phage display library).

In one embodiment of the invention, one of ordinary skill in the art could start with a single chain antibody of known specificity and build a Fab library using techniques known in the art or, alternatively, the skilled artisan could start with an Fab fragment of known specificity and build a single chain library using techniques known in the art. It is known in the art that libraries from nonimmunized sources and prepared by synthetic recombination of V-gene sequences (preferably recombination of VH with, DH and JH, and VL with JL sequences) can be used to isolate antibodies to any antigen. For example, patent application WO92/01047 teaches that antibody fragments can be displayed on the surface of bacteriophage and that they will bind antigen. Antibody fragments (e.g., Fab, Fv, ScFv and VH) can be directly selected using this characteristic. Other methods known in the art include those taught, e.g., in U.S. Pat. Nos. 5,698,426; 6,291,159; 5,658,727; 5,667,988; and 5,969,108.

In another embodiment, scFv which recognize a known target can be dimerized with scFv isolated from a semi-synthetic human phage antibody display library. (see, e.g., Kruif and Logtenberg 1996. J. Biol. Chem. 271:7630).

In one embodiment, the subject bispecific molecule is expressed in any expression system used to express antibody molecules, for example mammalian cells, yeast such as Pichia, E. coli, Baccoulovirus, etc. In one embodiment, the subject bispecific molecule is expressed in the NEOSPLA vector system (see, e.g., U.S. Pat. No. 6,159,730). This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence.

In one embodiment, the subject bispecific molecules comprise a synthetic connecting peptide.

These bispecific molecules have one or more binding sites for a known target and express a library at one or more binding sites. Such bispecific molecules can be used, e.g., to identify molecules in close proximity to or associated with the known target. For example, the skilled artisan could use the subject bispecific molecules in an assay to select for those that induce a particular response, e.g., apoptosis or cellular activation, using screening methods well known in the art. The bispecific molecule identified as producing the response screened for can then be identified and its specificity determined. Using such methods it is possible to identify molecules in close association with particular targets of interest, e.g., T cell markers or other signaling molecules (such as CRIPTO-I, death domain molecules, or molecules involved in apoptosis). The proximity of the known target and the molecule newly identified as a "nearest neighbor" can be confirmed using immunoprecipitation or other techniques known to those of skill in the art. Using these methods it is possible to identify molecules as targets for modulating a particular cellular response.

In one embodiment, a polypeptide molecule of the invention comprises an amino acid sequence encoded by a nucleic acid molecule comprising a nucleic acid sequence shown in FIG. 8A (SEQ ID NO:16), FIG. 8B (SEQ ID NO:17), FIG. 8C (SEQ ID NO:18), FIG. 10A (SEQ ID NO:22), FIG. 10B (SEQ ID NO:23). In another embodiment, a nucleic acid molecule of the invention comprises a nucleotide sequence shown in FIG. 8A (SEQ ID NO:16), FIG. 8B (SEQ ID NO:17), FIG. 8C (SEQ ID NO:18), FIG. 10A (SEQ ID NO:22), FIG. 10B (SEQ ID NO:23).

In another embodiment, a polypeptide of the invention comprises an amino acid sequence shown in FIG. 9A (SEQ ID NO:19), FIG. 9B (SEQ ID NO:20), FIG. 9C (SEQ ID NO:21), FIG. 11A (SEQ ID NO:24), or FIG. 11B (SEQ ID NO:25).

In another embodiment, a polypeptide of the invention is encoded by a nucleic acid molecule comprising the nucleotide sequence shown in FIG. 12A (SEQ ID NO:26), FIG. 12B (SEQ ID NO:27), FIG. 14 (SEQ ID NO:30), or FIG. 15 (SEQ ID NO:31). In another embodiment, a nucleic acid molecule of the invention comprises a nucleotide sequence shown in FIG. 12A (SEQ ID NO:26), FIG. 12B (SEQ ID NO:27), FIG. 14 (SEQ ID NO:30), or FIG. 15 (SEQ ID NO:31). In one embodiment, a polypeptide molecule of the invention comprises an amino acid sequence shown in FIG. 13A (SEQ ID NO:28), FIG. 13B (SEQ ID NO:29), FIG. 16 (SEQ ID NO:32), or FIG. 17 (SEQ ID NO:33).

The other nucleic acid and amino acid sequences disclosed herein in the sequence listing and Figures are also embraced by the invention.

B. Expression of Polypeptides

Following manipulation of the isolated genetic material to provide polypeptides of the invention as set forth above, the genes are typically inserted in an expression vector for introduction into host cells that may be used to produce the desired quantity of modified antibody that, in turn, provides the claimed polypeptides.

The term "vector" or "expression vector" is used herein for the purposes of the specification and claims, to mean vectors used in accordance with the present invention as a vehicle for introducing into and expressing a desired gene in a cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements which are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Exemplary vectors include those taught in U.S. Pat. No. 6,159,730 or 6,413,777 or US 2003 0157641 A1). Additionally, cells which have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation.

In one embodiment, an inducible expression system can be employed.

Additional elements may also be needed for optimal synthesis of mRNA. These elements may include signal sequences, splice signals, as well as transcriptional promoters, enhancers, and termination signals.

In one embodiment, a secretion signal, e.g., any one of several well characterized bacterial leader peptides (e.g., pelB, phoA, or ompA), can be fused in-frame to the N terminus of a polypeptide of the invention to obtain optimal secretion of the polypeptide. (Lei et al. 1988 Nature 331:543; Better et al. Science 1988. 240:1041; Mullinax et al., 1990. Proc. Natl. Acad. Sci. USA 87:8095).

In one embodiment, a vector can be used which comprises a nucleic acid sequence encoding a peptide linker. In another embodiment, it might be desirable to first assemble the desired coding sequences (e.g., secretion signal, VL, linker peptide, VH, etc.) into a single sequence, for example, by PCR amplification using overlapping primers, followed by ligation into a plasmid or other vector.

In particularly preferred embodiments the cloned variable region genes are inserted into an expression vector along with the heavy and light chain constant region genes (preferably human) modified as discussed above. Preferably, this is effected using a proprietary expression vector of IDEC, Inc., referred to as NEOSPLA see U.S. Pat. No. 6,159,730. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. As seen in the examples below, this vector has been found to result in very high level expression of antibodies upon incorporation of variable and constant region genes, transfection in CHO cells, followed by selection in G418 containing medium and methotrexate amplification. Vector systems are also taught in U.S. Pat. Nos. 5,736,137 and 5,658,570, each of which is incorporated by reference in its entirety herein. This system provides for high expression levels, e.g., >30 pg/cell/day. Other exemplary vector systems are disclosed e.g., in U.S. Pat. No. 6,413,777.

In other preferred embodiments the polypeptides of the invention of the instant invention may be expressed using polycistronic constructs such as those disclosed in U.S. provisional application No. 60/331,481 filed Nov. 16, 2001 and incorporated herein in its entirety. In these novel expression systems, multiple gene products of interest such as heavy and light chains of antibodies may be produced from a single polycistronic construct. These systems advantageously use an internal ribosome entry site (IRES) to provide relatively high levels of polypeptides of the invention in eukaryotic host cells. Compatible IRES sequences are disclosed in U.S. Pat. No. 6,193,980 which is also incorporated herein. Those skilled in the art will appreciate that such expression systems may be used to effectively produce the full range of polypeptides disclosed in the instant application.

More generally, once the vector or DNA sequence encoding a monomeric subunit of the polypeptide (e.g. a modified antibody) has been prepared, the expression vector may be introduced into an appropriate host cell. That is, the host cells may be transformed. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

As used herein, the term "transformation" shall be used in a broad sense to refer to any introduction of DNA into a recipient host cell that changes the genotype and consequently results in a change in the recipient cell.

Along those same lines, "host cells" refers to cells that have been transformed with vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

The host cell line used for protein expression is most preferably of mammalian origin; those skilled in the art are credited with ability to preferentially determine particular host cell lines which are best suited for the desired gene product to be expressed therein. Exemplary host cell lines include, but are not limited to, DG44 and DUXB11 (Chinese Hamster Ovary lines, DHFR minus), BELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). CHO cells are particularly preferred. Host cell lines are typically available from commercial services, the American Tissue Culture Collection or from published literature.

In another embodiment, a host cell is a prokaryotic cell, e.g., a strain which allows the formation of disulfide bonds (Derman, A I, et al. 1993. Science. 262:1744; Bessette, P H. Et al. 1999. Proc. Natl. Acad. Sci. USA 96:13703).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a modified hinge region polypeptide or prior to or subsequent to the HIC chromatography step described herein.

Genes encoding the polypeptide of the invention can also be expressed non-mammalian cells such as bacteria or yeast or plant cells. In this regard it will be appreciated that various unicellular non-mammalian microorganisms such as bacteria can also be transformed; i.e. those capable of being grown in cultures or fermentation. Bacteria, which are susceptible to transformation, include members of the enterobacteriaceae, such as strains of *Escherichia coli* or *Salmonella*; Bacillaceae, such as *Bacillus subtilis; Pneumococcus; Streptococcus*, and *Haemophilus influenzae*. It will further be appreciated that, when expressed in bacteria, the polypeptides typically become part of inclusion bodies. The polypeptides must be isolated, purified and then assembled into functional molecules. Where tetravalent forms of antibodies are desired, the subunits will then self-assemble into tetravalent antibodies (WO02/096948A2).

In addition to prokaryates, eukaryotic microbes may also be used. *Saccharomyces cerevisiae*, or common baker's yeast, is the most commonly used among eukaryotic microorganisms although a number of other strains are commonly available. For expression in *Saccharomyces*, the plasmid YRp7, for example, (Stinchcomb et al., Nature, 282:39 (1979); Kingsman et al., Gene, 7:141 (1979); Tschemper et al., Gene, 10:157 (1980)) is commonly used. This plasmid already contains the TRP1 gene which provides a selection marker for a mutant strain of yeast lacking the ability to grow in tryptophan, for example ATCC No. 44076 or PEP4-1 (Jones, Genetics, 85:12 (1977)). The presence of the trp1 lesion as a characteristic of the yeast host cell genome then provides an effective environment for detecting transformation by growth in the absence of tryptophan.

IV. SEPARATION OF POLYPEPTIDES COMPRISING AT LEAST ONE INTERCHAIN DISULFIDE LINKAGE FROM THOSE LACKING INTERCHAIN DISULFIDE LINKAGES

In one aspect, the invention pertains to separation of molecules having two heavy chain portions from a mixture, where a fraction of the molecules are present in a form in which the two heavy chain portions are linked via at least one interchain disulfide linkage and a fraction of the molecules comprise heavy chain portions that are not linked via at least one disulfide linkage by hydrophobic interaction chromatography.

Hydrophobic interaction chromatography was first developed following the observation that proteins could be retained on affinity gels which comprised hydrocarbon spacer arms but lacked the affinity ligand. Elution from HIC supports can be effected by alterations in solvent, pH, ionic strength, or by the addition of chaotropic agents or organic modifiers, such as ethylene or propylene glycol. A description of the general principles of hydrophobic interaction chromatography can be found e.g., in U.S. Pat. No. 3,917,527 and in U.S. Pat. No. 4,000,098. HIC in the context of high performance liquid chromatography (HPLC) has been used to separate antibody fragments lacking heavy chain portions (e.g., F(ab')$_2$) from intact antibody molecules in a single step protocol. (Morimoto, K. et al., L Biochem. Biophys. Meth. 24: 107 (1992)).

The separation method of the invention can be performed on an unpurified population of polypeptides (e.g., culture supernatants or preparations or preparations of polypeptides isolated from prokaryotic inclusion bodies). Alternatively, the instant separation methods can be used on polypeptide mixtures obtained after one or more initial purification steps, e.g., after a preparation comprising forms A and B has been eluted from an affinity matrix.

In one embodiment, the binding molecules subjected to HIC chromatography comprise a connecting peptide of the invention.

In a preferred embodiment, HIC can be applied to mixtures that have been partially purified by other protein purification procedures. The term "partially purified" as used herein includes a protein preparation in which the protein of interest is present in at least 5% by weight, more preferably at least 10% and most preferably at least 45%. Initial or subsequent purification steps can be used to remove, e.g., immunoglobulin aggregates, misfolded species, host cell protein, residue material from preceding chromatographic steps (such as Protein A when employed). In one embodiment, HIC can be performed on polypeptides comprising a connecting peptide of the invention. Accordingly, the application of HIC can also be appreciated in the context of an overall purification protocol. Exemplary purification steps that can be used prior to or subsequent to HIC include: affinity chromatography (for example, PROSEP-A® (BioProces sing Ltd., U.K.) which consists of Protein A covalently coupled to controlled pore glass or Protein A SEPHAROSE® Fast Flow (Pharmacia) or TOYOPEARL 650M Protein A (TosoHaas)). Protein A is preferred for human γ1, γ 2, or γ 4 heavy chains and protein G for mouse isotypes. Bakerbond ABXtm resin can be used if the molecule comprises a CH3 domain. In addition or alternatively, ion exchange chromatography may be employed. In this regard various anionic or cationic substituents. may be attached to matrices in order to form anionic or cationic supports for chromatography. Anionic exchange substituents include diethylaminoethyl(DEAE), quaternary aminoethyl (QAE) and quaternary amine (Q) groups. Cationic exchange substituents. include carboxymethyl (CM), sulfoethyl (SE), sulfopropyl (SP), phosphate (P) and sulfonate (S). Cellulose ion exchange resins such as DE23, DE32, DE52, CM-23, CM-32 and CM-52 are available from Whatman Ltd. Maidstone, Kent, U. K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow are all available from Pharmacia AB. Further, both DEAF and CM derivitized ethylene glycol-methacrylate copolymer such as TOYOPEARL DEAE-650S or M and TOYOPEARL CM-650S or M are available from Toso Haas Co., Philadelphia, Pa. Because elution from ion exchange supports usually involves addition of salt and because HIC is enhanced under increased salt concentrations, the introduction of a HIC step following an ionic exchange chromatographic step or other salt mediated purification step is preferred. Additional purification protocols may be added including but not necessarily limited to: further ionic exchange chromatography, size exclusion chromatography, viral inactivation, concentration and freeze drying, hydroxylapatite chromatography, gel electrophoresis, dialysis, ethanol precipitation, reverse phase HPLC, chromatography on silica, chromatography on heparin SEQHAROSE™, chromatofocusing, or ammonium sulfate precipitation.

Prior to purification using the subject methods, the composition comprising the mixture of polypeptides to be separated will preferably be placed in a buffer of acidic or approximately neutral pH. This can be done, for example, by adding concentrated buffer, resuspending the sample in the buffer, exchanging the buffer (e.g., using dialysis or ultrafiltration). Alternatively, the pH of the sample buffer can simply be adjusted to be within the desired range.

Hydrophobic interactions are strongest at high ionic strength, therefore, this form of separation is conveniently performed following salt precipitations or ion exchange procedures. Adsorption of the proteins to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++}$<; $Ca^{++}$<; $Mg^{++}$<; $Li^+$<; $Cs^+$<; $Na^+$<; $K^+$<; $Rb^+$<; $NH_4^+$, while anions may be ranked in terms of increasing chaotropic effect as $PO^{---}$<; $SO_4^{--}$<; $CH_3COO^-$<; $Cl^-$<; $Br^-$<; $NO_3^-$<; $ClO_4^-$<; $I^-$<; $SCN^-$ In general, Na, K or $NH_4$ sulfates effectively promote ligand-protein interaction in HIC. Salts may be formulated that influence the strength of the interaction as given by the following relationship: $(NH_4)_2SO_4>$; $Na_2SO_4>$; $NaCl>$; $NH_4Cl>$; $NaBr>$; $NaSCN$. In general, salt concentrations of between about 0.75 and about 2M ammonium sulfate or between about 1 and 4M NaCl are useful.

A number of chromatographic supports may be employed in the preparation of HIC columns, the most extensively used are agarose, silica and organic polymer or co-polymer resins. The hydrophobic interaction material is generally a base matrix (e.g., a hydrophilic carbohydrate (such as cross-linked agarose) or synthetic copolymer material) to which hydrophobic ligands (e.g., alkyl or aryl groups) are coupled. The preferred HIC material comprises an agarose resin substituted with phenyl groups. Exemplary HIC material includes: phenyl SEPHAROSE™, FAST FLOW with low or high substitution (Pharmacia LKB Biotechnology, AB, Sweden); phenyl SEPHAROSE™ High Performance column; phenyl or butyl-SEPHAROSE® CL-4B, butyl-SEPHAROSE® FF, octyl-SEPHAROSE® FF and phenyl-SEPHAROSE® FF (Pharmacia LKB Biotechnology AB, Sweden); Fractogel™ EMD Propyl or FRACTOGEL™ EMC Phenyl columns (E. Merck, Germany); MACROPREP™ Methyl or MACROPREP™ t-Butyl Supports (Bio-Rad, California); WP HI-Propyl (C3)™ column (J. T. Baker, New Jersey). Exemplary HIC materials are also available from Tosoh Corporation, Tokyo, Japan under the product names TOYOPEARL ether 650, phenyl 650, butyl 650 (Fractogel), ether-5PW-HR, or phenyl-5PW-HR; Miles-Yeda, Rehovot, Israel under the product name alkyl-agarose, wherein the alkyl group contains from 2-10 carbon atoms, and J. T. Baker, Phillipsburg, N.J. under the product name Bakerbond WP-HI-propyl. It is also possible to prepare the desired HIC column using conventional chemistry. (Sa: for example, Er-el. Z. gl all, Biochem. Biophys. Res. Comm. 49:383 (1972) or Ulbrich, V. rd gL Coll. Czech. Chem. Commum. 9:1466 (1964)).

The choice of a particular gel can be determined by the skilled artisan. In general the strength of the interaction of the protein and the HIC ligand increases with the chain length of the alkyl ligands but ligands having from about 4 to about 8 carbon atoms are suitable for most separations. A phenyl group has about the same hydrophobicity as a pentyl group, although the selectivity can be different owing to the possibility of pi-pi orbital interaction with aromatic groups on the protein. Selectively may also be affected by the chemistry of the supporting resin.

Ligand density is an important parameter in that it influences not only the strength of the interaction but the capacity of the column as well. The ligand density of the commercially available phenyl or octyl phenyl gels is on the order of 40 pmoles/ml gel bed. Gel capacity is a function of the particular protein in question as well as pH, temperature and salt type and concentration but generally can be expected to fall in the range of 3-20 mg/ml of gel.

In general, a decrease in temperature decreases the interaction with HIC material. However, any benefit that would accrue by increasing the temperature must also be weighed against adverse effects such an increase may have on the stability of the protein.

In one embodiment, the polypeptides of the invention can be eluted isocratically. In isocratic elution, all compounds begin migration through the column at onset. However, each migrates at a different rate, resulting in faster or slower elution rate. For example, as described in the instant examples, form A can be eluted with the flow through of the column.

In another embodiment, one or more polypeptides of the invention can be bound to the column and eluted, e.g., using stepwise elution or gradient elution. Elution, whether stepwise or in the form of a gradient, can be accomplished in a variety of ways: (a) by changing the salt concentration, (b) by changing the polarity of the solvent or (c) by adding detergents. By decreasing salt concentration adsorbed proteins are eluted in order of increasing hydrophobicity. Changes in polarity may be affected by additions of solvents such as ethylene or propylene glycol or (iso)propanol, thereby decreasing the strength of the hydrophobic interactions. Detergents function as displacers of proteins and have been used primarily in connection with the purification of membrane proteins In performing the separation, the polypeptide mixture can be contacted with the HIC material e.g., using a batch purification technique or using a column. Prior to HIC purification it may be desirable to remove any chaotropic agents or very hydrophobic substances, e.g., by passing the mixture through a precolumn.

For example, for batch purification, HIC material is prepared in or equilibrated to the desired starting buffer. A slurry of the HIC material is obtained. The polypeptide solution is contacted with the slurry to adsorb at least one of the polypeptides to be separated to the HIC material. The solution containing the polypeptides that do not bind to the HIC material is separated from the slurry, e.g., by allowing the slurry to settle and removing the supernatant. The slurry can be subjected to one or more washing steps. If desired, the slurry can be contacted with a solution of lower conductivity to desorb polypeptides that have bound to the HIC material. In order to elute bound polypeptides, the salt concentration can be decreased.

In one embodiment, the HIC material can be packed in a column. A mixture comprising the polypeptides to be separated can be applied to the column allowing at least one of the polypeptides to be separated to adsorb to the column. The polypeptides that do not adsorb to the column pass through and can be collected. In order to elute bound polypeptides, the salt concentration can be decreased, e.g., in a step-wise fashion or using a salt gradient.

Since form B is more hydrophobic than form A, it adsorbs irreversibly to the stationary phase using approximately 0.7 M (e.g., 0.73M) Ammonium Sulfate/20 mM Sodium Phosphate, pH 4.0 to pH 8.0 as the mobile phase. Form A binds to a lesser extent to the stationary phase under these conditions and is therefore eluted isocratically, i.e. it leaves the column with the flowthrough fraction. Subsequent to the isocratic elution of form A, omitting Ammonium sulfate from the mobile phase desorbs form B.

In an exemplary purification scheme, the HIC material is equilibrated in a buffer comprising a salt concentration yielding a conductivity of from between about 160 to about 110, preferably from between about 140 to about 115, even more preferably from between about 130 or about 120 to about 117 mS/cm. For example, an exemplary starting solution comprises a salt concentration of approximately 1M to 0.7M, e.g., 1M to 0.7M ammonium sulfate. In a preferred embodiment, the solution comprising the mixture of polypeptides to be separated is also brought to the same, or approximately the same conductivity (e.g., using a concentrated stock solution of salt). Under these conditions, Form A is eluted from the column at a conductivity of about 120 mS/cm. In order to elute Form B, a stepwise or linear gradient of reducing ammonium sulfate content can be applied to the column. Form B elutes at a conductivity of approximately 115 to approximately 100 mS/cm.

In one embodiment, the subject purification method yields a composition comprising polypeptide molecules having at least two target binding sites and two heavy chain portions, wherein the heavy chain portions lack CH2 domains and wherein greater than about 50% of the molecules are present in a form in which the two heavy chain portions are linked via at least one interchain disulfide linkage. In another embodiment, greater than about 60% of the molecules are present in a form in which the two heavy chain portions are linked via at least one interchain disulfide linkage. In another embodiment, greater than about 70% of the molecules are present in a form in which the two heavy chain portions are linked via at least one interchain disulfide linkage. In another embodiment, greater than about 80% of the molecules are present in a form in which the two heavy chain portions are linked via at least one interchain disulfide linkage. In another embodiment, greater than about 90% of the molecules are present in a form in which the two heavy chain portions are linked via at least one interchain disulfide linkage.

In one embodiment, the subject purification method yields a composition comprising recombinant polypeptide molecules having at least two target binding sites and two heavy chain portions, wherein greater than about 99% of the molecules are present in a form in which the two heavy chain portions are linked via at least one interchain disulfide linkage.

In one embodiment, the subject purification method yields a composition comprising polypeptide molecules having at least two target binding sites and two heavy chain portions, wherein greater than about 95% of the molecules are present in a form in which the two heavy chain portions are linked via at least one interchain disulfide linkage, and wherein the heavy chain portions of the polypeptides are derived from an antibody of the IgG4 isotype.

In one embodiment, the subject purification method yields a composition comprising polypeptide molecules having two light chain portions and two heavy chain portions, wherein the heavy chain portions lack CH2 domains and wherein greater than about 80% of the molecules are present in a form in which the two heavy chain portions are not linked via at least one interchain disulfide linkage.

In another aspect, the instant invention also provides methods for monitoring the results of purification and/or preferential biosynthesis comprising measuring the relative amounts of Form A and Form B in a composition. Form A and Form B can be measured, e.g., as described herein using non-reducing SDS polyacrylamide gel electrophoresis or mass spectrometry.

V. LABELING OR CONJUGATION OF POLYPEPTIDES

The polypeptide molecules of the present invention may be used in non-conjugated form or may conjugated to at least one of a variety of molecules, e.g., to facilitate antigen detection or for imaging or therapy of the patient. The polypeptides of the invention can be labeled or conjugated either before or after purification, when purification is performed. In particular, the polypeptides of the present invention may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or antibodies wherein the resulting molecule binds to both the neoplastic cell and an effector cell such as a T cell), or PEG. In another embodiment, a polypeptide of the invention can be conjugated to a molecule that decreases vascularization of tumors. In other embodiments, the disclosed compositions may comprise polypeptides of the invention coupled to drugs or prodrugs. Still other embodiments of the present invention comprise the use of polypeptides of the invention conjugated to specific biotoxins or their cytotoxic fragments such as ricin, gelonin, pseudomonas exotoxin or diphtheria toxin. The selection of which conjugated or unconjugated polypeptide to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that, in previous studies, anti-tumor antibodies labeled with isotopes have been used successfully to destroy cells in solid tumors as well as lymphomas/leukemias in animal models, and in some cases in humans. Exemplary radioisotopes include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

With respect to the use of radiolabeled conjugates in conjunction with the present invention, polypeptides of the invention may be directly labeled (such as through iodination) or may be labeled indirectly through the use of a chelating agent. As used herein, the phrases "indirect labeling" and "indirect labeling approach" both mean that a chelating agent is covalently attached to a molecule and at least one radionuclide is associated with the chelating agent. Such chelating agents are typically referred to as bifunctional chelating agents as they bind both the polypeptide and the radioisotope. Particularly preferred chelating agents comprise 1-isothiocymatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

As used herein, the phrases "direct labeling" and "direct labeling approach" both mean that a radionuclide is covalently attached directly to a polypeptide (typically via an amino acid residue). More specifically, these linking technologies include random labeling and site-directed labeling. In the latter case, the labeling is directed at specific sites on the polypeptide, such as the N-linked sugar residues present only on the Fc portion of the conjugates. Further, various direct labeling techniques and protocols are compatible with the instant invention. For example, Technetium-99m labeled polypeptides may be prepared by ligand exchange processes, by reducing pertechnate ($TcO_4^-$) with stannous ion solution, chelating the reduced technetium onto a Sephadex column and applying the polypeptides to this column, or by batch labeling techniques, e.g. by incubating pertechnate, a reducing agent such as $SnCl_2$, a buffer solution such as a sodium-potassium phthalate-solution, and the molecules. In any event, preferred radionuclides for directly labeling polypeptides are well known in the art and a particularly preferred radionuclide for direct labeling is $^{131}$I covalently attached via tyrosine residues. Polypeptides according to the invention may be derived, for example, with radioactive sodium or potassium iodide and a chemical oxidizing agent, such as sodium hypochlorite, chloramine T or the like, or an enzymatic oxidizing agent, such as lactoperoxidase, glucose oxidase and glucose. However, for the purposes of the present invention, the indirect labeling approach is particularly preferred. Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, 5,434,287 and 5,124,471 of Gansow also relate to polysubstituted DTPA chelates. These patents are incorporated herein in their entirety. Other examples of compatible metal chelators are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like. Cyclohexyl-DTPA or CHX-DTPA is particularly preferred. Still other compatible chelators, including those yet to be discovered, may easily be discerned by a skilled artisan and are clearly within the scope of the present invention.

Compatible chelators, including the specific bifunctional chelator used to facilitate chelation in co-pending application Ser. Nos. 08/475,813, 08/475,815 and 08/478,967, are preferably selected to provide high affinity for trivalent metals, exhibit increased tumor-to-non-tumor ratios and decreased bone uptake as well as greater in vivo retention of radionuclide at target sites, i.e., B-cell lymphoma tumor sites. However, other bifunctional chelators that may or may not possess all of these characteristics are known in the art and may also be beneficial in tumor therapy. It will also be appreciated that, in accordance with the teachings herein, polypeptides may be conjugated to different radiolabels for diagnostic and therapeutic purposes. To this end the aforementioned co-pending applications, herein incorporated by reference in their entirety, disclose radiolabeled therapeutic conjugates for diagnostic "imaging" of tumors before administration of therapeutic molecule. "In2B8" conjugate comprises a murine monoclonal antibody, 2B8, specific to human CD20 antigen, that is attached to $^{111}$In via a bifunctional chelator, i.e., MX-DTPA (diethylenetriaminepentaacetic acid), which comprises a 1:1 mixture of 1-isothiocyanatobenzyl-3-methyl-DTPA and 1-methyl-3-isothiocyanatobenzyl-DTPA. $^{111}$In is particularly preferred as a diagnostic radionuclide because between about 1 to about 10 mCi can be safely administered without detectable toxicity; and the imaging data is generally predictive of subsequent $^{90}$Y-labeled antibody distribution. Most imaging studies utilize 5 mCi $^{111}$In-labeled antibody, because this dose is both safe and has increased imaging efficiency compared with lower doses, with optimal imaging occurring at three to six days after antibody administration. See, for example, Murray, J. Nuc. Med. 26: 3328 (1985) and Carraguillo et al., J. Nuc. Med. 26: 67 (1985).

As indicated above, a variety of radionuclides are applicable to the present invention and those skilled in the can readily determine which radionuclide is most appropriate under various circumstances. For example, $^{131}$I is a well known radionuclide used for targeted immunotherapy. However, the clinical usefulness of $^{131}$I can be limited by several factors including: eight-day physical half-life; dehalogenation of iodinated antibody both in the blood and at tumor sites; and emission characteristics (e.g., large gamma component) which can be suboptimal for localized dose deposition in tumor. With the advent of superior chelating agents, the opportunity for attaching metal chelating groups to proteins has increased the opportunities to utilize other radionuclides such as $^{111}$In and $^{90}$Y. $^{90}$Y provides several benefits for utilization in radioimmunotherapeutic applications: the 64 hour half-life of $^{90}$Y is long enough to allow accumulation by tumor and, unlike e.g., $^{131}$I, $^{90}$Y is a pure beta emitter of high energy with no accompanying gamma irradiation in its decay, with a range in tissue of 100 to 1,000 cell diameters. Furthermore, the minimal amount of penetrating radiation allows for outpatient administration of $^{90}$Y-labeled molecules. Additionally, internalization of labeled polypeptides is not required for cell killing, and the local emission of ionizing radiation should be lethal for adjacent tumor cells lacking the target antigen.

Those skilled in the art will appreciate that these non-radioactive conjugates may also be assembled using a variety of techniques depending on the selected agent to be conjugated. For example, conjugates with biotin are prepared e.g. by reacting the polypeptides with an activated ester of biotin such as the biotin N-hydroxysuccinimide ester. Similarly, conjugates with a fluorescent marker may be prepared in the presence of a coupling agent, e.g. those listed above, or by reaction with an isothiocyanate, preferably fluorescein-isothiocyanate. Conjugates of the polypeptides of the invention with cytostatic/cytotoxic substances and metal chelates are prepared in an analogous manner.

Preferred agents for use in the present invention are cytotoxic drugs, particularly those which are used for cancer therapy. As used herein, "a cytotoxin or cytotoxic agent" means any agent that is detrimental to the growth and proliferation of cells and may act to reduce, inhibit or destroy a cell or malignancy. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. Any cytotoxin that acts to retard or slow the growth of immunoreactive cells or malignant cells is within the scope of the present invention.

Exemplary cytotoxins include, in general, cytostatic agents, alkylating agents, antimetabolites, anti-proliferative agents, tubulin binding agents, hormones and hormone antagonists, and the like. Exemplary cytostatics that are compatible with the present invention include alkylating substances, such as mechlorethamine, triethylenephosphoramide, cyclophosphamide, ifosfamide, chlorambucil, busulfan, melphalan or triaziquone, also nitrosourea compounds, such as carmustine, lomustine, or semustine. Other preferred classes of cytotoxic agents include, for example, the maytansinoid family of drugs. Other preferred classes of cytotoxic agents include, for example, the anthracycline family of drugs, the vinca drugs, the mitomycins, the bleomycins, the cytotoxic nucleosides, the pteridine family of drugs, diynenes, and the podophyllotoxins. Particularly useful members of those classes include, for example, adriamycin, caminomycin, daunorubicin (daunomycin), doxorubicin, aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, or podophyllotoxin derivatives such as etoposide or etoposide phosphate, melphalan, vinblastine, vincristine, leurosidine, vindesine, leurosine and the like. Still other cytotoxins that are compatible with the teachings herein include taxol, taxane, cytochalasin B, gramicidin D, ethidium bromide, emetine, tenoposide, colchicin, dihydroxy anthracin dione, mitoxantrone, procaine, tetracaine, lidocaine, propranolol, and puromycin and analogs or homologs thereof. Hormones and hormone antagonists, such as corticosteroids, e.g. prednisone, progestins, e.g. hydroxyprogesterone or medroprogesterone, estrogens, e.g. diethylstilbestrol, antiestrogens, e.g. tamoxifen, androgens, e.g. testosterone, and aromatase inhibitors, e.g. aminogluthetimide are also compatible with the teachings herein. As noted previously, one skilled in the art may make chemical modifications to the desired compound in order to make reactions of that compound more convenient for purposes of preparing conjugates of the invention.

One example of particularly preferred cytotoxins comprise members or derivatives of the enediyne family of anti-tumor antibiotics, including calicheamicin, esperamicins or dynemicins. These toxins are extremely potent and act by cleaving nuclear DNA, leading to cell death. Unlike protein toxins which can be cleaved in vivo to give many inactive but immunogenic polypeptide fragments, toxins such as calicheamicin, esperamicins and other enediynes are small molecules which are essentially non-immunogenic. These non-peptide toxins are chemically-linked to the dimers or tetramers by techniques which have been previously used to label monoclonal antibodies and other molecules. These linking technologies include site-specific linkage via the N-linked sugar residues present only on the Fc portion of the constructs. Such site-directed linking methods have the advantage of reducing the possible effects of linkage on the binding properties of the constructs.

As previously alluded to, compatible cytotoxins may comprise a prodrug. As used herein, the term "prodrug" refers to a precursor or derivative form of a pharmaceutically active substance that is less cytotoxic to tumor cells compared to the parent drug and is capable of being enzymatically activated or converted into the more active parent form. Prodrugs compatible with the invention include, but are not limited to, phosphate-containing prodrugs, thiophosphate-containing prodrugs, sulfate containing prodrugs, peptide containing prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs that can be converted to the more active cytotoxic free drug. Further examples of cytotoxic drugs that can be derivatized into a prodrug form for use in the present invention comprise those chemotherapeutic agents described above.

Among other cytotoxins, it will be appreciated that polypeptides can also be associated with a biotoxin such as ricin subunit A, abrin, diptheria toxin, botulinum, cyanginosins, saxitoxin, shigatoxin, tetanus, tetrodotoxin, trichothecene, verrucologen or a toxic enzyme. Preferably, such constructs will be made using genetic engineering techniques that allow for direct expression of the binding molecule-toxin construct. Other biological response modifiers that may be associated with the polypeptides of the invention of the present invention comprise cytokines such as lymphokines and interferons. In view of the instant disclosure it is submitted that one skilled in the art could readily form such constructs using conventional techniques.

Another class of compatible cytotoxins that may be used in conjunction with the disclosed polypeptides are radiosensitizing drugs that may be effectively directed to tumor or immunoreactive cells. Such drugs enhance the sensitivity to ionizing radiation, thereby increasing the efficacy of radiotherapy. An conjugate internalized by the tumor cell would deliver the radiosensitizer nearer the nucleus where radiosensitization would be maximal. The unbound radiosensitizer linked polypeptides of the invention would be cleared quickly from the blood, localizing the remaining radiosensitization agent in the target tumor and providing minimal uptake in normal tissues. After rapid clearance from the blood, adjunct radiotherapy would be administered in one of three ways: 1.) external beam radiation directed specifically to the tumor, 2.) radioactivity directly implanted in the tumor or 3.) systemic radioimmunotherapy with the same targeting molecule. A potentially attractive variation of this approach would be the attachment of a therapeutic radioisotope to the radiosensitized immunoconjugate, thereby providing the convenience of administering to the patient a single drug.

In one embodiment, a moiety that enhances the stability or efficacy of the polypeptide can be conjugated. For example, in one embodiment, PEG can be conjugated to the polypeptides of the invention to increase their half-life in vivo. Leong, S. R., et al. 2001. *Cytokine* 16:106; 2002; *Adv. in Drug Deliv. Rev.* 54:531; or Weir et al. 2002. Biochem. Soc. Transactions 30:512.

VI. ADMINISTRATION OF POLYPEPTIDES

Methods of preparing and administering polypeptides of the invention to a subject are well known to or are readily determined by those skilled in the art. The route of administration of the polypeptide of the invention may be oral, parenteral, by inhalation or topical. The term parenteral as used herein includes intravenous, intraarterial, intraperitoneal, intramuscular, subcutaneous, rectal or vaginal administration. The intravenous, intraarterial, subcutaneous and intramuscular forms of parenteral administration are generally preferred. While all these forms of administration are clearly contemplated as being within the scope of the invention, a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, the polypeptides can be delivered directly to the site of the adverse cellular population thereby increasing the exposure of the diseased tissue to the therapeutic agent.

Preparations for parenteral administration includes sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., a polypeptide by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in co-pending U.S. Ser. No. 09/259,337 and U.S. Ser. No. 09/259,338 each of which is incorporated herein by reference. Such articles of manufacture will preferably have labels or package inserts indicating that the associated compositions are useful for treating a subject suffering from, or predisposed to autoimmune or neoplastic disorders. Effective doses of the compositions of the present invention, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages may be titrated using routine methods known to those of skill in the art to optimize safety and efficacy. For passive immunization with an antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, preferably at least 1 mg/kg. Doses intermediate in the above ranges are also intended to be within the scope of the invention. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Polypeptides of the invention can be administered on multiple occasions. Intervals between single dosages can be weekly, monthly or yearly. Intervals can also be irregular as indicated by measuring blood levels of polypeptide or antigen in the patient. In some methods, dosage is adjusted to achieve a plasma polypeptide concentration of 1-1000 μg/ml and in some methods 25-300 μg/ml. Alternatively, binding molecules can be administered as a sustained release formulation, in which case less frequent administration is required. Dosage and frequency vary depending on the half-life of the molecule in the patient. In general, humanized antibodies show the longest half-life, followed by chimeric antibodies and non-human antibodies. In one embodiment, the binding molecules of the invention can be administered in unconjugated form, In another embodiment, the polypeptides of the invention can be administered multiple times in conjugated form. In still another embodiment, the binding molecules of the invention can be administered in unconjugated form, then in conjugated form, or vise versa.

The dosage and frequency of administration can vary depending on whether the treatment is prophylactic or therapeutic. In prophylactic applications, compositions containing the present polypeptides or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a polypeptide of the invention (e.g., in a vector). Doses for nucleic acids encoding polypeptides range from about 10 ng to 1 g, 100 ng to 100 mg, 1 μg to 10 mg, or 30-300 μg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection or intravenous infusion are preferred for administration of molecules. In some methods, particular therapeutic molecules are injected directly into the cranium. In some methods, molecules are administered as a sustained release composition or device, such as a Medipad™ device.

Agents of the invention can optionally be administered in combination with other agents that are effective in treating the disorder or condition in need of treatment (e.g., prophylactic or therapeutic).

Effective single treatment dosages (i.e., therapeutically effective amounts) of $^{90}$Y-labeled polypeptides of the invention range from between about 5 and about 75 mCi, more preferably between about 10 and about 40 mCi. Effective single treatment non-marrow ablative dosages of $^{131}$I-labeled antibodies range from between about 5 and about 70 mCi, more preferably between about 5 and about 40 mCi. Effective single treatment ablative dosages (i.e., may require autologous bone marrow transplantation) of $^{131}$I-labeled antibodies range from between about 30 and about 600 mCi, more preferably between about 50 and less than about 500 mCi. In conjunction with a chimeric antibody, owing to the longer circulating half life vis-á-vis murine antibodies, an effective single treatment non-marrow ablative dosages of iodine-131 labeled chimeric antibodies range from between about 5 and about 40 mCi, more preferably less than about 30 mCi. Imaging criteria for, e.g., the $^{111}$In label, are typically less than about 5 mCi.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$Cu, $^{77}$Br, $^{81}$Rb, $^{81}$Kr, $^{87}$Sr, $^{113}$In, $^{127}$Cs, $^{129}$Cs, $^{132}$I, $^{197}$Hg, $^{203}$Pb, $^{206}$Bi, $^{177}$Lu, $^{186}$Re, $^{212}$Pd, $^{212}$Bi, $^{47}$Sc, $^{105}$Rh, $^{109}$Pd, $^{153}$Sm, $^{188}$Re, $^{199}$Au, $^{225}$Ac, $^{211}$At, and $^{213}$Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{123}$I, $^{99}$Tc, $^{43}$K, $^{52}$Fe, $^{67}$Ga, $^{68}$Ga, as well as $^{111}$In. Antibodies have also been labeled with a variety of radionuclides for potential use in targeted immunotherapy (Peirersz et al. *Immunol. Cell Biol.* 65: 111-125 (1987)). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

Whether or not the polypeptides of the invention are used in a conjugated or unconjugated form, it will be appreciated that a major advantage of the present invention is the ability to use these polypeptides in myelosuppressed patients, especially those who are undergoing, or have undergone, adjunct therapies such as radiotherapy or chemotherapy. That is, the beneficial delivery profile (i.e. relatively short serum dwell time, high binding affinity and enhanced localization) of the polypeptides makes them particularly useful for treating patients that have reduced red marrow reserves and are sensitive to myelotoxicity. In this regard, the unique delivery profile of the polypeptides make them very effective for the administration of radiolabeled conjugates to myelosuppressed cancer patients. As such, the polypeptides of the invention are useful in a conjugated or unconjugated form in patients that have previously undergone adjunct therapies such as external beam radiation or chemotherapy. In other preferred embodiments, the polypeptides (again in a conjugated or unconjugated form) may be used in a combined therapeutic regimen with chemotherapeutic agents. Those skilled in the art will appreciate that such therapeutic regimens may comprise the sequential, simultaneous, concurrent or coextensive administration of the disclosed molecules and one or more chemotherapeutic agents. Particularly preferred embodiments of this aspect of the invention will comprise the administration of a radiolabeled polypeptide.

While the polypeptides may be administered as described immediately above, it must be emphasized that in other embodiments conjugated and unconjugated polypeptides may be administered to otherwise healthy patients as a first line therapeutic agent. In such embodiments the polypeptides may be administered to patients having normal or average red marrow reserves and/or to patients that have not, and are not, undergoing adjunct therapies such as external beam radiation or chemotherapy.

However, as discussed above, selected embodiments of the invention comprise the administration of polypeptides to myelosuppressed patients or in combination or conjunction with one or more adjunct therapies such as radiotherapy or chemotherapy (i.e. a combined therapeutic regimen). As used herein, the administration of polypeptides in conjunction or combination with an adjunct therapy means the sequential, simultaneous, coextensive, concurrent, concomitant or contemporaneous administration or application of the therapy and the disclosed molecules. Those skilled in the art will appreciate that the administration or application of the various components of the combined therapeutic regimen may be timed to enhance the overall effectiveness of the treatment. For example, chemotherapeutic agents could be administered in standard, well known courses of treatment followed within a few weeks by radioimmunoconjugates of the present invention. Conversely, cytotoxin associated polypeptides could be administered intravenously followed by tumor localized external beam radiation. In yet other embodiments, the polypeptide may be administered concurrently with one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard it will be appreciated that the combination of the polypeptide (with or without cytotoxin) and the chemotherapeutic agent may be administered in any order and within any time frame that provides a therapeutic benefit to the patient. That is, the chemotherapeutic agent and polypeptide may be administered in any order or concurrently. In selected embodiments the polypeptides of the present invention will be administered to patients that have previously undergone chemotherapy. In yet other embodiments, the polypeptides and the chemotherapeutic treatment will be administered substantially simultaneously or concurrently. For example, the patient may be given the binding molecule while undergoing a course of chemotherapy. In preferred embodiments the binding molecule will be administered within 1 year of any chemotherapeutic agent or treatment. In other preferred embodiments the polypeptide will be administered within 10, 8, 6, 4, or 2 months of any chemotherapeutic agent or treatment. In still other preferred embodiments the polypeptide will be administered within 4, 3, 2 or 1 week of any chemotherapeutic agent or treatment. In yet other embodiments the polypeptide will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

Moreover, in accordance with the present invention a myelosuppressed patient shall be held to mean any patient exhibiting lowered blood counts. Those skilled in the art will appreciate that there are several blood count parameters conventionally used as clinical indicators of myelosuppresion and one can easily measure the extent to which myelosuppresion is occurring in a patient. Examples of art accepted myelosuppression measurements are the Absolute Neutrophil Count (ANC) or platelet count. Such myelosuppression or partial myeloablation may be a result of various biochemical disorders or diseases or, more likely, as the result of prior chemotherapy or radiotherapy. In this respect, those skilled in the art will appreciate that patients who have undergone traditional chemotherapy typically exhibit reduced red marrow reserves. As discussed above, such subjects often cannot be treated using optimal levels of cytotoxin (i.e. radionuclides) due to unacceptable side effects such as anemia or immunosuppression that result in increased mortality or morbidity.

More specifically conjugated or unconjugated polypeptides of the present invention may be used to effectively treat patients having ANCs lower than about $2000/mm^3$ or platelet counts lower than about $150,000/mm^3$. More preferably the polypeptides of the present invention may be used to treat patients having ANCs of less than about $1500/mm^3$, less than about $1000/mm^3$ or even more preferably less than about $500/mm^3$. Similarly, the polypeptides of the present invention may be used to treat patients having a platelet count of less than about $75,000/mm^3$, less than about $50,000/mm^3$ or even less than about $10,000/mm^3$. In a more general sense, those skilled in the art will easily be able to determine when a patient is myelosuppressed using government implemented guidelines and procedures.

As indicated above, many myelosuppressed patients have undergone courses of treatment including chemotherapy, implant radiotherapy or external beam radiotherapy. In the case of the latter, an external radiation source is for local irradiation of a malignancy. For radiotherapy implantation methods, radioactive reagents are surgically located within the malignancy, thereby selectively irradiating the site of the disease. In any event, the disclosed polypeptides may be used to treat disorders in patients exhibiting myelosuppression regardless of the cause.

In this regard it will further be appreciated that the polypeptides of the instant invention may be used in conjunction or combination with any chemotherapeutic agent or agents (e.g. to provide a combined therapeutic regimen) that eliminates, reduces, inhibits or controls the growth of neoplastic cells in vivo. As discussed, such agents often result in the reduction of red marrow reserves. This reduction may be offset, in whole or in part, by the diminished myelotoxicity of the compounds of the present invention that advantageously allow for the aggressive treatment of neoplasias in such patients. In other preferred embodiments the radiolabeled immunoconjugates disclosed herein may be effectively used with radiosensitizers that increase the susceptibility of the neoplastic cells to radionuclides. For example, radiosensitizing compounds may be administered after the radiolabeled binding molecule has been largely cleared from the bloodstream but still remains at therapeutically effective levels at the site of the tumor or tumors.

With respect to these aspects of the invention, exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), Ch1VPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas*, in HARRISON'S PRINCIPLES OF INTERNAL MEDICINE 1774-1788 (Kurt J. Isselbacher et al., eds., $13^{th}$ ed. 1994) and V. T. DeVita et al., (1997) and the references cited therein for standard dosing and scheduling. These therapies can be used unchanged, or altered as needed for a particular patient, in combination with one or more polypeptides of the invention as described herein.

Additional regimens that are useful in the context of the present invention include use of single alkylating agents such as cyclophosphamide or chlorambucil, or combinations such as CVP (cyclophosphamide, vincristine and prednisone), CHOP (CVP and doxorubicin), C-MOPP (cyclophosphamide, vincristine, prednisone and procarbazine), CAP-BOP (CHOP plus procarbazine and bleomycin), m-BACOD (CHOP plus methotrexate, bleomycin and leucovorin), ProMACE-MOPP (prednisone, methotrexate, doxorubicin, cyclophosphamide, etoposide and leucovorin plus standard MOPP), ProMACE-CytaBOM (prednisone, doxorubicin, cyclophosphamide, etoposide, cytarabine, bleomycin, vincristine, methotrexate and leucovorin) and MACOP-B (methotrexate, doxorubicin, cyclophosphamide, vincristine, fixed dose prednisone, bleomycin and leucovorin). Those skilled in the art will readily be able to determine standard dosages and scheduling for each of these regimens. CHOP has also been combined with bleomycin, methotrexate, procarbazine, nitrogen mustard, cytosine arabinoside and etoposide. Other compatible chemotherapeutic agents include, but are not limited to, 2-chlorodeoxyadenosine (2-CDA), 2'-deoxycoformycin and fludarabine.

For patients with intermediate- and high-grade NHL, who fail to achieve remission or relapse, salvage therapy is used. Salvage therapies employ drugs such as cytosine arabinoside, cisplatin, etoposide and ifosfamide given alone or in combination. In relapsed or aggressive forms of certain neoplastic disorders the following protocols are often used: IMVP-16 (ifosfamide, methotrexate and etoposide), MIME (methylgag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the polypeptides of the instant invention may vary by subject or may be administered according to what is known in the art. See for example, Bruce A Chabner et al., *Antineoplastic Agents*, in GOODMAN & GILMAN'S THE PHARMACOLOGICAL BASIS OF THERAPEUTICS 1233-1287 ((Joel G. Hardman et al., eds., $9^{th}$ ed. 1996).

As previously discussed, the polypeptides of the present invention, immunoreactive fragments or recombinants thereof may be administered in a pharmaceutically effective amount for the in vivo treatment of mammalian disorders. In this regard, it will be appreciated that the disclosed binding molecules will be formulated so as to facilitate administration and promote stability of the active agent. Preferably, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of the polypeptide, immunoreactive fragment or recombinant thereof, conjugated or unconjugated to a therapeutic agent, shall be held to mean an amount sufficient to achieve effective binding to an antigen and to achieve a benefit, e.g., to ameliorate symptoms of a disease or disorder or to detect a substance or a cell. In the case of tumor cells, the polypeptide will be preferably be capable of interacting with selected immunoreactive antigens on neoplastic or immunoreactive cells and provide for an increase in the death of those cells. Of course, the pharmaceutical compositions of the present invention may be administered in single or multiple doses to provide for a pharmaceutically effective amount of the polypeptide.

In keeping with the scope of the present disclosure, the polypeptides of the invention may be administered to a human or other animal in accordance with the aforementioned methods of treatment in an amount sufficient to produce a therapeutic or prophylactic effect. The binding molecules of the invention can be administered to such human or other animal in a conventional dosage form prepared by combining the binding molecule of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of polypeptides according to the present invention may prove to be particularly effective.

VII. METHODS OF USE

The polypeptides of the invention can be used for diagnostic or therapeutic purposes. Preferred embodiments of the present invention provide compounds, compositions, kits and methods for the diagnosis and/or treatment of disorders, e.g., neoplastic disorders in a mammalian subject in need of such treatment. Preferably, the subject is a human.

The polypeptides of the instant invention will be useful in a number of different applications. For example, in one embodiment, the subject binding molecules should be useful for reducing or eliminating cells bearing an epitope recognized by a binding molecule of the invention. In another embodiment, the subject binding molecules are effective in reducing the concentration of or eliminating soluble antigen in the circulation In one embodiment, tumor size, inhibiting tumor growth and/or prolonging the survival time of tumor-bearing animals. Accordingly, this invention also relates to a method of treating tumors in a human or other animal by administering to such human or animal an effective, non-toxic amount of polypeptide. One skilled in the art would be able, by routine experimentation, to determine what an effective, non-toxic amount of polypeptide would be for the purpose of treating malignancies. For example, a therapeutically active amount of a polypeptide may vary according to factors such as the disease stage (e.g., stage I versus stage IV), age, sex, medical complications (e.g., immunosuppressed conditions or diseases) and weight of the subject, and the ability of the molecule to elicit a desired response in the subject. The dosage regimen may be adjusted to provide the optimum therapeutic response. For example, several divided doses may be administered daily, or the dose may be proportionally reduced as indicated by the exigencies of the therapeutic situation. Generally, however, an effective dosage is expected to be in the range of about 0.05 to 100 milligrams per kilogram body weight per day and more preferably from about 0.5 to 10, milligrams per kilogram body weight per day.

For purposes of clarification "mammal" refers to any animal classified as a mammal, including humans, domestic and farm animals, and zoo, sports, or pet animals, such as dogs, horses, cats, cows, etc. Preferably, the mammal is human.

"Treatment" refers to both therapeutic treatment and prophylactic or preventative measures. Those in need of treatment include those already with the disease or disorder as well as those in which the disease or disorder is to be prevented. Hence, the mammal may have been diagnosed as having the disease or disorder or may be predisposed or susceptible to the disease.

As discussed above, the polypeptides of the present invention may be immunoreactive with one or more tumor antigens or antigens associated with immune disorders. For example, for neoplastic disorders, the antigen binding site (i.e. the variable region or immunoreactive fragment or recombinant thereof) of the disclosed polypeptides binds to a selected tumor associated antigen at the site of the malignancy. Similarly, in immune (including autoimmune) disorders the disclosed polypeptides will bind to selected markers on the offending cells. Given the number of reported antigens associated with neoplasias and immune disorders, and the number of related antibodies, those skilled in the art will appreciate that the presently disclosed polypeptides may therefore be derived from any one of a number of whole antibodies. More generally, polypeptides useful in the present invention may be obtained or derived from any antibody (including those previously reported in the literature) that reacts with a molecule or marker associated with the selected condition. Further, the parent or precursor antibody, or fragment thereof, used to generate the disclosed polypeptides may be murine, human, chimeric, humanized, non-human primate or primatized. In other preferred embodiments the polypeptides of the present invention may comprise single chain antibody constructs (such as that disclosed in U.S. Pat. No. 5,892,019 which is incorporated herein by reference) having altered constant domains as described herein. Consequently, any of these types of antibodies modified in accordance with the teachings herein is compatible with the instant invention.

As used herein, "tumor associated antigens" means any antigen which is generally associated with tumor cells, i.e., occurring at the same or to a greater extent as compared with normal cells. More generally, tumor associated antigens comprise any antigen that provides for the localization of immunoreactive antibodies at a neoplastic cell irrespective of its expression on non-malignant cells. Such antigens may be relatively tumor specific and limited in their expression to the surface of malignant cells. Alternatively, such antigens may be found on both malignant and non-malignant cells. For example, CD20 is a pan B antigen that is found on the surface of both malignant and non-malignant B cells that has proved to be an extremely effective target for immunotherapeutic antibodies for the treatment of non-Hodgkin's lymphoma. In this respect, pan T cell antigens such as CD2, CD3, CD5, CD6 and CD7 also comprise tumor associated antigens within the meaning of the present invention. Still other exemplary tumor associated antigens comprise but not limited to MAGE-1, MAGE-3, MUC-1, HPV 16, HPV E6 & E7, TAG-72, CEA, L6-Antigen, CD19, CD22, CD37, CD52, HLA-DR, EGF Receptor and HER2Receptor. In many cases immunoreactive antibodies for each of these antigens have been reported in the literature. Those skilled in the art will appreciate that each of these antibodies may serve as a precursor for polypeptides of the invention in accordance with the present invention.

The polypeptides of the present invention preferably associate with, and bind to, tumor or immune associated antigens as described above. Accordingly, as will be discussed in some detail below the polypeptides of the present invention may be derived, generated or fabricated from any one of a number of antibodies that react with tumor associated antigens. In preferred embodiments the polypeptides are modified or domain deleted antibodies that are derived using common genetic engineering techniques whereby at least a portion of one or more constant region domains are deleted or altered so as to provide the desired biochemical characteristics such as reduced serum half-life. More particularly, one skilled in the art may readily isolate the genetic sequence corresponding to the variable and/or constant regions of the subject antibody and delete or alter the appropriate nucleotides to provide polypeptides of the invention for use as monomeric subunits in accordance with the instant invention. It will further be appreciated that compatible polypeptides of the invention may be expressed and produced on a clinical or commercial scale using well-established protocols.

Previously reported antibodies that react with tumor associated antigens may be altered as described herein to provide the polypeptides of the present invention. Exemplary antibodies that may be used to provide antigen binding regions for, generate or derive the disclosed polypeptides include, but are not limited to 2B8 and C2B8 (Zevalin® and Rituxan®, IDEC Pharmaceuticals Corp., San Diego), Lym 1 and Lym 2 (Techniclone), LL2 (Immunomedics Corp., New Jersey), HER2 (Herceptin®, Genentech Inc., South San Francisco), B1 (Bexxar®, Coulter Pharm., San Francisco), Campath®(Millennium Pharmaceuticals, Cambridge) MB1, BH3, B4, B72.3 (Cytogen Corp.), CC49 (National Cancer Institute) and 5E10 (University of Iowa). Other antibody binding sites that can be incorporated into the subject binding molecules include: Orthoclone OKT3 (CD3), ReoPro (GpIIb/gIIa), Zenapax (C25), Remicade (TNF-a), Simulect (CD25), Synagis (RSV), Mylotarg (CD33), and Campath (CD52). In preferred embodiments, the polypeptides of the present invention will bind to the same tumor associated antigens as the antibodies enumerated immediately above. In particularly preferred embodiments, the polypeptides will be derived from or bind the same antigens as 2B8, C2B8, CC49 and C5E10 and, even more preferably, will lack all or part of a CH2 domain.

In one embodiment, a binding molecule of the invention binds to the CD23 (U.S. Pat. No. 6,011,138). In a preferred embodiment, a binding molecule of the invention binds to the same epitope as the 5E8 antibody. In another embodiment, a binding molecule of the invention comprises at least one CDR from an anti-CD23 antibody, e.g., the 5E8 antibody.

In one embodiment, a binding molecule of the invention binds to the CRIPTO-I antigen (WO02/088170A2 or WO03/083041A2). In a preferred embodiment, a binding molecule of the invention binds to the same epitope as the B3F6 antibody. In another embodiment, a binding molecule of the invention comprises at least one CDR from an anti-CRIPTO-I antibody, e.g., the B3F6 antibody.

In a first preferred embodiment, the polypeptide will bind to the same tumor associated antigen as Rituxan®. Rituxan® (also known as, rituximab, IDEC-C2B8 and C2B8) was the first FDA-approved monoclonal antibody for treatment of human B-cell lymphoma (see U.S. Pat. Nos. 5,843,439; 5,776,456 and 5,736,137 each of which is incorporated herein by reference). Y2B8 (90Y labeled 2B8; Zevalin®; ibritumomab tiuxetan) is the murine parent of C2B8. Rituxan® is a chimeric, anti-CD20 monoclonal antibody which is growth inhibitory and reportedly sensitizes certain lymphoma cell lines for apoptosis by chemotherapeutic agents in vitro. The antibody efficiently binds human complement, has strong FcR binding, and can effectively kill human lymphocytes in vitro via both complement dependent (CDC) and antibody-dependent (ADCC) mechanisms (Reff et al., Blood 83: 435-445 (1994)). Those skilled in the art will appreciate that dimeric variants (homodimers or heterodimers) of C2B8 or 2B8, modified according to the instant disclosure, may be used in conjugated or unconjugated forms to effectively treat patients presenting with CD20+ malignancies. More generally, it must be reiterated that the polypeptides disclosed herein may be used in either a "naked" or unconjugated state or conjugated to a cytotoxic agent to effectively treat any one of a number of disorders. In other preferred embodiments of the present invention, the polypeptide of the invention will be derived from, or bind to, the same tumor associated antigen as CC49. As previously alluded to, CC49 binds human tumor associated antigen TAG-72 which is associated with the surface of certain tumor cells of human origin, specifically the LS174T tumor cell line. LS174T [American Type Culture Collection (herein ATCC) No. CL 188] is a variant of the LS180 (ATCC No. CL 187) colon adenocarcinoma line. It will further be appreciated that numerous murine monoclonal antibodies have been developed which have binding specificity for TAG-72. One of these monoclonal antibodies, designated B72.3, is a murine IgG1 produced by hybridoma B72.3 (ATCC No. HB-8108). B72.3 is a first generation monoclonal antibody developed using a human breast carcinoma extract as the immunogen (see Colcher et al., Proc. Natl. Acad. Sci. (USA), 78:3199-3203 (1981); and U.S. Pat. Nos. 4,522,918 and 4,612,282 each of which is incorporated herein by reference). Other monoclonal antibodies directed against TAG-72 are designated "CC" (for colon cancer). As described by Schlom et al. (U.S. Pat. No. 5,512,443 which is incorporated herein by reference) CC monoclonal antibodies are a family of second generation murine monoclonal antibodies that were prepared using TAG-72 purified with B72.3. Because of their relatively good binding affinities to TAG-72, the following CC antibodies have been deposited at the ATCC, with restricted access having been requested: CC49 (ATCC No. HB 9459); CC 83 (ATCC No. HB 9453); CC46 (ATCC No. HB 9458); CC92 (ATTCC No. HB 9454); CC30 (ATCC No. HB 9457); CC11 (ATCC No. 9455); and CC15 (ATCC No. E1B 9460). U.S. Pat. No. 5,512,443 further teaches that the disclosed antibodies may be altered into their chimeric form by substituting, e.g., human constant regions (Fc) domains for mouse constant regions by recombinant DNA techniques known in the art. Besides disclosing murine and chimeric anti-TAG-72 antibodies, Schlom et al. have also produced variants of a humanized CC49 antibody as disclosed in PCT/US99/25552 and single chain constructs as disclosed in U.S. Pat. No. 5,892,019 each of which is also incorporated herein by reference. Those skilled in the art will appreciate that each of the foregoing antibodies, constructs or recombinants, and variations thereof, may be modified and used to provide polypeptides in accordance with the present invention.

In addition to the anti-TAG-72 antibodies discussed above, various groups have also reported the construction and partial characterization of domain-deleted CC49 and B72.3 antibodies (e.g., Calvo et al. Cancer Biotherapy, 8(1):95-109 (1993), Slavin-Chiorini et al. Int. J. Cancer 53:97-103 (1993) and Slavin-Chiorini et al. Cancer. Res. 55:5957-5967 (1995

Still other preferred embodiments of the present invention comprise modified antibodies that are derived from or bind to the same tumor associated antigen as C5E10. As set forth in co-pending application Ser. No. 09/104,717, C5E10 is an antibody that recognizes a glycoprotein determinant of approximately 115 kDa that appears to be specific to prostate tumor cell lines (e.g. DU145, PC3, or ND1). Thus, in conjunction with the present invention, polypeptides (e.g. CH2 domain-deleted antibodies) that specifically bind to the same tumor associated antigen recognized by C5E10 antibodies could be produced and used in a conjugated or unconjugated form for the treatment of neoplastic disorders. In particularly preferred embodiments, the modified antibody will be derived or comprise all or part of the antigen binding region of the C5E10 antibody as secreted from the hybridoma cell line having ATCC accession No. PTA-865. The resulting modified antibody could then be conjugated to a radionuclide as described below and administered to a patient suffering from prostate cancer in accordance with the methods herein.

In general, the disclosed invention may be used to prophylactically or therapeutically treat any neoplasm comprising an antigenic marker that allows for the targeting of the cancerous cells by the binding molecule. Exemplary cancers that may be treated include, but are not limited to, prostate, gastric carcinomas such as colon, skin, breast, ovarian, lung and pancreatic. More particularly, the binding molecules of the instant invention may be used to treat Kaposi's sarcoma, CNS neoplasias (capillary hemangioblastomas, meningiomas and cerebral metastases), melanoma, gastrointestinal and renal sarcomas, rhabdomyosarcoma, glioblastoma (preferably glioblastoma multiforme), leiomyosarcoma, retinoblastoma, papillary cystadenocarcinoma of the ovary, Wilm's tumor or small cell lung carcinoma. It will be appreciated that appropriate polypeptides may be derived for tumor associated antigens related to each of the forgoing neoplasias without undue experimentation in view of the instant disclosure. Exemplary hematologic malignancies that are amenable to treatment with the disclosed invention include Hodgkins and non-Hodgkins lymphoma as well as leukemias, including ALL-L3 (Burkitt's type leukemia), chronic lymphocytic leukemia (CLL) and monocytic cell leukemias. It will be appreciated that the compounds and methods of the present invention are particularly effective in treating a variety of B-cell lymphomas, including low grade/follicular non-Hodgkin's lymphoma (NHL), cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL and Waldenstrom's Macroglobulinemia. It should be clear to those of skill in the art that these lymphomas will often have different names due to changing systems of classification, and that patients having lymphomas classified under different names may also benefit from the combined therapeutic regimens of the present invention. In addition to the aforementioned neoplastic disorders, it will be appreciated that the disclosed invention may advantageously be used to treat additional malignancies bearing compatible tumor associated antigens.

Besides neoplastic disorders, the polypeptides of the instant invention are particularly effective in the treatment of autoimmune disorders or abnormal immune responses. In this regard, it will be appreciated that the polypeptide of the present invention may be used to control, suppress, modulate or eliminate unwanted immune responses to both external and autoantigens. For example, in one embodiment, the antigen is an autoantigen. In another embodiment, the antigen is an allergen. In yet other embodiments, the antigen is an alloantigen or xenoantigen. Use of the disclosed polypeptides to reduce an immune response to alloantigens and xenoantigens is of particular use in transplantation, for example to inhibit rejection by a transplant recipient of a donor graft, e.g. a tissue or organ graft or bone marrow transplant. Additionally, suppression or elimination of donor T cells within a bone marrow graft is useful for inhibiting graft versus host disease.

In yet other embodiments the polypeptides of the present invention may be used to treat immune disorders that include, but are not limited to, allergic bronchopulmonary aspergillosis; Allergic rhinitis Autoimmune hemolytic anemia; Acanthosis nigricans; Allergic contact dermatitis; Addison's disease; Atopic dermatitis; Alopecia greata; Alopecia universalis; Amyloidosis; Anaphylactoid purpura; Anaphylactoid reaction; Aplastic anemia; Angioedema, hereditary; Angioedema, idiopathic; Ankylosing spondylitis; Arteritis, cranial; Arteritis, giant cell; Arteritis, Takayasu's; Arteritis, temporal; Asthma; Ataxia-telangiectasia; Autoimmune oophoritis; Autoimmune orchitis; Autoimmune polyendocrine failure; Behcet's disease; Berger's disease; Buerger's disease; bronchitis; Bullous pemphigus; Candidiasis, chronic mucocutaneous; Caplan's syndrome; Post-myocardial infarction syndrome; Post-pericardiotomy syndrome; Carditis; Celiac sprue; Chagas's disease; Chediak-Higashi syndrome; Churg-Strauss disease; Cogan's syndrome; Cold agglutinin disease; CREST syndrome; Crohn's disease; Cryoglobulinemia; Cryptogenic fibrosing alveolitis; Dermatitis herpetifomis; Dermatomyositis; Diabetes mellitus; Diamond-Blackfan syndrome; DiGeorge syndrome; Discoid lupus erythematosus; Eosinophilic fasciitis; Episcleritis; Drythema elevatum diutinum; Erythema marginatum; Erythema multiforme; Erythema nodosum; Familial Mediterranean fever; Felty's syndrome; Fibrosis pulmonary; Glomerulonephritis, anaphylactoid; Glomerulonephritis, autoimmune; Glomerulonephritis, post-streptococcal; Glomerulonephritis, post-transplantation; Glomerulopathy, membranous; Goodpasture's syndrome; Granulocytopenia, immune-mediated; Granuloma annulare; Granulomatosis, allergic; Granulomatous myositis; Grave's disease; Hashimoto's thyroiditis; Hemolytic disease of the newborn; Hemochromatosis, idiopathic; Henoch-Schoenlein purpura; Hepatitis, chronic active and chronic progressive; Histiocytosis X; Hypereosinophilic syndrome; Idiopathic thrombocytopenic purpura; Job's syndrome; Juvenile dermatomyositis; Juvenile rheumatoid arthritis (Juvenile chronic arthritis); Kawasaki's disease; Keratitis; Keratoconjunctivitis sicca; Landry-Guillain-Barre-Strohl syndrome; Leprosy, lepromatous; Loeffler's syndrome; lupus; Lyell's syndrome; Lyme disease; Lymphomatoid granulomatosis; Mastocytosis, systemic; Mixed connective tissue disease; Mononeuritis multiplex; Muckle-Wells syndrome; Mucocutaneous lymph node syndrome; Mucocutaneous lymph node syndrome; Multicentric reticulohistiocytosis; Multiple sclerosis; Myasthenia gravis; Mycosis fungoides; Necrotizing vasculitis, systemic; Nephrotic syndrome; Overlap syndrome; Panniculitis; Paroxysmal cold hemoglobinuria; Paroxysmal nocturnal hemoglobinuria; Pemphigoid; Pemphigus; Pemphigus erythema-tosus; Pemphigus foliaceus; Pemphigus vulgaris; Pigeon breeder's disease; Pneumonitis, hypersensitivity; Polyarteritis nodosa; Polymyalgia rheumatic; Polymyositis; Polyneuritis, idiopathic; Portuguese familial polyneuropathies; Pre-eclampsia/eclampsia; Primary biliary cirrhosis; Progressive systemic sclerosis (Scleroderma); Psoriasis; Psoriatic arthritis; Pulmonary alveolar proteinosis; Pulmonary fibrosis, Raynaud's phenomenon/syndrome; Reidel's thyroiditis; Reiter's syndrome, Relapsing polychrondritis; Rheumatic fever; Rheumatoid arthritis; Sarcoidosis; Scleritis; Sclerosing cholangitis; Serum sickness; Sezary syndrome; Sjogren's syndrome; Stevens-Johnson syndrome; Still's disease; Subacute sclerosing panencephalitis; Sympathetic ophthalmia; Systemic lupus erythematosus; Transplant rejection; Ulcerative colitis; Undifferentiated connective tissue disease; Urticaria, chronic; Urticaria, cold; Uveitis; Vitiligo; Weber-Christian disease; Wegener's granulomatosis and Wiskott-Aldrich syndrome.

In another embodiment, the binding molecules of the invention can be used for pretargeting applications. For example, the same advantages will be apparent in pretargeting applications for chemotherapeutic drug delivery.

For example, in pretargeting a tumor is pretargeted with a binding construct that has affinity for the tumor-associated antigen on the one hand and for, e.g., a radiolabeled hapten on the other. The radiolabeled hapten is administered later, preferably after the binding molecule has cleared (see, e.g., Boerman et al. 2003. J. Nuclear Med. 44:400). In another example, an antibody which is non-toxic, but has been derivitized to react with a drug or prodrug that is toxic only when bound by the binding molecule. Given the biodistribution data in the instant examples, the binding molecules of the invention are well suited to use in pretargeting applications. In one embodiment, a clearing agent could be eliminated from the pretargeting methodology by using the instant binding molecules.

This invention is further illustrated by the following examples which should not be construed as limiting. The contents of all references, patents and published patent applications cited throughout this application are incorporated herein by reference.

EXAMPLES

Example 1

Identification of A and B Isoforms

Solutions of antibody molecules comprise two different isoforms. One form, Form A comprises heavy chain molecules that are linked via at least one disulfide linkage. The other form, Form B, comprises heavy chain molecules that are not linked via at least one disulfide linkage. Form B does not appear or appears at a very low frequency in with intact gamma 1 MAbs, such as Rituxan®. However with domain deleted (dd) constructs having a similar hinge, the frequency of Form B is much higher. These forms can be distinguished using denaturing, non-reducing SDS page. In domain deleted antibody preparations, Form A appears as a 120 kDa dimer while Form B appears as a 60 kDa monomer (FIG. 1).

Example 2

Identification of Hinge Region Heterogeneity in CH2 Domain Deleted MAb Fragments Hinge domains can be subdivided into three distinct regions: upper, middle, and lower hinge regions (Roux et al. J. Immunol. 1998 161:4083). Polypeptide sequences encompassing these regions for IgG1 and IgG3 hinges are shown in Table 1. The IgG3 hinge middle region contains, in addition to the two conserved cysteine residues, a 15 amino acid motif that repeats three times. Amino acid sequences from these regions were used to design synthetic IgG1/IgG3 connecting peptides. These consisted of IgG1 upper hinge residues corresponding to positions 226 through 238, an IgG1 middle hinge corresponding to positions 239 through 241, and a single IgG3 middle hinge repeat motif corresponding to positions 241EE through 242 combined with either an added proline at position 243 or an added proline, alanine, proline at positions 243, 244, and 245, respectively (Kabat numbering system), followed by a flexible Gly/Ser spacer (Table 2). In addition, novel connecting peptides were designed consisting of a serine amino acid residue substituted for the cysteine at positions 239 or 242 combined with either an added proline at position 243 or an added proline, alanine, proline at positions 243, 244, and 245, respectively (Kabat numbering system). Pro243Ala244Pro245 and Pro 243 connecting peptides were also made. The amino acid sequence of the parent CH2 domain deleted humanized CC49 connecting peptide beginning at the first residue of the IgG1 hinge (position 226, Kabat numbering system) to the last residue of the hinge/GlySer connecting peptide is shown in Table 2. Also shown are the various connecting peptide designs by alignment to CC49 with positions of the cysteine residues indicated in Kabat numbering system.

TABLE 1

IgG1, IgG3 and IgG4 Hinge Regions

| IgG | Upper Hinge | Middle Hinge | Lower Hinge |
|---|---|---|---|
| IgG1 | EPKSCDKTHT (SEQ ID NO: 2) | CPPCP (SEQ ID NO: 3) | APELLGGP (SEQ ID NO: 4) |
| IgG3 | ELKTPLGDTTHT (SEQ ID NO: 5) | CPRCP(EPKSCDTPPPCPRCP)$_3$ (SEQ ID NO: 6) | APELLGGP (SEQ ID NO: 4) |
| IgG4 | ESKYGPP (SEQ ID NO: 45) | CPSCP (SEQ ID NO: 46) | APEFLGGP (SEQ ID NO: 47) |

TABLE 2

Hinge Region Connecting Peptide Sequences

| Kabat hinge position: | 226 | 227 | 228 | 229 | 230 | 232 | 235 | 236 | 237 | 238 | 239 | 240 | 241 | 241EE | 241FF | 241GG | 241HH | 241II | 241JJ | 241KK | 241LL |
|---|---|---|---|---|---|---|---|---|---|---|---|---|---|---|---|---|---|---|---|---|---|
| IgG1 hinge sequence | E | P | K | S | C | D | K | T | H | T | C | P | P | | | | | | | | |
| IgG4 hinge sequence | E | S | K | Y | G | | | | | | P | P | C | P | S | | | | | | |
| IgG3 middle hinge sequence | | | | | | | | | | | | | | C | P | E | P | K | S | C | D |

TABLE 2-continued

Hinge Region Connecting Peptide Sequences

| Connecting peptide: | Connecting peptide sequences |
|---|---|
| G1 (Seq. ID NO: 7) | E P K S C D K T H T C P P |
| G1/G3/Pro243 (Seq. ID NO: 8) | E P K S C D K T H T C P P C P E P K S C D |
| G1/G3/Pro243 Ala244Pro245 (Seq. ID NO: 9) | E P K S C D K T H T C P P C P E P K S C D |
| G1/Cys239Ser:Pro243 (Seq. ID NO: 10) | E P K S C D K T H T S P P |
| G1/Cys239Ser:Pro243 Ala244Pro245 (Seq. ID NO: 11) | E P K S C D K T H T S P P |
| G1/Cys242Ser:Pro243 (Seq. ID NO: 12) | E P K S C D K T H T C P P |
| G1/Cys242Ser:Pro243 Ala244Pro245 (Seq. ID NO: 13) | E P K S C D K T H T C P P |
| G1/Pro243Ala244Pro245 (Seq. ID NO: 14) | E P K S C D K T H T C P P |
| G1/Pro243 (Seq. ID NO: 15) | E P K S C D K T H T C P P |
| G4/G3/Pro243Ala244Pro245 (Seq. ID NO: 48) | E S K Y G     P P C P S C P E P K S C D |

| Kabat hinge position: | 241MM | 241NN | 241OO | 241PP | 241QQ | 241RR | 241SS | 242 | 243 | 244 | 245 | |
|---|---|---|---|---|---|---|---|---|---|---|---|---|
| IgG1 hinge sequence | | | | | | | | C | P | A | P | |
| IgG4 hinge sequence | | | | | | | | C | P | A | P | |
| IgG3 middle hinge sequence | T | P | P | P | | C | P | R | | | | |
| Connecting peptide: | | | | | Connecting peptide sequences | | | | | | | |
| G1 (Seq. ID NO: 7) | | | | | | | | C | | | | GGGSSGGGSG |
| G1/G3/Pro243 (Seq. ID NO: 8) | T | P | P | P | | C | P | R | C | P | | GGGSSGGGSG |
| G1/G3/Pro243 Ala244Pro245 (Seq. ID NO: 9) | T | P | P | P | | C | P | R | C | P | A | P | GGGSSGGGSG |
| G1/Cys239Ser:Pro243 (Seq. ID NO: 10) | | | | | | | | C | P | | | GGGSSGGGSG |
| G1/Cys239Ser:Pro243 Ala244Pro245 (Seq. ID NO: 11) | | | | | | | | C | P | A | P | GGGSSGGGSG |
| G1/Cys242Ser:Pro243 (Seq. ID NO: 12) | | | | | | | | S | P | | | GGGSSGGGSG |
| G1/Cys242Ser:Pro243 Ala244Pro245 (Seq. ID NO: 13) | | | | | | | | S | P | A | P | GGGSSGGGSG |
| G1/Pro243Ala244Pro245 (Seq. ID NO: 14) | | | | | | | | C | P | A | P | GGGSSGGGSG |
| G1/Pro243 (Seq. ID NO: 15) | | | | | | | | C | P | | | GGGSSGGGSG |
| G4/G3/Pro243Ala244Pro245 (Seq. ID NO: 48) | T | P | P | P | | C | P | R | C | P | A | P | |

Example 3

Construction of Connecting Polypeptides and Preferential Synthesis of Isoforms Nucleic acid sequences encoding the hinge region connecting peptides shown in Table 2 were introduced into CH2 domain deleted huCC49 gene sequences using the Splicing by Overlap Extension (SOE) method (Horton, R. M. 1993 Methods in Molecular Biology, Vol 15:PCR Protocols: Current Methods and applications. Ed. B. A. White). Correct modifications to the hinge region were confirmed by DNA sequence analysis. Plasmid DNA was used to transform CHO DG44 cells for stable production of antibody protein.

CH2 domain deleted huCC49 antibodies containing the eight designed synthetic connecting peptides indicated in Table 2 were constructed and antibody produced in CHO DG44 cells. Supernatants were collected from isolated cell lines and concentration of antibody in the culture supernatants determined by immunoassay. Supernatants containing antibody ranging from 0 to 30 ng of total antibody protein from each cell line was analyzed by non-reducing SDS-PAGE electrophoresis followed by Western Blot with anti-human kappa HRP conjugated antibody to detect CH2 domain deleted huCC49 Form A and Form B isoforms. Under these conditions, Form A migrates as a single 120 kDa homodimer and Form B as a 60 kDa doublet. Also visible are kappa chain monomer and dimers. Connecting peptides shown in SEQ ID NOs: 8, 9, 14, and 15 were all found to increase the proportion of Form A produced.

TABLE 3

The percentage of Form A antibody after affinity chromatography (Protein G) and after HIC purification

| CH2 domain deleted Antibody | % Form A Antibody | |
|---|---|---|
| | After Protein G | After HIC purification |
| HuCC49 (connecting peptide SEQ ID NO: 7) | 60 | 98 |
| HuCC49 PAP (connecting peptide SEQ ID NO: 14) | 83 | 98 |
| HuCC49 V2 PAP (connecting peptide SEQ ID NO: 14) | 90 | 99 |
| HuCC49 G1/G3/PAP (connecting peptide SEQ ID NO: 9) | 98 | Not done |
| HuCC49 V2 G1/G3/PAP (connecting peptide SEQ ID NO: 9) | 96 | Not done |

These data show that novel, engineered synthetic hinge region connecting peptides can be used to preferentially favor the formation of the A or B isoform. These studies also reveal the importance of the cysteine residues at position 242 (Kabat numbering system) in synthesizing the CH2 domain-deleted antibody Form A isoform. Substituting the cysteine at either position 239 or 242 with serine (e.g., using connecting peptides shown in SEQ ID NOs:10, 11, 12, or 13) shifts CH2 domain-deleted antibody biosynthesis to the Form B isoform. Accordingly, in one embodiment, a connecting peptide of the invention comprises a cysteine at at least one of position 239 or 242. The use of connecting peptides which increase the proportion of Form A produced will lead to a beneficial improvement in process, yield and/or stability. These synthetic hinge region connecting peptides are useful for favoring synthesis of CH2 domain deleted antibody Form A isoform for any antibody isotype, e.g., IgG1, IgG2, IgG3, or IgG4, based on the extremely high degree of homology among the CH3 domains for all four human isotypes. Including identical and conserved amino acid residues, IgG1 CH3 domain is 98.13% homologous to IgG2 CH3, 97.20% homologous to IgG3 CH3, and 96.26% homologous to IgG4 CH3.

Example 4

Purification of Form A and Form B from a Monoclonal Antibody Mixture Containing Both Isoforms 10 mL of ddCC49 supernatant was titrated with 1M Tris pH 9.0 to a final pH of 7.5. This material was filtered through a series of Sol-Vac 0.8μ and 0.4μ membranes. A 100 mL XK50 Protein G column was pre-equilibrated with 1×PBS at a flow rate of 80 ml/min. The titrated, filtered supernatant was loaded onto the column at 80 ml/min. Bound protein was washed with the equilibrium buffer for 2 column volumes and then eluted with 100 mM Glycine at pH 3.0. The fractions containing the ddCC49 peak were collected and immediately titrated with 1 M Tris pH 9.0 to a final pH of 7.0.

A Toso Biosep Phenyl 5PW-HR column was pre-equilibrated with 20 mM Phosphate pH 7.2; 1 M Ammonium Sulfate. The Protein G eluate was titrated to 1 M Ammonium Sulfate using a 3.5 M Ammonium Sulfate pH 7.2 stock and loaded at a concentration of 2 mg/ml of gel bed. Bound protein was washed with a 20 mM Phosphate pH 4 or 7.2 Ammonium Sulfate to adjust the conductivity to 116.4 mS/cm. The material eluted from this condition has an apparent molecular weight about 120 kD (Form A) on a non-reducing SDS-PAGE. The remaining bound antibody was further eluted with a linear gradient of reducing Ammonium Sulfate content in the Phosphate buffer. This method separates Forms A and B in two separate peaks. The latter eluted antibody apparently lacks the disulfide linkage between the heavy chains and its molecular weight is about 60 kDa (Form B).

Both of the above purified materials can be recaptured by bringing the ammonium sulfate concentration to 1M and reloading it onto the cleaned Phenyl 5PW-HR column. Bound protein is eluted with 20 mM Phosphate pH 7.2 and dialyzed into 1×PBS.

Example 5

Comparison of Stability of Form A and Form B

The biologic activity of Forms A and B (as measured in preliminary experiments e.g., using direct binding or competition studies) revealed that Forms A and B have similar biologic activity.

The stability of Forms A and B was also compared. Purified ddCC49 molecules were concentrated to about 5 mg/ml by Amicon concentrator fitted with YM30 membrane (Millipore). The concentrated materials were equally divided into four portions for each isoforms and each fraction was put into 10K dialysis cassette (Pierce, cat#66410) for 16 h dialysis in the following buffers: 1) 10 mM Sodium Phosphate, pH3; 2) 10 mM Sodium acetate, pH 5; 3) 10 mM Sodium Phosphate, pH 7; and 4) 10 mM Sodium Borate, pH 9. After dialysis, the protein concentration of each solution was adjusted to 3 mg/ml. In addition to the pure A and B isoform solution, a portion of A and B solutions from each pH were mixed to create a mixture containing 50% each isoform. Total of 12 formulations were created (four pH levels times 3 antibody solutions). The solutions were filtered and filled in 3 ml Type-1 glass serum vials (West Pharmaceuticals) with gray butyl stopper.

Three temperatures, 2-8° C., 20-25° C., and 38-42° C. were chosen to store the protein solutions for stability testing. Prior to storage, 500 µl samples were drawn from each formulation for physical and chemical analyses, these zero-time point data were referred to as control. Once in storage, samples were drawn at the following schedule, 2 weeks, 1 month, 2 months and 3 months and submitted for testing immediately.

To evaluate the physical and chemical stability of the two isoforms, the following methods were used: turbidity measured at $OD_{320}$, non-reducing SDS-PAGE, and size-exclusion chromatography.

Non-reducing SDS-PAGE was performed on for samples stored at 2-8° C., 20-25° C. and 38-42° C. for various time points. Both A and B form are relatively stable at pH 5 when stored at 2-8° C. However, when formulated at pH 7 and 9, both A and B forms showed degradation as indicated by increasing in number of bands that were smaller than the original major bands (120 kDa for form A and 60 kDa for form B). It was noticed that, particularly for pH 7 and 9 samples stored at low and intermediate temperatures, the intensity and number of bands that were less than 55 kDa were higher in B-isoform than A. This indicated that under these conditions the A-isoform is more stable than B-isoform. However, this seems not to be the case for A-isoform in pH 5 and stored at 20-25° C. This sample seemed to have more fragments than B-isoform. This appears to have been an artifact due to microbial contamination (discussed in more detail below). At high storage temperature, both forms at pH 9 were significantly degraded and there was almost no difference in gel patterns among the samples. Under this condition, trace amount of smear bands showed up at top of the gel which indicated the formation of aggregates. Because aggregates could be dissolved by SDS, the aggregation was investigated using the methods described in the following sections.

Table 4A through Table 4C list the turbidity data for ddCC49 stored at three different temperatures. The turbidity measures both the soluble and non-soluble aggregates and it is based on the amount of light scattered by these particles. When present, aggregates will scatter light and result in an increase in $A_{320}$. As showed in Table 4A-C, the turbidity of ddCC49 molecules stored at 2-8° C. increases as pH increased for both A and B isoforms, with the former being less turbid than the latter. This trend held true for samples stored for less than a month at higher temperatures (20-25° C. and 38-40° C.). As storage time reached 3 months, the turbidity increased significantly for samples at high pH and temperature, and the difference between A and B forms diminished. These results parallel those of SDS-PAGE and indicate that both isoforms are relatively stable (in terms of not forming aggregates) at pH 3 and 5, and that A-isoform is less susceptible to aggregation than the B isoform.

TABLE 4A

Turbidity measured at $A_{320}$ for ddCC49 samples stored at 2-8° C.

| Time (month) | A-isoform | | | | B-isoform | | | | Mixture | | | |
|---|---|---|---|---|---|---|---|---|---|---|---|---|
| pH = | 3 | 5 | 7 | 9 | 3 | 5 | 7 | 9 | 3 | 5 | 7 | 9 |
| 0 | 0.030 | 0.038 | 0.044 | 0.056 | 0.034 | 0.042 | 0.046 | 0.066 | 0.036 | 0.042 | 0.051 | 0.061 |
| ½ | 0.029 | 0.029 | 0.046 | 0.045 | 0.030 | 0.038 | 0.048 | 0.058 | 0.034 | 0.033 | 0.043 | 0.055 |
| 1 | 0.033 | 0.039 | 0.035 | 0.055 | 0.033 | 0.035 | 0.044 | 0.059 | 0.032 | 0.040 | 0.039 | 0.066 |
| 2 | 0.042 | 0.022 | 0.042 | 0.044 | 0.039 | 0.037 | 0.055 | 0.067 | 0.042 | 0.024 | 0.040 | 0.058 |
| 3 | 0.035 | 0.047 | 0.051 | 0.050 | 0.038 | 0.041 | 0.066 | 0.081 | 0.027 | 0.048 | 0.051 | 0.065 |

TABLE 4B

Turbidity measured at $A_{320}$ for ddCC49 samples stored at 20-25° C.

| Time (month) | A-isoform | | | | B-isoform | | | | Mixture | | | |
|---|---|---|---|---|---|---|---|---|---|---|---|---|
| pH = | 3 | 5 | 7 | 9 | 3 | 5 | 7 | 9 | 3 | 5 | 7 | 9 |
| ½ | 0.031 | 0.032 | 0.056 | 0.066 | 0.039 | 0.034 | 0.064 | 0.083 | 0.034 | 0.039 | 0.060 | 0.071 |
| 1 | 0.025 | 0.043 | 0.055 | 0.090 | 0.034 | 0.042 | 0.070 | 0.084 | 0.028 | 0.039 | 0.055 | 0.094 |
| 2 | 0.034 | 0.053 | 0.077 | 0.113 | 0.046 | 0.032 | 0.090 | 0.087 | 0.037 | 0.038 | 0.066 | 0.108 |
| 3 | 0.036 | 0.056 | 0.156 | 0.143 | 0.029 | 0.060 | 0.121 | 0.125 | 0.044 | 0.050 | 0.101 | 0.142 |

TABLE 4C

Turbidity measured at $A_{320}$ for ddCC49 samples stored at 38-42° C.

| Time (month) | A-isoform | | | | B-isoform | | | | Mixture | | | |
|---|---|---|---|---|---|---|---|---|---|---|---|---|
| pH = | 3 | 5 | 7 | 9 | 3 | 5 | 7 | 9 | 3 | 5 | 7 | 9 |
| ½ | 0.041 | 0.042 | 0.068 | 0.063 | 0.041 | 0.044 | 0.080 | 0.067 | 0.041 | 0.039 | 0.070 | 0.064 |
| 1 | 0.041 | 0.043 | 0.071 | 0.065 | 0.036 | 0.040 | 0.079 | 0.069 | 0.032 | 0.048 | 0.078 | 0.070 |
| 2 | 0.047 | 0.030 | 0.066 | 0.060 | 0.046 | 0.045 | 0.087 | 0.082 | 0.051 | 0.034 | 0.078 | 0.079 |
| 3 | 0.058 | 0.051 | 0.098 | 0.105 | 0.046 | 0.057 | 0.101 | 0.157 | 0.056 | 0.057 | 0.101 | 0.126 |

Size exclusion chromatography (SEC) is a powerful method for revealing the percent of intact molecules and the degraded products (both fragments and soluble aggregates) and is highly reproducible. In Table 4A-C the percent of intact monomer of A-isoform, B-isoform and the mixture stored at different temperatures are listed. For samples stored at 2-8° C., it is clear that Form A has a higher percentage of monomer as compared to Form B, and the mixture of Form A and Form B was somewhere in between. At this storage temperature, both forms were relatively stable at pH 3, 5 and 7 (with pH 5 being the most stable condition) for about three months. However, at pH 9 there was a significant decrease in percentage of monomer for Form B but only a slight decrease for Form A.

At elevated temperatures, all samples showed a significant decrease in percent of monomer as storage time increased; the A-isoform outperformed the B-isoform. However there was an exception, the sample of A-isoform in pH 5 stored at room temperature exhibited much more degradation than the B-isoform or the mixture under similar storage conditions. A close examination of this particular A-isoform vial, the data from SDS-PAGE, and SEC of the sample suggested that microbial contamination might have caused this unexpected result. First, both the SEC and SDS-PAGE results indicated that the degradation for this sample was primarily accounted for by a increase in fragmentation, presumably resulting from microbial digestion, otherwise some degree of increase in aggregation would have been expected. Second, the fact that the mixture sample, which contained 50% each of A and B-isoform, showed a better stability profile than B-isoform indicating that a more stable A-isoform must have contributed to the higher percent of monomer. Finally, A-isoform in pH 5 stored at 2-8° C. and 38-42° C. both showed higher percent of monomer than B-isoform under similar conditions. Therefore, intermediate storage temperature should have yielded similar results. Due to the limited amount of sample, an assay for microbial contamination could not be performed.

It was also noted that for both isoforms of IDEC-159 stored in high pH (9) and at 40° C., the percent of monomer reduced to about 30%. Under these severe conditions, the stability differences between the two isoforms disappeared. This SEC result mirrors of the results found using SDS-PAGE. Both results indicate that, although some chemical and physical characteristics differ between the two isoforms, the mechanism and by-products of degradation for both isoforms are similar, if not identical.

In summary, the SEC results indicate that both A and B-isoforms have optimal pH at about 5, and that A-isoform is more stable than B-isoform in terms of retaining higher percent of intact monomer at similar storage conditions.

TABLE 5A

Percent of monomer for ddCC49 samples stored at 2-8° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| 0 | 98.81 | 99.13 | 98.16 | 97.93 | 97.02 | 97.70 | 96.88 | 93.51 | 97.83 | 98.27 | 97.44 | 95.81 |
| ½ | 98.98 | 99.16 | 98.25 | 98.00 | 97.15 | 97.87 | 96.96 | 91.95 | 98.15 | 98.49 | 97.68 | 95.59 |
| 1 | 98.80 | 99.20 | 97.99 | 97.11 | 97.02 | 97.81 | 96.62 | 88.99 | 98.04 | 98.45 | 97.41 | 94.45 |
| 2 | 98.74 | 99.01 | 98.00 | 95.67 | 97.15 | 97.69 | 95.50 | 84.84 | 98.06 | 98.34 | 96.81 | 92.17 |
| 3 | 98.28 | 98.89 | 97.88 | 95.31 | 96.69 | 98.14 | 95.37 | 85.98 | 97.61 | 98.15 | 96.65 | 89.90 |

TABLE 5B

Percent of monomer for ddCC49 samples stored at 20-25° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| ½ | 97.83 | 99.04 | 97.12 | 93.65 | 95.84 | 97.62 | 93.71 | 79.61 | 96.75 | 98.30 | 95.37 | 87.67 |
| 1 | 96.60 | 96.63 | 95.65 | 88.09 | 94.38 | 97.23 | 90.69 | 72.26 | 95.36 | 97.99 | 93.05 | 80.92 |
| 2 | 93.62 | 92.79 | 93.17 | 80.06 | 91.71 | 96.96 | 85.51 | 66.53 | 92.78 | 97.51 | 89.33 | 73.91 |
| 3 | 92.81 | 89.56 | x | 74.31 | 89.30 | 96.04 | 82.57 | 63.25 | 90.46 | 97.02 | 86.80 | 69.36 |

TABLE 5C

Percent of monomer for ddCC49 samples stored at 38-42° C.

| Time (month) | A-isoform | | | | B-isoform | | | | Mixture | | | |
|---|---|---|---|---|---|---|---|---|---|---|---|---|
| | pH = 3 | 5 | 7 | 9 | 3 | 5 | 7 | 9 | 3 | 5 | 7 | 9 |
| ½ | 86.31 | 97.50 | 85.06 | 66.42 | 79.85 | 94.29 | 69.68 | 63.64 | 82.09 | 95.70 | 76.24 | 63.95 |
| 1 | 78.71 | 95.19 | 73.77 | 51.55 | 66.73 | 89.37 | 54.70 | 50.10 | 68.53 | 92.02 | 62.93 | 49.28 |
| 2 | 66.64 | 91.63 | 60.45 | 38.43 | 60.29 | 81.08 | 42.98 | 37.09 | 61.33 | 85.81 | 51.08 | 36.68 |
| 3 | 57.87 | 86.99 | 52.82 | 30.81 | 43.61 | 74.23 | 36.68 | 29.73 | 46.75 | 80.93 | 44.35 | 30.18 |

Example 7

Preparative Purification of Forms A and B

IDEC-159 (ddCC49) is a CH2 domain deleted monoclonal antibody directed against TAG-72 antigen, which is expressed on the surface of tumors. IDEC-159 contains two isoforms of the antibody, called Form A and Form B. The current cell culture process for IDEC-159 produces an approximate 50:50 ratio of Form A to Form B. The Form A isoform is an antibody with a deleted CH2 region in the $F_C$ portion of the heavy chain. In addition to having a deleted CH2 region, Form B also lacks the disulfide bond linkage across the $F_C$ region and is only held together by hydrophobic interactions and salt bridges.

The third and final chromatography step in the IDEC-159 purification process was developed to separate the two isoforms of IDEC-159. The separation is achieved by hydrophobic interaction chromatography (HIC), using a Phenyl TSK-gel 5PW-HR adsorbent. Since form B is more hydrophobic than form A, it adsorbs irreversibly to the stationary phase using approximately 0.73 M Ammonium Sulfate/20 mM Sodium Phosphate, pH 4.0-pH 7.0 as the mobile phase. Form A binds to a lesser extent to the stationary phase under these conditions and is therefore eluted isocratically, i.e. it leaves the column with the flowthrough fraction. Subsequent to the isocratic elution of Form A, omitting Ammonium sulfate from the mobile phase des orbs Form B. The following method was used to separate the two isoforms of IDEC-159:

The column was sanitized using ≥3 CVs of 0.5 N NaOH, at ≤150 cm/hr.

The column was equilibrated using ≥5 CVs of 0.73 M Ammonium Sulfate/20 mM Sodium Phosphate, pH 4.0, at ≤150 cm/hr.

The column was loaded with room temperature TMAE Flowthrough that has been adjusted to include 0.43 volumes of 2.5 M Ammonium Sulfate/20 mM Sodium Phosphate, pH 4.0 liquid stock solution, at 5 mg per ml of resin.

The antibody was loaded onto the column at pH 4.0, at ≤100 cm/hr.

Collection of the antibody started when the outlet O.D. at 280 nm reaches 10 mAU.

The column was washed using 15 CVs of 0.73 M Ammonium Sulfate/20 mM Sodium Phosphate, pH 4.0, at ≤100 cm/hr.

Continue antibody collection throughout the 15 CV wash, then the outlet was diverted back to waste.

The column was stripped using ≥5CVs of 20 mM Sodium Phosphate, pH 4.0, at ≤100 cm/hr. 6. The column was cleaned with ≥3 CVs 0.5 N NaOH, at ≤150 cm/hr.

The column was equilibrated with ≥3 CVs of 0.73 M Ammonium Sulfate/20 mM Sodium Phosphate, pH 4.0, at ≤150 cm/hr.

The column was stored in ≥3 CVs of 20% Ethanol, at ≥150 cm/hr.

The separation of the two forms at a preparative scale (5 L column volume, total IDEC-159 load approximately 20 g) is shown in FIGS. 13 (A and B). The first two peaks comprise the isocratic elution of Form A, the second peak shows the eluted Form B, while the third peak contains impurities, which are removed from the stationary phase during cleaning.

The capability of this method to separate Forms A and B at preparative scale was also demonstrated by SDS PAGE.

Example 8

Preparation of a CH2 Domain-Deleted Tetravalent Antibody

HuCC49 CH2 domain-deleted sc(Fv)2 tetravalent antibody design was based on appending a huCC49 single chain Fv (scFv) to the carboxyl terminus of the HuCC49 CH2 domain-deleted antibody CH3 domain. A schematic diagram of HuCC49 CH2 domain-deleted sc(Fv)2 tetravalent antibody is shown in FIG. 4. An equivalent reference to this design is C-scFv Tetravalent CH2 Domain Deleted antibody. The preparation of single polypeptide chain binding molecules of the Fv region, single-chain Fv molecules, is described in U.S. Pat. No. 4,946,778. A CC49 scFv immunoglobulin-like antibody is described in U.S. Pat. No. 5,892,019. The huCC49 scFv is comprised of a VL and a VH region sequence tethered by a short synthetic linker (VL→(Gly$_4$Ser)$_3$ linker→VH orientation) and was synthesized by PCR amplification. The 5' VL PCR primer included a Bam HI restriction endonuclease site followed by sequence encoding a (Gly$_4$Ser)$_2$ linker peptide. The 3' VL PCR primer included sequence partially encoding a (Gly$_4$Ser)$_3$ linker peptide used to connect the two VL and VH regions. The 5' VH PCR primer also included sequence partially encoding a (Gly$_4$Ser)$_3$ linker peptide used to connect the VL and VH regions. Finally, the 3' VH PCR primer included a stop codon followed by a Bam HI site. The two V regions were amplified with the two sets of PCR primers from plasmid DNA substrate containing huCC49 CH2 domain-deleted antibody and assembly of the scFv was accomplished in a second PCR reaction through the common overlapping sequences encoding the (Gly$_4$Ser)$_3$ linker. The huCC49 scFv gene fragment was gel isolated, digested with Bam HI restriction endonuclease and cloned into a single Bam HI site previously introduced into the huCC49 CH2 domain-deleted antibody Polycistronic expression vector. (See US 2003 0157641 A1.). Briefly, the vector was modified by removing an existing stop codon at the 3' end of the gene coding for the CH3 domain and replacing with nucleotides coding for the amino acid sequence Ser-Gly-Gly-Gly immediately followed by a Bam HI restriction endonuclease site (coding for Gly-Ser). The Bam HI digested huCC49 scFv fragment was cloned into the Bam HI site of the vector resulting in a fusion product of the huCC49 scFv to the carboxyl terminus of the huCC49 CH2 domain-deleted antibody CH3 domain through a 16 amino acid Ser(Gly$_4$Ser)$_3$ linker. Correct sequences were confirmed by DNA sequence analysis. Plasmid DNA was used to transform CHO DG44 cells for stable production of antibody protein. The engineered antibody was designated huCC49 domain-deleted sc(Fv)2 tetravalent antibody. FIG. 8A shows the DNA sequence of heavy chain huCC49 domain-deleted sc(Fv)2 tetravalent antibody. FIG. 8C shows the DNA sequence of light chain huCC49 domain-deleted sc(Fv)2 tetravalent antibody. FIG. 9A shows the amino acid sequence of heavy chain huCC49 domain-deleted sc(Fv)2 tetravalent antibody. FIG. 9C shows the amino sequence of light chain huCC49 domain-deleted sc(Fv)2 tetravalent antibody.

Figure 18:
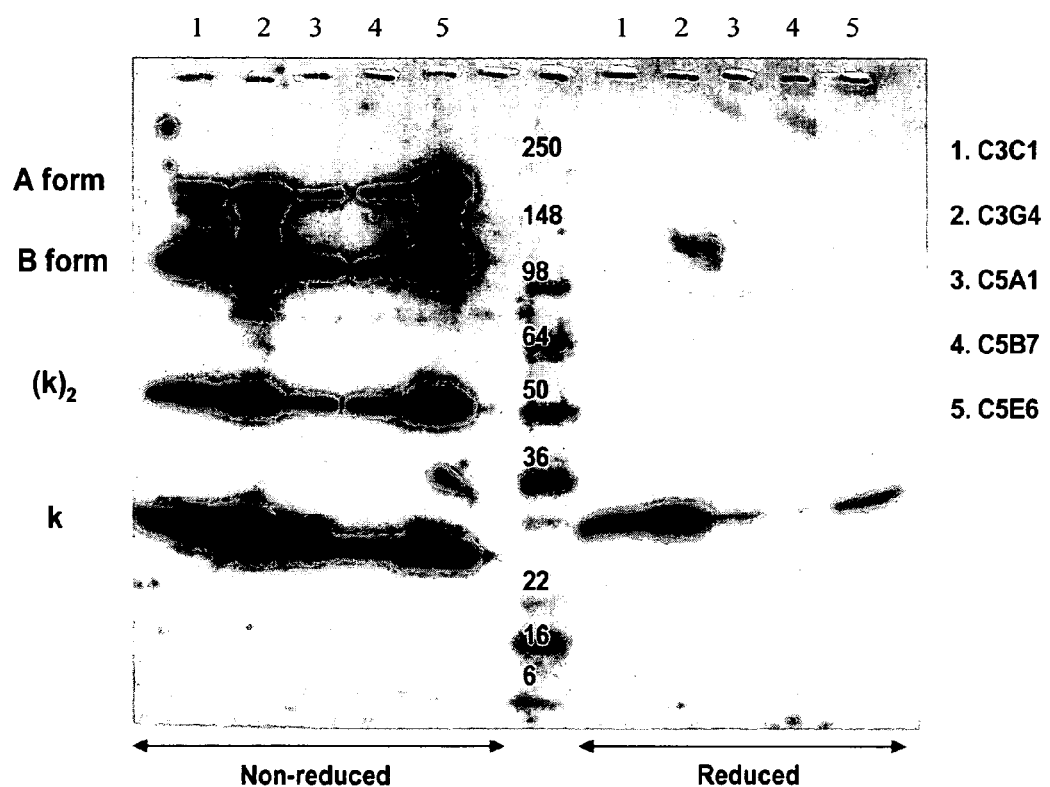
FIG. 18 shows a Western Blot of supernatants from five independent clones producing huCC49 domain-deleted sc(Fv)2 tetravalent (C-scFv tetravalent CH2 domain deleted) antibody. Each supernatant was electrophoresed under both reducing and non-reducing conditions.
Figure 19:
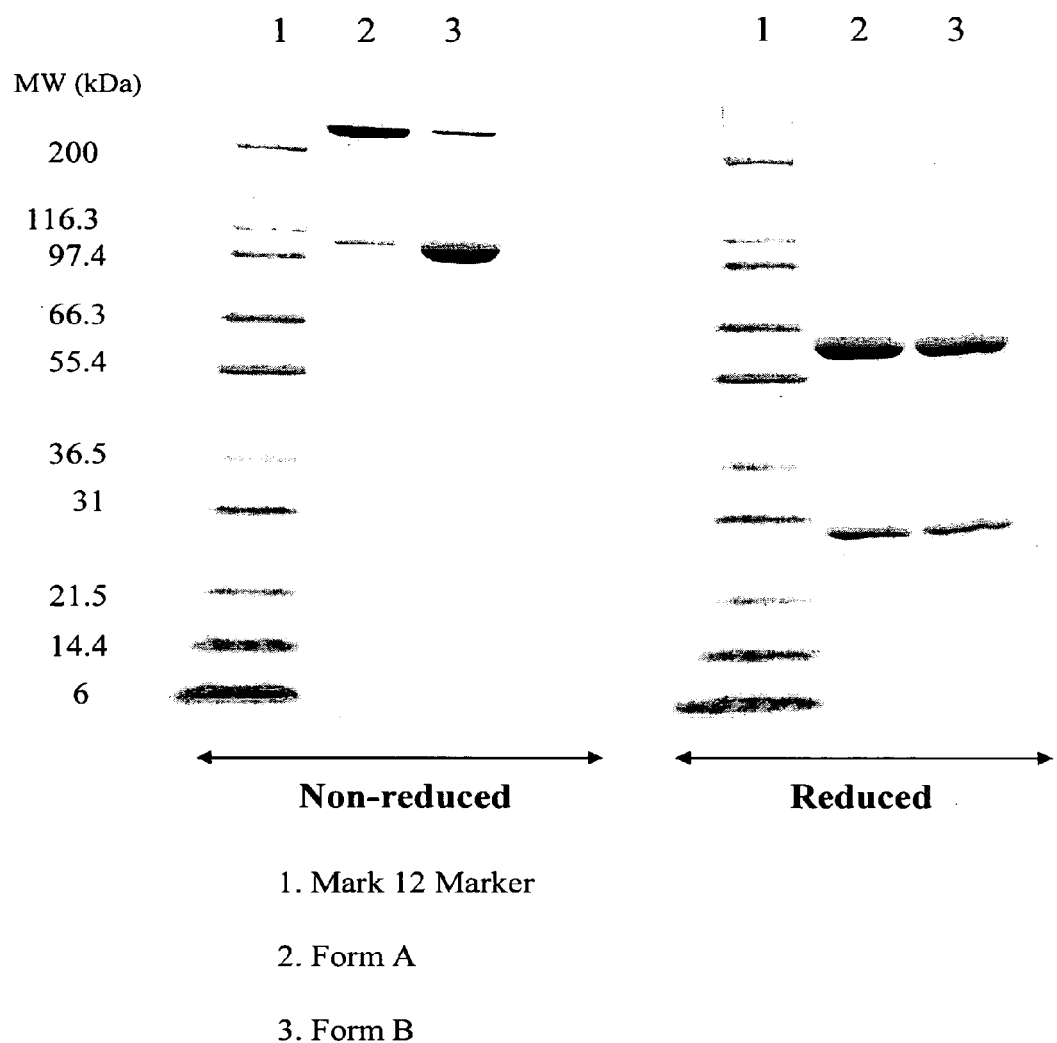
FIG. 19 shows a Coomassie Blue stained gel of purified Forms A and B huCC49 domain-deleted sc(Fv)2 tetravalent (C-scFv tetravalent CH2 domain deleted) antibodies. Each antibody was electrophoresed under reducing and non-reducing conditions.
Figure 20:
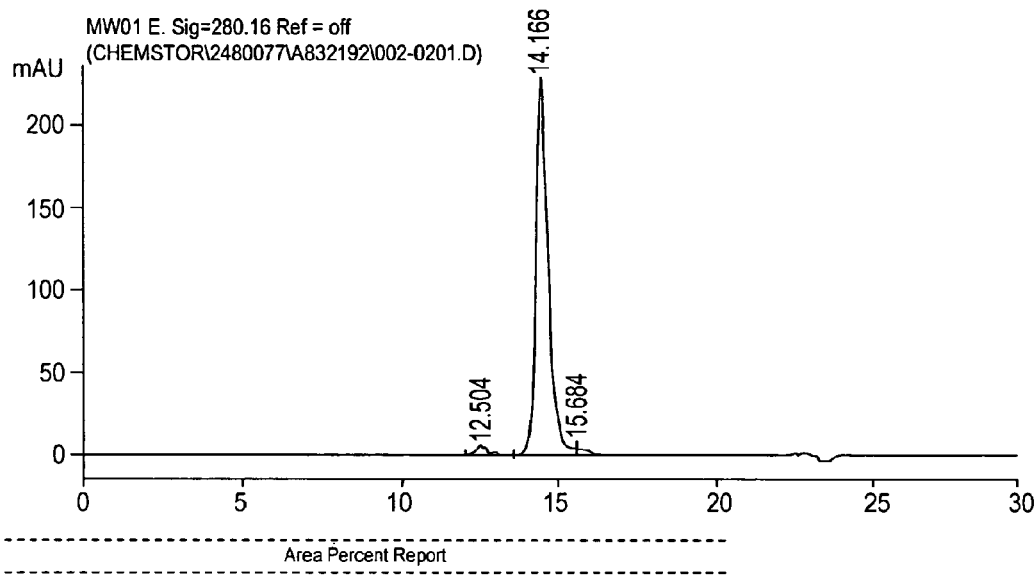
FIG. 20 shows that purified Form A huCC49 domain-deleted sc(Fv)2 tetravalent (C-scFv tetravalent CH2 domain deleted) antibody predominantly elutes as a single peak by HPLC size-exclusion chromatography.

Supernatants were collected from isolated cell lines and concentration of antibody in the culture supernatants determined by immunoassay. Supernatants were analyzed by non-reducing SDS-PAGE electrophoresis followed by Western Blot with anti-human kappa-HRP conjugated antibody to detect huCC49 CH2 domain-deleted sc(Fv)2 tetravalent antibody Form A and Form B isoforms. Under these conditions, Form A was observed to migrate as a single ~170 kDa homodimer and Form B as a ~85 kDa doublet in approximately a 50:50 ratio of A to B isoform. As shown in FIG. 18, five individually isolated clones were all found to produce an A and B CH2 domain-deleted sc(Fv)2 tetravalent antibody isoform. One of the clones was selected for antibody production and purification using HIC chromatography as described in Example 4. Purified huCC49 CH2 domain-deleted sc(Fv)2 tetravalent antibody Forms A and B were analyzed by non-reducing and reducing SDS-PAGE and the results are shown in FIG. 19. Form A huCC49 domain-deleted sc(Fv)2 tetravalent antibody was effectively separated from Form B in excess of 95% purity. As expected, both purified Forms behaved identically under reducing SDS-PAGE conditions. HuCC49 CH2 domain-deleted sc(Fv)2 tetravalent antibody Form A was examined by size exclusion chromatography and found to elute primarily as a single peak (96%) indicating that there was no significant aggregation or decomposition of antibody product (FIG. 20).

Example 9

Biodistribution Profile of HuCC49 CH2 Domain-Deleted Tetravalent Antibody

Figure 21:
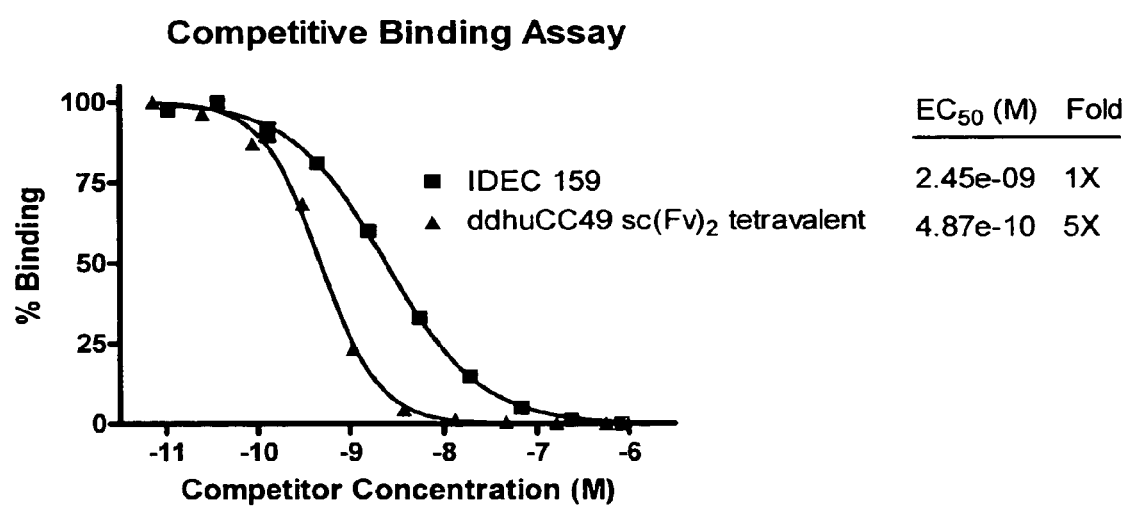
FIG. 21 shows the results of a competitive binding assay of Form A huCC49 domain-deleted sc(Fv)2 tetravalent (C-scFv tetravalent CH2 domain deleted) antibody to bovine submaxillary mucin, a source of the TAG-72 antigen, by time-resolved fluorometic immunoassay using a Delphia fluorimeter (Wallac Inc, Gaithersburg, Md.).

HuCC49 CH2 domain-deleted sc(Fv)2 tetravalent antibody Form A was tested in a competitive binding assay for it's ability to bind to bovine submaxillary mucin, a source of the TAG-72 antigen, by time-resolved fluorometric immunoassay using a Delphia fluorimeter (Wallac Inc., Gaithersburg, Md.). Competitive binding curves are shown in FIG. 21. HuCC49 CH2 domain-deleted sc(Fv)2 tetravalent antibody Form A and control parent CH2 domain-deleted huCC49 (referred to as HuCC49 or IDEC 159) antibodies were evaluated. Relative binding activity for the tetravalent antibody was found to be 5-fold more avid than the control parent CC49 antibody (GraphPad Prism 4.0 for Windows, GraphPad, Software, San Diego Calif. USA. www.graphpad.com), consistent with an expected increase in the number of antigen binding sites.

Biodistribution of $^{90}$Y-radiolabeled huCC49 CH2 domain-deleted sc(Fv)2 tetravalent antibody was compared to results previously generated with control parent huCC49 antibody in athymic nude mice bearing LS-174T human tumor xenografts. HuCC49 CH2 domain-deleted sc(Fv)2 tetravalent antibody was conjugated with the chelator Chx-DTPA and binding activity assessed. Conjugated huCC49 CH2 domain-deleted sc(Fv)2 tetravalent antibody showed a 5-6 fold higher avidity than the conjugated control parent huCC49 demonstrating that the tetravalent antibody could be derivatized without losing significant binding activity. HuCC49 CH2 domain-deleted sc(Fv)2 tetravalent antibody was labeled with $^{90}$Y and a single dose of radiolabeled antibody was administered by i.v. tail vein injection to mice presenting pre-established tumors of approximately 250 mm$^3$. Samples were harvested and processed for beta counting. Percentage injected dose (% ID) of $^{90}$Y radiolabeled antibody per grain of tumor or normal tissue was determined from 3 to 72 hours and is shown in Table 6.

TABLE 6

| | 5-7 mice/group % ID/gm-tissue | | | | |
|---|---|---|---|---|---|
| | Blood | Spleen | Kidney | Liver | Tumor |
| HuCC49 (domain deleted) | | | | | |
| 3-5 hrs | 18.24 | 5.39 | 9.15 | 8.83 | 13.66 |
| 12 hrs | 3.21 | 5.01 | 15.50 | 14.20 | 17.33 |
| 24 hrs | 1.03 | 6.21 | 14.09 | 10.84 | 20.53 |
| 48 hrs | 0.17 | 6.92 | 11.15 | 11.85 | 13.17 |
| 72 hrs | 0.10 | 6.22 | 9.01 | 10.59 | 10.55 |
| Tetravalent HuCC49 | | | | | |
| 3 hrs | 20.3 | 12.60 | 7.60 | 9.60 | 10.80 |
| 6 hrs | 15.4 | 12.20 | 6.70 | 12.40 | 12.10 |
| 12 hrs | 7.20 | 15.10 | 5.10 | 13.90 | 13.10 |

TABLE 6-continued

| | 5-7 mice/group % ID/gm-tissue | | | | |
|---|---|---|---|---|---|
| | Blood | Spleen | Kidney | Liver | Tumor |
| 24 hrs | 2.40 | 9.50 | 3.90 | 12.10 | 14.00 |
| 48 hrs | 0.50 | 10.00 | 2.60 | 11.90 | 11.50 |
| 72 hrs | 0.10 | ** | 1.90 | 12.70 | 6.40 |

Figure 35A:
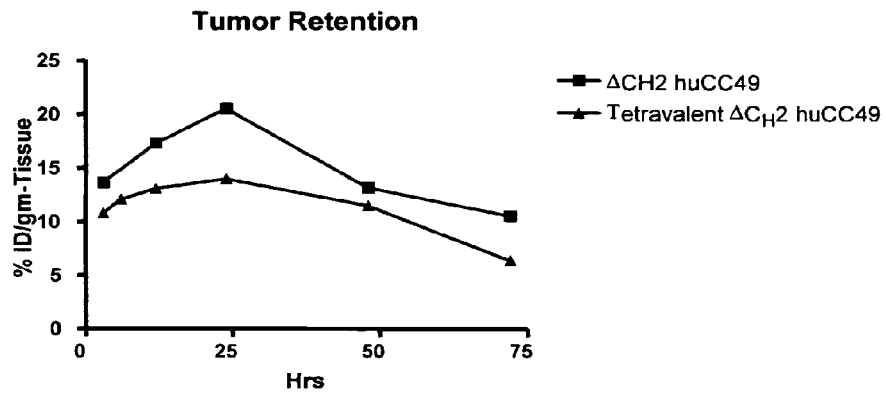
FIG. 35 A shows tumor retention for control parent huCC49 and huCC49 CH2 domain-deleted sc(Fv)2 tetravalent antibody as measured by % ID/gm.
Figure 35B:
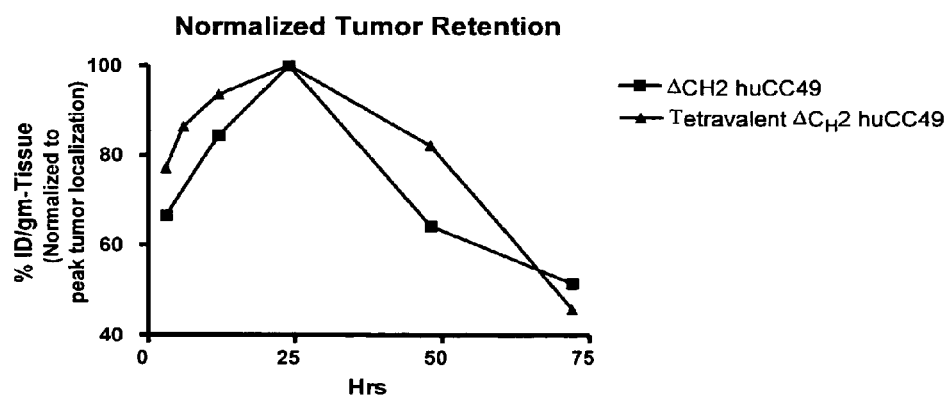

Data represent mean values +/− standard errors.
 technical problem with sample HuCC49 CH2 domain-deleted sc(Fv)2 tetravalent (C-scFv tetravalent CH2 domain deleted) antibody showed lower accumulation in the kidney than control huCC49 antibody, likely due to the increased molecular mass of the antibody. Tumor accumulation of huCC49 CH2 domain-deleted sc(Fv)2 tetravalent antibody was similar to that achieved with the control parent huCC49 (Table 6). However, as mentioned, these two biodistribution studies were not conducted simultaneously and are subject to experimental variation. A figure showing tumor retention for control parent huCC49 and huCC49 CH2 domain-deleted sc(Fv)2 tetravalent antibody as measured by % ID/gm is shown in FIG. 35. FIG. 35 also shows the same tumor retention data normalized to peak accumulation of radioactivity. AUC analysis of the two normalized retention curves in FIG. 35** was calculated using GraphPad Prism 4.0 for Windows, GraphPad, Software, San Diego Calif. USA. www.graphpad.com. Control parent huCC49 had a Total Peak Area of 2037 units and huCC49 CH2 domain-deleted sc(Fv)2 tetravalent antibody had a Total Peak Area of 2562 units representing a 25.8% increase in area for the tetravalent protein. Representation of the data in this format suggests that there is improved retention of tetravalent antibody in the tumor compartment compared to the parent divalent molecule.

The tetrameric HuCC49 construct affords certain advantages for pretargeting, e.g., radioimmunotherapeutic (RIT) pretargeting. This advantage is defined by three observations derived from Table 6. First, the tetrameric HuCC49 CH2 domain-deleted construct has a blood clearance rate comparable to that of the current CH2 domain-deleted HuCC49 construct. This fast blood clearance may obviate the need for a "clearing agent" to expedite removal of the antibody from the blood prior to administration of the radiolabeled ligand that localizes to the tumor-bound antibody. Elimination of the clearing agent significantly reduces the complexity of this modality of treatment in the clinical setting. Second, tumor retention for the tetrameric construct is comparable to the current dimeric construct. Therefore, radiation dose delivered will be comparable for the two constructs ((Table 6). Third, the lower kidney and liver uptake compared to the CH2 domain-deleted HuCC49 may enable larger input doses of the radiolabeled ligand before reaching organ-limiting toxicity.

Example 10

Preparation of a HuCC49 CH2 Domain-Deleted Tetravalent Antibody Comprising a Novel Connecting Peptide and Preferential Synthesis of Isoform A A huCC49 CH2 domain-deleted sc(Fv)2 tetravalent antibody similar to the design shown in the bottom half of FIG. 4 but containing the G1/G3/Pro243Ala244Pro245+[Gly/Ser] synthetic connecting peptide indicated in Table 2 was constructed. Briefly, gene sequences coding for partial G1/G3/

Pro243Ala244Pro245+[Gly/Ser] connecting peptide was synthesized by PCR amplification using a 5' connecting peptide PCR primer encoding a Sal I restriction endonuclease site and a 3' connecting peptide PCR primer encoding an Xho I site. Plasmid DNA containing the gene sequence coding for the G1/G3/Pro243Ala244Pro245+[Gly/Ser] connecting peptide was used as substrate. The PCR product encodes all of G1/G3/Pro243Ala244Pro245 and part of [Gly/Ser] connecting peptide. The G1/G3/Pro243Ala244Pro245 hinge fragment was gel isolated, digested with Sal I and Xho I restriction endonucleases and cloned into the Sal I and Xho I vector sites reconstituting the full length G1/G3/Pro243Ala244Pro245+[Gly/Ser] connecting peptide. Correct sequences were confirmed by DNA sequence analysis. Plasmid DNA was used to transform CHO DG44 cells for stable production of antibody protein. FIG. 8B shows the DNA sequence of heavy chain huCC49 domain-deleted sc(Fv)2 tetravalent antibody containing the G1/G3/Pro243Ala244Pro245+[Gly/Ser] connecting peptide. FIG. 8C shows the DNA sequence of light chain huCC49 domain-deleted sc(Fv)2 tetravalent antibody containing the G1/G3/Pro243Ala244Pro245+[Gly/Ser] connecting peptide. FIG. 9B shows the amino acid sequence of heavy chain huCC49 domain-deleted sc(Fv)2 tetravalent antibody containing the G1/G3/Pro243Ala244Pro245+[Gly/Ser] connecting peptide. FIG. 9C shows the amino sequence of light chain huCC49 domain-deleted sc(Fv)2 tetravalent antibody containing the G1/G3/Pro243Ala244Pro245+[Gly/Ser] connecting peptide.

Figure 22:
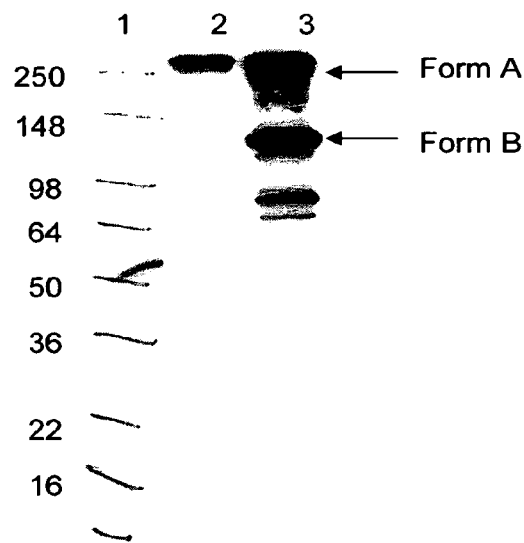
FIG. 22 shows a Western Blot of supernatant from a representative clone producing huCC49 CH2 domain-deleted sc(Fv)2 tetravalent (C-scFv tetravalent CH2 domain deleted) antibody containing the G1/G3/Pro243Ala244Pro245+[Gly/Ser] hinge connecting peptide.

Supernatants were collected from isolated cell lines and concentration of antibody in the culture supernatants determined by immunoassay. Supernatants were analyzed by non-reducing SDS-PAGE electrophoresis followed by Western Blot with anti-IgG-HRP conjugated antibody to detect huCC49 CH2 domain-deleted sc(Fv)2 tetravalent (C-scFv tetravalent CH2 domain-deleted) antibody Form A and Form β isoforms. Under these conditions, Form A is expected to migrate as a single ~170 kDa homodimer and Form B as a ~85 kDa doublet in approximately a 50:50 ratio of A to B isoform. As shown in FIG. 22, a representative CH2 domain-deleted sc(Fv)2 tetravalent antibody containing the G1/G3/Pro243Ala244Pro245+[Gly/Ser] connecting peptide was found to produce all Form A tetravalent antibody isoform.

Figure 23:
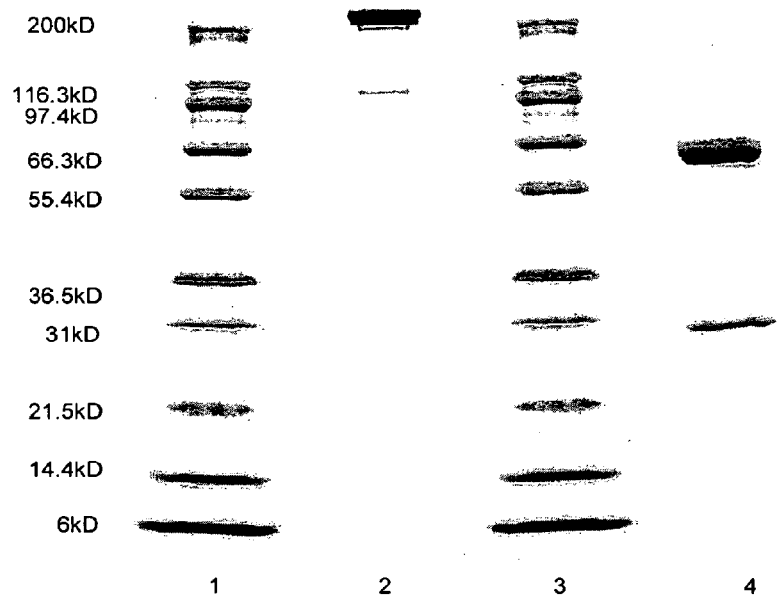
FIG. 23 shows a Coomassie Blue stained gel of purified Form A huCC49 CH2 domain-deleted sc(Fv)2 tetravalent G1/G3/PAP (C-scFv tetravalent CH2 domain deleted) antibody containing the G1/G3/Pro243Ala244Pro245+[Gly/Ser] hinge connecting peptide.
Figure 24:
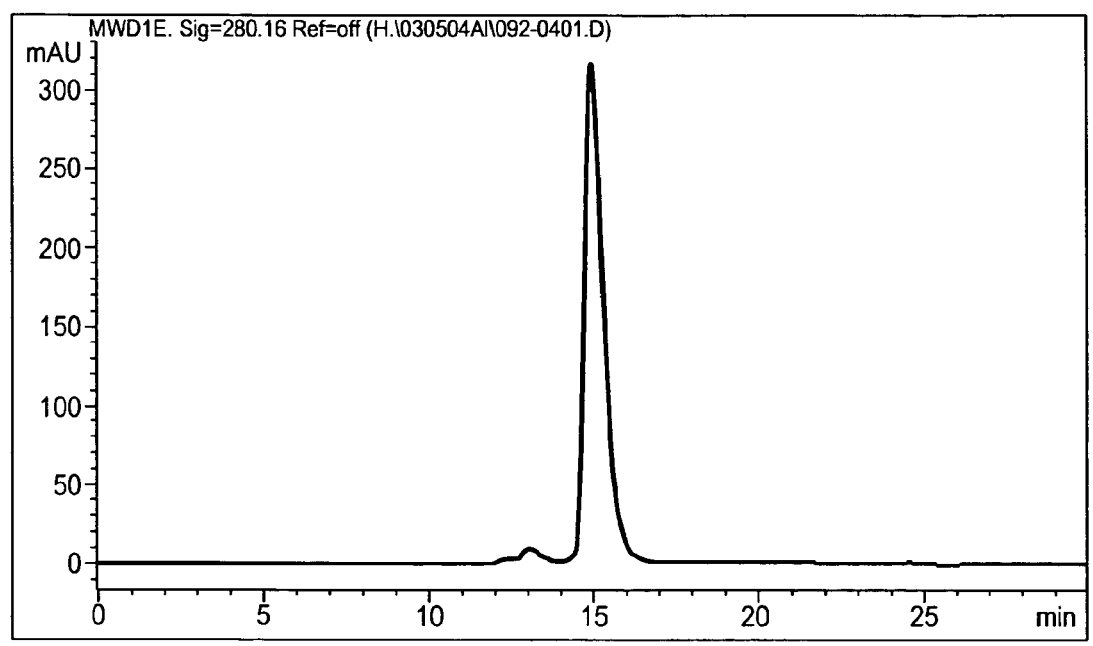
FIG. 24 shows that purified Form A huCC49 CH2 domain-deleted sc(Fv)2 tetravalent G1/G3/PAP (C-scFv tetravalent CH2 domain deleted) antibody containing the G1/G3/Pro243Ala244Pro245+[Gly/Ser] hinge connecting peptide predominantly elutes as a single peak by HPLC size-exclusion chromatography.
Figure 25:
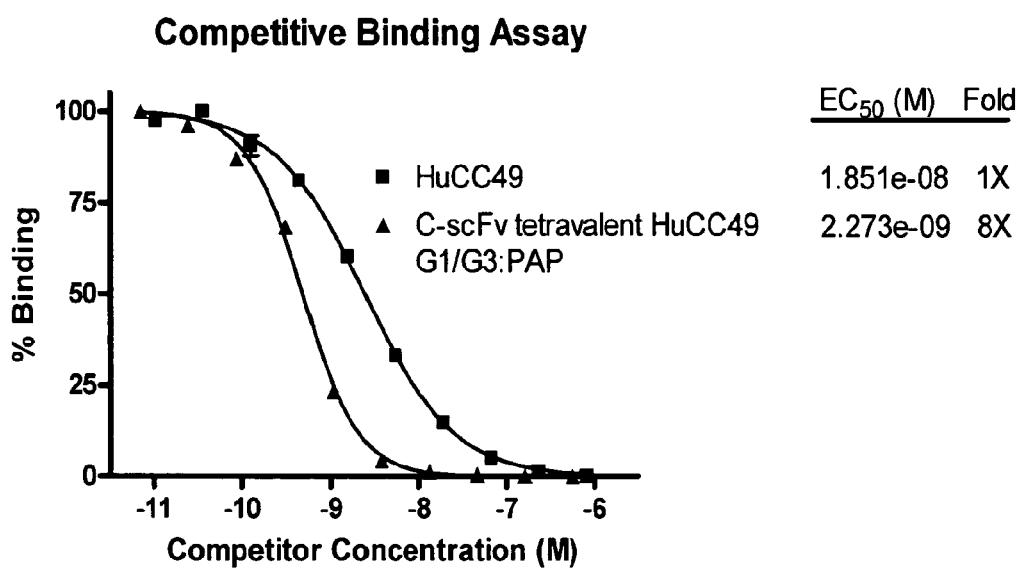
FIG. 25 shows the results of a competitive binding assay of Form A huCC49 CH2 domain-deleted sc(Fv)2 tetravalent G1/G3/PAP (C-scFv tetravalent CH2 domain deleted) antibody containing the G1/G3/Pro243Ala244Pro245+[Gly/Ser] hinge connecting peptide to bovine submaxillary mucin, a source of the TAG-72 antigen, by time-resolved fluorometic immunoassay using a Delphia fluorimeter (Wallac Inc, Gaithersburg, Md.).

A cell line containing the G1/G3/Pro243Ala244Pro245+[Gly/Ser] (SEQ ID NO:9) connecting peptide introduced into the huCC49 CH2 domain-deleted sc(Fv)2 tetravalent antibody sequence was used for antibody production. Antibody was produced and purified using methods described in Example 4 above. HuCC49 CH2 domain-deleted sc(Fv)2 tetravalent antibody containing the G1/G3/Pro243Ala244Pro245+[Gly/Ser] (SEQ ID NO:9) connecting peptide was purified using only the Protein G column, eluted essentially as a single peak at 96% purity without further HIC purification. Reduced and non-reduced purified protein samples were analyzed by SDS-PAGE electrophoresis. Under non-reducing conditions, Form A is expected to migrate as a single 170 kDa homodimer and Form B as a 85 kDa doublet. The connecting peptide shown in SEQ ID NO: 9 was found to substantially increase the proportion of Form A produced. Exemplary results are shown in FIG. 23. This result shows that the G1/G3/Pro243Ala244Pro245+[Gly/Ser] hinge (SEQ ID NO:9) resulted in the production of essentially all Form A huCC49 CH2 domain-deleted sc(Fv)2 tetravalent (C-scFv tetravalent CH2 domain deleted) antibody with little or no detectable Form B, demonstrating that the utility of this hinge for producing the Form A isoform is generally applicable to complex antibodies such as multivalent antibodies. It is clear that this invention is also applicable to bispecific tetravalent antibody formats as well. HuCC49 CH2 domain-deleted sc(Fv)2 tetravalent G1/G3/Pro243Ala244Pro245 antibody was examined by size exclusion chromatography and found to essentially elute as a single peak containing 84% monomer. The fraction containing the residual aggregates was removed by preparative size exclusion chromatography with the resulting preparation containing essentially 95% monomer (FIG. 24) HuCC49 CH2 domain-deleted sc(Fv)2 tetravalent G1/G3/Pro243Ala244Pro245 antibody was tested in a competitive binding assay for it's ability to bind to bovine submaxillary mucin, a source of the TAG-72 antigen, by time-resolved fluorometric immunoassay using a Delphia fluorimeter (Wallac Inc., Gaithersburg, Md.). Competitive binding curves are shown in FIG. 25. HuCC49 CH2 domain-deleted sc(Fv)2 tetravalent antibody Form A and control parent CH2 domain-deleted huCC49 (referred to as HuCC49 or IDEC 159) antibodies were evaluated. Relative binding activity for the tetravalent antibody was found to be 8-fold more avid than the control parent HuCC49 antibody (GraphPad Prism 4.0 for Windows, GraphPad, Software, San Diego Calif. USA. www.graphpad.com), consistent with an expected increase in the number of antigen binding sites.

These results show that the G1/G3/Pro243Ala244Pro245+[Gly/Ser] connecting peptide (SEQ ID NO:9) resulted in the production of essentially all Form A huCC49 CH2 domain-deleted sc(Fv)2 tetravalent antibody with no detectable Form B. The purified antibody demonstrated an increase in avidity towards antigen.

Example 11

Preparation of a CH2 Domain-Deleted Tetravalent Antibody

A huCC49 minibody and a huCC49 2 sc(Fv)2 tetravalent antibody (N-scFv tetravalent minibody) as shown in FIG. 2 were both constructed. Briefly, huCC49 2 sc(Fv)2 tetravalent antibody (N-scFv tetravalent minibody) design was based on inserting a huCC49 single chain Fv (scFv) between the carboxyl end of the first scFv domain and the amino-end of the hinge connecting peptide in the huCC49 minibody. The preparation of single polypeptide chain binding molecules of the Fv region, single-chain Fv molecules, is described in U.S. Pat. No. 4,946,778. A CC49 scFv immunoglobulin-like antibody is described in U.S. Pat. No. 5,892,019. The preparation of a minibody construct is described in U.S. Pat. No. 5,837, 821. The huCC49 scFv is comprised of a VL and a VH region sequence tethered by a short synthetic linker (VL→(Gly$_4$Ser)$_3$ linker→VH orientation) and was synthesized by PCR amplification and used to construct a huCC49 minibody. Second, the minibody vector was modified by adding a modified (Gly$_4$Ser)$_5$ linker to the carboxyl end of the amino-terminal scFv domain of the huCC49 minibody by PCR amplification, replacing nucleotides coding for the last two amino acids residues of the linker with an Nhe I restriction endonuclease site. This results in a (Gly$_4$Ser)$_4$-Gly$_3$-Ala-Ser linker followed by a Sal I restriction endonuclease site separated by several nucleotides. A second huCC49 scFv was amplified using PCR from plasmid DNA substrate containing huCC49 scFv gene with the 5' VL PCR primer encoding an Nhe I restriction endonuclease site and the 3' VH PCR primer encoding a Sal I site. The huCC49 scFv fragment was gel isolated, digested with Nhe I and Sal I restriction endonucleases and cloned into Nhe I and Sal I sites between the first scFv and the hinge connecting peptide. This results in a fusion product consisting of a leader peptide to two serial huCC49 scFvs to a hinge connecting peptide to a CH3 domain. Correct sequences were confirmed by DNA sequence analysis. Plasmid DNA was used to transform CHO DG44 cells for stable production of antibody protein. FIG. 10A shows the DNA sequence of huCC49 tetravalent (N-scFv tetravalent) minibody gene. FIG. 11A shows the amino acid sequence of huCC49 tetravalent (N-scFv tetravalent) minibody.

Figure 26:
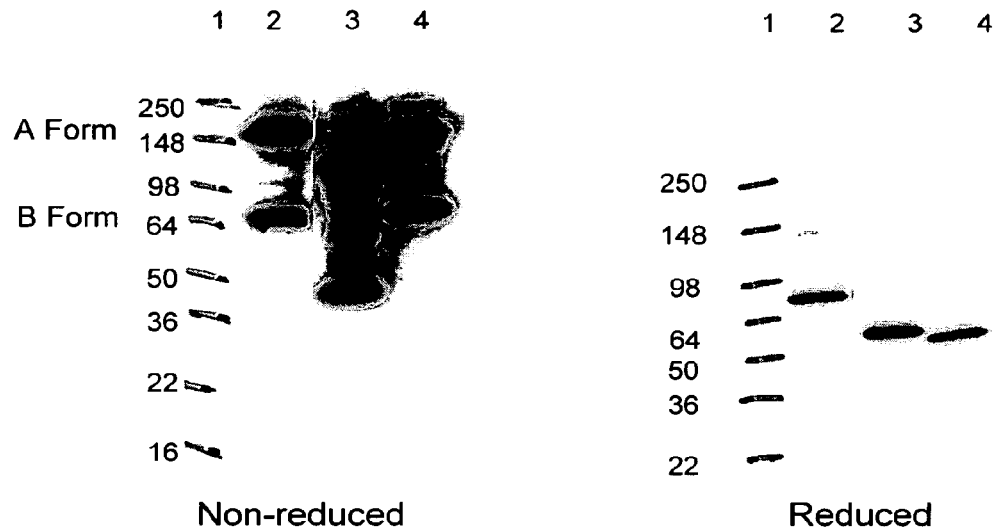
FIG. 26 shows Western Blots of supernatants from representative clones producing huCC49 minibody, huCC49 2 sc(Fv)2 tetravalent antibody (N-scFv tetravalent huCC49 minibody), and huCC49 CH2 domain deleted antibody. A Western Blot was performed on supernatants that were electrophoresed under reducing and non-reducing conditions.

Supernatants were collected from isolated cell lines and concentration of antibody in the culture supernatants determined by immunoassay. Supernatants were analyzed by non-reducing SDS-PAGE electrophoresis followed by Western Blot with anti-IgG-HRP conjugated antibody to detect heavy chain constant sequences in the Form A and Form B isoforms. Under these conditions, huCC49 minibody Form A is expected to migrate as a single ~82 kDa homodimer and half molecules or Form B as a ~41 kDa doublet. HuCC49 2 sc(Fv)2 tetravalent minibody Form A is expected to migrate as a single ~138 kDa homodimer and Form B as a ~69 kDa doublet in approximately a 50:50 ratio of A to B isoform. By comparison, huCC49 CH2 domain deleted antibody (expected to migrate as a single ~120 kDa homodimer and Form B as a ~60 kDa doublet in approximately a 50:50 ratio of A to B isoform) was used as control. As shown in FIG. 26, representative isolated minibody and 2 sc(Fv)2 tetravalent minibody clones were found to secrete both A and B isoforms consistent with the expected molecular masses under both non-reducing and reducing SDS-PAGE conditions.

Example 12

Preparation of a HuCC49 CH2 Domain-Deleted Tetravalent Antibody Comprising a Novel Connecting Peptide and Preferential Synthesis of Isoform A A huCC49 2 sc(Fv)2 tetravalent antibody (N-scFv tetravalent minibody) similar to the design shown in the bottom of FIG. 2 but containing the G1/G3/Pro243Ala244Pro245+[Gly/Ser] connecting peptide indicated in Table 2 was constructed. Briefly, gene sequences coding for partial G1/G3/Pro243Ala244Pro245+[Gly/Ser] connecting peptide was synthesized by PCR amplification using a 5' connecting peptide PCR primer encoding a Sal I restriction endonuclease site and a 3' connecting peptide PCR primer encoding an Xho I site. Plasmid DNA containing the gene sequence coding for the G1/G3/Pro243Ala244Pro245+[Gly/Ser] connecting peptide was used as substrate. The PCR product encodes all of G1/G3/Pro243Ala244Pro245 and part of [Gly/Ser] connecting peptide. The G1/G3/Pro243Ala244Pro245 hinge fragment was gel isolated, digested with Sal I and Xho I restriction endonucleases and cloned into the Sal I and Xho I vector sites reconstituting the full length G1/G3/Pro243Ala244Pro245+[Gly/Ser] connecting peptide. Correct sequences were confirmed by DNA sequence analysis. Plasmid DNA was used to transform CHO DG44 cells for stable production of antibody protein. FIG. 10B shows the DNA sequence of huCC49 2 sc(Fv)2 tetravalent antibody (N-scFv tetravalent minibody) gene containing the G1/G3/Pro243Ala244Pro245+[Gly/Ser] connecting peptide. FIG. 11B shows the amino acid sequence of huCC49 2 sc(Fv)2 tetravalent antibody (N-scFv tetravalent minibody) gene containing the G1/G3/Pro243Ala244Pro245+[Gly/Ser] connecting peptide.

Figure 27:
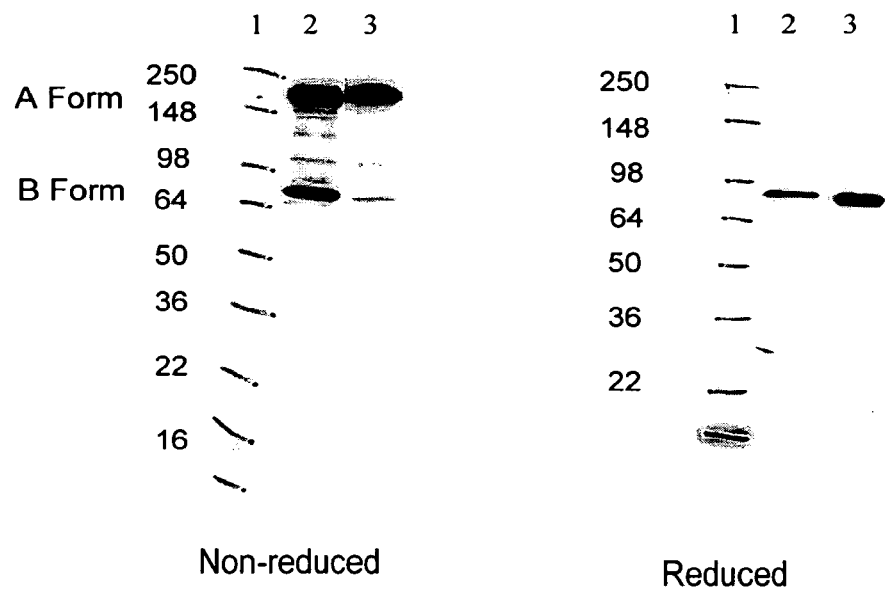
FIG. 27 shows a Western Blot of supernatants from representative clones producing huCC49 2 sc(Fv)2 tetravalent antibody (N-scFv tetravalent huCC49 minibody) and huCC49 2 sc(Fv)2 tetravalent antibody (N-scFv tetravalent huCC49 minibody) containing the G1/G3/Pro243Ala244Pro245+[Gly/Ser] hinge connecting peptide.

Supernatants were collected from isolated cell lines and concentration of antibody in the culture supernatants determined by immunoassay. Supernatants were analyzed by non-reducing SDS-PAGE electrophoresis followed by Western Blot with anti-IgG-HRP conjugated antibody to anti-IgG-HRP conjugated antibody to detect huCC49 2 sc(Fv)2 tetravalent minibody (N-scFv tetravalent minibody) Form A and Form B isoforms. Under these conditions, huCC49 2 sc(Fv)2 tetravalent minibody Form A is expected to migrate as a single ~138 kDa homodimer and Form B as a ~69 kDa doublet in approximately a 50:50 ratio of A to B isoform. As shown in FIG. 27, a representative huCC49 2 sc(Fv)2 tetravalent minibody containing the G1/G3/Pro243Ala244Pro245+[Gly/Ser] connecting peptide was found to produce essentially all Form A tetravalent minibody isoform.

Figure 28:
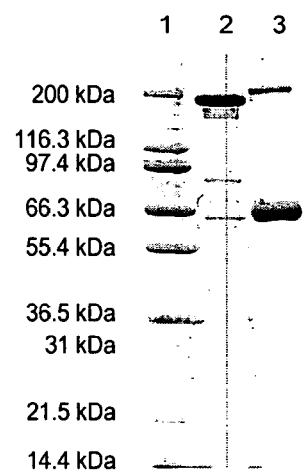
FIG. 28 shows a Coomassie Blue stained gel of purified Form A huCC49 domain-deleted sc(Fv)2 tetravalent antibody (N-scFv tetravalent minibody) containing the G1/G3/Pro243Ala244Pro245+[Gly/Ser] hinge connecting peptide.
Figure 29:
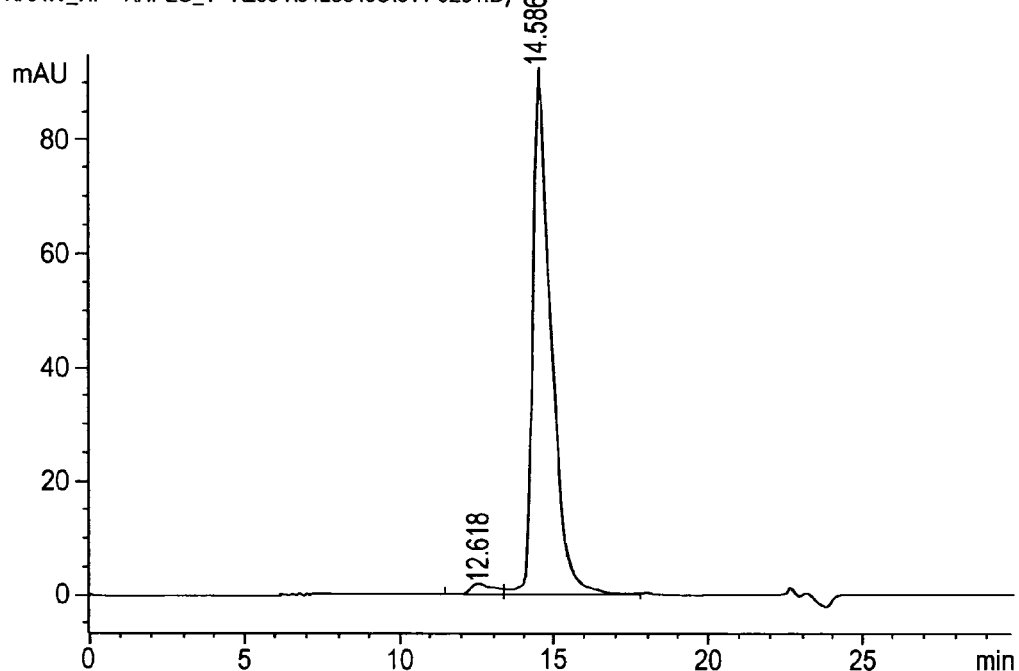
FIG. 29 shows purified Form A huCC49 domain-deleted sc(Fv)2 tetravalent antibody (N-scFv tetravalent minibody) containing the G1/G3/Pro243Ala244Pro245+[Gly/Ser] hinge connecting peptide predominantly elutes as a single peak by HPLC size-exclusion chromatography.

A cell line containing the G1/G3/Pro243Ala244Pro245+[Gly/Ser] (SEQ ID NO:9) connecting peptide introduced into the huCC49 2 sc(Fv)2 tetravalent minibody sequence was used for antibody production. Because huCC49 2 sc(Fv)2 tetravalent minibody lacks a CH1 domain, protein cannot be purified using Protein G chromatography. Antibody was subsequently purified using a combination of anion exchange, hydrophobic interaction, and size exclusion chromatography methods. HuCC49 2 sc(Fv)2 tetravalent minibody containing the G1/G3/Pro243Ala244Pro245+[Gly/Ser] (SEQ ID NO:9) connecting peptide was purified essentially as a single peak at 97.6% purity. Reduced and non-reduced purified protein samples were analyzed by SDS-PAGE electrophoresis. Under non-reducing conditions, Form A is expected to migrate as a single ~138 kDa homodimer and Form B as a ~69 kDa doublet. The connecting peptide shown in SEQ ID NO: 9 was found to substantially increase the proportion of Form A produced. Exemplary results are shown in FIG. 28. This result shows that the G1/G3/Pro243Ala244Pro245+[Gly/Ser] hinge (SEQ ID NO:9) resulted in the production of essentially all Form A huCC49 2 sc(Fv)2 tetravalent minibody (N-scFv tetravalent minibody) with little or no detectable Form B, demonstrating that the utility of this hinge for producing the Form A isoform is generally applicable to complex antibodies such as multivalent antibodies. It is clear that this invention is also applicable to bispecific tetravalent antibody formats as well. Purified huCC49 2 sc(Fv)2 tetravalent G1/G3/Pro243Ala244Pro245 minibody was examined by size exclusion chromatography and found to essentially elute as a single peak containing 97.6% monomer (FIG. 29).

Figure 30:
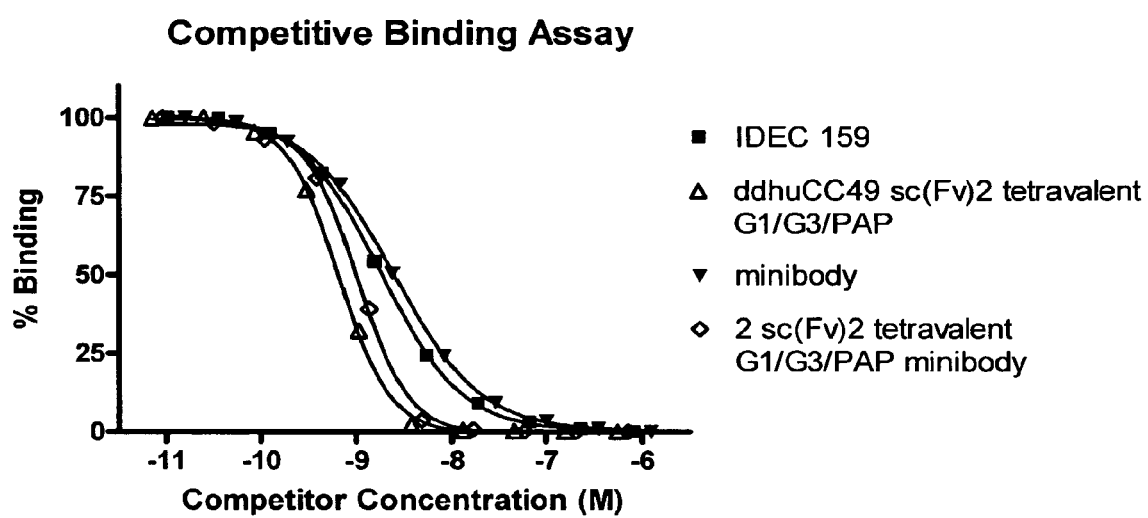
FIG. 30 shows the results of a competitive binding assay of huCC49 domain-deleted sc(Fv)2 tetravalent antibody (N-scFv tetravalent minibody) containing the G1/G3/Pro243Ala244Pro245+[Gly/Ser] hinge connecting peptide, huCC49 minibody, huCC49 CH2 domain-deleted sc(Fv)2 tetravalent antibody (C-scFv tetravalent antibody) containing the G1/G3/Pro243Ala244Pro245+[Gly/Ser] hinge connecting peptide, and control parent CH2 domain-deleted huCC49 (referred to as HuCC49 or IDEC 159) to bovine submaxillary mucine, a source of the TAG-72 antigen, by time-resolved fluorometic immunoassay using a Delphia fluorimeter (Wallac Inc, Gaithersburg, Md.).

Purified huCC49 2 sc(Fv)2 tetravalent G1/G3/Pro243Ala244Pro245 minibody was tested in a competitive binding assay for it's ability to bind to bovine submaxillary mucin, a source of the TAG-72 antigen, by time-resolved fluorometric immunoassay using a Delphia fluorimeter (Wallac Inc., Gaithersburg, Md.). Competitive binding curves are shown in FIG. 30. HuCC49 2 sc(Fv)2 tetravalent G1/G3/Pro243Ala244Pro245 minibody, huCC49 minibody, huCC49 CH2 domain-deleted sc(Fv)2 tetravalent G1/G3/Pro243Ala244Pro245 antibody, and control parent CH2 domain-deleted huCC49 (referred to as HuCC49 or IDEC 159) antibodies were evaluated. Relative binding activities for both tetravalent antibodies were found to be more avid than the control parent huCC49 antibody or minibody (GraphPad Prism 4.0 for Windows, GraphPad, Software, San Diego Calif. USA. www.graphpad.com), consistent with an expected increase in the number of antigen binding sites.

Example 13

Preparation of a PRIMATIZED® p5E8 CH2 Domain-Deleted Tetravalent Antibody Comprising a Novel Connecting Peptide and Preferential Synthesis of Isoform A PRIMATIZED® p5E8G1 is a chimeric macaque/human (PRIMATIZED®) monoclonal antibody containing macaque heavy and light variable regions fused to human gamma 1 and kappa constant regions, respectively. PRIMATIZED® p5E8G1 binds to human CD23, the low affinity receptor for IgE (FcεRII) (Mavromatis and Cheson. 2003. J. Clin. Oncol. 21:1874; US Patent Application 20030059424). CH2 domain-deleted PRIMATIZED® p5E8 sc(Fv)2 tetravalent antibody containing the G1/G3/Pro243Ala244Pro245+[Gly/Ser] synthetic connecting peptide indicated in Table 2 (SEQ ID NO:9) was constructed using a similar strategy as that described in Example 10. The PRIMATIZED® p5E8 scFv used for constructing the sc(Fv)2 tetravalent antibody is comprised of a p5E8 VL and a VH region sequence tethered by a short synthetic linker in the VL→(Gly$_4$Ser)$_3$ linker→VH orientation and is described in greater detail in Example 12. Correct sequences were confirmed by DNA sequence analysis. Plasmid DNA was used to transform CHO DG44 cells for stable production of antibody protein. FIG. 12A shows the DNA sequence of heavy chain CH2 domain-deleted PRIMATIZED® p5E8 sc(Fv)2 tetravalent antibody containing the G1/G3/Pro243Ala244Pro245+[Gly/Ser] connecting peptide. FIG. 12B shows the DNA sequence of light chain CH2 domain-deleted PRIMATIZED® p5E8 sc(Fv)2 tetravalent antibody. FIG. 13A shows the amino acid sequence of heavy chain CH2 domain-deleted PRIMATIZED® p5E8 sc(Fv)2 tetravalent antibody containing the G1/G3/Pro243Ala244Pro245+[Gly/Ser] connecting peptide. FIG. 13B shows the amino sequence of light chain CH2 domain-deleted PRIMATIZED® p5E8 sc(Fv)2 tetravalent antibody containing the G1/G3/Pro243Ala244Pro245+[Gly/Ser] connecting peptide.

Figure 31:
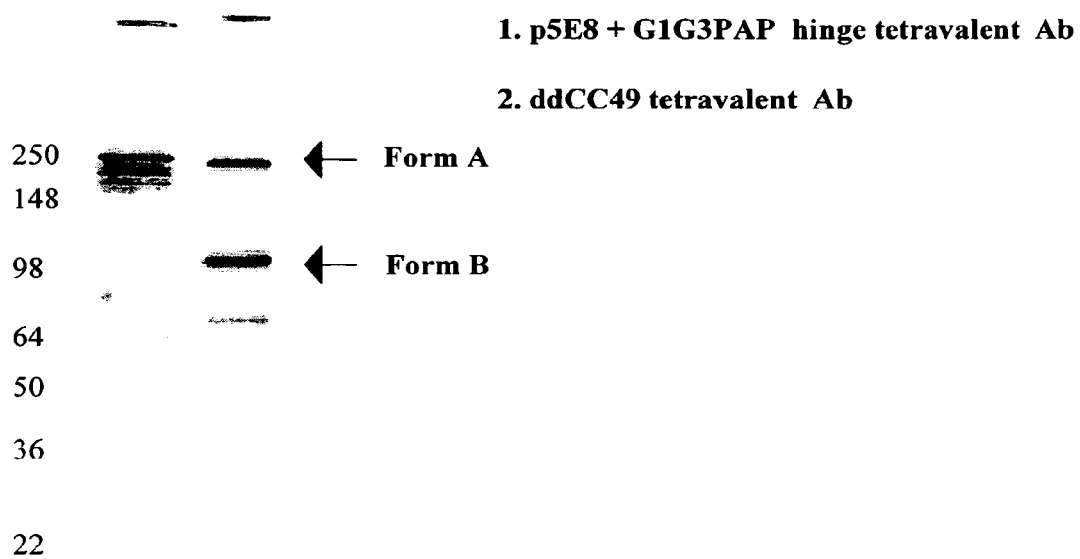
FIG. 31 shows a Western Blot of supernatant from a cell line producing CH2 domain-deleted (C-scFv tetravalent CH2 domain deleted) PRIMATIZED® p5E8 sc(Fv)2 antibody containing the G1/G3/Pro243Ala244Pro245+[Gly/Ser] hinge connecting peptide.

Supernatant was collected from a stably transfected cell line and concentration of antibody in the culture supernatant determined by immunoassay. Supernatant was analyzed by non-reducing SDS-PAGE electrophoresis followed by Western Blot with anti-human IgG-HRP conjugated antibody to detect Form A and Form B isoforms of CH2 domain-deleted PRIMATIZED® p5E8 sc(Fv)2 tetravalent antibody containing the G1/G3/Pro243Ala244Pro245+[Gly/Ser] connecting peptide. Under these conditions, Form A is expected to migrate as a single ~170 kDa homodimer and Form B as a ~85 kDa doublet. The connecting peptide shown in SEQ ID NO: 9 was found to substantially increase the proportion of Form A tetravalent antibody produced. Exemplary results are shown in FIG. 31. These results show that the G1/G3/Pro243Ala244Pro245+[Gly/Ser] connecting peptide (SEQ ID NO:9) resulted in the production of essentially all Form A CH2 domain-deleted PRIMATIZED® p5E8 sc(Fv)2 tetravalent antibody with no detectable Form B, demonstrating that the utility of this hinge for producing the Form A isoform CH2 domain-deleted sc(Fv)2 tetravalent antibodies is generally applicable to antibodies of varying specificities.

Example 14

Preparation of PRIMATIZED® p5E8 Minibodies Comprising a Novel Connecting Peptide and Preferential Synthesis of Isoform A Minibodies are single chain polypeptides consisting of an scFv fused to immunoglobulin hinge region and CH3 domain. The preparation of minibody single polypeptide chain binding molecules is described in U.S. Pat. No. 5,837,821. Normally, in intact IgG molecules the cysteine residue at position 230 in the hinge region forms a covalent disulfide bond with the carboxyl-terminal light chain constant domain cysteine residue at position 214, joining heavy and light chain polypeptides (Kabat numbering system). In the minibody design the light chain constant domain is absent, eliminating one of the two cysteines that participate in forming the disulfide bond. The single remaining cysteine in the hinge region at position 230, however, has been proposed to participate in a homotypic interchain disulfide bond possibly contributing to hinge region structure and therefore was left in place.

Figure 32:
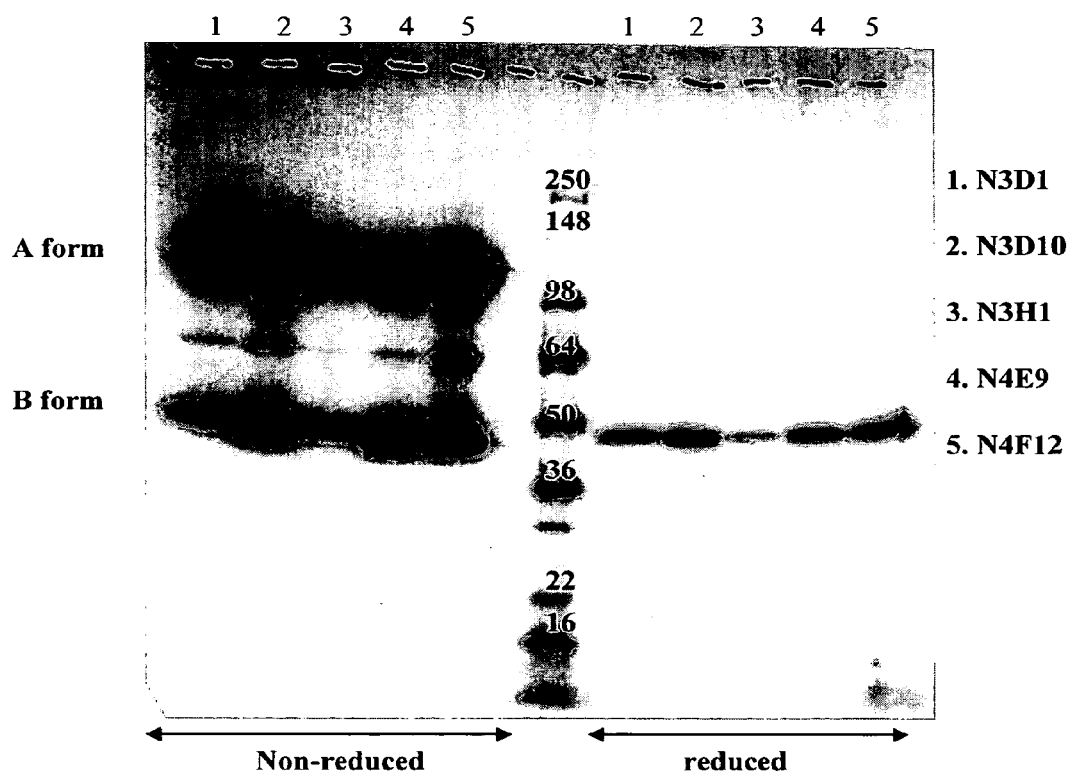
FIG. 32 shows a Western Blot of supernatants from five independent cell lines producing CH2 domain-deleted huCC49 VL/VH minibody. Minibody samples were analyzed under non-reducing, denaturing conditions revealing the presence of Form A and Form B isoforms.

Minibodies, which lack a CH2 domain, are secreted from cells and accumulate in culture supernatant as a mixture containing Form A and Form B isoforms and perhaps unassembled half molecules as shown in FIG. 32. The ratio of these forms is highly variable and presents a challenge for preparing a reproducibly pure product. The absence of the immunoglobulin CH1/CL domains precludes isolation of total minibody using Protein G immunoaffinity matrices. While the unassembled half molecules (MW ~40-45 kD) can be separated from the homodimers (MW ~80-90 kD) using a number of chromatographic strategies, the remaining intact A and B isoforms cannot be efficiently separated from one another using techniques such as HIC chromatography (described herein) also due to the absence of CH1/CL domains. These isoforms also cannot be separated by size exclusion chromatography because the molecular masses of the two isoforms are nearly identical, prohibiting separation based on this characteristic. Thus the composition of minibody preparations may actually be complex, consisting of a mixture of A and B isoforms. The production of CH2 domain-deleted PRIMATIZED® p5E8 minibodies engineered to contain the G1/G3/Pro243Ala244Pro245+[Gly/Ser] connecting peptide indicated in Table 2 (SEQ ID NO:9) was examined.

PRIMATIZED® p5E8 scFvs were constructed by PCR amplification. ScFvs were built in both orientations (VL→(Gly$_4$Ser)$_3$→linker VH (VL/VH) and VH→(Gly$_4$Ser)$_3$ linker→VL (VH/VL)). Oligonucleotides used in the construction are shown the tables below:

TABLE 7

PCR primers used to construct CH2 domain-deleted PRIMATIZED ® p5E8 VL/VH minibody containing the G1/G3/Pro243Ala244Pro245 + [Gly/Ser] connecting peptide.

N-23VL-1F                     (SEQ ID NO: 37)
5'-AGAGAG<u>ACATGT</u>GGCGACATCCAGATGACCCAGTC-3'

23-VL-1R                      (SEQ ID NO: 38)
5'-GGAGCCACCCCCACCGGACCCGCCACCGCCTTTGATTTCCACCTTGG TCC-3'

23-VH-2F                      (SEQ ID NO: 39)
5'-GGGTCCGGTGGGGGTGGCTCCGGGGGCGGTGGCTCCGAGGTGCAGCT GGTGGAGTC-3'

N-23-VH-2R                   (SEQ ID NO: 40)
5'-AGAGAG<u>GTCGAC</u>TGAGGAGACGGTGACCAGGAC-3'

In SEQ ID NO: 37 the BspLU11 I restriction endonuclease site is underlined. In SEQ ID NO:40 the Sal I restriction endonuclease site is underlined.

TABLE 8

PCR primers used to construct CH2 domain-deleted PRIMATIZED ® p5E8 VH/VL minibody containing the G1/G3/Pro243Ala244Pro245 + [Gly/Ser] connecting peptide.

N-23VH-1F                     (SEQ ID NO: 41)
5'-AGAGAG<u>ACATGT</u>GGCGAGGTGCAGCTGGTGGAGTC-3'

23-VH-1R                      (SEQ ID NO: 42)
5'-GGAGCCACCCCCACCGGACCCGCCACCGCCTGAGGAGACGGTGACCA GGAC-3'

TABLE 8-continued

PCR primers used to construct CH2 domain-deleted
PRIMATIZED ® p5E8 VH/VL minibody containing the
G1/G3/Pro243Ala244Pro245 + [Gly/Ser] connecting
peptide.

```
23-VL-2F                    (SEQ ID NO: 43)
5'-GGGTCCGGTGGGGGTGGCTCCGGGGGCGGTGGCTCCGACATCCAGAT
GACCCAGTC-3'

N-23-VL-2R                  (SEQ ID NO: 44)
5'-AGAGAGGTCGACTTTGATTTCCACCTTGGTCC-3
```

In SEQ ID NO: 41 the BspLU11 I restriction endonuclease site is underlined. In SEQ ID NO:44 the Sal I restriction endonuclease site is underlined.

The VL/VH scFv was constructed in two steps. The 5' VL PCR forward primer N-23VL-1F (SEQ ID NO:37) included a BspLU11 I restriction endonuclease site to permit joining of the scFv to the immunoglobulin signal peptide in the expression vector. The 3' VL PCR reverse primer 23-VL-1R (SEQ ID NO:38) included sequence partially encoding the (Gly$_4$Ser)$_3$ linker peptide used to join the VL and VH regions. The 5' forward VH PCR primer 23-VH-2F (SEQ ID NO:30) also included sequence partially encoding a (Gly$_4$Ser)$_3$ linker peptide used to connect the VL and VH regions and the 3' VH PCR reverse primer N-23-VH-2R (SEQ ID NO:40) included a Sal I restriction endonuclease site to join the scFv to the hinge region. The two V regions were amplified with the two sets of PCR primers from plasmid DNA substrate containing PRIMATIZED® p5E8G1 antibody and assembly of the scFv was accomplished in a second PCR reaction through the common overlapping sequences encoding the (Gly$_4$Ser)$_3$ linker. The PRIMATIZED® p5E8 scFv gene fragment was gel isolated, digested with BspLU11 I and Sal I restriction endonucleases and cloned into the BspLU11 I and Sal I double-digested CH2 domain-deleted antibody Polycistronic expression vector containing the G1/G3/Pro243Ala244Pro245+[Gly/Ser] connecting peptide. The PRIMATIZED® p5E8 VH/VL scFv was constructed in a similar manner using PCR primer pairs N-23VH-1F (SEQ ID NO:41) and 23-VH-1R (SEQ ID NO:36) and 23-VL-2F (SEQ ID NO:43) and N-23-VL-2R (SEQ ID NO:44) shown in Tables 7 and 8. Correct sequences of both completed constructs were confirmed by DNA sequence analysis. Plasmid DNA was used to transform CHO DG44 cells for transient production of antibody protein. FIG. 14 shows the DNA sequence of CH2 domain-deleted PRIMATIZED® p5E8 VL/VH minibody containing the G1/G3/Pro243Ala244Pro245+[Gly/Ser] connecting peptide in the VL VH orientation (VL/VH). FIG. 15 shows the DNA sequence of CH2 domain-deleted PRIMATIZED® p5E8 VH/VL minibody containing the G1/G3/Pro243Ala244Pro245+[Gly/Ser] connecting peptide in the VH VL orientation (VH/VL). FIG. 16 shows the amino acid sequence of CH2 domain-deleted PRIMATIZED® p5E8 VL/VH minibody containing the G1/G3/Pro243Ala244Pro245+[Gly/Ser] connecting peptide. FIG. 17 shows the amino acid sequence of CH2 domain-deleted PRIMATIZED® p5E8 VH/VL minibody containing the G1/G3/Pro243Ala244Pro245+[Gly/Ser] connecting peptide.

Figure 33:
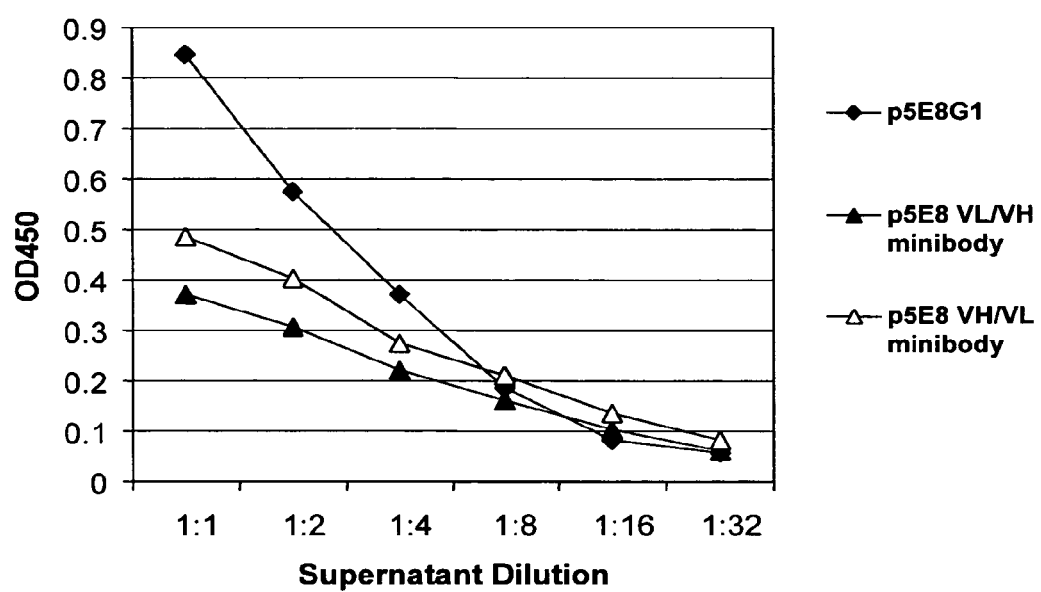
FIG. 33 show the results of an ELISA binding assay of PRIMATIZED® p5E8 VH/VL and VL/VH minibodies containing the G1/G3/Pro243Ala244Pro245+[Gly/Ser] connecting peptide binding to the CD23 antigen. p5E8G1 is intact full length PRIMATIZED® IgG1.

Supernatant was collected from the transfected cell lines and concentration of antibody in the culture supernatant determined by immunoassay. Minibody molecules present in culture supernatant were analyzed for binding to soluble CD23 antigen immobilized on plastic microtiter plates by ELISA. Results shown in FIG. 33 demonstrate that both PRIMATIZED® p5E8 VH/VL and VL/VH minibodies containing the G1/G3/Pro243Ala244Pro245+[Gly/Ser] connecting peptide are equally capable of binding to the CD23 antigen in a dose-responsive manner.

Figure 34:
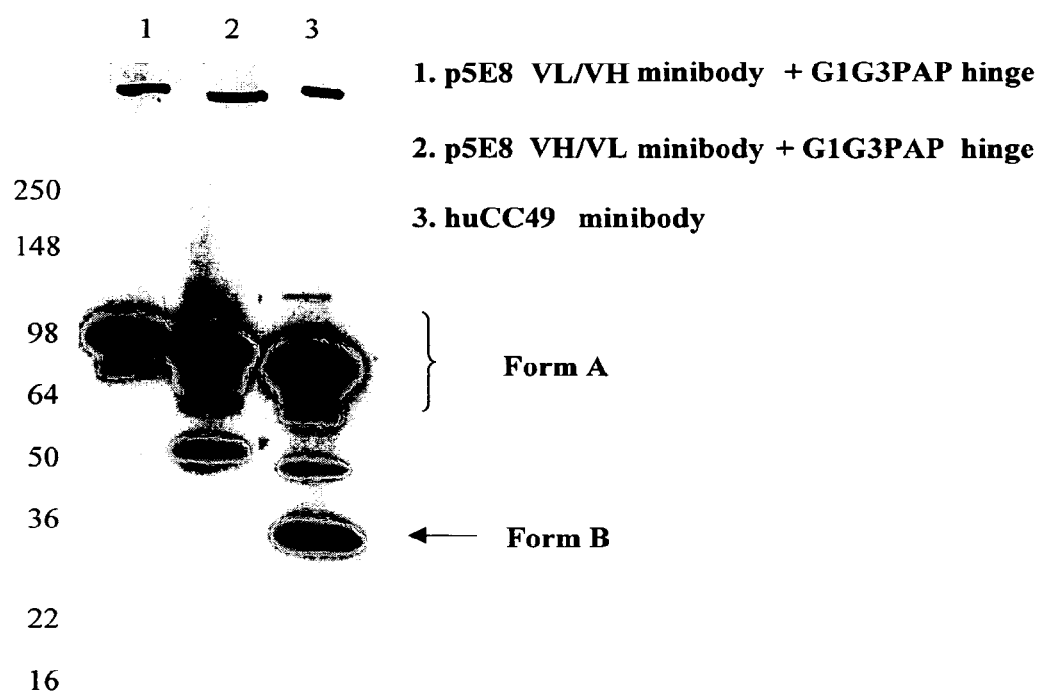
FIG. 34 shows a Western Blot of supernatant from cell lines producing PRIMATIZED® p5E8 VH/VL and VL/VH minibodies containing the G1/G3/Pro243Ala244Pro245+[Gly/Ser] connecting peptide.

Supernatants were analyzed by non-reducing SDS-PAGE electrophoresis followed by Western Blot with anti-human IgG-HRP conjugated antibody to detect Form A and Form B isoforms of CH2 domain-deleted PRIMATIZED® p5E8 minibodies containing the G1/G3/Pro243Ala244Pro245+ [Gly/Ser] connecting peptide. Under these conditions, Form A is expected to migrate as a single-80-90 kDa homodimer and Form B as a ~40-45 kDa doublet. The connecting peptide shown in SEQ ID NO: 9 was found to substantially increase the proportion of Form A for both minibodies produced. Exemplary results are shown in FIG. 34. These results show that the G1/G3/Pro243Ala244Pro245+[Gly/Ser] connecting peptide (SEQ ID NO:9) resulted in the production of essentially all Form A CH2 domain-deleted PRIMATIZED® p5E8 minibody with no detectable Form B.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising polypeptide dimers having at least four antigen binding sites and at least two polypeptide chains, wherein said at least two polypeptide chains each comprise a complete Ig heavy chain, and a chimeric hinge,
   wherein said chimeric hinge connects the CH1 and the CH2 domain of the Ig heavy chain, and
   wherein greater than about 50% of the dimers comprise polypeptide chains that are linked via at least one interchain disulfide linkage, and
   wherein amino acids at positions 226-242 (Kabat numbering) comprise: (i) the human IgG1 upper hinge region sequence EPKSCDKTHT (SEQ ID NO:2) or the human IgG4 upper hinge region sequence ESKYGPP (SEQ ID NO:45) at Kabat hinge positions 226-238; (ii) a cysteine residue (C) at Kabat hinge position 239; (iii) a proline residue (P) at Kabat hinge position 240; (iv) a proline (P) or serine (S) residue at Kabat hinge position 241; (v) the human IgG3 middle hinge sequence CPEPKSCDTPP-PCPR (SEQ ID NO:49) at Kabat hinge positions 241EE-241SS; and (vi) a cysteine residue (C) at Kabat hinge position 242.

2. The composition of claim 1 wherein greater than about 90% of the dimers are linked via at least one interchain disulfide linkage.

3. The composition of claim 1, wherein the dimers are linked via two or more interchain disulfide linkages.

4. The composition of claim 1, wherein the heavy chain is from an antibody of an isotype selected from the group consisting of: IgG1, IgG2, IgG3, and IgG4.

5. The composition of claim 1, wherein the dimers are bispecific.

6. The composition of claim 1, wherein at least one of said antigen-binding sites is specific for a soluble ligand.

7. The composition of claim 1, wherein at least one of said antigen binding sites is specific for a cell surface molecule.

8. The composition of claim 1, wherein at least one of said antigen binding sites is specific for a tumor cell antigen.

9. The composition of claim 1, wherein the chimeric hinge comprises a proline residue at position 243, Kabat numbering system.

10. The composition of claim 9, wherein the chimeric hinge further comprises an alanine residue at position 244 and a proline residue at position 245, Kabat numbering system.

11. The composition of claim 1, wherein the chimeric hinge comprises at least a portion of an IgG1 hinge domain and at least a portion of an IgG3 hinge domain.

12. The composition of claim 1, wherein the chimeric hinge comprises an amino acid sequence selected from the group consisting of: SEQ ID NOs: 8-15 and 48.

13. A composition comprising tetravalent binding molecules comprising at least two polypeptide chains and at least four antigen binding sites, wherein two of the polypeptide chains comprise an Ig heavy chain CH3 domain and a chimeric hinge interposed between the antigen binding site and the CH3 domain, and wherein the polypeptide chains lack all or part of a CH2 domain,
   and wherein greater than about 50% of the molecules are present in a form in which two of the polypeptide chains are linked via at least one interchain disulfide linkage and
   wherein amino acids at positions 226-242 (Kabat numbering) comprise: (i) the human IgG1 upper hinge region sequence EPKSCDKTHT (SEQ ID NO:2) or the human IgG4 upper hinge region sequence ESKYGPP (SEQ ID NO:45) at Kabat hinge positions 226-238; (ii) a cysteine residue (C) at Kabat hinge position 239; (iii) a proline residue (P) at Kabat hinge position 240; (iv) a proline (P)

or serine (S) residue at Kabat hinge position 241; (v) the human IgG3 middle hinge sequence CPEPKSCDTPP-PCPR (SEQ ID NO:49) at Kabat hinge positions 241EE-241SS; and (vi) a cysteine residue (C) at Kabat hinge position 242.

14. The composition of claim 13, wherein greater than about 90% of the binding molecules are linked via at least one interchain disulfide linkage.

15. The composition of claim 13 wherein at least one of the polypeptide chains comprises a CH3 domain genetically fused to a VL, VH or CH1 domain via the chimeric hinge.

16. The composition of claim 13, wherein the Ig heavy chains lack the entire CH2 domain.

17. The composition of claim 13, wherein two of the Ig heavy chains are linked via two or more interchain disulfide linkages.

18. The composition of claim 13, wherein the Ig heavy chain is from an antibody of an isotype selected from the group consisting of: IgG1, IgG2, IgG3, and IgG4.

19. The composition of claim 13, wherein the Ig heavy chain comprises an amino acid sequence from a hinge region selected from the group consisting of: a γ1 hinge, a γ 2 hinge a γ 3 hinge, and a γ 4 hinge.

20. The composition of claim 13, wherein the dimers are bispecific.

21. The composition of claim 13, wherein the chimeric hinge comprises a proline residue at position 243, Kabat numbering system.

22. The composition of claim 13, wherein the chimeric hinge comprises at least a portion of an IgG1 hinge domain and at least a portion of an IgG3 hinge domain.

23. A composition comprising polypeptide dimers having at least four binding sites and at least two polypeptide chains, wherein said at least two polypeptide chains comprise (i) an Ig heavy chain lacking a CH2 domain, and (ii) a chimeric hinge,
wherein said chimeric hinge comprises an amino acid sequence selected from the group consisting of SEQ ID NOs: 8-15 and 48 and wherein said chimeric hinge connects said heavy chain to at least one of said binding sites, and
wherein greater than 50% of the polypeptide dimers comprise polypeptide chains that are linked via at least one interchain disulfide linkage.

24. The composition of claim 23, wherein greater than 90% of the polypeptide dimers are linked via at least one interchain disulfide linkage.

25. The composition of claim 23, wherein the dimers are linked via two or more interchain disulfide linkages.

26. The composition of claim 23, wherein the heavy chain is from an antibody of an isotype selected from the group consisting of IgG1, IgG2, IgG3, and IgG4.

27. The composition of claim 23, wherein the polypeptide dimers comprise four polypeptide chains and wherein two of the polypeptide chains comprise at least one heavy chain and a chimeric hinge.

28. The composition of claim 23, wherein the dimers are bispecific.

29. The composition of claim 23, wherein at least one of said binding sites is specific for a soluble ligand.

30. The composition of claim 23, wherein at least one of said binding sites is specific for a cell surface molecule.

31. The composition of claim 23, wherein at least one of said binding sites is specific for a tumor cell antigen.

32. The composition of claim 1, wherein at least one antigen binding site binds to an antigen expressed on the surface of tumor cells.

33. The composition of claim 13, wherein at least one antigen binding site binds to an antigen expressed on the surface of tumor cells.

34. The composition of claim 23, wherein at least one antigen binding site binds to an antigen expressed on the surface of tumor cells.

35. The composition of claim 1, wherein the heavy chain is from an antibody of an IgG3 isotype.

36. The composition of claim 13, wherein the heavy chain is from an antibody of an IgG3 isotype.

37. The composition of claim 23, wherein the heavy chain is from an antibody of an IgG3 isotype.

38. The composition of claim 1, wherein the chimeric hinge further comprises a gly-ser linker.

39. The composition of claim 33, wherein the gly-ser linker consists of the amino acid sequence GGGSSGGGSG (SEQ ID NO:1).

40. The composition of claim 13, wherein the chimeric hinge further comprises a gly-ser linker.

41. The composition of claim 40, wherein the gly-ser linker consists of the amino acid sequence GGGSSGGGSG (SEQ ID NO:1).

42. The composition of claim 1, wherein the Ig heavy chain is from an IgG4 molecule.

43. The composition of claim 13, wherein the Ig heavy chain is from an IgG4 molecule.

44. The composition of claim 23, wherein the Ig heavy chain is from an IgG4 molecule.

45. The composition of claim 1, wherein the polypeptide dimers comprise four polypeptide chains and wherein two of the polypeptide chains comprise at least one heavy chain and a chimeric hinge.

46. The composition of claim 13, wherein the chimeric hinge comprises the amino acid sequence of SEQ ID NO:8.

47. The composition of claim 13, wherein the chimeric hinge comprises the amino acid sequence of SEQ ID NO:9.

48. The composition of claim 13, wherein the chimeric hinge comprises the amino acid sequence of SEQ ID NO:48.

49. The composition of claim 13, wherein the binding molecule is a minibody consisting of two polypeptide chains, wherein said polypeptide chains each lack a CH1 domain and wherein the antigen binding sites are scFv molecules.

50. The composition of claim 13, wherein the binding molecule is a CH2 domain-deleted antibody consisting of four polypeptide chains, wherein said polypeptide chains lack the entire CH2 domain.

* * * * *